US012703701B2

(12) United States Patent
Xiao et al.

(10) Patent No.: US 12,703,701 B2
(45) **Date of Patent: *Aug. 11, 2026**

(54) PYRAZOLE-CONTAINING POLYCYCLIC DERIVATIVE INHIBITOR, PREPARATION METHOD THEREFOR AND APPLICATION THEREOF

(71) Applicants: Shanghai Hansoh Biomedical Co., Ltd., Shanghai (CN); Jiangsu Hansoh Pharmaceutical Group Co., Ltd., Lianyungang (CN)

(72) Inventors: Hualing Xiao, Shanghai (CN); Qiang Liu, Shanghai (CN); Xingyun Lu, Shanghai (CN); Jiaqiang Cai, Shanghai (CN); Rudi Bao, Shanghai (CN)

(73) Assignees: Shanghai Hansoh Biomedical Co., Ltd., Shanghai (CN); Jiangsu Hansoh Pharmaceutical Group Co., Ltd., Lianyungang (CN)

( * ) Notice: Subject to any disclaimer, the term of this patent is extended or adjusted under 35 U.S.C. 154(b) by 931 days.

This patent is subject to a terminal disclaimer.

(21) Appl. No.: 17/784,256

(22) PCT Filed: Dec. 7, 2020

(86) PCT No.: PCT/CN2020/134264
§ 371 (c)(1),
(2) Date: Jun. 10, 2022

(87) PCT Pub. No.: WO2021/115225
PCT Pub. Date: Jun. 17, 2021

(65) Prior Publication Data

US 2023/0118497 A1 Apr. 20, 2023

(30) Foreign Application Priority Data

| | | |
|---|---|---|
| Dec. 10, 2019 | (CN) | 201911261871.8 |
| Jan. 8, 2020 | (CN) | 202010019465.7 |
| Apr. 10, 2020 | (CN) | 202010280611.1 |
| Apr. 30, 2020 | (CN) | 202010364846.9 |
| Jul. 1, 2020 | (CN) | 202010627864.1 |

(51) Int. Cl.

| | |
|---|---|
| ***C07D 471/14*** | (2006.01) |
| ***A61K 31/519*** | (2006.01) |
| ***A61P 11/00*** | (2006.01) |
| ***A61P 13/00*** | (2006.01) |
| ***A61P 15/00*** | (2006.01) |
| ***A61P 25/00*** | (2006.01) |
| ***C07D 487/04*** | (2006.01) |
| ***C07D 487/14*** | (2006.01) |
| ***C07D 498/14*** | (2006.01) |
| ***C07D 513/14*** | (2006.01) |

(52) U.S. Cl.
CPC ......... *C07D 471/14* (2013.01); *C07D 498/14* (2013.01); *C07D 513/14* (2013.01)

(58) Field of Classification Search
CPC .. C07D 471/14; C07D 487/04; C07D 487/14; C07D 498/14; C07D 513/14; A61K 31/519; A61P 11/00; A61P 13/00; A61P 15/00; A61P 25/00
See application file for complete search history.

(56) References Cited

U.S. PATENT DOCUMENTS 4,070,466 A 1/1978 Denzel et al.
4,105,766 A * 8/1978 Alexander ............ C07C 243/00 514/820
9,434,734 B2 * 9/2016 Mayer ..................... A61P 25/02
(Continued)

FOREIGN PATENT DOCUMENTS

CN 104540828 A 4/2015
CN 105683190 A 6/2016

OTHER PUBLICATIONS

El-Feky, S. A., Novel Quinazolinones from 2-Cyanomethyl-3-Phenyl-4(3H) quinazolinone, Bollettino Chimico Farmaceutico, vol. 137, No. 7, pp. 286-289 (Year: 1998).*
(Continued)

*Primary Examiner* — Brenda L Coleman
(74) *Attorney, Agent, or Firm* — Taft Stettinius & Hollister LLP

(57) ABSTRACT

Provided are a pyrazole-containing polycyclic derivative inhibitor, a preparation method therefor and an application thereof. In particular, provided are a compound as represented by formula (I), a preparation method therefor, a pharmaceutical composition containing the compound, and an application thereof as a P2X3 inhibitor in treatment of P2X3 receptor function disorders, particularly in treatment of neurogenic diseases, wherein the substituents in the formula (I) are the same as those in the description in definition.

(I)

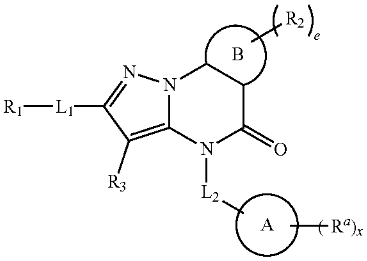

25 Claims, No Drawings

(56) References Cited

U.S. PATENT DOCUMENTS

| | | | | |
|---|---|---|---|---|
| 9,708,332 | B2 * | 7/2017 | Sturino | C07D 413/06 |
| 11,136,321 | B2 * | 10/2021 | Vendeville | C07D 471/14 |
| 11,820,773 | B2 * | 11/2023 | Vendeville | C07D 471/16 |
| 2024/0376108 | A1 * | 11/2024 | Dong | A61K 31/519 |

OTHER PUBLICATIONS

CAS Printout of Registry Numbers obtained in the search performed on Dec. 4, 2024.*

International Search Report; China National Intellectual Property Administration; International Application No. PCT/CN2020/134264; Feb. 19, 2021; 10 pages.

Chen, Dingben et al.; Cascade synthesis of azoquinazolinones by Cu(I)-catalyzed C—N coupling/C—H activation/C—N formation reactions under O2; Tetrahedron; 2013; pp. 6461-6467; vol. 69.

Quang Dao, Pham Duy et al.; Microwave-assisted Copper Powder-Catalyzed Synthesis of Azole-Fused Pyrimidinones; Current Organic Chemistry; 2018; pp. 85-93; vol. 22.

Guerrini, Gabriella et al.; Pyrazolo[1,5-a]quinazoline scaffold as 5-deaza analogue of pyrazolo[5,1-c][1,2,4] benzotriazine system: synthesis of new derivatives, biological activity on GABAA receptor subtype and molecular dynamic study; Journal of Enzyme Inhibition and Medicinal Chemistry; 2016; pp. 195-204; vol. 31, No. 2.

Unzue, Andrea et al.; Fragment-based Design of Selective Nanomolar Ligands of the CREBBP Bromodomain; Journal of Medicinal Chemistry; 2015; 21 pages.

Taliani, Sabrina et al.; Phenylpyrazolo[1,5-a]quinazolin-5(4H)-one: a suitable scaffold for the development of non-camptothecin Topoisomerase I (Top1) inhibitors; J Med Chem.; Sep. 26, 2013; pp. 7458-7462; vol. 56, No. 18.

Written Opinion of the International Searching Authority; China National Intellectual Property Administration; International Application No. PCT/CN2020/134264; Mar. 16, 2021; 14 pages.

International Preliminary Report on Patentability; The International Bureau of WIPO; International Application No. PCT/CN2020/134264; Jun. 23, 2022; 16 pages.

* cited by examiner

PYRAZOLE-CONTAINING POLYCYCLIC DERIVATIVE INHIBITOR, PREPARATION METHOD THEREFOR AND APPLICATION THEREOF

CROSS-REFERENCE TO RELATED APPLICATIONS

This application is a U.S. National Phase of International PCT Application No. PCT/CN2020/134264 filed on Dec. 7, 2020, which claims priority to Chinese Patent Application Serial No. 201911261871.8 filed on Dec. 10, 2019, Chinese Patent Application Serial No. 202010019465.7 filed on Jan. 8, 2020, Chinese Patent Application Serial No. 202010280611.1 filed on Apr. 10, 2020, Chinese Patent Application Serial No. 202010364846.9 filed on Apr. 30, 2020, and Chinese Patent Application Serial No. 202010627864.1 filed on Jul. 1, 2020, the contents of each application are incorporated herein by reference in their entireties.

FIELD OF THE INVENTION

The present invention belongs to the field of pharmaceutical synthesis, and specifically relates to a pyrazole-containing polycyclic derivative inhibitor, a method for preparing the same, and a use thereof.

BACKGROUND OF THE INVENTION

P2X receptors, also known as P2X purinoreceptors, are a family of cation-permeable ATP ligand-gated ion channels that can bind to extracellular ATP. P2X receptors have seven subunits, and exist in the form of homotrimers or heterotrimers. P2X receptors are mainly expressed on nerve endings (presynaptic and postsynaptic) of the nervous system, and regulate synaptic transmission. P2X3 receptor is a member of the P2X family, and is a key sensory receptor for sensing upper airway stimuli and triggering the cough reflex. P2X3 receptor is thought to play a key role in the sensitisation of specific sensory nerves, involve in pain and cough, and in the perception of bone cancer pain. Blocking P2X3 can suppress cough signaling.

Cough is a defensive nerve reflex of the body, which helps to clear respiratory secretions and harmful factors. However, frequent and severe cough will seriously affect the patient's work, life and social activities. Cough is divided into acute, subacute, and chronic cough. Chronic cough is defined as coughing for more than 8 weeks, with cough as the main or only symptom, and no obvious lesions in the lungs on chest imaging examination. Chronic cough has long been considered a consequence of various diseases such as asthma/eosinophilic bronchitis, rhinitis and gastroesophageal acid reflux disease. However, recent evidences show that chronic cough is a clinical symptom of neuroticism with unique intrinsic pathophysiological features. Unexplained chronic cough or idiopathic cough is mainly manifested by chronic irritating dry cough. It is sensitive to external stimuli and generally has high cough sensitivity. Cough hypersensitivity is its physiological and pathological mechanism. Cough-related afferent nerve abnormalities may be the cause of refractory or unexplained chronic cough. Chronic cough can cause complications in cardiovascular, digestive, neurological, urinary, musculoskeletal systems, such as urinary incontinence, syncope, insomnia, anxiety, etc.

In view of the pathophysiology of cough hypersensitivity syndrome, treatment should aim to reduce cough sensitivity. Current treatment options are limited, including pharmacological and non-pharmacological approaches. Clinical study results have shown that the neuromodulator drug gabapentin is effective. Other drugs such as amitriptyline, baclofen, carbamazepine and pregabalin can also be used. Severe cough can be treated by appropriate antitussives. Antitussives are mainly divided into central antitussives and peripheral antitussives. Central antitussives are divided into dependent antitussives (morphine alkaloids and their derivatives) and non-dependent antitussives (synthetic dextromethorphan and pentoverine). Dependent antitussives have side effects such as addiction and anesthesia. Non-dependent antitussives are widely used in clinical practice. Peripheral antitussives, also known as ending antitussives, act by inhibiting a certain link in the cough reflex arc, including local anesthetics (narcotine, benzonatate) and mucosal protectants (benproperine and moguisteine).

At present, there are no approved P2X3 receptor antagonist small molecule drugs on the market. P2X3 receptor antagonist drugs currently in clinical stage include MK-7264 developed by Merck & Co. It is used to treat diseases such as chronic cough, pain and pulmonary fibrosis. It has low selectivity to P2X3/P2X2/3 and good safety, but has side effects such as loss of taste. At present, it has entered the phase III clinical study for the indication of chronic cough. BLU5937 developed by Bellus Health has high selectivity, and no side effects such as taste side effects appeared in phase I clinical trials. On Jul. 6, 2020, Bellus Health announced the main results of the phase 2 RELIEF trial of BLU-5937 in patients with refractory chronic cough: in the phase II clinical study, the RELIEF trial failed to achieve statistical significance for the primary endpoint of placebo-adjusted reduction in cough frequency at any dose. In addition, BAY-1817080 and BAY-1902607 developed by Bayer and S-600918 developed by Shionogi are currently in clinical phase I/II for the indication of chronic cough. Therefore, there is an urgent need to develop safe, non-addictive, non-narcotic and highly selective P2X3 receptor inhibitor drugs for treating diseases such as chronic cough to meet the huge market demand.

SUMMARY OF THE INVENTION

The object of the present invention is to provide a compound of formula (I), a stereoisomer thereof or a pharmaceutically acceptable salt thereof, wherein the structure of the compound of formula (I) is shown as following:

(I)

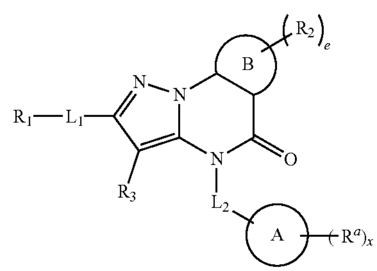

wherein:

$L_1$ is selected from the group consisting of a bond, $-(CH_2)_{n1}-$, $-(CH_2)_{n1}C(O)(CR_{aa}R_{bb})_{n2}-$, $-(CH_2)_{n1}C(O)NR_{aa}(CH_2)_{n2}-$, $-(CH_2)_{n1}(CR_{aa}R_{bb})_{n2}-$, $-(CR_{aa}R_{bb})_{n1}O(CH_2)_{n2}-$, $-(CH_2)_{n1}O(CR_{aa}R_{bb})_{n2}-$, $-(CR_{aa}R_{bb})_{n1}S(CH_2)_{n2}-$, $-$ $(CH_2)_{n1}S(CR_{aa}R_{bb})_{n2}$—, —$(CR_{aa}R_{bb})_{n1}(CH_2)_{n2}NR_{cc}$—, —$(CH_2)_{n1}NR_{aa}(CR_{bb}R_{cc})_{n2}$—, —$(CH_2)_{n1}NR_{aa}C(O)$—, —$(CH_2)_{n1}P(O)R_{aa}$—, —$(CH_2)_{n1}S(O)_{n2}$—, —$(CH_2)_{n1}S(O)_{n2}NR_{aa}$— and —$(CH_2)_{n1}NR_{aa}S(O)_{n2}$—;

$R_{aa}$ to $R_{cc}$ are each independently selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

or, any two of $R_{aa}$ to $R_{cc}$ are bonded to form a cycloalkyl, heterocyclyl, aryl or heteroaryl, wherein the cycloalkyl, heterocyclyl, aryl or heteroaryl can be optionally further substituted;

$L_2$ is selected from the group consisting of a bond, —$(CH_2)_{n3}$—, —$(CH_2)_{n3}C(O)(CR_{dd}R_{ee})_{n4}$—, —$(CH_2)_{n3}C(O)NR_{dd}(CH_2)_{n4}$—, —$(CH_2)_{n3}(CR_{dd}R_{ee})_{n4}$—, —$(CR_{dd}R_{ee})_{n3}O(CH_2)_{n4}$—, —$(CH_2)_{n3}O(CR_{dd}R_{ee})_{n4}$—, —$(CR_{dd}R_{ee})_{n3}S(CH_2)_{n4}$—, —$(CH_2)_{n3}S(CR_{dd}R_{ee})_{n4}$—, —$(CR_{dd}R_{ee})_{n3}(CH_2)_{n4}NR_{ff}$—, —$(CH_2)_{n3}NR_{dd}(CR_{ee}R_{ff})_{n4}$—, —$(CH_2)_{n3}NR_{dd}C(O)$—, —$(CH_2)_{n3}P(O)R_{dd}$—, —$(CH_2)_{n3}S(O)_{n4}$—, —$(CH_2)_{n3}S(O)_{n4}NR_{dd}$— and —$(CH_2)_{n3}NR_{dd}S(O)_{n4}$—;

$R_{dd}$ to $R_{ff}$ are each independently selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

or, any two of $R_{dd}$ to $R_{ff}$ are bonded to form a cycloalkyl, heterocyclyl, aryl or heteroaryl, wherein the cycloalkyl, heterocyclyl, aryl or heteroaryl can be optionally further substituted;

ring A is selected from the group consisting of cycloalkyl, heterocyclyl, aryl and heteroaryl;

$R_1$ is selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

ring B is selected from the group consisting of cycloalkyl, heterocyclyl, aryl and heteroaryl;

$R_2$ is selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

$R_3$ is selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl and heteroaryl can be each optionally further substituted;

$R^a$ is selected from the group consisting of hydrogen, deuterium, halogen, amino, nitro, hydroxy, cyano, oxo, thioxo, alkyl, deuterated alkyl, haloalkyl, hydroxyalkyl, alkoxy, haloalkoxy, alkenyl, alkynyl, heterocyclylalkyl, cycloalkyl, heterocyclyl, aryl, heteroaryl, —$(CH_2)_{n5}R_{gg}$, —$(CH_2)_{n5}OR_{gg}$, —$(CH_2)_{n5}C(O)OR_{gg}$, —$(CH_2)_{n5}SR_{gg}$, —$(CH_2)_{n5}NR_{gg}C(O)(CH_2)_{n6}R_{hh}$, —$(CH_2)_{n5}NR_{gg}C(O)OR_{hh}$, —$(CH_2)_{n5}NR_{gg}C(O)NR_{hh}R_{ii}$, —$(CH_2)_{n5}NR_{gg}R_{hh}$, —$NR_{gg}(CH_2)_{n5}R_{hh}$, —$(CH_2)_{n5}C(O)NR_{gg}(CH_2)_{n6}R_{hh}$, —$(CH_2)_{n5}C(O)R_{gg}$, —$OC(R_{gg}R_{hh})_{n5}(CH_2)_{n6}R_{ii}$, —$(CH_2)_{n5}S(O)_{n6}R_{gg}$, —$(CH_2)_{n5}NR_{gg}S(O)_{n6}R_{hh}$, —CH═$CH(CH_2)_{n5}R_{gg}$, —CH═$CH(CH_2)_{n5}NR_{gg}R_{hh}$, —CH═$CH(CH_2)_{n5}NR_{gg}C(O)R_{hh}$ and —CH═$CH(CH_2)_{n5}NR_{gg}C(O)NR_{hh}R_{ii}$, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl and heteroaryl can be each optionally further substituted;

$R_{gg}$ to $R_{ii}$ are each independently selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

or, any two of $R_{gg}$ to $R_{ii}$ are bonded to form a cycloalkyl, heterocyclyl, aryl or heteroaryl, wherein the cycloalkyl, heterocyclyl, aryl or heteroaryl can be optionally further substituted;

x is an integer from 0 to 6;

e is an integer from 0 to 6;

n1, n3, and n5 are each independently an integer from 0 to 3; and n2, n4, and n6 are each independently an integer from 0 to 2.

In a further preferred embodiment of the present invention, the compound of formula (I), the stereoisomer thereof or the pharmaceutically acceptable salt thereof is characterized in that $L_1$ is selected from the group consisting of a bond, —$(CH_2)_{n1}$—, —$(CH_2)_{n1}C(O)(CR_{aa}R_{bb})_{n2}$—, —$(CH_2)_{n1}C(O)NR_{aa}(CH_2)_{n2}$—, —$(CH_2)_{n1}(CR_{aa}R_{bb})_{n2}$—, —$(CR_{aa}R_{bb})_{n1}O(CH_2)_{n2}$—, —$(CH_2)_{n1}O(CR_{aa}R_{bb})_{n2}$—, —$(CR_{aa}R_{bb})_{n1}S(CH_2)_{n2}$—, —$(CH_2)_{n1}S(CR_{aa}R_{bb})_{n2}$—, —$(CR_{aa}R_{bb})_{n1}(CH_2)_{n2}NR_{cc}$—, —$(CH_2)_{n1}NR_{aa}(CR_{bb}R_{cc})_{n2}$—, —$(CH_2)_{n1}C(O)(CR_{aa}R_{bb})_{n2}$—, —$(CH_2)_{n1}NR_{aa}C(O)$—, —$(CH_2)_{n1}P(O)R_{aa}$—, —$(CH_2)_{n1}S(O)_{n2}$—, —$(CH_2)_{n1}S(O)_{n2}NR_{aa}$— and —$(CH_2)_{n1}NR_{aa}S(O)_{n2}$—;

preferably selected from the group consisting of a bond, —$(CH_2)_{n1}$—, —$(CH_2)_{n1}O(CR_{aa}R_{bb})_{n2}$—, —$(CH_2)_{n1}S(CR_{aa}R_{bb})_{n2}$—, —$(CH_2)_{n1}C(O)$—, —$(CH_2)_{n1}NR_{aa}$—, $-(CH_2)_{n1}S(O)_{n2}-$, $-(CH_2)_{n1}C(O)NR_{aa}-$, $-C(O)NR_{aa}(CH_2)_{n2}-$ and $-(CH_2)_{n1}NR_{aa}C(O)-$;

and more preferably selected from the group consisting of a bond, —NH—, $-C(O)NHCH_2-$ and $-C(O)N(CH_3)CH_2-$;

$R_{aa}$ to $R_{cc}$ are each independently selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, deuterated $C_{1-6}$ alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of hydrogen, deuterium, halogen, amino, hydroxy, cyano, nitro, $C_{1-6}$ alkyl, $C_{2-6}$ alkenyl, $C_{2-6}$ alkynyl, deuterated $C_{1-6}$ alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

or, any two of $R_{aa}$ to $R_{cc}$ are bonded to form a $C_{3-12}$ cycloalkyl, 3 to 12 membered heterocyclyl, $C_{6-14}$ aryl or 5 to 14 membered heteroaryl, wherein the $C_{3-12}$ cycloalkyl, 3 to 12 membered heterocyclyl, $C_{6-14}$ aryl or 5 to 14 membered heteroaryl is optionally substituted by one or more substituents selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

n1 is an integer from 0 to 3; and n2 is an integer from 0 to 2.

In a further preferred embodiment of the present invention, the compound of formula (I), the stereoisomer thereof or the pharmaceutically acceptable salt thereof is characterized in that $L_1$ is selected from the group consisting of a bond and —C(O)—.

In a further preferred embodiment of the present invention, the compound of formula (I), the stereoisomer thereof or the pharmaceutically acceptable salt thereof is characterized in that $L_2$ is selected from the group consisting of a bond, $-(CH_2)_{n3}-$, $-(CH_2)_{n3}C(O)(CR_{dd}R_{ee})_{n4}-$, $-(CH_2)_{n3}C(O)NR_{dd}(CH_2)_{n4}-$, $-(CH_2)_{n3}(CR_{dd}R_{ee})_{n4}-$, $-(CR_{dd}R_{ee})_{n3}O(CH_2)_{n4}-$, $-(CH_2)_{n3}O(CR_{dd}R_{ee})_{n4}-$, $-(CR_{dd}R_{ee})_{n3}S(CH_2)_{n4}-$, $-(CH_2)_{n3}S(CR_{dd}R_{ee})_{n4}-$, $-(CR_{dd}R_{ee})_{n3}(CH_2)_{n4}NR_{ff}-$, $-(CH_2)_{n3}NR_{dd}(CR_{ee}R_{ff})_{n4}-$, $-(CH_2)_{n3}NR_{dd}C(O)-$, $-(CH_2)_{n3}P(O)R_{dd}-$, $-(CH_2)_{n3}S(O)_{n4}-$, $-(CH_2)_{n3}S(O)_{n4}NR_{dd}-$ and $-(CH_2)_{n3}NR_{dd}S(O)_{n4}-$;

preferably selected from the group consisting of $-(CH_2)_{n3}-$, $-(CH_2)_{n3}O-$, $-(CH_2)_{n3}S-$, $-(CH_2)_{n3}NR_{dd}-$, $-(CH_2)_{n3}C(O)NR_{dd}-$ and $-(CH_2)_{n3}NR_{dd}C(O)-$;

and more preferably selected from $-CH_2C(O)NH-$;

$R_{dd}$ to $R_{ff}$ are each independently selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

or, any two of $R_{dd}$ to $R_{ff}$ are bonded to form a $C_{3-12}$ cycloalkyl, 3 to 12 membered heterocyclyl, $C_{6-14}$ aryl or 5 to 14 membered heteroaryl, wherein the $C_{3-12}$ cycloalkyl, 3 to 12 membered heterocyclyl, $C_{6-14}$ aryl or 5 to 14 membered heteroaryl is optionally substituted by one or more substituents selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

n3 is an integer from 0 to 3; and n4 is an integer from 0 to 2.

In a further preferred embodiment of the present invention, in the compound of formula (I), the stereoisomer thereof or the pharmaceutically acceptable salt thereof, ring A is selected from the group consisting of $C_{3-8}$ cycloalkyl, 3 to 12 membered heterocyclyl, $C_{6-14}$ aryl and 5 to 14 membered heteroaryl; preferably selected from the group consisting of $C_{6-10}$ aryl and 5 to 10 membered heteroaryl; and more preferably selected from the group consisting of phenyl, oxadiazolyl and pyridyl.

In a further preferred embodiment of the present invention, in the compound of formula (I), the stereoisomer thereof or the pharmaceutically acceptable salt thereof, $R_1$ is selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl, $C_{6-14}$ aryloxy, 5 to 14 membered heteroaryl and 5 to 14 membered heteroaryloxy, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl, $C_{6-14}$ aryloxy, 5 to 14 membered heteroaryl and 5 to 14 membered heteroaryloxy are each optionally substituted by one or more substituents selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl, $C_{6-14}$ aryloxy, 5 to 14 membered heteroaryl, 5 to 14 membered heteroaryloxy, $-(CH_2)_{m1}OR_a$, $-(CH_2)_{m1}SR_a$, $-(CH_2)_{m1}C(O)R_a$, $-(CH_2)_{m1}NR_aR_b$, $-(CH_2)_{m1}C(O)NR_aR_b$, $-(CH_2)_{m1}NR_aC(O)R_b$ and $-(CH_2)_{m1}S(O)_{m2}R_a$;

preferably selected from the group consisting of hydrogen, halogen, amino, cyano, $C_{1-4}$ alkyl, $C_{1-4}$ alkoxy, $C_{2-4}$ alkenyl, $C_{2-4}$ alkynyl, $C_{1-4}$ haloalkyl, $C_{3-6}$ cycloalkyl, 3 to 6 membered heterocyclyl, $C_{6-10}$ aryl and 5 to 8 membered heteroaryl, wherein the $C_{2-4}$ alkenyl, $C_{2-4}$ alkynyl, $C_{3-6}$ cycloalkyl, 3 to 6 membered heterocyclyl, $C_{6-10}$ aryl and 5 to 8 membered heteroaryl are each optionally substituted by one or more substituents selected from the group consisting of hydrogen, deuterium, halogen, amino, hydroxy, cyano, nitro, oxo, thioxo, $C_{1-4}$ alkyl, $C_{2-4}$ alkenyl, $C_{2-4}$ alkynyl, $C_{1-4}$ deuterated alkyl, $C_{1-4}$ haloalkyl, $C_{1-4}$ alkoxy, $C_{1-4}$ haloalkoxy, $C_{1-4}$ hydroxyalkyl, $C_{3-6}$ cycloalkyl, 3 to 6 membered heterocyclyl, $C_{6-10}$ aryl, 5 to 8 membered heteroaryl, $-(CH_2)_{m1}C(O)R_a$, $-(CH_2)_{m1}NR_aR_b$, $-(CH_2)_{m1}C(O)NR_aR_b$, $-(CH_2)_{m1}NR_aC(O)R_b$ and $-(CH_2)_{m1}S(O)_{m2}R_a$;

more preferably selected from the group consisting of hydrogen, halogen, amino, cyano, $C_{1-4}$ alkyl, $C_{1-4}$ alkoxy, $C_{1-4}$ haloalkyl, $C_{3-6}$ cycloalkyl, 4 to 6 membered heterocyclyl containing 1 to 2 nitrogen atoms, phenyl and 5 to 7 membered heteroaryl containing 1 to 2 nitrogen atoms, optionally further substituted by one or more substituents selected from the group consisting of halogen, amino, hydroxy, cyano, nitro, oxo, thioxo, $C_{1-4}$ alkyl, $C_{1-4}$ deuterated alkyl, $C_{1-4}$ haloalkyl and $C_{1-4}$ alkoxy;

and further preferably selected from the group consisting of hydrogen, methyl, ethyl, isopropyl, isobutyl, tert-butyl, trifluoromethyl, fluorine, chlorine, bromine, amino, isopropenyl, cyclopropyl, cyclopentyl, cyclopentenyl, oxetanyl, tetrahydropyranyl, tetrahydrothiopyranyl, piperidinyl, phenyl, pyridyl,

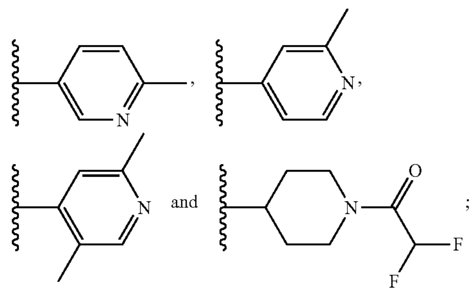

and ;

$R_a$ and $R_b$ are each independently selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

or, $R_a$ and $R_b$ are bonded to form a $C_{3-12}$ cycloalkyl, 3 to 12 membered heterocyclyl, $C_{6-14}$ aryl or 5 to 14 membered heteroaryl, wherein the $C_{3-12}$ cycloalkyl, 3 to 12 membered heterocyclyl, $C_{6-14}$ aryl or 5 to 14 membered heteroaryl is optionally substituted by one or more substituents selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

m1 is an integer from 0 to 3; and m2 is an integer from 0 to 2.

In a further preferred embodiment of the present invention, in the compound of formula (I), the stereoisomer thereof or the pharmaceutically acceptable salt thereof, $R_2$ is selected from the group consisting of hydrogen, deuterium, halogen, amino, hydroxy, cyano, oxo, thioxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl and 5 to 14 membered heteroaryl;

preferably selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 10 membered heterocyclyl, $C_{6-12}$ aryl and 5 to 12 membered heteroaryl;

more preferably selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 8 membered heterocyclyl containing 1 to 3 atoms selected from the group consisting of N, O and S, $C_{6-10}$ aryl and 5 to 10 membered heteroaryl containing 1 to 3 atoms selected from the group consisting of N, O and S;

and further preferably selected from the group consisting of hydrogen, deuterium, fluorine, chlorine, bromine, amino, hydroxy, cyano, oxo, thioxo, methyl, ethyl, propyl, vinyl, propenyl, allyl, ethynyl, propynyl, propargyl, deuterated methyl, deuterated ethyl, deuterated propyl, fluoromethyl, fluoroethyl, fluoropropyl, chloromethyl, chloroethyl, chloropropyl, bromomethyl, bromoethyl, bromopropyl, hydroxymethyl, hydroxyethyl, hydroxypropyl, methoxy, ethoxy, propoxy, fluoromethoxy, fluoroethoxy, fluoropropoxy, chloromethoxy, chloroethoxy, chloropropoxy, cyclopropyl, cyclobutyl, cyclopentyl, cyclohexyl, cycloheptyl, epoxypropyl, epoxybutyl, epoxypentyl, epoxyhexyl, epoxyheptyl, aziridinyl, azetidinyl, azacyclopentyl, azacyclohexyl, azacycloheptyl, thienyl, pyrrolyl, pyridyl, pyranyl, piperazinyl, phenyl and naphthyl.

In a further preferred embodiment of the present invention, in the compound of formula (I), the stereoisomer thereof or the pharmaceutically acceptable salt thereof, $R_3$ is selected from the group consisting of hydrogen, deuterium, halogen, amino, hydroxy, cyano, oxo, thioxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl and 5 to 14 membered heteroaryl;

preferably selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 10 membered heterocyclyl, $C_{6-12}$ aryl and 5 to 12 membered heteroaryl;

more preferably selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 8 membered heterocyclyl containing 1 to 3 atoms selected from the group consisting of N, O and S, $C_{6-10}$ aryl and 5 to 10 membered heteroaryl containing 1 to 3 atoms selected from the group consisting of N, O and S;

and further preferably selected from the group consisting of hydrogen, deuterium, fluorine, chlorine, bromine, amino, hydroxy, cyano, oxo, thioxo, methyl, ethyl, propyl, vinyl, propenyl, allyl, ethynyl, propynyl, propargyl, deuterated methyl, deuterated ethyl, deuterated propyl, fluoromethyl, fluoroethyl, fluoropropyl, chloromethyl, chloroethyl, chloropropyl, bromomethyl, bromoethyl, bromopropyl, hydroxymethyl, hydroxyethyl, hydroxypropyl, methoxy, ethoxy, propoxy, fluoromethoxy, fluoroethoxy, fluoropropoxy, chloromethoxy, chloroethoxy, chloropropoxy, cyclopropyl, cyclobutyl, cyclopentyl, cyclohexyl, cycloheptyl, epoxypropyl, epoxybutyl, epoxypentyl, epoxyhexyl, epoxyheptyl, aziridinyl, azetidinyl, azacyclopentyl, azacyclohexyl, azacycloheptyl, thienyl, pyrrolyl, pyridyl, pyranyl, piperazinyl, phenyl and naphthyl.

In a further preferred embodiment of the present invention, in the compound of formula (I), the stereoisomer thereof or the pharmaceutically acceptable salt thereof, $R^a$ is selected from the group consisting of hydrogen, deuterium, halogen, amino, hydroxy, cyano, oxo, thioxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl, 5 to 14 membered heteroaryl, $-(CH_2)_{n5}R_{gg}$, $-(CH_2)_{n5}OR_{gg}$, $-(CH_2)_{n5}C(O)OR_{gg}$, $-(CH_2)_{n5}SR_{gg}$, $-(CH_2)_{n5}NR_{gg}C(O)(CH_2)_{n6}R_{hh}$, $-(CH_2)_{n5}NR_{gg}C(O)OR_{hh}$, $-(CH_2)_{n5}NR_{gg}C(O)NR_{hh}R_{ii}$, $-(CH_2)_{n5}NR_{gg}R_{hh}$, $-NR_{gg}(CH_2)_{n5}R_{hh}$, $-(CH_2)_{n5}C(O)NR_{gg}(CH_2)_{n6}R_{hh}$, $-(CH_2)_{n5}C(O)R_{gg}$ and $-OC(R_{gg}R_{hh})_{n5}(CH_2)_{n6}R_{ii}$;

preferably selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 10 membered heterocyclyl, $C_{6-12}$ aryl and 5 to 12 membered heteroaryl;

more preferably selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 8 membered heterocyclyl containing 1 to 3 atoms selected from the group consisting of N, O and S, $C_{6-10}$ aryl and 5 to 10 membered heteroaryl containing 1 to 3 atoms selected from the group consisting of N, O and S;

and further preferably selected from the group consisting of hydrogen, deuterium, fluorine, chlorine, bromine, amino, hydroxy, cyano, oxo, thioxo, methyl, ethyl, propyl, vinyl, propenyl, allyl, ethynyl, propynyl, propargyl, deuterated methyl, deuterated ethyl, deuterated propyl, fluoromethyl, fluoroethyl, fluoropropyl, chloromethyl, chloroethyl, chloropropyl, bromomethyl, bromoethyl, bromopropyl, hydroxymethyl, hydroxyethyl, hydroxypropyl, methoxy, ethoxy, propoxy, fluoromethoxy, fluoroethoxy, fluoropropoxy, chloromethoxy, chloroethoxy, chloropropoxy, cyclopropyl, cyclobutyl, cyclopentyl, cyclohexyl, cycloheptyl, epoxypropyl, epoxybutyl, epoxypentyl, epoxyhexyl, epoxyheptyl, aziridinyl, azetidinyl, azacyclopentyl, azacyclohexyl, azacycloheptyl, thienyl, pyrrolyl, pyridyl, pyranyl, piperazinyl, phenyl and naphthyl;

$R_{gg}$ to $R_{ii}$ are each independently selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

or, any two of $R_{gg}$ to $R_{ii}$ are bonded to form a $C_{3-12}$ cycloalkyl, 3 to 12 membered heterocyclyl, $C_{6-14}$ aryl or 5 to 14 membered heteroaryl, wherein the $C_{3-12}$ cycloalkyl, 3 to 12 membered heterocyclyl, $C_{6-14}$ aryl or 5 to 14 membered heteroaryl is optionally substituted by one or more substituents selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

n5 is an integer from 0 to 3; and n6 is an integer from 0 to 2.

In a further preferred embodiment of the present invention, in the compound of formula (I), the stereoisomer thereof or the pharmaceutically acceptable salt thereof, ring B is shown as following:

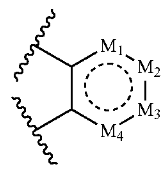

wherein:

$M_1$, $M_2$, $M_3$ and $M_4$ are each independently selected from the group consisting of $CR_{A1}$, C(O), N, $CR_{A1}R_{A2}$ and $NR_{A3}$;

$R_{A1}$ to $R_{A3}$ are each independently selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

preferably selected from the group consisting of hydrogen, deuterium, halogen, amino, hydroxy, cyano, oxo, thioxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl and 5 to 14 membered heteroaryl;

and more preferably selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 10 membered heterocyclyl, $C_{6-12}$ aryl and 5 to 12 membered heteroaryl.

In a further preferred embodiment of the present invention, in the compound of formula (I), the stereoisomer thereof or the pharmaceutically acceptable salt thereof, $M_1$, $M_2$, $M_3$ and $M_4$ are each independently $CR_{A1}$;

$R_{A1}$ is selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 8 membered heterocyclyl containing 1 to 3 atoms selected from the group consisting of N, O and S atoms, $C_{6-10}$ aryl and 5 to 10 membered heteroaryl containing 1 to 3 atoms selected from the group consisting of N, O and S;

and further preferably selected from the group consisting of hydrogen, deuterium, fluorine, chlorine, bromine, amino, hydroxy, cyano, oxo, thioxo, methyl, ethyl, propyl, vinyl, propenyl, allyl, ethynyl, propynyl, propargyl, deuterated methyl, deuterated ethyl, deuterated propyl, fluoromethyl, fluoroethyl, fluoropropyl, chloromethyl, chloroethyl, chloropropyl, bromomethyl, bromoethyl, bromopropyl, hydroxymethyl, hydroxyethyl, hydroxypropyl, methoxy, ethoxy, propoxy, fluoromethoxy, fluoroethoxy, fluoropropoxy, chloromethoxy, chloroethoxy, chloropropoxy, cyclopropyl, cyclobutyl, cyclopentyl, cyclohexyl, cycloheptyl, epoxypropyl, epoxybutyl, epoxypentyl, epoxyhexyl, epoxyheptyl, aziridinyl, azetidinyl, azacyclopentyl, azacyclohexyl, azacycloheptyl, thienyl, pyrrolyl, pyridyl, pyranyl, piperazinyl, phenyl and naphthyl.

In a further preferred embodiment of the present invention, in the compound of formula (I), the stereoisomer thereof or the pharmaceutically acceptable salt thereof, at least one of $M_1$, $M_2$, $M_3$ and $M_4$ is N;

preferably, $M_4$ is N, and $M_1$, $M_2$ and $M_3$ are each independently $CR_{A1}$;

or, $M_1$ is N, and $M_2$, $M_3$ and $M_4$ are each independently $CR_{A1}$;

$R_{A1}$ is selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 8 membered heterocyclyl containing 1 to 3 atoms selected from the group consisting of N, O and S, $C_{6-10}$ aryl and 5 to 10 membered heteroaryl containing 1 to 3 atoms selected from the group consisting of N, O and S;

and further preferably selected from the group consisting of hydrogen, deuterium, fluorine, chlorine, bromine, amino, hydroxy, cyano, oxo, thioxo, methyl, ethyl, propyl, vinyl, propenyl, allyl, ethynyl, propynyl, propargyl, deuterated methyl, deuterated ethyl, deuterated propyl, fluoromethyl, fluoroethyl, fluoropropyl, chloromethyl, chloroethyl, chloropropyl, bromomethyl, bromoethyl, bromopropyl, hydroxymethyl, hydroxyethyl, hydroxypropyl, methoxy, ethoxy, propoxy, fluoromethoxy, fluoroethoxy, fluoropropoxy, chloromethoxy, chloroethoxy, chloropropoxy, cyclopropyl, cyclobutyl, cyclopentyl, cyclohexyl, cycloheptyl, epoxypropyl, epoxybutyl, epoxypentyl, epoxyhexyl, epoxyheptyl, aziridinyl, azetidinyl, azacyclopentyl, azacyclohexyl, azacycloheptyl, thienyl, pyrrolyl, pyridyl, pyranyl, piperazinyl, phenyl and naphthyl.

In a further preferred embodiment of the present invention, ring B is shown as following:

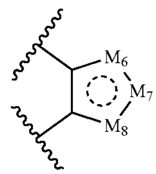

wherein:

$M_6$, $M_7$ and $M_8$ are each independently selected from the group consisting of $CR_{A4}$, C(O), N, O, S, $CR_{A4}R_{A5}$ and $NR_{A6}$;

$R_{A4}$ to $R_{A6}$ are each independently selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

preferably selected from the group consisting of hydrogen, deuterium, halogen, amino, hydroxy, cyano, oxo, thioxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl and 5 to 14 membered heteroaryl;

and more preferably selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 10 membered heterocyclyl, $C_{6-12}$ aryl and 5 to 12 membered heteroaryl.

In a further preferred embodiment of the present invention, ring B is selected from the group consisting of:

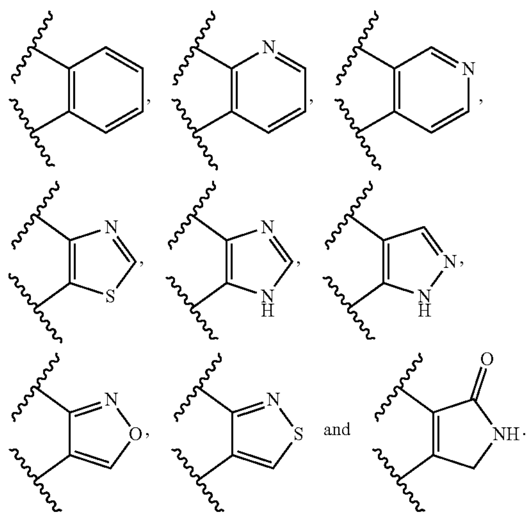

In a further preferred embodiment of the present invention, the compound of formula (I), the stereoisomer thereof or the pharmaceutically acceptable salt thereof is characterized in that ring A is selected from

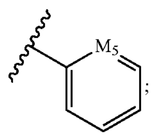

$M_5$ is selected from the group consisting of N and $CR_4$; and preferably selected from the group consisting of N and CH;

$R_4$ is selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-12}$ aryl and 5 to 12 membered heteroaryl;

preferably selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 10 membered heterocyclyl, $C_{6-12}$ aryl and 5 to 12 membered heteroaryl;

more preferably selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 8 membered heterocyclyl containing 1 to 3 atoms selected from the group consisting of N, O and S, $C_{6-10}$ aryl and 5 to 10 membered heteroaryl containing 1 to 3 atoms selected from the group consisting of N, O and S;

and further preferably selected from the group consisting of hydrogen, deuterium, fluorine, chlorine, bromine, amino, hydroxy, cyano, oxo, thioxo, methyl, ethyl, propyl, vinyl, propenyl, allyl, ethynyl, propynyl, propargyl, deuterated methyl, deuterated ethyl, deuterated propyl, fluoromethyl, fluoroethyl, fluoropropyl, chloromethyl, chloroethyl, chloropropyl, bromomethyl, bromoethyl, bromopropyl, hydroxymethyl, hydroxyethyl, hydroxypropyl, methoxy, ethoxy, propoxy, fluoromethoxy, fluoroethoxy, fluoropropoxy, chloromethoxy, chloroethoxy, chloropropoxy, cyclopropyl, cyclobutyl, cyclopentyl, cyclohexyl, cycloheptyl, epoxypropyl, epoxybutyl, epoxypentyl, epoxyhexyl, epoxyheptyl, aziridinyl, azetidinyl, azacyclopentyl, azacyclohexyl, azacycloheptyl, thienyl, pyrrolyl, pyridyl, pyranyl, piperazinyl, phenyl and naphthyl.

In a further preferred embodiment of the present invention, the formula (I) is further as shown in formula (II):

(II)

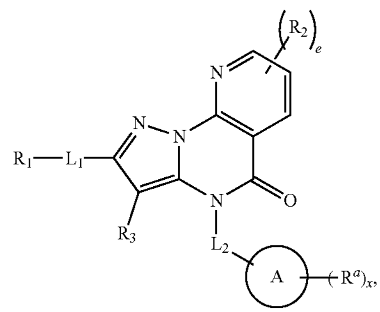

wherein e is an integer from 0 to 3.

In a further preferred embodiment of the present invention, the formula (I) is further as shown in formula (III):

(III)

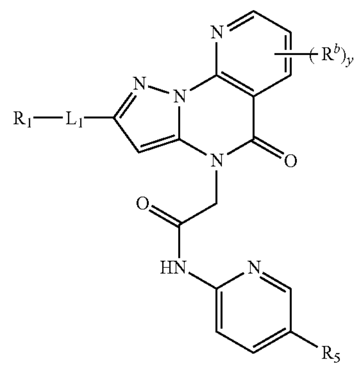

wherein:

$R_5$ is selected from the group consisting of hydrogen, deuterium, halogen, amino, hydroxy, cyano, oxo, thioxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl and 5 to 14 membered heteroaryl;

preferably selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 10 membered heterocyclyl, $C_{6-12}$ aryl and 5 to 12 membered heteroaryl;

more preferably selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 8 membered heterocyclyl containing 1 to 3 atoms selected from the group consisting of N, O and S, $C_{6-10}$ aryl and 5 to 10 membered heteroaryl containing 1 to 3 atoms selected from the group consisting of N, O and S;

and further preferably selected from the group consisting of hydrogen, deuterium, fluorine, chlorine, bromine, amino, hydroxy, cyano, oxo, thioxo, methyl, ethyl, propyl, vinyl, propenyl, allyl, ethynyl, propynyl, propargyl, deuterated methyl, deuterated ethyl, deuterated propyl, fluoromethyl, fluoroethyl, fluoropropyl, chloromethyl, chloroethyl, chloropropyl, bromomethyl, bromoethyl, bromopropyl, hydroxymethyl, hydroxyethyl, hydroxypropyl, methoxy, ethoxy, propoxy, fluoromethoxy, fluoroethoxy, fluoropropoxy, chloromethoxy, chloroethoxy, chloropropoxy, cyclopropyl, cyclobutyl, cyclopentyl, cyclohexyl, cycloheptyl, epoxypropyl, epoxybutyl, epoxypentyl, epoxyhexyl, epoxyheptyl, aziridinyl, azetidinyl, azacyclopentyl, azacyclohexyl, azacycloheptyl, thienyl, pyrrolyl, pyridyl, pyranyl, piperazinyl, phenyl and naphthyl;

$R^b$ is selected from the group consisting of hydrogen, deuterium, halogen, amino, hydroxy, cyano, oxo, thioxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl and 5 to 14 membered heteroaryl;

preferably selected from the group consisting of hydrogen, deuterium, halogen, amino, hydroxy, cyano, oxo, thioxo, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 10 membered heterocyclyl, $C_{6-12}$ aryl and 5 to 12 membered heteroaryl;

and more preferably selected from the group consisting of hydrogen, deuterium, fluorine, chlorine, bromine, amino, hydroxy, cyano, oxo, thioxo, methyl, ethyl, propyl, vinyl, propenyl, allyl, ethynyl, propynyl, propargyl, deuterated methyl, deuterated ethyl, deuterated propyl, fluoromethyl, fluoroethyl, fluoropropyl, chloromethyl, chloroethyl, chloropropyl, bromomethyl, bromoethyl, bromopropyl, hydroxymethyl, hydroxyethyl, hydroxypropyl, methoxy, ethoxy, propoxy, fluoromethoxy, fluoroethoxy, fluoropropoxy, chloromethoxy, chloroethoxy, chloropropoxy, cyclopropyl, cyclobutyl, cyclopentyl, cyclohexyl, cycloheptyl, epoxypropyl, epoxybutyl, epoxypentyl, epoxyhexyl, epoxyheptyl, aziridinyl, azetidinyl, azacyclopentyl, azacyclohexyl, azacycloheptyl, thienyl, pyrrolyl, pyridyl, pyranyl, piperazinyl, phenyl and naphthyl; and y is an integer from 0 to 3.

In a further preferred embodiment of the present invention, in the compound of formula (III), the stereoisomer thereof or the pharmaceutically acceptable salt thereof, $L_1$ is a bond or —C(O)—.

In a further preferred embodiment of the present invention, in the compound of formula (III), the stereoisomer thereof or the pharmaceutically acceptable salt thereof, $R_1$ is selected from the group consisting of hydrogen, halogen, amino, cyano, $C_{1-4}$ alkyl, $C_{1-4}$ alkoxy, $C_{1-4}$ hydroxyalkyl, $C_{1-4}$ haloalkyl, $C_{3-6}$ cycloalkyl, 4 to 6 membered heterocyclyl containing 1 to 2 nitrogen atoms, phenyl and 5 to 7 membered heteroaryl containing 1 to 2 nitrogen atoms, optionally further substituted by one or more substituents selected from the group consisting of halogen, amino, hydroxy, cyano, nitro, oxo, thioxo, $C_{1-4}$ alkyl, $C_{1-4}$ deuterated alkyl, $C_{1-4}$ haloalkyl and $C_{1-4}$ alkoxy.

In a further preferred embodiment of the present invention, the formula (I) is further as shown in formula (IV):

(IV)

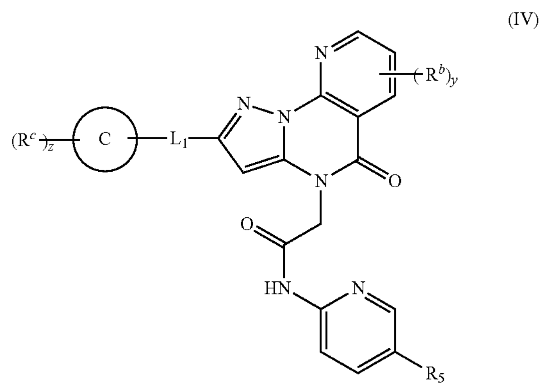

wherein:

ring C is selected from the group consisting of $C_{3-12}$ cycloalkyl, 3 to 12 membered heterocyclyl, $C_{6-14}$ aryl and 5 to 14 membered heteroaryl, or ring C is absent;

preferably selected from the group consisting of $C_{3-8}$ cycloalkyl, 3 to 10 membered heterocyclyl, $C_{6-12}$ aryl and 5 to 12 membered heteroaryl;

more preferably selected from the group consisting of $C_{3-6}$ cycloalkyl, 3 to 8 membered heterocyclyl containing 1 to 3 atoms selected from the group consisting of N, O and S, $C_{6-10}$ aryl and 5 to 10 membered heteroaryl containing 1 to 3 atoms selected from the group consisting of N, O and S;

and further preferably selected from the group consisting of cyclopropyl, cyclopentyl, cyclopentenyl, oxetanyl, tetrahydropyranyl, tetrahydrothiopyranyl, piperidinyl, phenyl and pyridyl;

$R^c$ is selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl, $C_{6-14}$ aryloxy, 5 to 14 membered heteroaryl, 5 to 14 membered heteroaryloxy, $-(CH_2)_{m3}OR_c$, $-(CH_2)_{m3}SR_c$, $-(CH_2)_{m3}C(O)R_c$, $-(CH_2)_{m3}NR_cR_d$, $-(CH_2)_{m3}C(O)NR_cR_d$, —

$(CH_2)_{m3}NR_cC(O)R^a$ and $-(CH_2)_{m3}S(O)_{m4}R_c$, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl, $C_{6-14}$ aryloxy, 5 to 14 membered heteroaryl and 5 to 14 membered heteroaryloxy are each optionally substituted by one or more substituents selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl, $C_{6-14}$ aryloxy, 5 to 14 membered heteroaryl and 5 to 14 membered heteroaryloxy;

preferably selected from the group consisting of hydrogen, halogen, amino, cyano, $C_{1-4}$ alkyl, $C_{1-4}$ alkoxy, $C_{2-4}$ alkenyl, $C_{2-4}$ alkynyl, $C_{1-4}$ haloalkyl, $C_{3-6}$ cycloalkyl, 3 to 6 membered heterocyclyl, $C_{6-10}$ aryl, 5 to 8 membered heteroaryl, $-(CH_2)_{m3}OR_c$, $-(CH_2)_{m3}SR_c$, $-(CH_2)_{m3}C(O)R_c$, $-(CH_2)_{m3}NR_cR_d$, $-(CH_2)_{m3}C(O)NR_cR_d$ and $-(CH_2)_{m3}NR_cC(O)R^a$, wherein the amino, $C_{1-4}$ alkyl, $C_{1-4}$ alkoxy, $C_{2-4}$ alkenyl, $C_{2-4}$ alkynyl, $C_{3-6}$ cycloalkyl, 3 to 6 membered heterocyclyl, $C_{6-10}$ aryl and 5 to 8 membered heteroaryl are each optionally substituted by one or more substituents selected from the group consisting of hydrogen, deuterium, halogen, amino, hydroxy, cyano, nitro, oxo, thioxo, $C_{1-4}$ alkyl, $C_{2-4}$ alkenyl, $C_{2-4}$ alkynyl, $C_{1-4}$ deuterated alkyl, $C_{1-4}$ haloalkyl, $C_{1-4}$ alkoxy, $C_{1-4}$ haloalkoxy, $C_{1-4}$ hydroxyalkyl, $C_{3-6}$ cycloalkyl, 3 to 6 membered heterocyclyl, $C_{6-10}$ aryl and 5 to 8 membered heteroaryl;

and further preferably selected from the group consisting of hydrogen, methyl, ethyl, isopropyl, isobutyl, tert-butyl, trifluoromethyl, fluorine, chlorine, bromine, amino and $-C(O)CHF_2$;

$R_c$ and $R_d$ are each independently selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and to 14 membered heteroaryl are each optionally substituted by one or more substituents selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

or, $R_c$ and $R_d$ are bonded to form a $C_{3-12}$ cycloalkyl, 3 to 12 membered heterocyclyl, $C_{6-14}$ aryl or 5 to 14 membered heteroaryl, wherein the $C_{3-12}$ cycloalkyl, 3 to 12 membered heterocyclyl, $C_{6-14}$ aryl or 5 to 14 membered heteroaryl is optionally substituted by one or more substituents selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

m3 is an integer from 0 to 3;

m4 is an integer from 0 to 2; and z is an integer from 0 to 6.

In a further preferred embodiment of the present invention, the formula (II) is further as shown in formula (V):

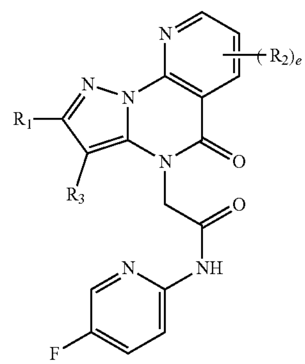

(V)

wherein:

$R_1$ is selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of hydrogen, deuterium, halogen, amino, hydroxy, cyano, nitro, oxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-12}$ aryl and 5 to 12 membered heteroaryl;

$R_2$ is selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of hydrogen, deuterium, halogen, amino, hydroxy, cyano, nitro, oxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-12}$ aryl and 5 to 12 membered heteroaryl;

$R_3$ is selected from the group consisting of hydrogen, deuterium, halogen, amino, hydroxy, cyano, oxo, thioxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl and 5 to 14 membered heteroaryl; and e is an integer from 0 to 3.

In a preferred embodiment of the present invention, $R_1$ is selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-8}$ cycloalkyl, 3 to 8 membered heterocyclyl, $C_{6-10}$ aryl and 5 to 10 membered heteroaryl are each optionally substituted by one or more substituents selected from the group consisting of hydrogen, deuterium, halogen, amino, hydroxy, cyano, nitro, oxo, $C_{1-3}$ alkyl, $C_{2-3}$ alkenyl, $C_{2-3}$ alkynyl, $C_{1-3}$ deuterated alkyl, $C_{1-3}$ haloalkyl, $C_{1-3}$ alkoxy, $C_{1-3}$ haloalkoxy, $C_{1-3}$ hydroxyalkyl, cyano-substituted $C_{1-3}$ alkyl, $C_{3-8}$ cycloalkyl, 3 to 8 membered heterocyclyl, $C_{6-10}$ aryl and 5 to 10 membered heteroaryl.

In a further preferred embodiment of the present invention, $R_1$ is selected from the group consisting of:

—H, —$NH_2$, —F, —Cl, —Br, —$CH_3$, —$CH_2CH_3$, —$CF_3$,

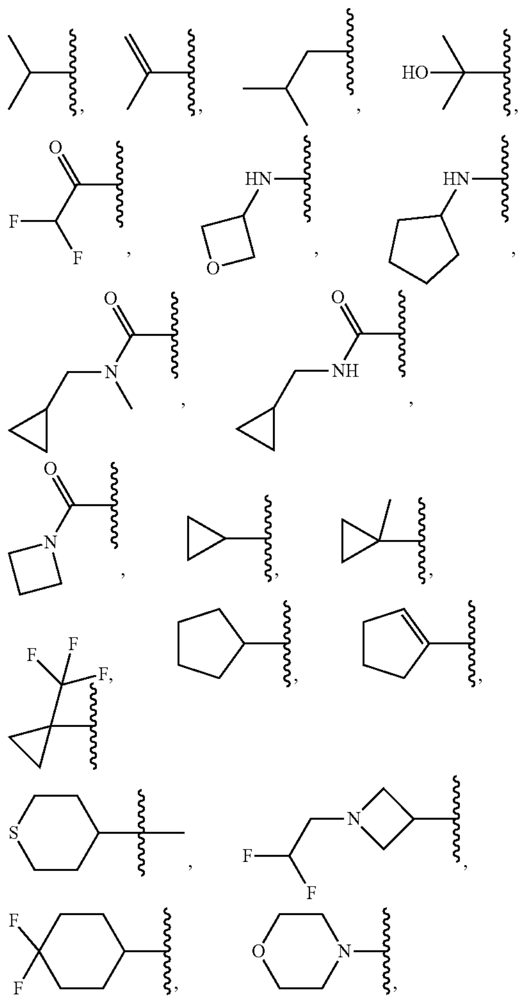

-continued

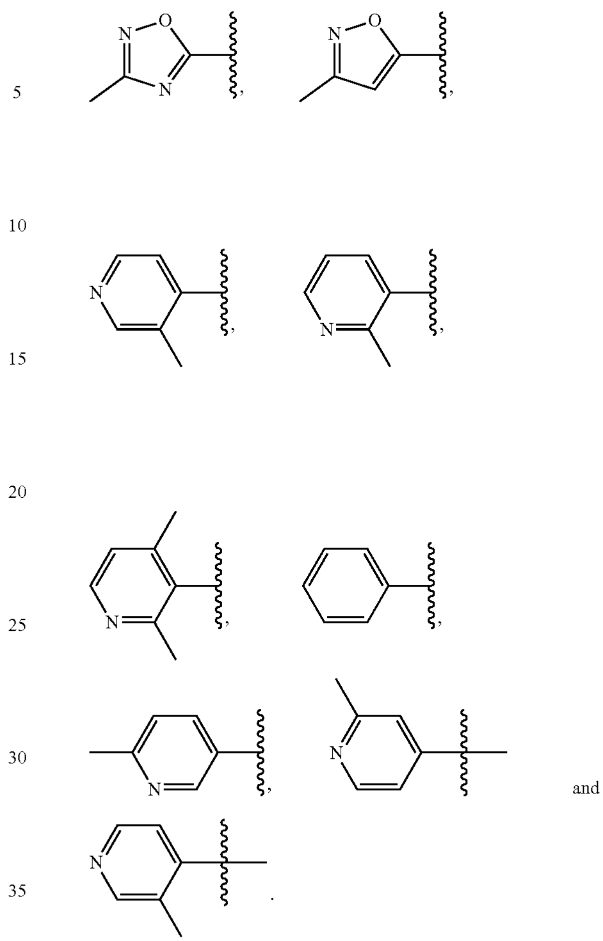

and

In a preferred embodiment of the present invention, $R_2$ is selected from the group consisting of hydrogen, deuterium, halogen, amino, hydroxy, cyano, nitro, $C_{1-3}$ alkyl, $C_{2-3}$ alkenyl, $C_{2-3}$ alkynyl, $C_{1-3}$ deuterated alkyl, $C_{1-3}$ haloalkyl, $C_{1-3}$ alkoxy, $C_{1-3}$ haloalkoxy, $C_{1-3}$ hydroxyalkyl, $C_{3-8}$ cycloalkyl, 3 to 8 membered heterocyclyl, $C_{6-10}$ aryl and 5 to 10 membered heteroaryl.

In a further preferred embodiment of the present invention, $R_2$ is selected from the group consisting of hydrogen, amino, cyano, fluorine, chlorine, bromine, methyl, isopropyl, trifluoromethyl, methoxy, cyclopropyl and morpholinyl.

In a preferred embodiment of the present invention, $R_3$ is selected from the group consisting of hydrogen, deuterium, halogen, amino, hydroxy, cyano, oxo, thioxo, C1-3 alkyl, C2-3 alkenyl, C2-3 alkynyl, C1-3 deuterated alkyl, C1-3 haloalkyl, C1-3 hydroxyalkyl, C1-3 alkoxy, C1-3 haloalkoxy, C3-8 cycloalkyl, 3 to 8 membered heterocyclyl, C6-10 aryl and 5 to 10 membered heteroaryl.

In a further preferred embodiment of the present invention, $R_3$ is selected from the group consisting of hydrogen and cyano; and e is an integer from 0 to 3.

In a preferred embodiment of the present invention, the compound of formula (I), the stereoisomer thereof or the pharmaceutically acceptable salt thereof is selected from the group consisting of:

-continued
1
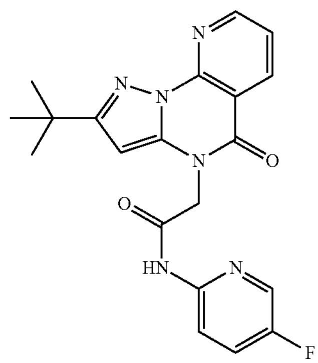
2
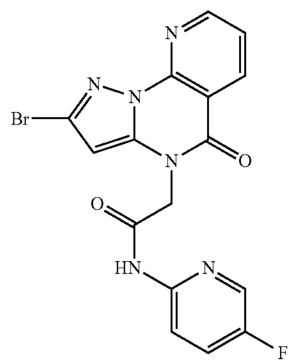
3
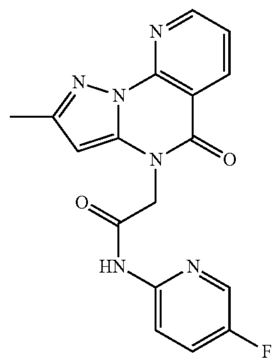
4
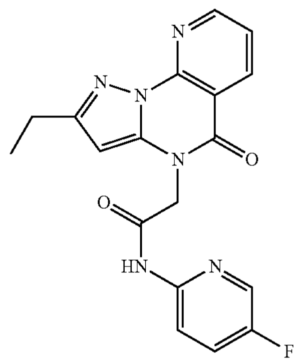
5
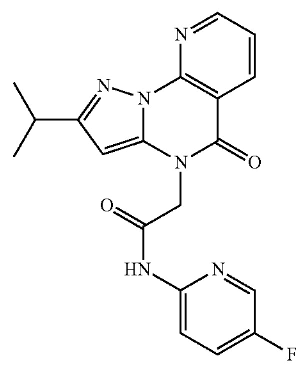
6
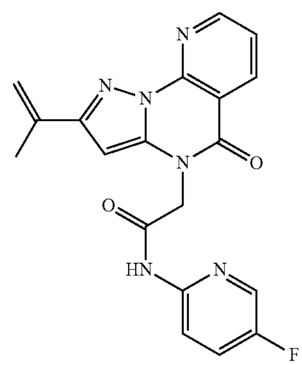
7
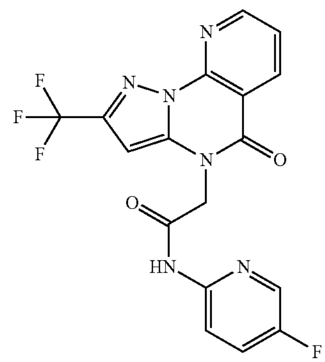
8
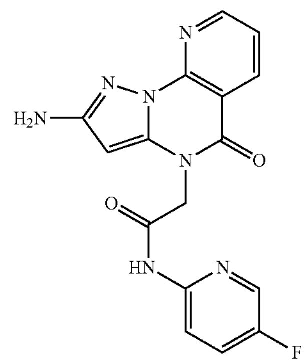

-continued
9
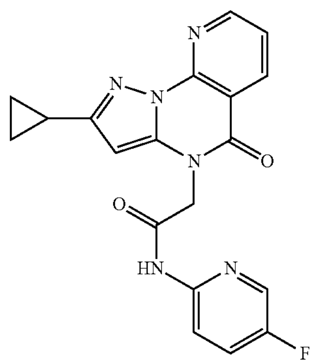
10
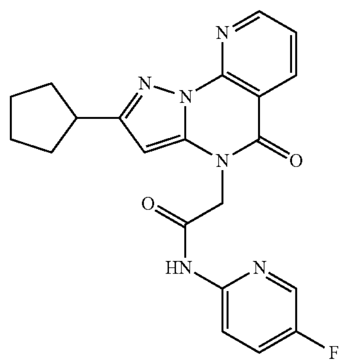
11
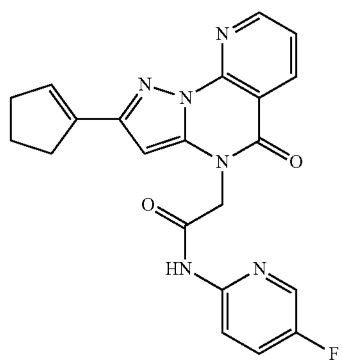
12
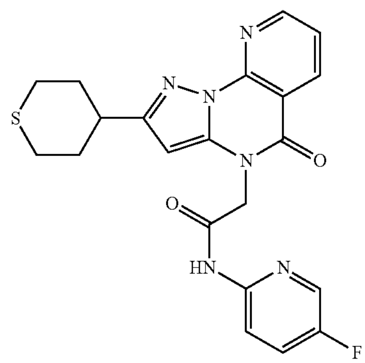
-continued
13
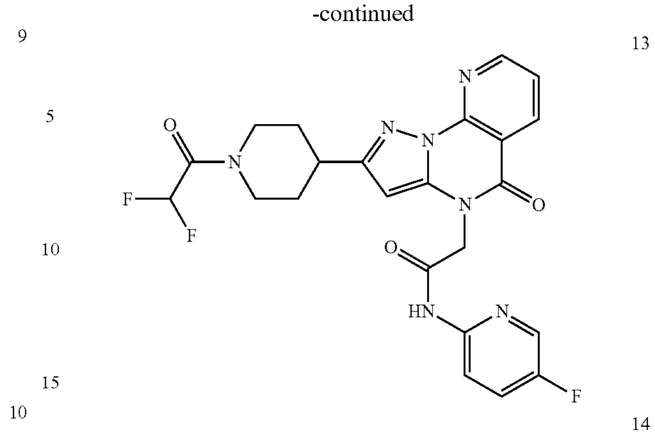
14
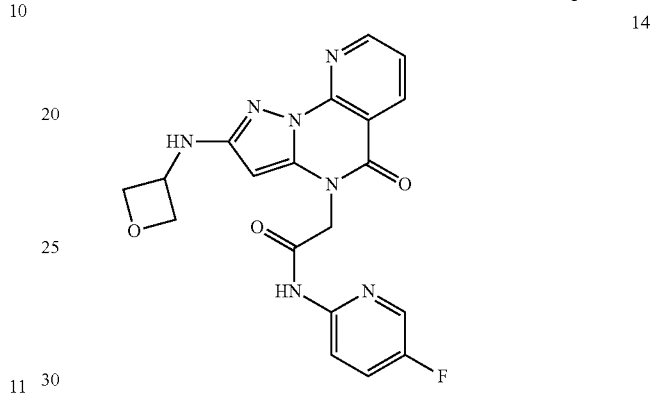
15
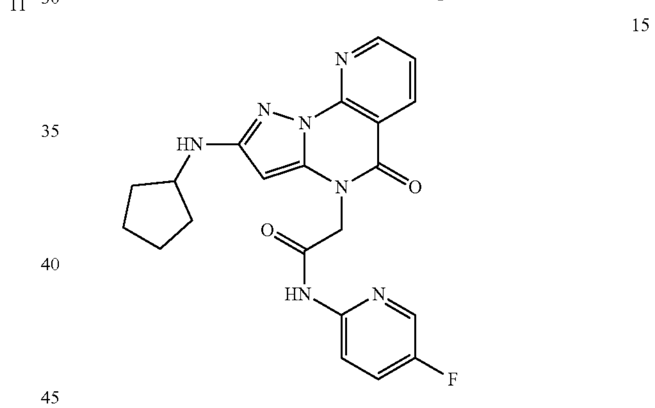
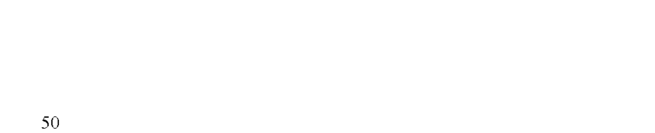
16
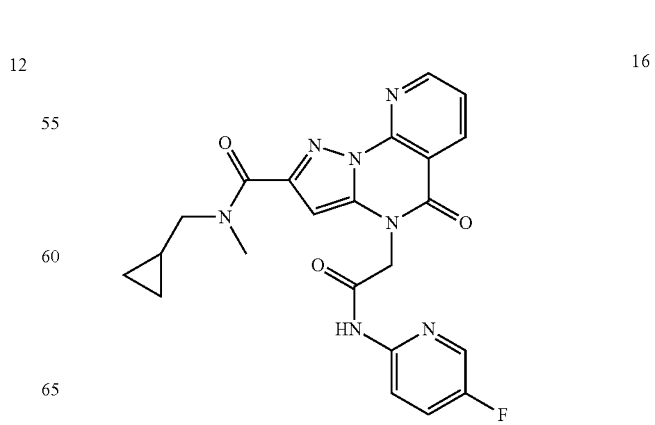

-continued
17
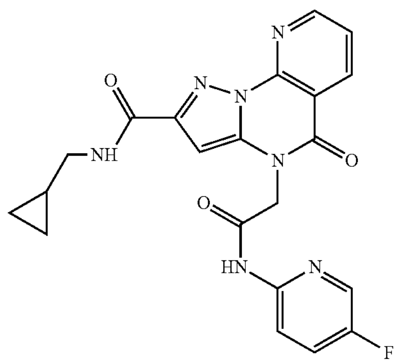
18
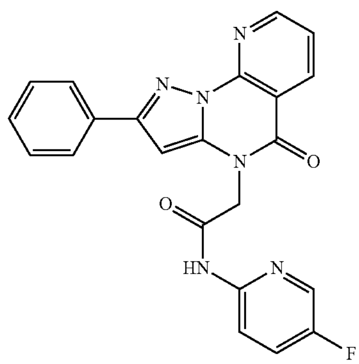
19
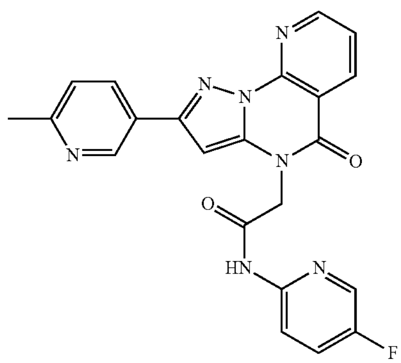
20
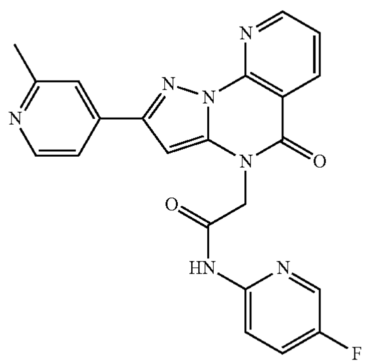
-continued
21
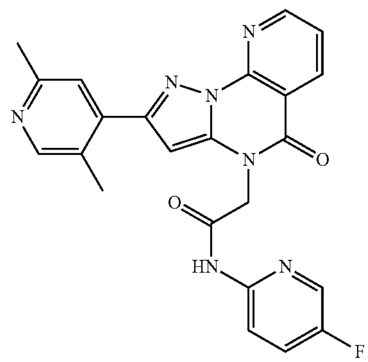
22
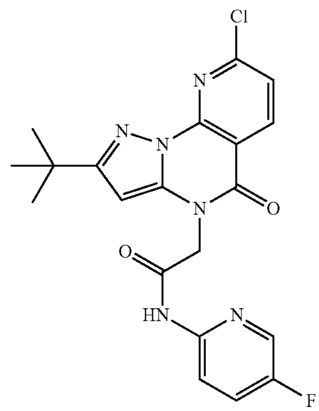
23
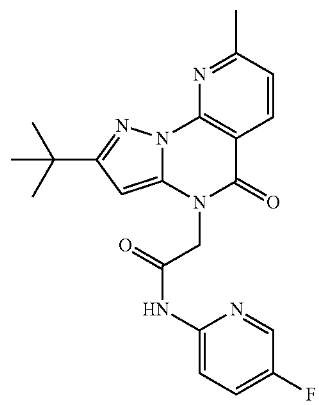
24
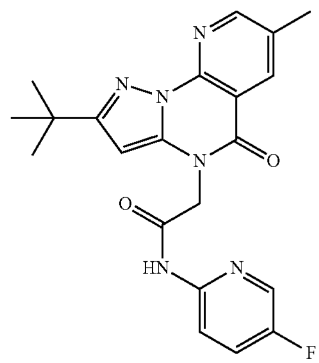

25
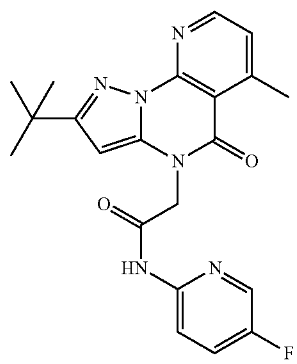
26
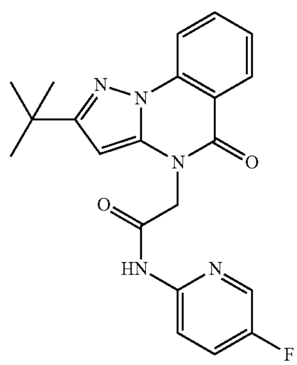
27
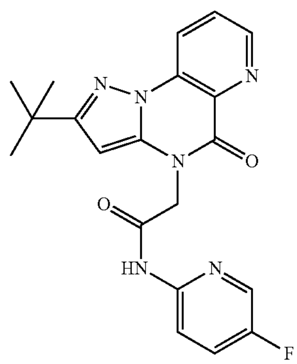
28
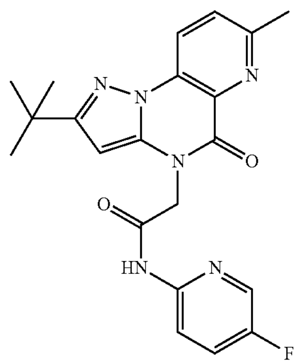
29
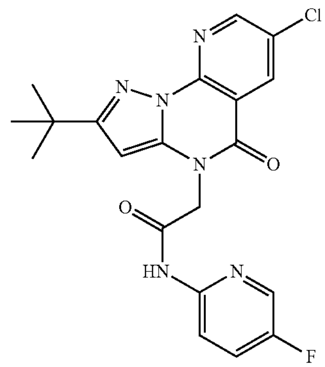
30
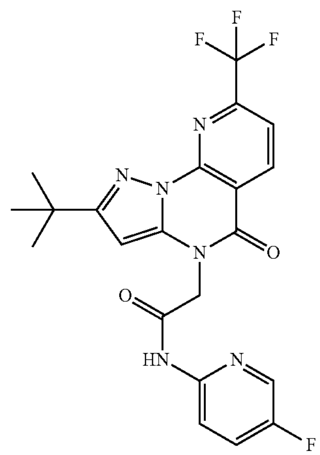
31
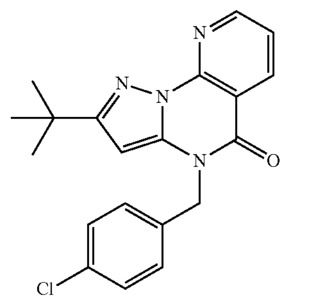
32
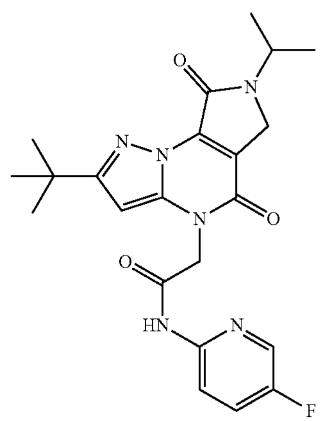

-continued
33
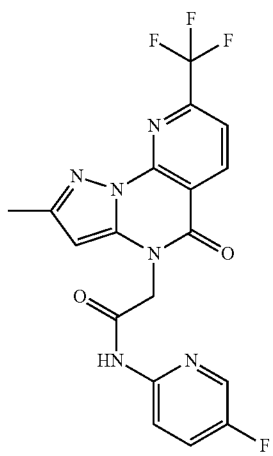
34
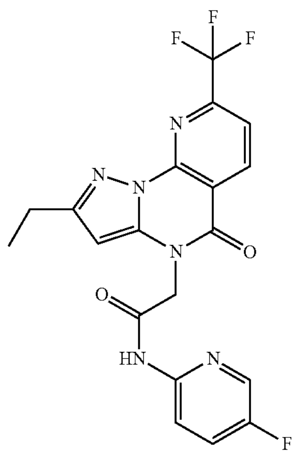
35
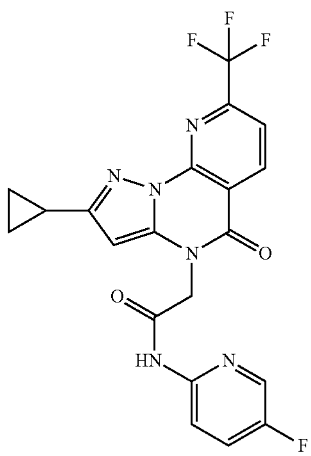
-continued
36
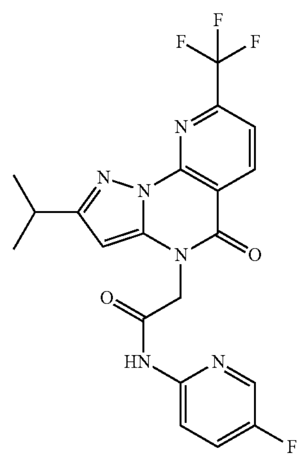
37
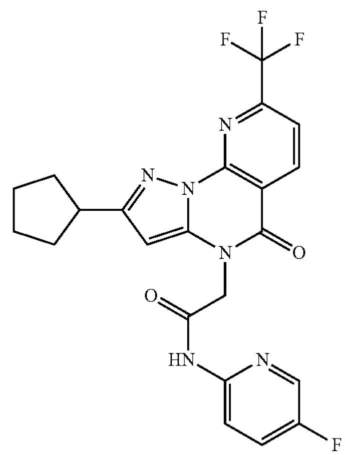
38
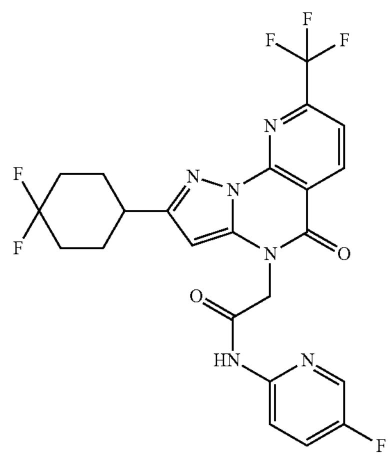

-continued
39
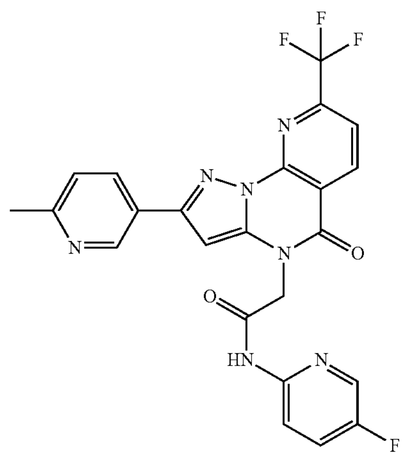
40
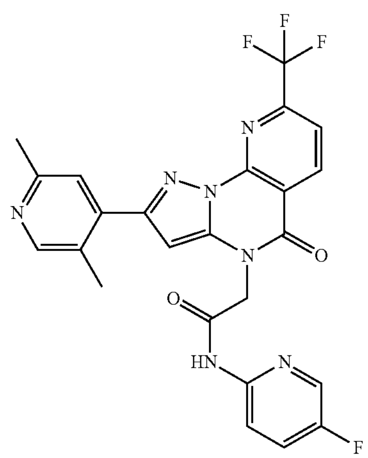
41
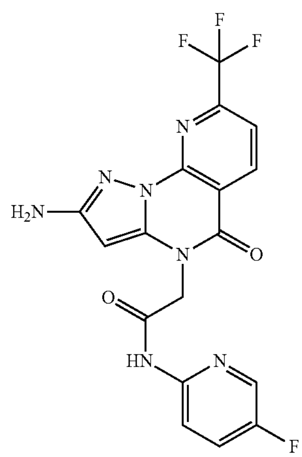
-continued
42
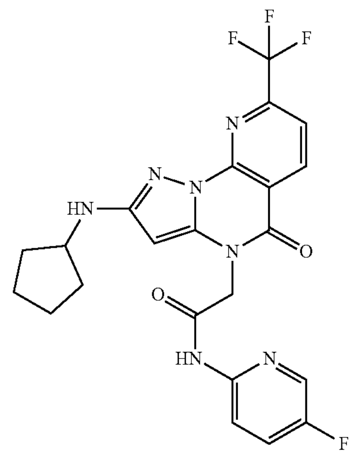
43
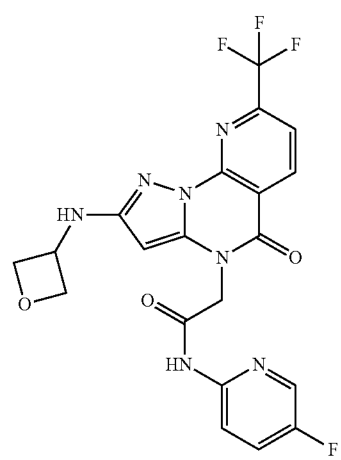
44
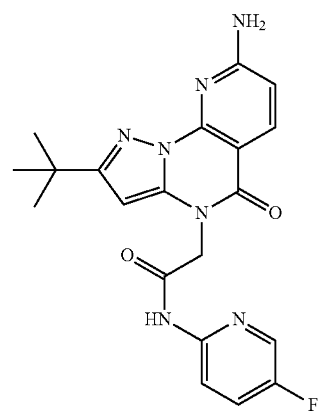

-continued
45
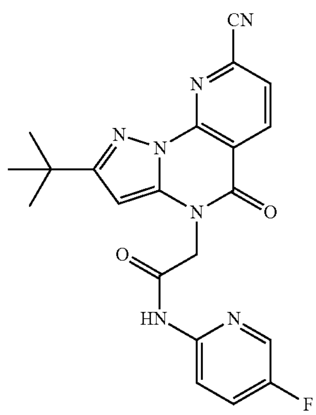
46
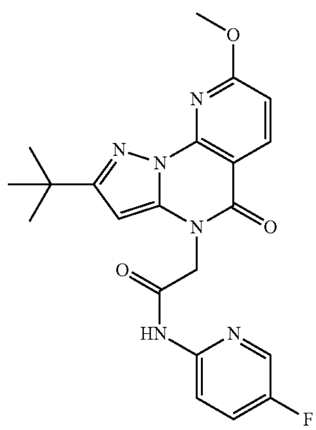
47
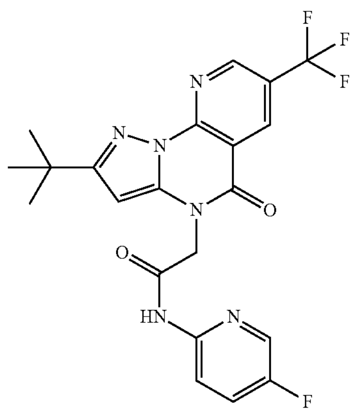
48
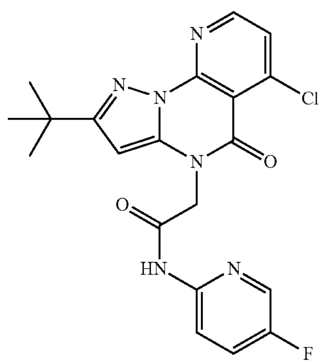
-continued
49
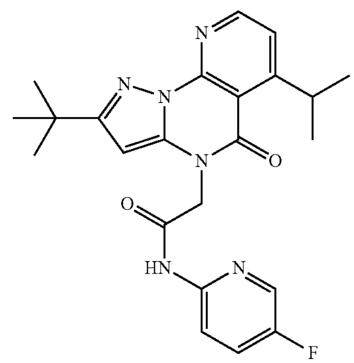
50
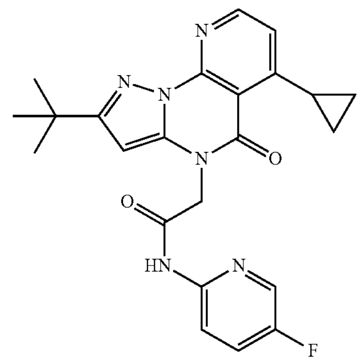
51
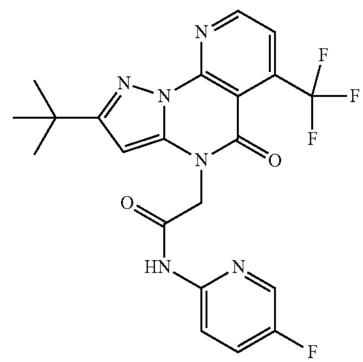
52
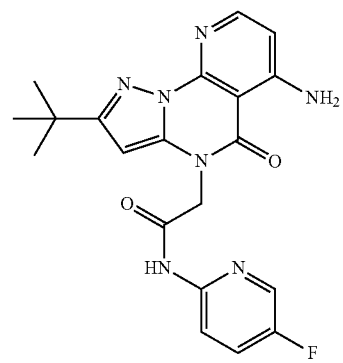

-continued
53
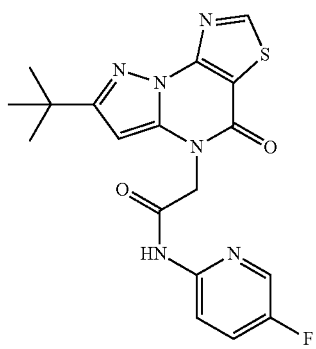
54
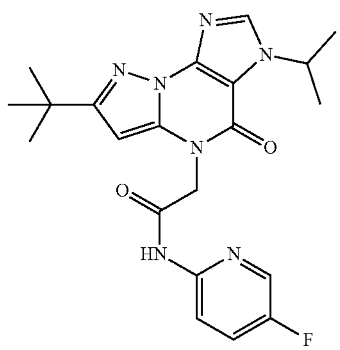
55
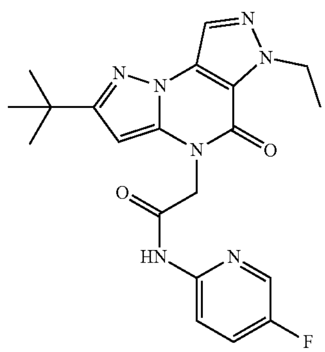
56
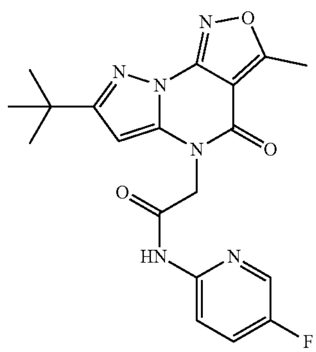
-continued
57
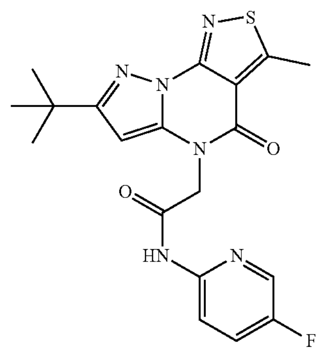
58
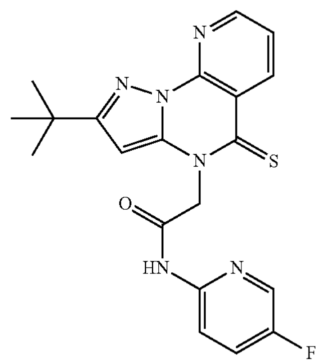
59
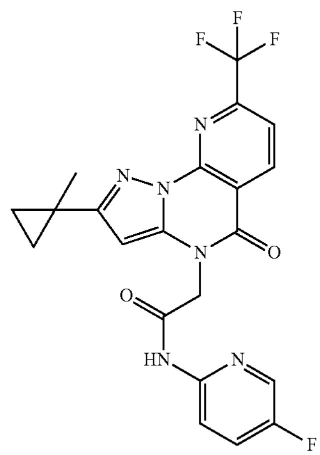
61-0
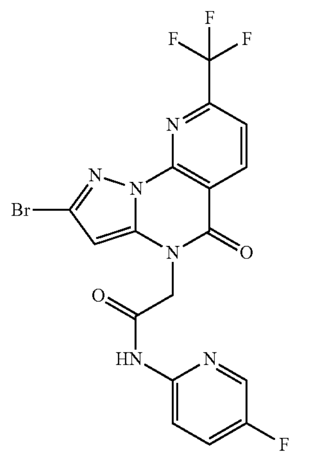

-continued
60
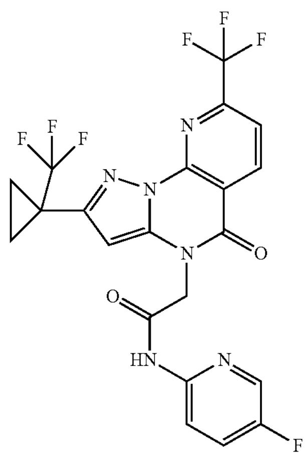
61
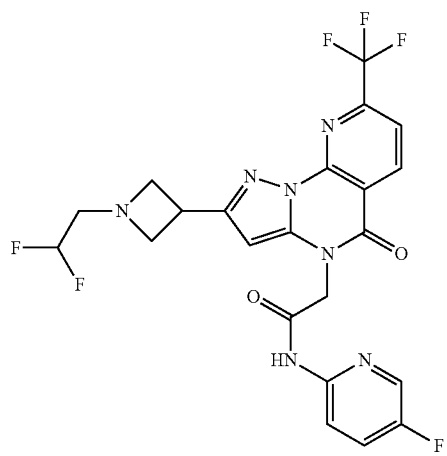
62
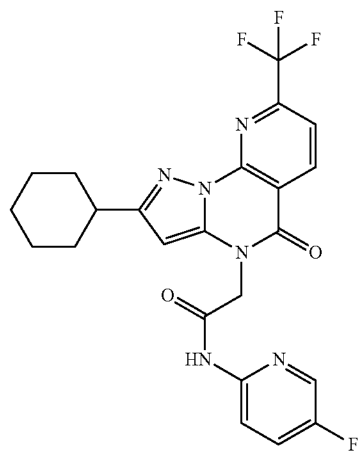
-continued
63
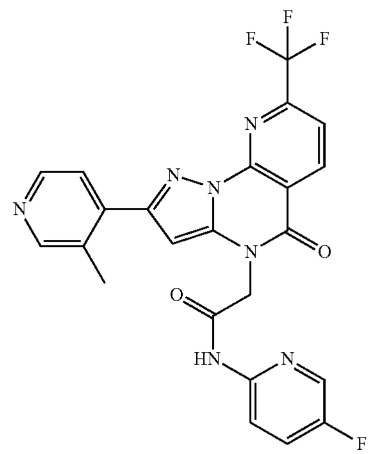
64
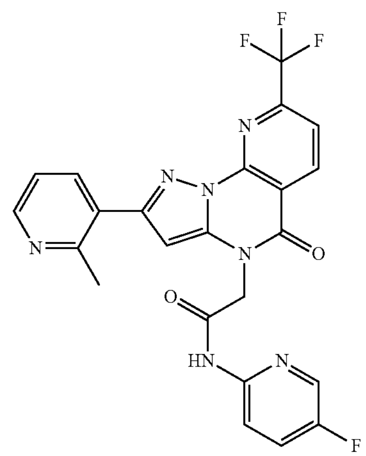
65
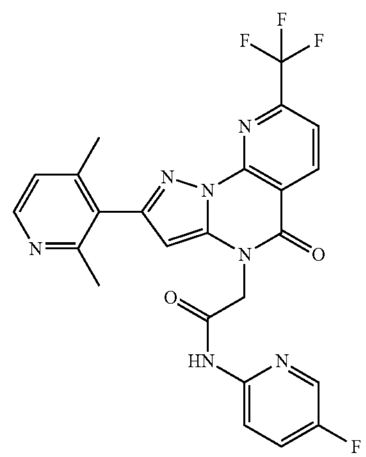

66
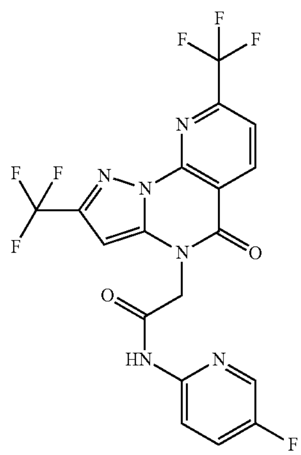
67
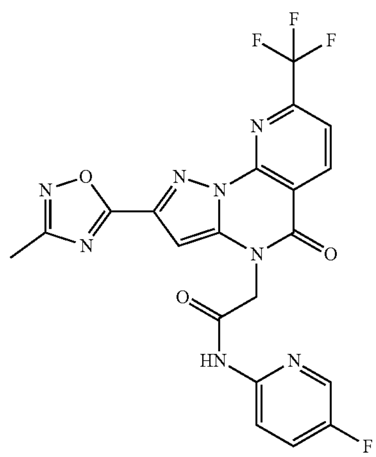
68
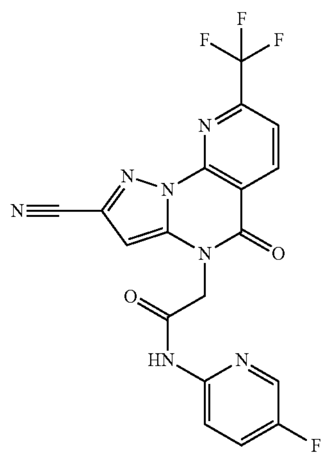
69
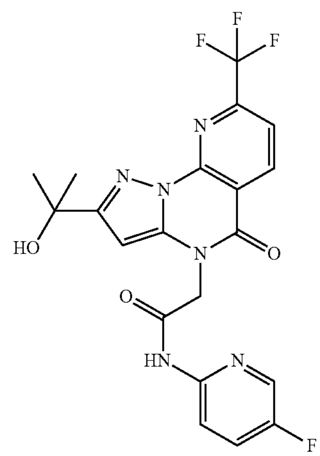
70
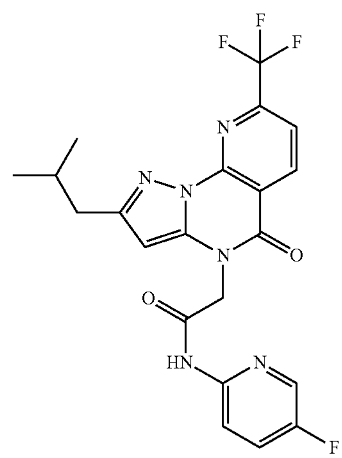
71
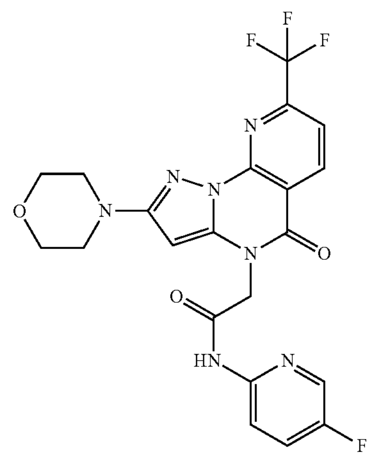

-continued
72
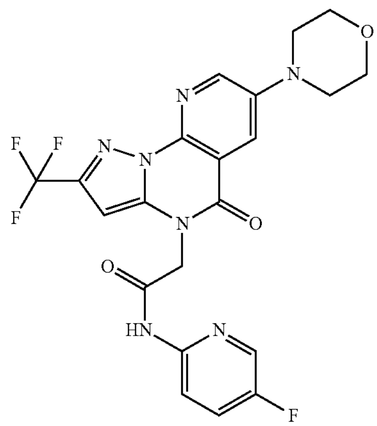
73
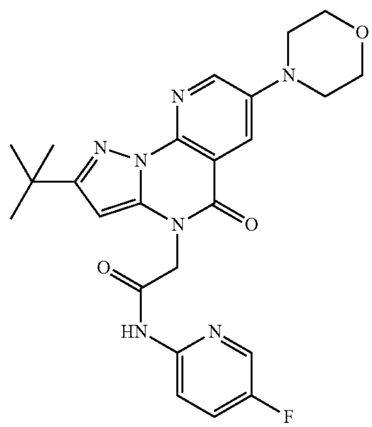
74
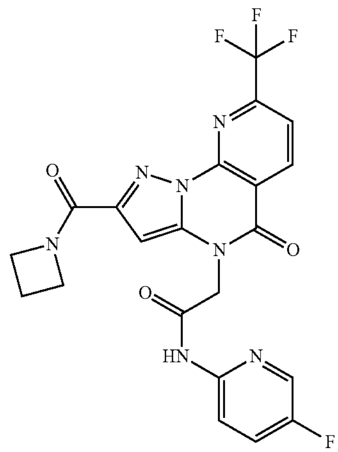
-continued
75
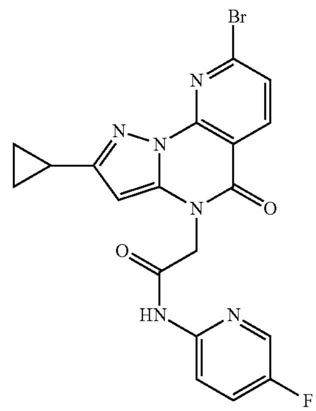
76
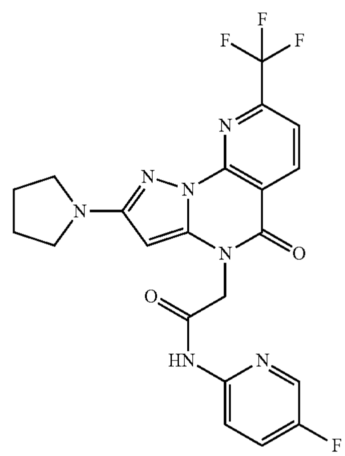
77
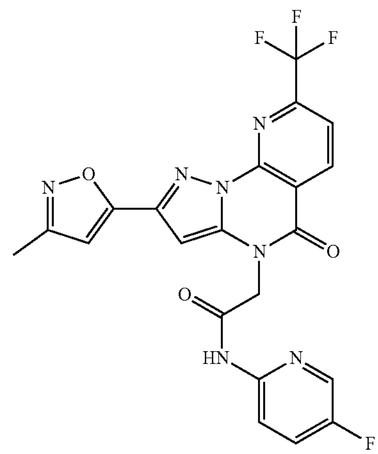

-continued
78
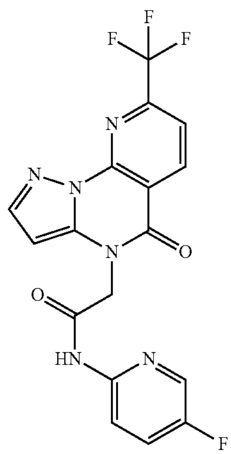
79
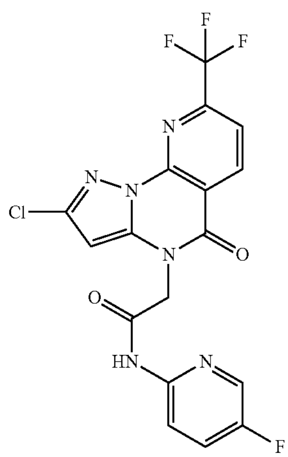
80
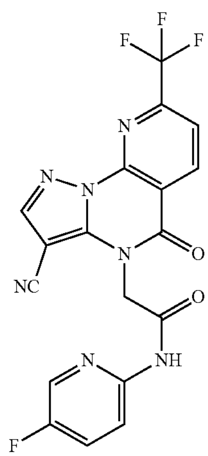
-continued
81
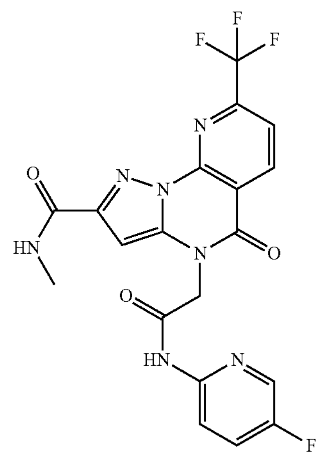
82
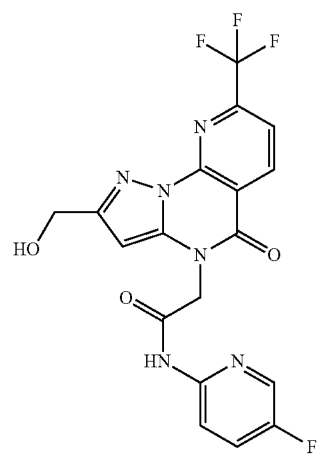
83
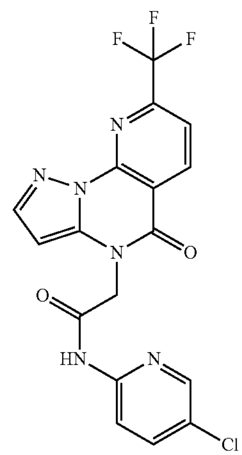

-continued
84
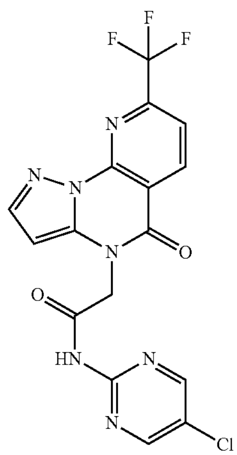
85
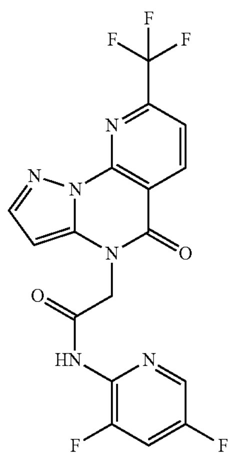
86
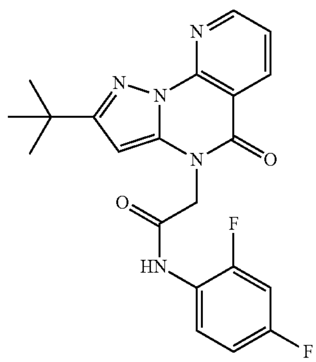
-continued
87
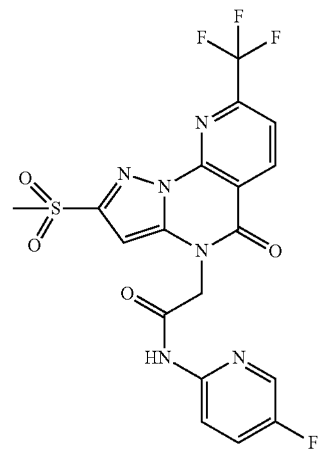
88
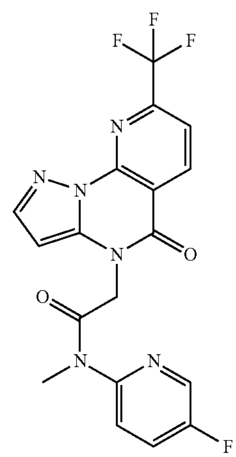
89
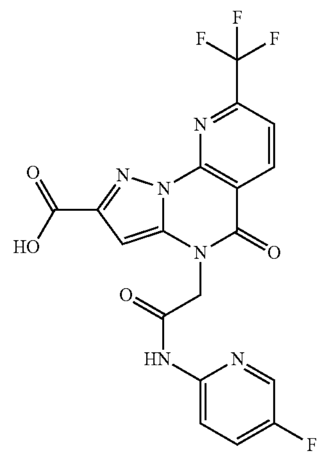

-continued
90
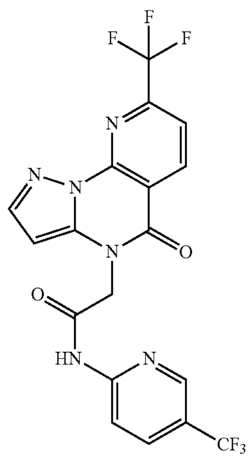
91
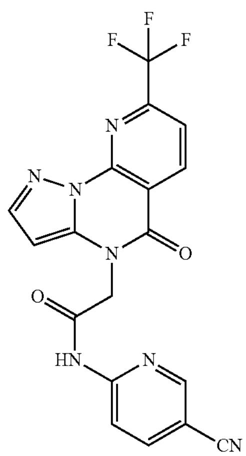
92
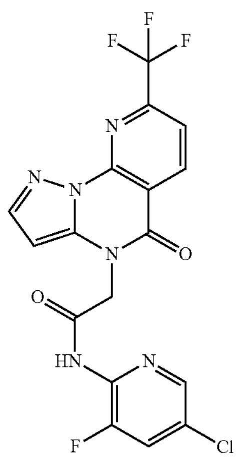
-continued
93
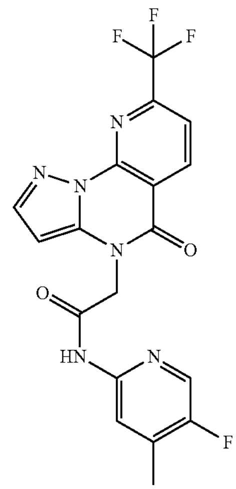
94
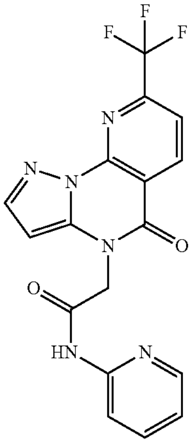
and
95
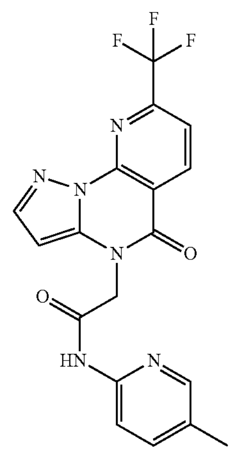
.
The present invention further relates to a method for preparing the compound of formula (III), the stereoisomer thereof or the pharmaceutically acceptable salt thereof, characterized by comprising the following step of:

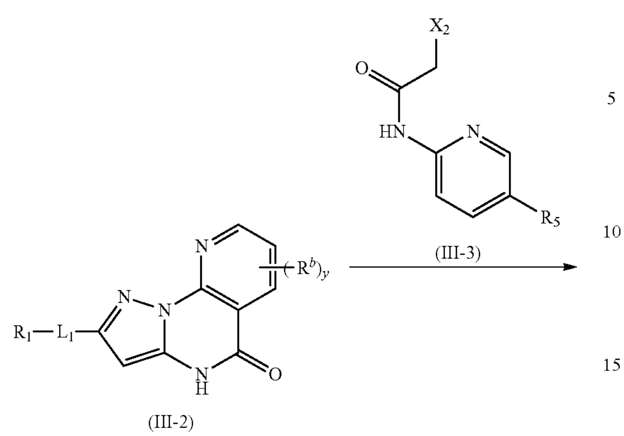

(III-2)

(III-3)

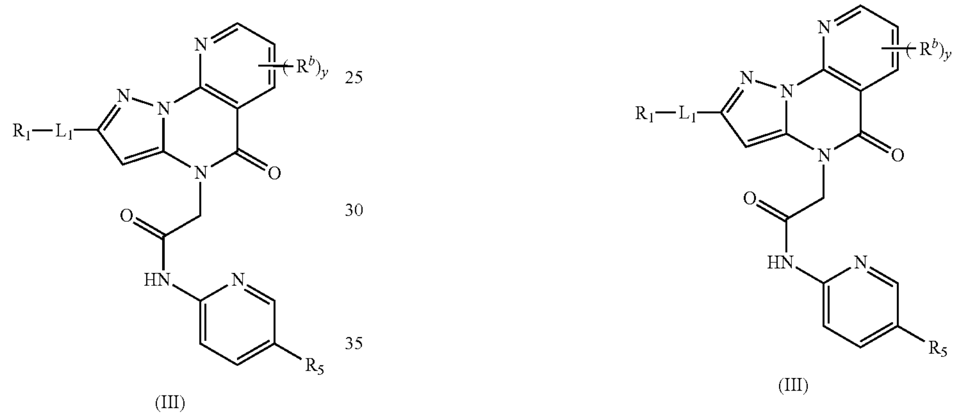

(III)

reacting a compound of formula (III-2) with a compound of formula (III-3) to obtain the target compound of formula (III);

wherein:

$X_2$ is halogen, preferably chlorine or bromine.

The present invention further relates to a method for preparing the compound of formula (III), the stereoisomer thereof or the pharmaceutically acceptable salt thereof, comprising the following steps of:

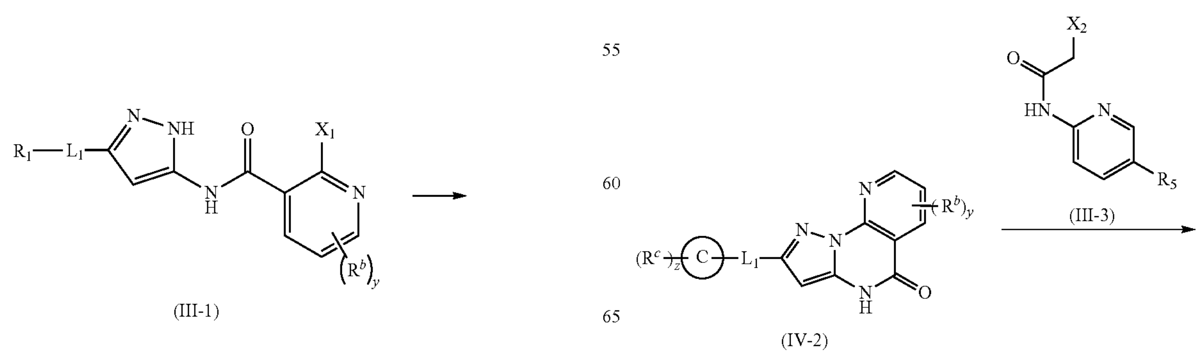

(III-1)

-continued

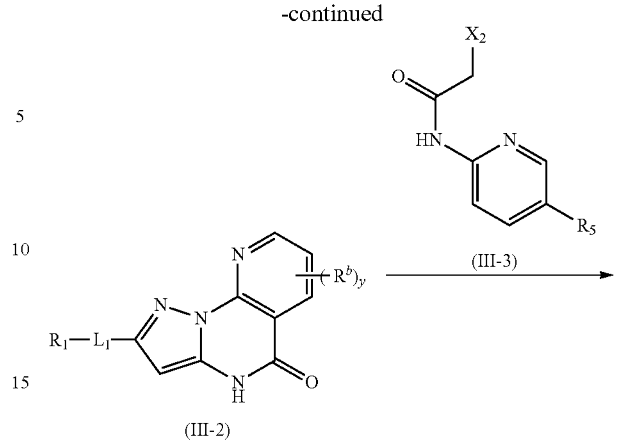

(III-2)

(III-3)

(III)

condensing a compound of formula (III-1) to obtain a compound of formula (III-2), and reacting the compound of formula (III-2) with a compound of formula (III-3) to obtain the target compound of formula (III);

wherein:

$X_1$ is halogen, preferably chlorine or bromine;

$X_2$ is halogen, preferably chlorine or bromine.

The present invention further relates to a method for preparing the compound of formula (IV), the stereoisomer thereof or the pharmaceutically acceptable salt thereof, comprising the following step of:

(IV-2)

(III-3)

-continued

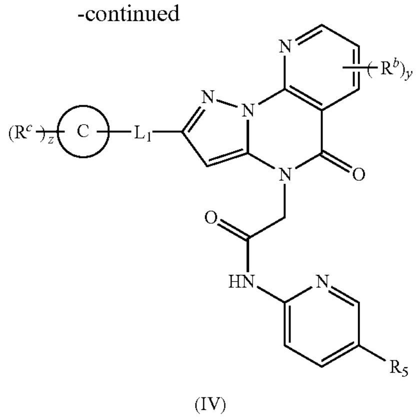

(IV)

reacting a compound of formula (IV-2) with a compound of formula (III-3) to obtain the target compound of formula (IV);

wherein:

$X_2$ is halogen, preferably chlorine or bromine.

The present invention further relates to a method for preparing the compound of formula (IV), the stereoisomer thereof or the pharmaceutically acceptable salt thereof, comprising the following steps of:

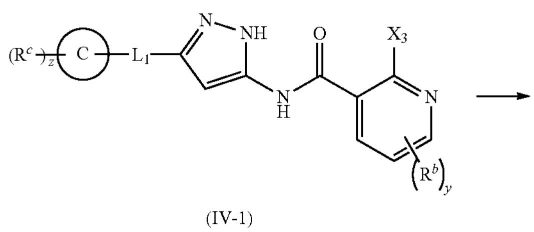

(IV-1)

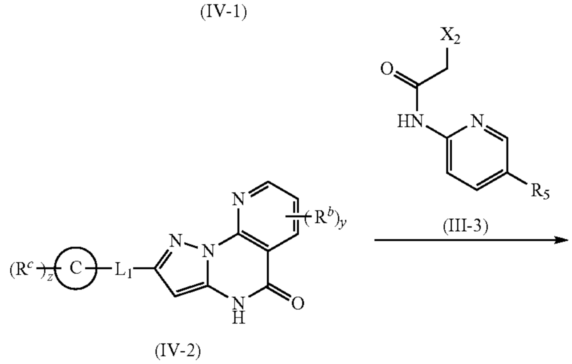

(III-3)

(IV-2)

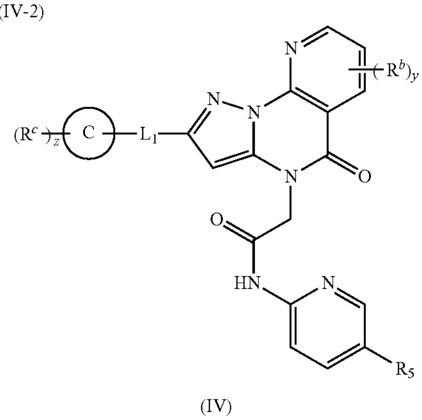

(IV)

condensing a compound of formula (IV-1) to obtain a compound of formula (IV-2), and reacting the compound of formula (IV-2) with a compound of formula (III-3) to obtain the target compound of formula (IV);

wherein:

$X_2$ is halogen, preferably chlorine or bromine;

$X_3$ is halogen, preferably chlorine or bromine.

The present invention further relates to a method for preparing the compound of formula (V), the stereoisomer thereof or the pharmaceutically acceptable salt thereof, characterized by comprising the following step of:

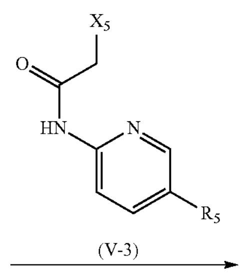

(V-3)

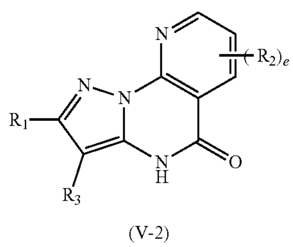

(V-2)

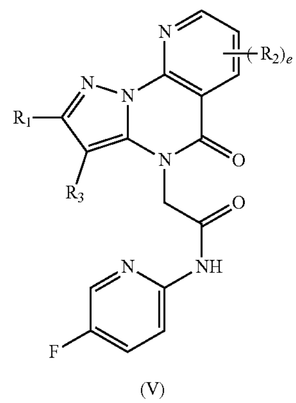

(V)

reacting a compound of formula (V-2) with a compound of formula (V-3) to obtain the target compound of formula (V);

wherein:

$X_5$ is halogen, preferably chlorine or bromine.

The present invention further relates to a method for preparing the compound of formula (V), the stereoisomer thereof or the pharmaceutically acceptable salt thereof, characterized by comprising the following steps of:

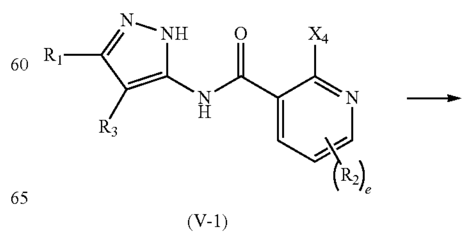

(V-1)

-continued

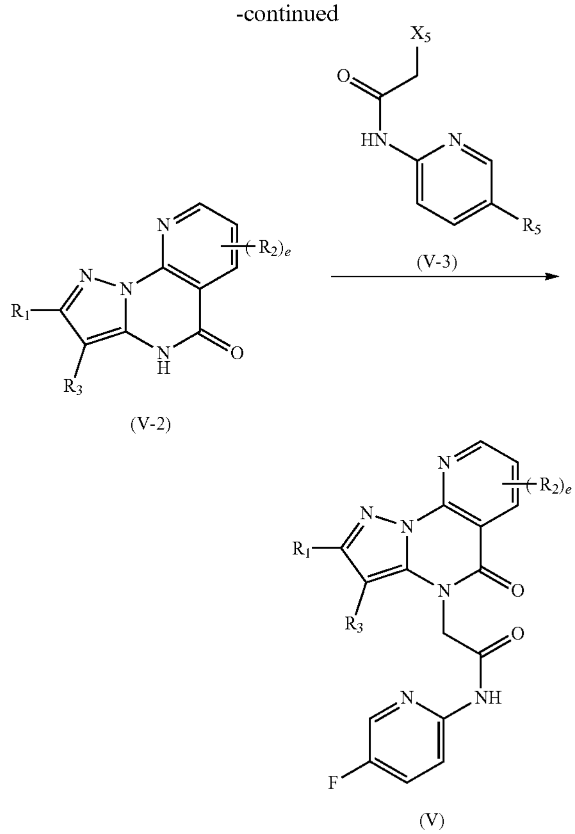

(V-3)

(V-2)

(V)

condensing a compound of formula (V-1) to obtain a compound of formula (V-2), and reacting the compound of formula (V-2) with a compound of formula (V-3) to obtain the target compound of formula (V);

wherein:

$X_4$ is halogen, preferably chlorine or bromine;

$X_5$ is halogen, preferably chlorine or bromine.

The present invention further relates to a pharmaceutical composition comprising a therapeutically effective dose of any one of the compound of formula (I), the stereoisomer thereof or the pharmaceutically acceptable salt thereof, and one or more pharmaceutically acceptable carriers, diluents or excipients.

The present invention further relates to a use of any one of the compound of formula (I), the stereoisomer thereof or the pharmaceutically acceptable salt thereof, or the pharmaceutical composition in the preparation of a P2X3 receptor inhibitor drug.

The present invention further relates to a use of the compound of formula (I), the stereoisomer thereof or the pharmaceutically acceptable salt thereof, or the pharmaceutical composition thereof in the preparation of a medicament for treating a neurogenic disease, wherein the neurogenic disease is selected from the group consisting of gynecological diseases, urinary tract disease states, respiratory disorders, pulmonary fibrosis and pain related diseases or conditions.

The present invention further relates to a method for treating a neurogenic disease by the compound of formula (I), the stereoisomer thereof or the pharmaceutically acceptable salt thereof or the pharmaceutical composition thereof.

The present invention also relates to a method for preventing and/or treating a neurogenic disease, comprising a step of administration of a therapeutically effective dose of the compound of formula (I), the stereoisomer thereof or the pharmaceutically acceptable salt thereof or the pharmaceutical composition thereof to a patient.

The present invention also provides a method for treating a disease condition by using the compound or pharmaceutical composition according to the present invention, wherein the disease condition includes, but is not limited to a condition related to P2X3 receptor dysfunction.

The present invention also relates to a method for treating a neurogenic disease in a mammal, comprising a step of administration of a therapeutically effective amount of the compound or the pharmaceutically acceptable salt, ester, prodrug, solvate, hydrate or derivative thereof according to the present invention to the mammal.

In some embodiments, the method involves gynecological diseases, urinary tract disease states, respiratory disorders and pain related diseases or conditions.

In some embodiments, the method involves the treatment of endometriosis, overactive bladder, pulmonary fibrosis or chronic cough.

In some embodiments, the method involves neuropathic pain, and pain and discomfort related to uterine fibroid.

Chronic cough and neuropathic pain are preferred.

Chronic cough is more preferred.

Definitions

Unless otherwise stated, the terms used in the specification and claims have the meanings described below.

The term “alkyl” refers to a saturated aliphatic hydrocarbon group, which is a straight or branched chain group comprising 1 to 20 carbon atoms, preferably an alkyl having 1 to 8 carbon atoms, more preferably an alkyl having 1 to 6 carbon atoms, and most preferably an alkyl having 1 to 3 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, the alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl group can be substituted or unsubstituted. When substituted, the substituent group(s) can be substituted at any available connection point. The substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl. The alkyl of the present invention is preferably selected from the group consisting of methyl, ethyl, isopropyl, tert-butyl, haloalkyl, deuterated alkyl, alkoxy-substituted alkyl and hydroxy-substituted alkyl.

The term "alkylene" refers to an alkyl of which a hydrogen atom is further substituted, for example, "methylene" refers to $—CH_2—$, "ethylene" refers to $—(CH_2)_2—$, "propylene" refers to $—(CH_2)_3—$, "butylene" refers to $—(CH_2)_4—$ and the like.

The term "alkenyl" refers to an alkyl as defined above that consists of at least two carbon atoms and at least one carbon-carbon double bond, for example, ethenyl, 1-propenyl, 2-propenyl, 1-, 2- or 3-butenyl and the like. The alkenyl group can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio and heterocyclylthio.

The term "cycloalkyl" refers to a saturated or partially unsaturated monocyclic or polycyclic hydrocarbon substituent group having 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring. The cycloalkyl is preferably cyclopropyl, cyclobutyl, cyclohexyl, cyclopentyl and cycloheptyl.

The term "spiro cycloalkyl" refers to a 5 to 20 membered polycyclic group with individual rings connected through one shared carbon atom (called a spiro atom), wherein the rings can contain one or more double bonds, but none of the rings has a completely conjugated π-electron system. The spiro cycloalkyl is preferably a 6 to 14 membered spiro cycloalkyl, and more preferably a 7 to 10 membered spiro cycloalkyl. According to the number of the spiro atoms shared between the rings, the spiro cycloalkyl can be divided into a mono-spiro cycloalkyl, a di-spiro cycloalkyl, or a poly-spiro cycloalkyl, and the spiro cycloalkyl is preferably a mono-spiro cycloalkyl or di-spiro cycloalkyl, and more preferably a 3-membered/6-membered, 3-membered/5-membered, 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

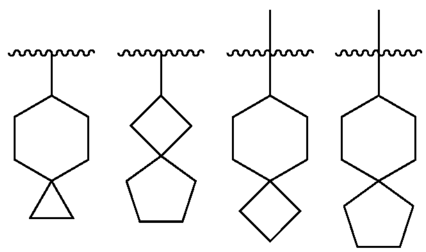

-continued

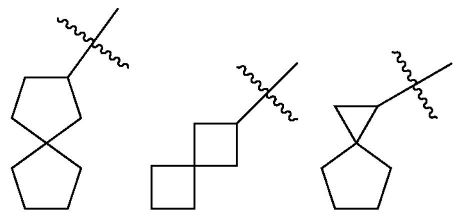

and the like;

and also include spiro cycloalkyl in which a cycloalkyl and a heterocyclyl are connected through one spiro atom, non-limiting examples thereof include:

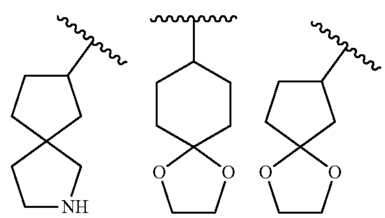

and the like.

The term "fused cycloalkyl" refers to a 5 to 20 membered all-carbon polycyclic group, wherein each ring in the system shares an adjacent pair of carbon atoms with another ring, one or more rings can contain one or more double bonds, but none of the rings has a completely conjugated π-electron system. The fused cycloalkyl is preferably a 6 to 14 membered fused cycloalkyl, and more preferably a 7 to 10 membered fused cycloalkyl. According to the number of membered rings, the fused cycloalkyl can be divided into a bicyclic, tricyclic, tetracyclic or polycyclic fused cycloalkyl, and the fused cycloalkyl is preferably a bicyclic or tricyclic fused cycloalkyl, and more preferably a 5-membered/5-membered or 5-membered/6-membered bicyclic fused cycloalkyl. Non-limiting examples of fused cycloalkyl include:

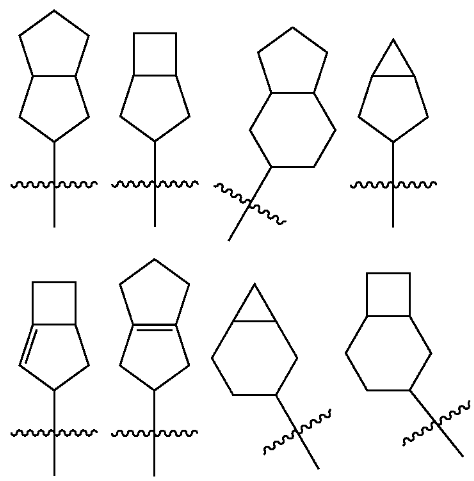

-continued

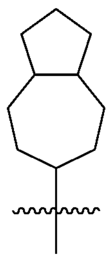

and the like.

The term "bridged cycloalkyl" refers to a 5 to 20 membered all-carbon polycyclic group, wherein every two rings in the system share two disconnected carbon atoms, the rings can have one or more double bonds, but none of the rings has a completely conjugated π-electron system. The bridged cycloalkyl is preferably a 6 to 14 membered bridged cycloalkyl, and more preferably a 7 to 10 membered bridged cycloalkyl. According to the number of membered rings, the bridged cycloalkyl can be divided into a bicyclic, tricyclic, tetracyclic or polycyclic bridged cycloalkyl, and the bridged cycloalkyl is preferably a bicyclic, tricyclic or tetracyclic bridged cycloalkyl, and more preferably a bicyclic or tricyclic bridged cycloalkyl. Non-limiting examples of bridged cycloalkyl include:

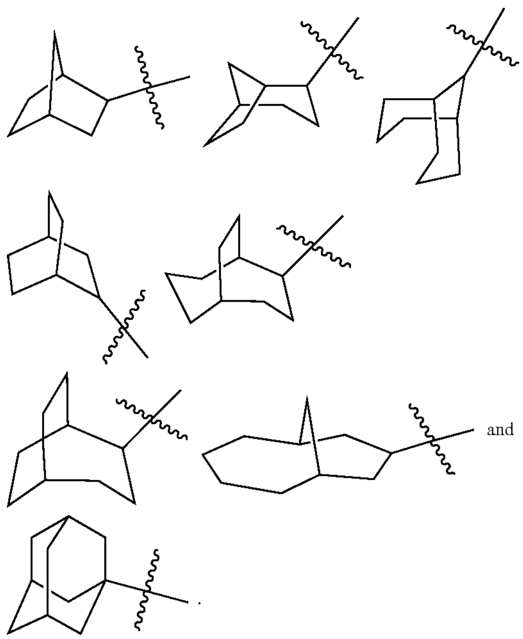

and

The cycloalkyl ring can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "heterocyclyl" refers to a 3 to 20 membered saturated or partially unsaturated monocyclic or polycyclic hydrocarbon group, wherein one or more ring atoms are heteroatoms selected from the group consisting of nitrogen, oxygen and $S(O)_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; more preferably, 3 to 8 ring atoms; most preferably 3 to 8 ring atoms; and further preferably, 3 to 8 ring atoms with 1 to 3 nitrogen atoms. Optionally, the heterocyclyl is substituted by 1 to 2 oxygen atom, sulfur atom, oxo. The heterocyclyl includes nitrogen-containing monocyclic heterocyclyl, nitrogen-containing spiro heterocyclyl and nitrogen-containing fused heterocyclyl.

Non-limiting examples of monocyclic heterocyclyl include oxetanyl, thietanyl, pyrrolidinyl, imidazolidinyl, tetrahydrofuranyl, tetrahydrothienyl, tetrahydropyranyl, dihydroimidazolyl, dihydrofuranyl, dihydropyrazolyl, dihydropyrrolyl, piperidinyl, piperazinyl, morpholinyl, thiomorpholinyl, homopiperazinyl, azetyl, 1,4-diazacycloheptyl, pyranyl, tetrahydrothiapyran dioxide group and the like, preferably oxetanyl, thietanyl, tetrahydrofuranyl, tetrahydropyranyl, tetrahydrothienyl, tetrahydrothiapyranyl, tetrahydrothiapyranyl dioxide group, pyrrolidinyl, morpholinyl, piperidinyl, azetyl, 1,4-diazacycloheptyl and piperazinyl, and more preferably oxetanyl, piperidinyl, tetrahydropyranyl and tetrahydrothiapyranyl. Polycyclic heterocyclyl includes a heterocyclyl having a spiro ring, fused ring or bridged ring. The heterocyclyl having a spiro ring, fused ring or bridged ring is optionally bonded to other group via a single bond, or further bonded to other cycloalkyl, heterocyclyl, aryl and heteroaryl via any two or more atoms on the ring.

The term "spiro heterocyclyl" refers to a 5 to 20 membered polycyclic heterocyclyl group with individual rings connected through one shared atom (called a spiro atom), wherein one or more ring atoms are heteroatoms selected from the group consisting of nitrogen, oxygen and $S(O)_m$ (wherein m is an integer of 0 to 2), with the remaining ring atoms being carbon atoms, and the rings can contain one or more double bonds, but none of the rings has a completely conjugated π-electron system. The spiro heterocyclyl is preferably a 6 to 14 membered spiro heterocyclyl, and more preferably a 7 to 10 membered spiro heterocyclyl. According to the number of the spiro atoms shared between the rings, the spiro heterocyclyl can be divided into a mono-spiro heterocyclyl, di-spiro heterocyclyl, or poly-spiro heterocyclyl, and the spiro heterocyclyl is preferably a mono-spiro heterocyclyl or di-spiro heterocyclyl, and more preferably a 3-membered/5-membered, 3-membered/6-membered, 4-membered/4-membered, 4-membered/5-membered, 4-membered/6-membered, 5-membered/5-membered, or 5-membered/6-membered mono-spiro heterocyclyl. Non-limiting examples of spiro heterocyclyl include:

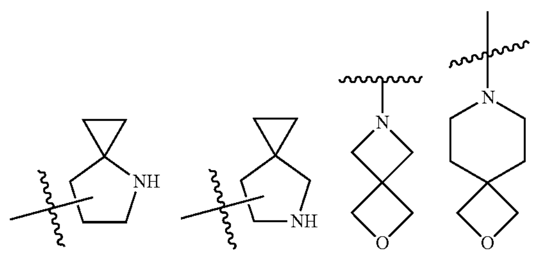

-continued

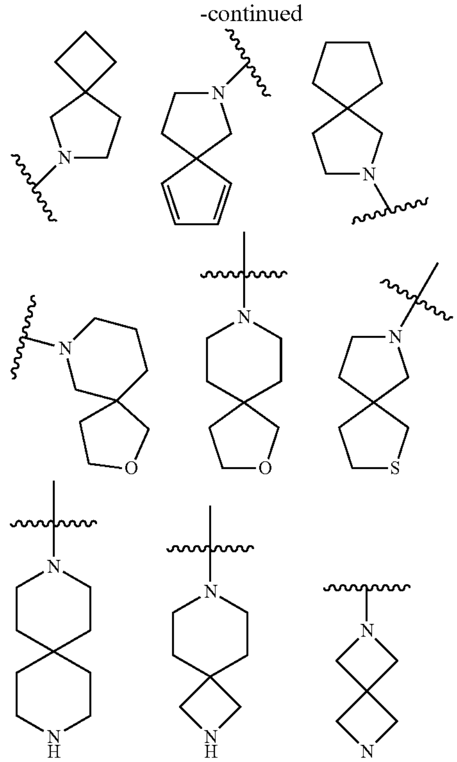

and the like.

The term “fused heterocyclyl” refers to a 5 to 20 membered polycyclic heterocyclyl group, wherein each ring in the system shares an adjacent pair of atoms with another ring, one or more rings can contain one or more double bonds, but none of the rings has a completely conjugated π-electron system, and one or more ring atoms are heteroatoms selected from the group consisting of nitrogen, oxygen and $S(O)_m$ (wherein m is an integer of 0 to 2), with the remaining ring atoms being carbon atoms. The fused heterocyclyl is preferably a 6 to 14 membered fused heterocyclyl, and more preferably a 7 to 10 membered fused heterocyclyl. According to the number of membered rings, the fused heterocyclyl can be divided into a bicyclic, tricyclic, tetracyclic or polycyclic fused heterocyclyl, and preferably a bicyclic or tricyclic fused heterocyclyl, and more preferably a 5-membered/5-membered or 5-membered/6-membered bicyclic fused heterocyclyl. Non-limiting examples of fused heterocyclyl include:

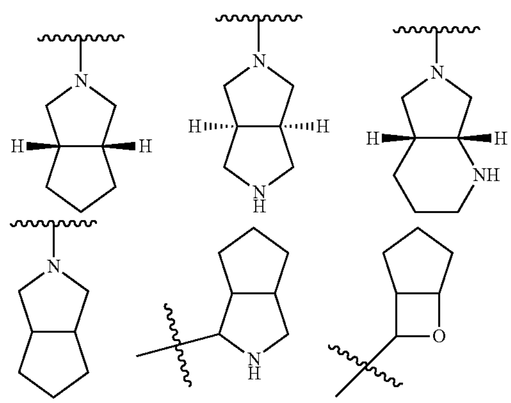

-continued

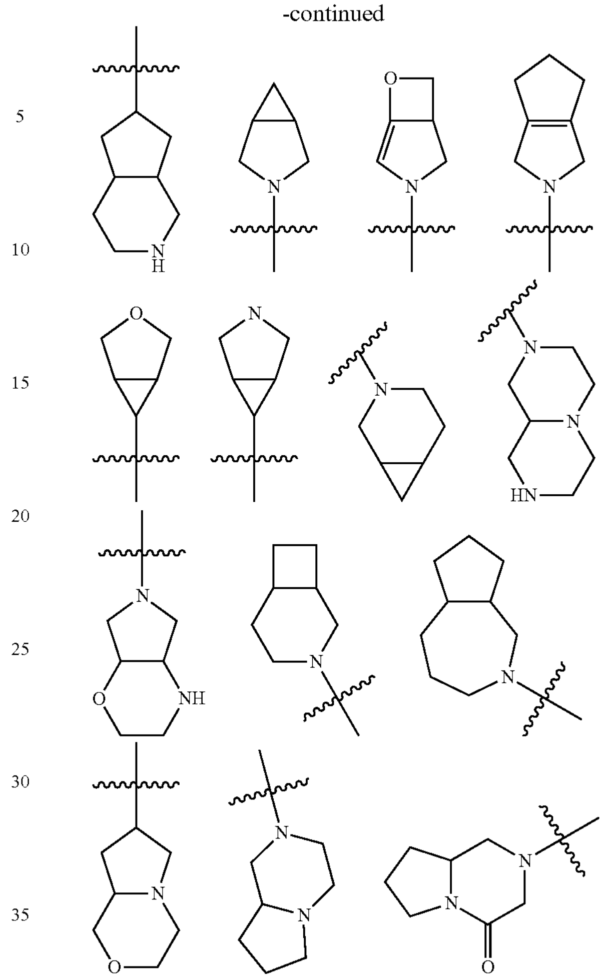

and the like.

The term “bridged heterocyclyl” refers to a 5 to 14 membered polycyclic heterocyclyl group, wherein every two rings in the system share two disconnected atoms, wherein the rings can have one or more double bond(s), but none of the rings has a completely conjugated π-electron system, and one or more ring atoms are heteroatoms selected from the group consisting of nitrogen, oxygen and $S(O)_m$ (wherein m is an integer of 0 to 2), with the remaining ring atoms being carbon atoms. The bridged heterocyclyl is preferably a 6 to 14 membered bridged heterocyclyl, and more preferably a 7 to 10 membered bridged heterocyclyl. According to the number of membered rings, the bridged heterocyclyl can be divided into a bicyclic, tricyclic, tetracyclic or polycyclic bridged heterocyclyl, and the bridged heterocyclyl is preferably a bicyclic, tricyclic or tetracyclic bridged heterocyclyl, and more preferably a bicyclic or tricyclic bridged heterocyclyl. Non-limiting examples of bridged heterocyclyl include:

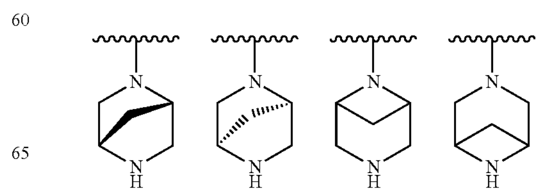

-continued

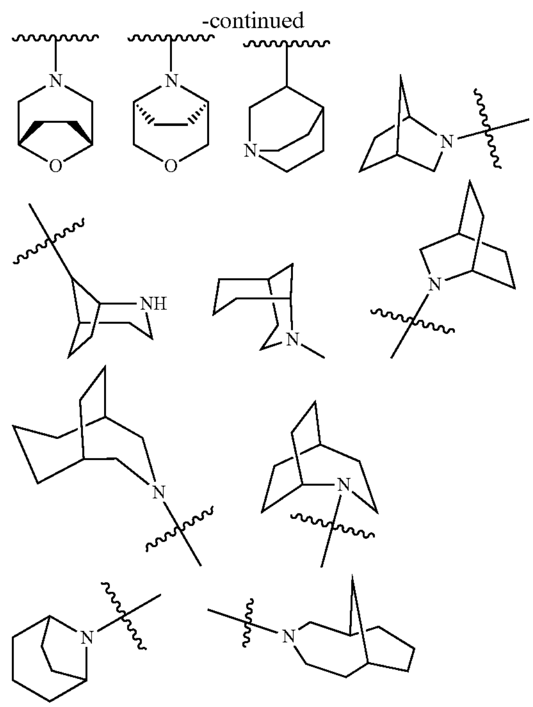

and the like.

The heterocyclyl ring can be fused to the ring of aryl, heteroaryl or cycloalkyl, wherein the ring bound to the parent structure is heterocyclyl. Non-limiting examples include:

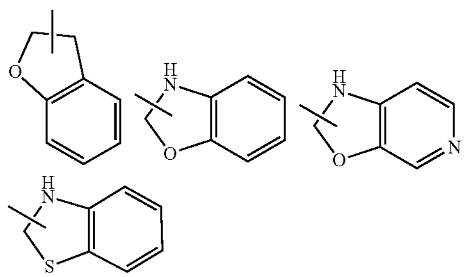

and the like.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term “aryl” refers to a 6 to 14 membered all-carbon monocyclic ring or polycyclic fused ring (i.e. each ring in the system shares an adjacent pair of carbon atoms with another ring in the system) having a conjugated π-electron system, preferably a 6 to 12 membered aryl, for example, phenyl and naphthyl. The aryl is more preferably phenyl. The aryl ring can be fused to the ring of heteroaryl, heterocyclyl or cycloalkyl. The aryl includes benzo 5 to 10 membered heteroaryl, benzo 3 to 8 membered cycloalkyl and benzo 3 to 8 membered heterocyclyl, preferably benzo 5 to 6 membered heteroaryl, benzo 3 to 6 membered cycloalkyl and benzo 3 to 6 membered heterocyclyl, wherein the heterocyclyl is a heterocyclyl containing 1 to 3 nitrogen atoms, oxygen atoms or sulfur atoms. The aryl also includes 3 membered nitrogen-containing fused ring containing a benzene ring.

The ring bound to the parent structure is aryl ring. Non-limiting examples thereof include:

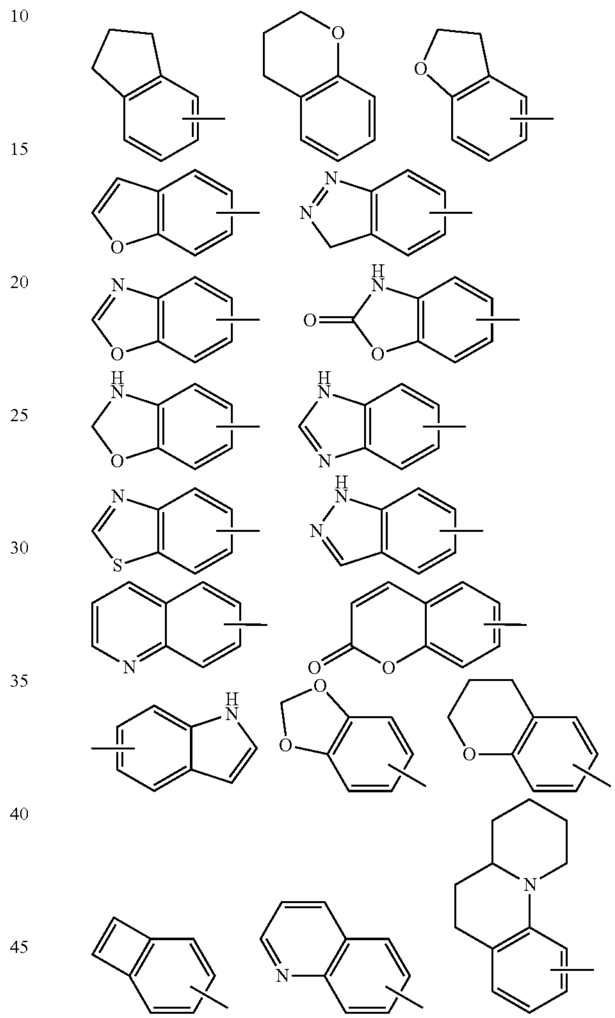

and the like.

The aryl can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term “heteroaryl” refers to a 5 to 14 membered heteroaromatic system having 1 to 4 heteroatoms selected from the group consisting of oxygen, sulfur and nitrogen. The heteroaryl is preferably a 5 to 12 membered heteroaryl, and more preferably a 5 or 6 membered heteroaryl, for example imidazolyl, furanyl, thienyl, thiazolyl, pyrazolyl, oxazolyl, pyrrolyl, triazolyl, tetrazolyl, pyridyl, pyrimidinyl, thiadiazolyl, pyridazinyl, pyrazinyl and the like, preferably pyridyl, oxadiazolyl, triazolyl, thienyl, imidazolyl, pyrazolyl, oxazolyl, pyrimidinyl, furyl, thienyl, pyridazinyl, pyrazinyl and thiazolyl, and more preferably pyridyl, furyl, thienyl, pyrimidinyl, oxazolyl, oxadiazolyl, pyrazolyl, pyrrolyl, thiazolyl, pyridazinyl, pyrazinyl and oxazolyl. The heteroaryl ring can be fused to the ring of aryl, heterocyclyl or cycloalkyl, wherein the ring bound to the parent structure is heteroaryl ring. Non-limiting examples thereof include:

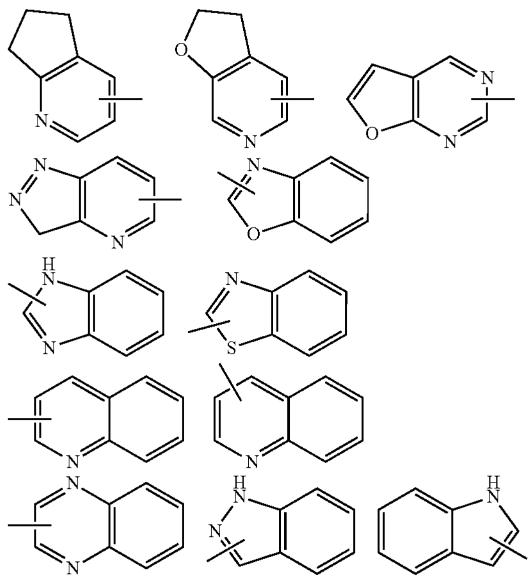

and the like.

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "alkoxy" refers to an —O-(alkyl) or an —O-(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "alkylthio" refers to an —S-(alkyl) or an —S-(unsubstituted cycloalkyl) group, wherein the alkyl is as defined above. Non-limiting examples of alkylthio include methoxy, ethoxy, propoxy, butoxy, cyclopropyloxy, cyclobutyloxy, cyclopentyloxy, cyclohexyloxy. The alkylthio can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

"Haloalkyl" refers to an alkyl group substituted by one or more halogen(s), wherein the alkyl is as defined above.

"Haloalkoxy" refers to an alkoxy group substituted by one or more halogen(s), wherein the alkoxy is as defined above.

"Hydroxyalkyl" refers to an alkyl group substituted by hydroxy(s), wherein the alkyl is as defined above.

"Alkenyl" refers to a chain olefin, also known as alkene group. The alkenyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy or alkoxycarbonyl.

"Alkynyl" refers to (CH≡C—). The alkynyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy or alkoxycarbonyl.

The term "alkenylcarbonyl" refers to —C(O)-(alkenyl), wherein the alkenyl is as defined above. Non-limiting examples of alkenylcarbonyl include: vinylcarbonyl, propenylcarbonyl, butenylcarbonyl. The alkenylcarbonyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

"Hydroxy" refers to an —OH group.

"Halogen" refers to fluorine, chlorine, bromine or iodine.

"Amino" refers to a $—NH_2$ group.

"Cyano" refers to a —CN group.

"Nitro" refers to a $—NO_2$ group.

"Carbonyl" refers to a —C(O)— group.

"Carboxy" refers to a —C(O)OH group.

"THF" refers to tetrahydrofuran.

"EtOAc" refers to ethyl acetate.

"MeOH" refers to methanol.

"DMF" refers to N,N-dimethylformamide.

"DIPEA" refers to diisopropylethylamine.

"TFA" refers to trifluoroacetic acid.

"MeCN" refers to acetonitrile.

"DMA" refers to N,N-dimethylacetamide.

"$Et_2O$" refers to diethyl ether.

"DCE" refers to 1,2-dichloroethane.

"DIPEA" refers to N,N-diisopropylethylamine.

"NBS" refers to N-bromosuccinimide.

"NIS" refers to N-iodosuccinimide.

"Cbz-Cl" refers to benzyl chloroformate.

"$Pd_2(dba)_3$" refers to tris(dibenzylideneacetone)dipalladium.

"Dppf" refers to 1,1'-bisdiphenylphosphinoferrocene.

"HATU" refers to 2-(7-azabenzotriazol-1-yl)-N,N,N',N'-tetramethyluronium hexafluorophosphate.

"KHMDS" refers to potassium hexamethyldisilazide.

"LiHMDS" refers to lithium bis(trimethylsilyl)amide.

"MeLi" refers to methyl lithium.

"n-BuLi" refers to n-butyl lithium.

"$NaBH(OAc)_3$" refers to sodium triacetoxyborohydride.

Different expressions such as "X is selected from the group consisting of A, B or C", "X is selected from the group consisting of A, B and C", "X is A, B or C", "X is A, B and C" are the same meaning, that is, X can be any one or more of A, B and C.

The hydrogen atom of the present invention can be replaced by its isotope deuterium. Any of the hydrogen atoms in the compounds of the examples of the present invention can also be substituted by deuterium atom.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, and more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without excessive efforts. For example, the combination of amino or hydroxy having free hydrogen and carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components such as physiologically/pharmaceutically acceptable carriers and excipients. The purpose of the pharmaceutical composition is to facilitate administration of a compound to an organism, which is conducive to the absorption of the active ingredient so as to exert biological activity.

A "pharmaceutically acceptable salt" refers to a salt of the compound of the present invention, which is safe and effective in mammals and has the desired biological activity.

DETAILED DESCRIPTION OF THE INVENTION

The present invention will be further described with reference to the following examples, but the examples should not be considered as limiting the scope of the present invention.

EXAMPLES

The structures of the compounds of the present invention were identified by nuclear magnetic resonance (NMR) and/or liquid chromatography-mass spectrometry (LC-MS). NMR shifts (δ) are given in parts per million (ppm). NMR is determined by a Bruker AVANCE-400 instrument. The solvents for determination are deuterated-dimethyl sulfoxide (DMSO-$d_6$), deuterated-methanol ($CD_3OD$) and deuterated-chloroform ($CDCl_3$), and the internal standard is tetramethylsilane (TMS).

Liquid chromatography-mass spectrometry (LC-MS) is determined on an Agilent 1200 Infinity Series mass spectrometer. High performance liquid chromatography (HPLC) is determined on an Agilent 1200DAD high pressure liquid chromatograph (Sunfire C18 150×4.6 mm column), and a Waters 2695-2996 high pressure liquid chromatograph (Gimini $C_{18}$ 150×4.6 mm column).

Yantai Huanghai HSGF254 or Qingdao GF254 silica gel plate is used as the thin-layer silica gel chromatography (TLC) plate. The dimension of the silica gel plate used in TLC is 0.15 mm to 0.2 mm, and the dimension of the silica gel plate used in product purification is 0.4 mm to 0.5 mm. Yantai Huanghai 200 to 300 mesh silica gel is generally used as a carrier for column chromatography.

The raw materials used in the examples of the present invention are known and commercially available, or can be synthesized by or according to known methods in the art.

Unless otherwise stated, all reactions of the present invention are carried out under continuous magnetic stirring under a dry nitrogen or argon atmosphere. The solvent is dry, and the reaction temperature is in degrees celsius.

Example 1

2-(2-(Tert-butyl)-5-oxopyrazolo[1,5-a]pyrido[3,2-e]pyrimidin-4(5H)-yl)-N-(5-fluoropyridin-2-yl)acetamide

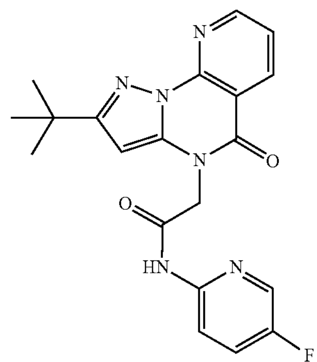 [SMILES: CC(C)(C)c1cc2n(CC(=O)Nc3ccc(F)cn3)c(=O)c3cccnc3n2n1]

Step 1: Preparation of N-(3-(tert-butyl)-1H-pyrazol-5-yl)-2-chloronicotinamide

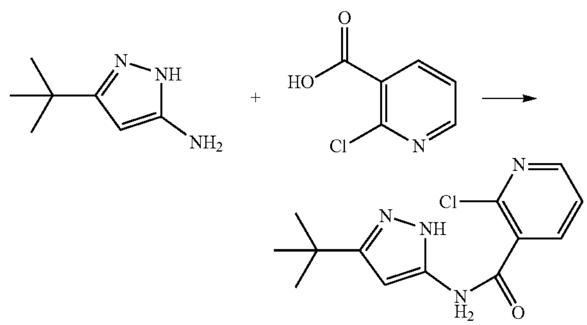

Example 1-1

3-(Tert-butyl)-1H-pyrazol-5-amine (2.77 g, 19.93 mmol), DIPEA (6.2 g, 49.8 mmol) and HATU (5.4 g, 0.144 mmol) were added successively to a solution of 2-chloronicotinic acid (1.57 g, 9.96 mmol) in DMF (30 mL) under an ice bath condition. The ice bath was removed, and the reaction solution was stirred for 1 h. The mixture was treated to obtain Example 1-1 (2.5 g, 90%).

MS m/z (ESI): 279.7 $[M+H]^+$.

Step 2: Preparation of 2-(tert-butyl)pyrazolo[1,5-a]pyrido[3,2-e]pyrimidin-5(4H)-one

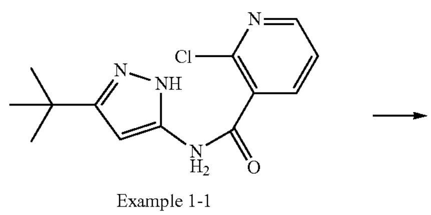

Example 1-1

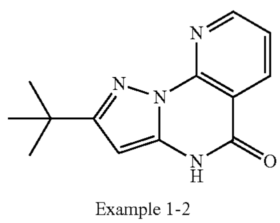

Example 1-2

Potassium carbonate (1.61 g, 11.66 mmol) and 1,4-diazabicyclo[2.2.2]octane (DABCO) (150.9 mg, 1.35 mmol) were added to a solution of Example 1-1 (2.5 g, 8.97 mmol) in DMF (50 mL). The reaction solution was stirred at room temperature for 16 hours. The mixture was treated to obtain Example 1-2 (2.1 g, 97%).

MS m/z (ESI): 279.7 $[M+H]^+$.

Step 3: Preparation of 2-(2-(tert-butyl)-5-oxopyrazolo[1,5-a]pyrido[3,2-e]pyrimidin-4(5H)-yl)-N-(5-fluoropyridin-2-yl)acetamide

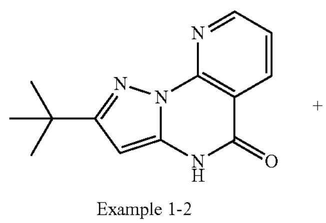

Example 1-2

+

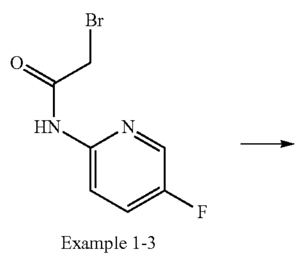

Example 1-3

-continued

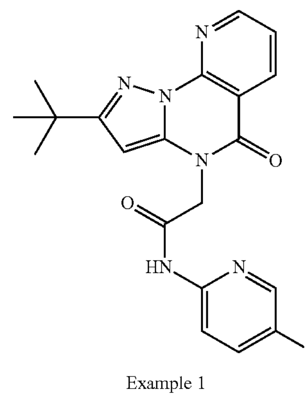

Example 1

Potassium carbonate (4.28 g, 30.96 mmol) and Example 1-3 (4.33 g, 18.57 mmol) were added to a solution of Example 1-2 (1.5 g, 6.19 mmol) in DMF (30 mL) at room temperature. The mixture was heated to 80° C. and stirred for 2 h. The reaction solution was cooled followed by addition of water. The precipitate was filtered, washed with ethyl acetate, and purified to obtain Example 1 (656 mg, yield: 27%).

MS m/z (ESI): 395.4 $[M+H]^+$.

$^1$H NMR (400 MHz, DMSO-d6) δ 11.01 (s, 1H), 8.80-8.78 (m, 1H), 8.47 (d, J=7.6 Hz, 1H), 8.30 (d, J=2.8 Hz, 1H), 8.01-7.94 (m, 1H), 7.73-7.66 (m, 1H), 7.49 (dd, J=8.0, 4.8 Hz, 1H), 6.34 (s, 1H), 4.87 (s, 2H), 1.26 (s, 9H).

Example 2

2-(2-Bromo-5-oxopyrazolo[1,5-a]pyrido[3,2-e]pyrimidin-4(5H)-yl)-N-(5-fluoropyridin-2-yl)acetamide

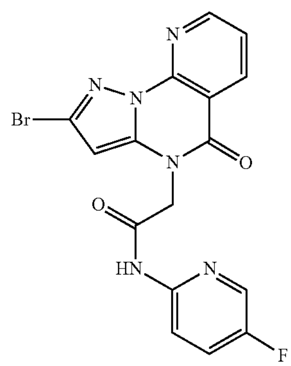 [SMILES: O=C(Cn1c(=O)c2cccnc2n2nc(Br)cc12)Nc1ccc(F)cn1]

Example 2 was synthesized according to the method of Example 1. The target compound (500 mg, yield: 68%) was obtained by replacing 3-(tert-butyl)-1H-pyrazol-5-amine with 3-bromo-1H-pyrazol-5-amine.

MS m/z (ESI): 418.2 $[M+H]^+$.

$^1$H NMR (400 MHz, DMSO-d6) δ 11.32 (s, 1H), 9.85 (d, J=7.6 Hz, 1H), 8.74 (d, J=6.4 Hz, 1H), 8.40 (d, J=2.8 Hz, 1H), 8.05-8.00 (m, 1H), 7.78-7.73 (m, 1H), 7.23-7.17 (m, 1H), 6.31 (s, 1H), 5.52 (s, 2H).

Example 3

N-(5-Fluoropyridin-2-yl)-2-(2-methyl-5-oxopyrazolo[1,5-a]pyrido[3,2-e]pyrimidin-4(5H)-yl)acetamide

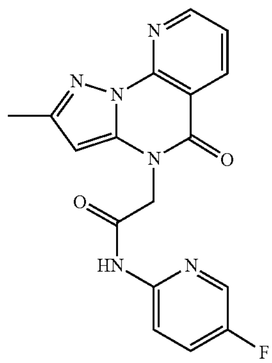 [SMILES: Cc1cc2n(CC(=O)Nc3ccc(F)cn3)c(=O)c3cccnc3n2n1]

Example 3 was synthesized according to the method of Example 1. The target compound (20 mg, yield: 26%) was obtained by replacing 3-(tert-butyl)-1H-pyrazol-5-amine with 3-methyl-1H-pyrazol-5-amine.

MS m/z (ESI): 353.3 $[M+H]^+$.

Example 4

N-(5-Fluoropyridin-2-yl)-2-(2-ethyl-5-oxopyrazolo[1,5-a]pyrido[3,2-e]pyrimidin-4(5H)-yl) acetamide

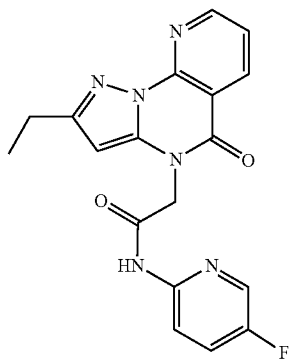 [SMILES: CCc1cc2n(CC(=O)Nc3ccc(F)cn3)c(=O)c3cccnc3n2n1]

Example 4 was synthesized according to the method of Example 1. The target compound (15 mg, yield: 36%) was obtained by replacing 3-(tert-butyl)-1H-pyrazol-5-amine with 3-ethyl-1H-pyrazol-5-amine.

MS m/z (ESI): 367.4 $[M+H]^+$.

Example 5

N-(5-Fluoropyridin-2-yl)-2-(2-isopropyl-5-oxopyrazolo[1,5-a]pyrido[3,2-e]pyrimidin-4(5H)-yl)acetamide

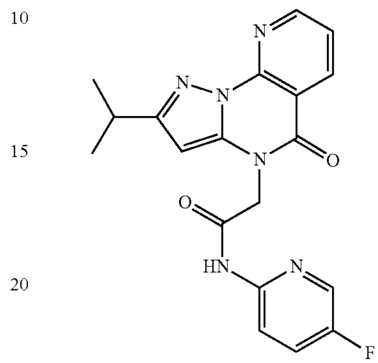

Example 5 was synthesized according to the method of Example 1. The target compound (15 mg, yield: 36%) was obtained by replacing 3-(tert-butyl)-1H-pyrazol-5-amine with 3-isopropyl-1H-pyrazol-5-amine.

MS m/z (ESI): 381.4 $[M+H]^+$.

Example 6

N-(5-Fluoropyridin-2-yl)-2-(2-isopropenyl-5-oxopyrazolo[1,5-a]pyrido[3,2-e]pyrimidin-4(5H)-yl)acetamide

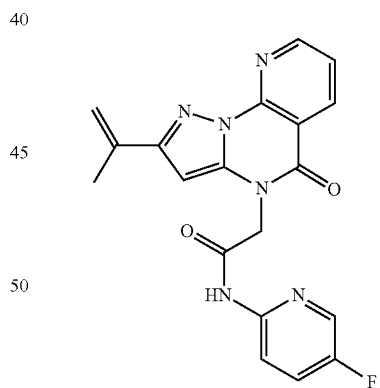

Example 2 (100 mg, 0.24 mmol), isopropenylboronic acid (41.2 mg, 0.48 mmol), [1,1'-bis(diphenylphosphino)ferrocene]dichloropalladium dichloromethane complex (19.2 mg, 0.024 mmol) and cesium carbonate (232.8 mg, 0.72 mmol) were stirred in dioxane (4 mL) and water (1 mL) at 100° C. under microwave for 1 h. The reaction solution was concentrated to dryness by rotary evaporation, and purified by preparative high performance liquid chromatography to obtain Example 6 (54 mg, yield: 60%).

MS m/z (ESI): 379.4 $[M+H]^+$.

Example 7

N-(5-Fluoropyridin-2-yl)-2-(5-oxo-2-(trifluoromethyl)pyrazolo[1,5-a]pyrido[3,2-e]pyrimidin-4(5H)-yl)acetamide

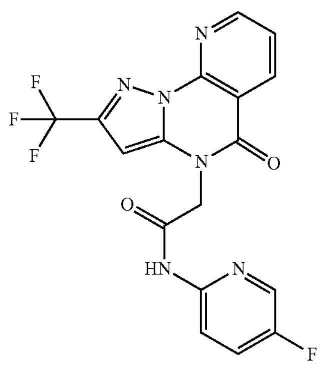 [SMILES: O=C(Cn1c(=O)c2cccnc2n2nc(C(F)(F)F)cc12)Nc1ccc(F)cn1]

Example 7 was synthesized according to the method of Example 1. The target compound (15 mg, yield: 36%) was obtained by replacing 3-(tert-butyl)-1H-pyrazol-5-amine with 3-trifluoromethyl-1H-pyrazol-5-amine.

MS m/z (ESI): 407.3 $[M+H]^+$.

$^1$H NMR (400 MHz, DMSO-d6) δ 11.08 (s, 1H), 8.96 (dd, J=8.0, 1.6 Hz, 1H), 8.65 (dd, J=8.0, 1.6 Hz, 1H), 8.37 (d, J=3.2 Hz, 1H), 8.07-8.02 (m, 1H), 7.78-7.73 (m, 2H), 7.05 (s, 1H), 5.02 (s, 2H).

Example 8

2-(2-Amino-5-oxopyrazolo[1,5-a]pyrido[3,2-e]pyrimidin-4(5H)-yl)-N-(5-fluoropyridin-2-yl)acetamide

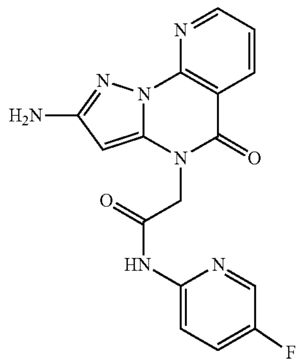 [SMILES: Nc1cc2n(CC(=O)Nc3ccc(F)cn3)c(=O)c3cccnc3n2n1]

Step 1: Preparation of methyl 5-oxo-4,5-dihydropyrazolo[1,5-a]pyrido[3,2-e]pyrimidine-2-carboxylate

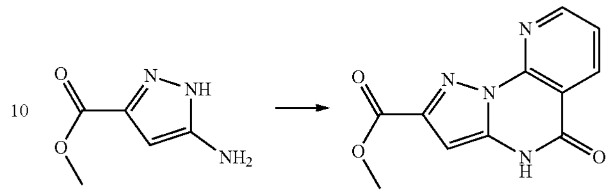

Example 8-1

The synthetic method of Example 8-1 was according to the synthetic method of Example 1-2. Example 8-1 (500 mg, 73%) was obtained by replacing 3-(tert-butyl)-1H-pyrazol-5-amine with methyl 5-amino-1H-pyrazole-3-carboxylate.

MS: m/z (ESI): 245.2 $[M+H]^+$.

Step 2: Preparation of methyl 4-(2-((5-fluoropyridin-2-yl)amino)-2-oxoethyl)-5-oxo-4,5-dihydropyrazolo[1,5-a]pyrido[3,2-e]pyrimidine-2-carboxylate

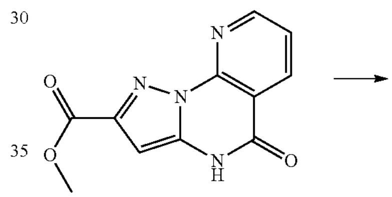

Example 8-1

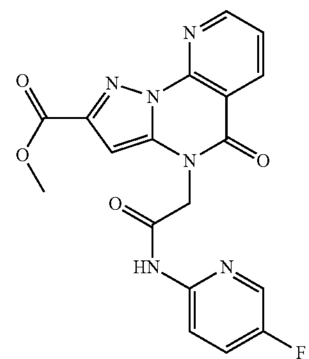

Example 8-2

The synthetic method of Example 8-2 was according to the synthetic method of Example 1. The title compound Example 8-2 (500 mg, 51%) was obtained by using Example 8-1 as the starting material.

MS m/z (ESI): 397.3 $[M+H]^+$.

Step 3: Preparation of 4-(2-((5-fluoropyridin-2-yl)amino)-2-oxoethyl)-5-oxo-4,5-dihydropyrazolo[1,5-a]pyrido[3,2-e]pyrimidine-2-carboxylic acid

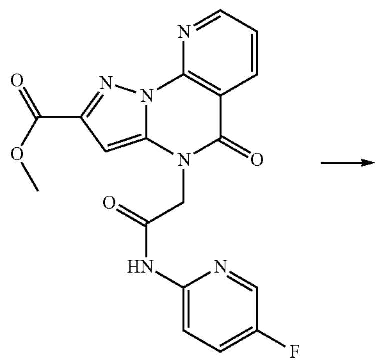

Example 8-2

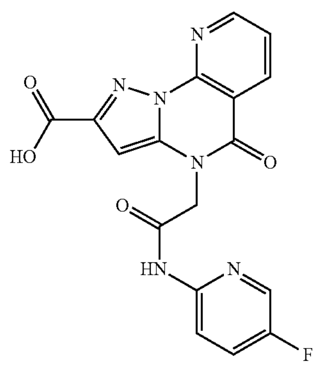

Example 8-3

A solution of LiOH (519 mg, 12.36 mmol) in water (2 mL) was added to a solution of Example 8-2 (490 mg, 1.24 mmol) in tetrahydrofuran (10 mL) at room temperature. The mixture was stirred at room temperature for 3 h, then the pH was adjusted to about 3 with 1M HCl. The solution was concentrated to dryness to obtain Example 8-3 (470 mg, 99%).

MS m/z (ESI): 383.3 $[M+H]^+$.

Step 4: Preparation of 2-(2-amino-5-oxopyrazolo[1,5-a]pyrido[3,2-e]pyrimidin-4(5H)-yl)-N-(5-fluoropyridin-2-yl)acetamide

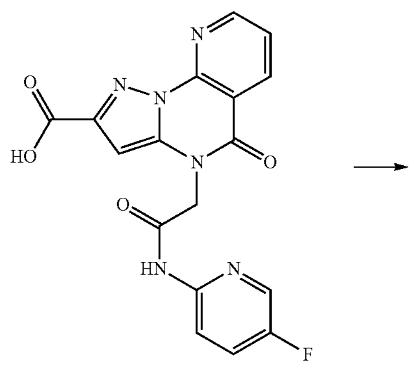

Example 8-3

-continued

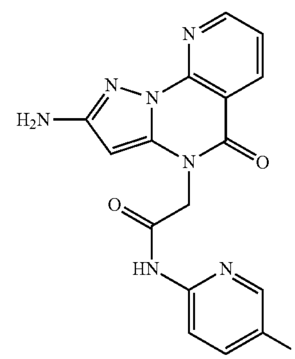

Example 8

Ammonia was added to a solution of Example 8-3 (450 mg, 1.2 mmol) in 1,4-dioxane (10 mL), $Et_3N$ (33 μL, 0.24 mmol) and BOP reagent (598 mg, 1.35 mmol), and stirred at room temperature for 20 min. Sodium azide (160 mg, 2.46 mmol) and tetrabutylammonium bromide (786 mg, 2.46 mmol) were added, and the reaction solution was stirred for 1 hour. The reaction solution was diluted with 1,4-dioxane (12 mL), followed by addition of 2 M aqueous $H_2SO_4$ solution (4 mL) and heating at 100° C. for 2 h. The solvent was evaporated, and the residues were diluted with water and extracted with ethyl acetate. The organic layer was washed with brine and dried over anhydrous sodium sulfate, and the solvent was evaporated. The resulting residues were purified by column chromatography to obtain Example 8 (360 mg, 86%).

MS m/z (ESI): 354.3 $[M+H]^+$.

Example 9

2-(2-Cyclopropyl-5-oxopyrazolo[1,5-a]pyrido[3,2-e]pyrimidin-4(5H)-yl)-N-(5-fluoropyridin-2-yl)acetamide

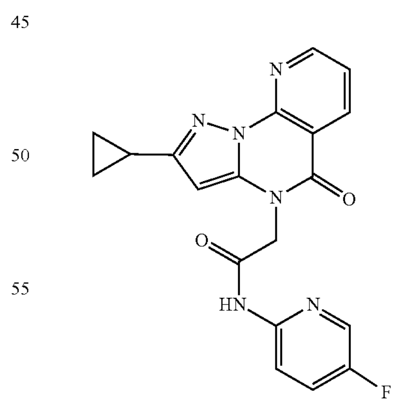

The synthetic method of Example 9 was according to the synthetic method of Example 6. The title compound Example 9 (8 mg, 51%) was obtained by replacing isopropenylboronic acid with cyclopropylboronic acid.

MS m/z (ESI): 378.4 $[M+H]^+$.

Example 10

2-(2-Cyclopentyl-5-oxopyrazolo[1,5-a]pyrido[3,2-e]pyrimidin-4(5H)-yl)-N-(5-fluoropyridin-2-yl)acetamide

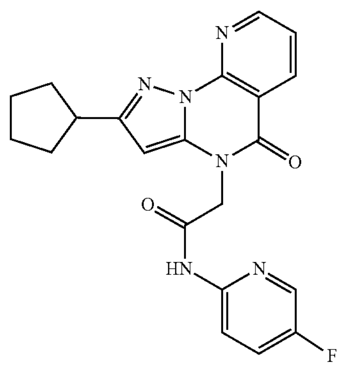 [SMILES: O=C(Cn1c(=O)c2cccnc2n2nc(C3CCCC3)cc12)Nc1ccc(F)cn1]

The synthetic method of Example 10 was according to the synthetic method of Example 1. The title compound Example 10 (9 mg, 28%) was obtained by replacing 3-bromo-1H-pyrazol-5-amine with 3-cyclopentyl-1H-pyrazol-5-amine.

MS m/z (ESI): 407.4 $[M+H]^+$.

Example 11

2-(2-Cyclopentenyl-5-oxopyrazolo[1,5-a]pyrido[3,2-e]pyrimidin-4(5H)-yl)-N-(5-fluoropyridin-2-yl)acetamide

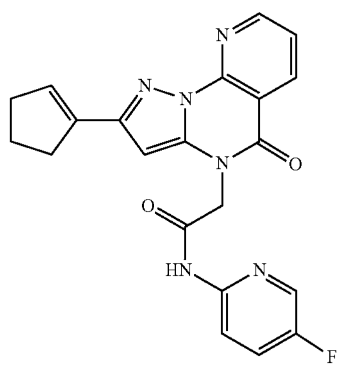 [SMILES: O=C(Cn1c(=O)c2cccnc2n2nc(C3=CCCC3)cc12)Nc1ccc(F)cn1]

The synthetic method of Example 11 was according to the synthetic method of Example 6. The title compound Example 11 (15 mg, 81%) was obtained by replacing isopropenylboronic acid with cyclopentenylboronic acid.

MS m/z (ESI): 405.4 $[M+H]^+$.

Example 12

N-(5-Fluoropyridin-2-yl)-2-(5-oxo-2-(tetrahydro-2H-thiopyran-4-yl)pyrazolo[1,5-a]pyrido[3,2-e]pyrimidin-4(5H)-yl)acetamide

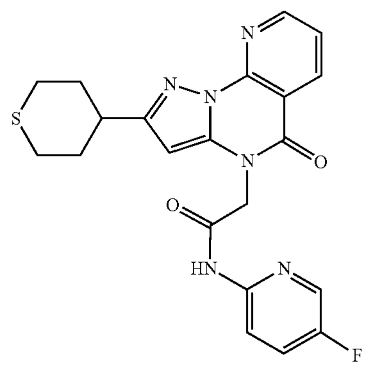 [SMILES: O=C(Cn1c(=O)c2cccnc2n2nc(C3CCSCC3)cc12)Nc1ccc(F)cn1]

Step 1: Preparation of 2-(2-(3,6-dihydro-2H-thiopyran-4-yl)-5-oxopyrazolo[1,5-a]pyrido[3,2-e]pyrimidin-4(5H)-yl)-N-(5-fluoropyridin-2-yl)acetamide

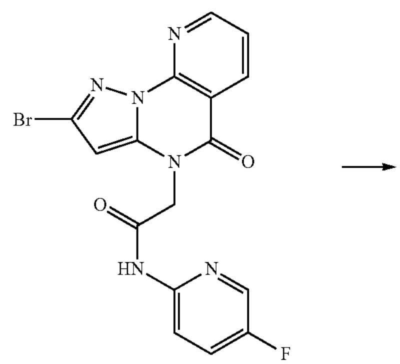

Example 2

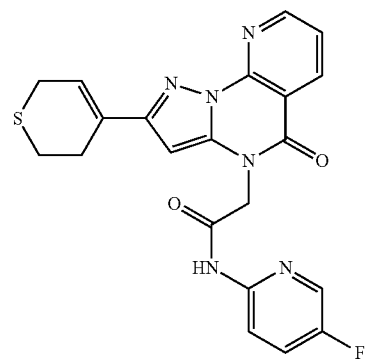

Example 12-1

The synthetic method of Example 12-1 was according to the synthetic method of Example 6. The title compound Example 12-1 (20 mg, 81%) was obtained by replacing isopropenylboronic acid with (3,6-dihydro-2H-thiopyran-4-yl)boronic acid.

MS m/z (ESI): 437.5 $[M+H]^+$.

Step 2: Preparation of N-(5-fluoropyridin-2-yl)-2-(5-oxo-2-(tetrahydro-2H-thiopyran-4-yl)pyrazolo[1,5-a]pyrido[3,2-e]pyrimidin-4(5H)-yl)acetamide

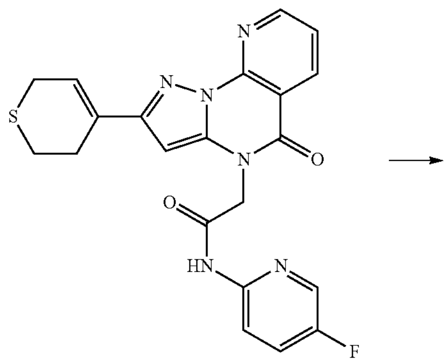

Example 12-1

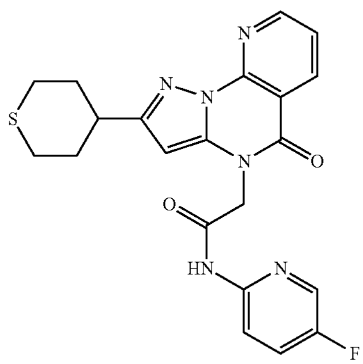

Example 12

Example 12-1 (20 mg, 0.045 mmol) was dissolved in methanol (1 mL). 10% wet palladium on carbon (2 mg) was added, and the reaction solution was heated to reflux under a hydrogen atmosphere. After completion of the reaction, the reaction solution was filtered through celite, and purified to obtain Example 12 (13 mg, 65%).

MS m/z (ESI): 439.5 $[M+H]^+$.

Example 13

2-(2-(2,2-Difluoroacetyl)piperidin-4-yl)-5-oxopyrazolo[1,5-a]pyrido[3,2-e]pyrimidin-4(5H)-yl)-N-(5-fluoropyridin-2-yl)acetamide

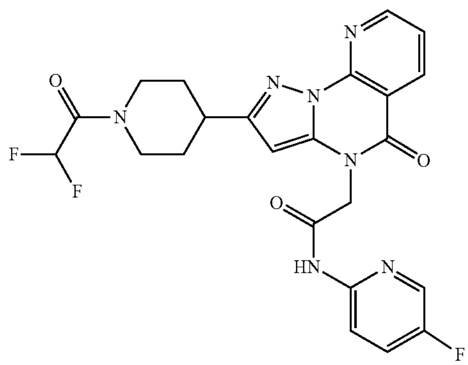 [SMILES: O=C(Cn1c(=O)c2cccnc2n2nc(C3CCN(C(=O)C(F)F)CC3)cc12)Nc1ccc(F)cn1]

The synthetic method of Example 13 was according to the synthetic method of Example 6. The title compound Example 13 (6 mg, 11%) was obtained.

MS m/z (ESI): 500.4 $[M+H]^+$.

Example 14

N-(5-Fluoropyridin-2-yl)-2-(2-(oxetan-3-ylamino)-5-oxopyrazolo[1,5-a]pyrido[3,2-e]pyrimidin-4(5H)-yl) acetamide

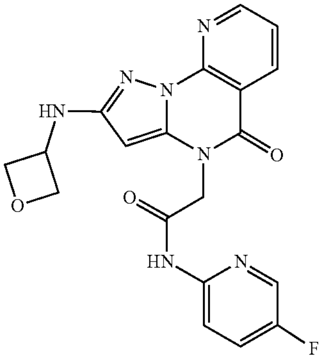 [SMILES: O=C(Cn1c(=O)c2cccnc2n2nc(NC3COC3)cc12)Nc1ccc(F)cn1]

Example 9 (35.3 mg, 0.1 mmol) and oxetanone (7.1 mg, 0.1 mmol) were dissolved in methanol (1 mL). Sodium borohydride (3.8 mg, 0.1 mmol) and p-toluenesulfonic acid monohydrate (0.1 mmol) were added to the resulting mixture, and the reaction solution was heated to reflux for 3 hours. The reaction mixture was quenched with saturated aqueous $NaHCO_3$ solution (10 mL), and extracted with dichloromethane (3*10 mL). The combined extracts were dried over anhydrous sodium sulfate, filtered and concentrated. The resulting crude product was purified to obtain Example 14 (20 mg, 50%).

MS m/z (ESI): 410.4 $[M+H]^+$.

Example 15

2-(2-(Cyclopentylamino)-5-oxopyrazolo[1,5-a]pyrido[3,2-e]pyrimidin-4(5H)-yl)-N-(5-fluoropyridin-2-yl)acetamide

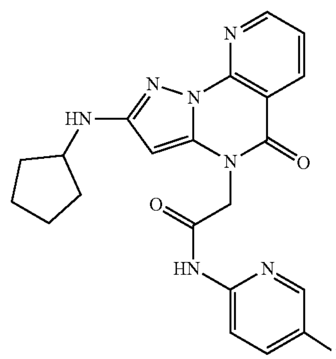

The synthetic method of Example 15 was according to the synthetic method of Example 14. The title compound Example 15 (7 mg, 13%) was obtained.

MS m/z (ESI): 422.4 $[M+H]^+$.

Example 16

N-(Cyclopropylmethyl)-4-(2-((5-fluoropyridin-2-yl)amino)-2-oxoethyl)-N-methyl-5-oxo-4,5-dihydropyrazolo[1,5-a]pyrido[3,2-e]pyrimidine-2-carboxamide

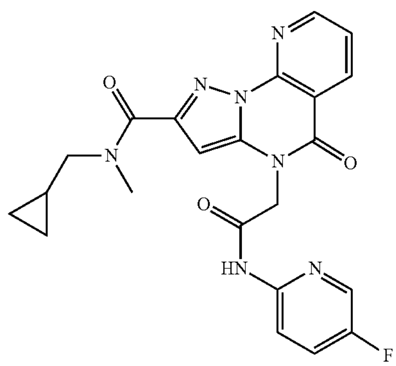 [SMILES: CN(CC1CC1)C(=O)c1cc2n(CC(=O)Nc3ccc(F)cn3)c(=O)c3cccnc3n2n1]

Example 8-3 (36.7 mg, 0.096 mmol) was dissolved in DMF (1 mL) under an ice bath condition, followed by successively adding 1-cyclopropyl-N-methylformamide (16.4 mg, 0.192 mmol), DIPEA (62 mg, 0.48 mmol) and HATU (54 mg, 0.144 mmol). The ice bath was removed, and the reaction solution was stirred for 1 h. The mixture was treated to obtain Example 16 (22 mg, 50%).

MS m/z (ESI): 450.5 $[M+H]^+$.

Example 17

N-(Cyclopropyl)-4-(2-((5-fluoropyridin-2-yl)amino)-2-oxoethyl)-N-methyl-5-oxo-4,5-dihydropyrazolo[1,5-a]pyrido[3,2-e]pyrimidine-2-carboxamide

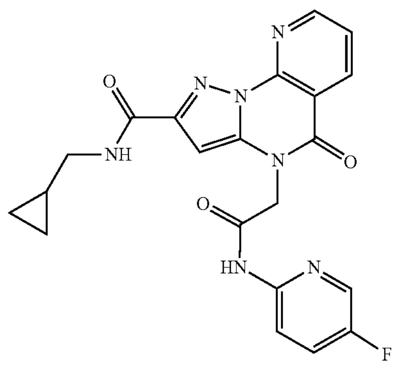 [SMILES: O=C(Cn1c(=O)c2cccnc2n2nc(C(=O)NCC3CC3)cc12)Nc1ccc(F)cn1]

The synthetic method of Example 17 was according to the synthetic method of Example 16. The title compound Example 17 (20 mg, 50%) was obtained.

MS m/z (ESI): 436.4 $[M+H]^+$.

Example 18

N-(5-Fluoropyridin-2-yl)-2-(5-oxo-2-phenylpyrazolo[1,5-a]pyrido[3,2-e]pyrimidin-4(5H)-yl)acetamide

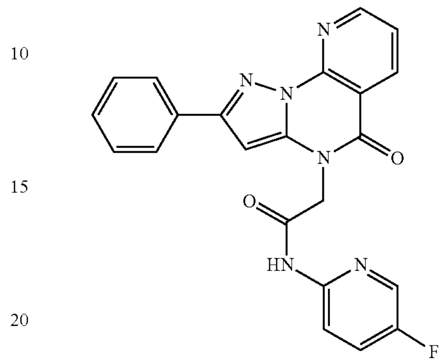

The synthetic method of Example 18 was according to the synthetic method of Example 6. The title compound Example 18 (6 mg, 54%) was obtained.

MS m/z (ESI): 415.4 $[M+H]^+$.

Example 19

N-(5-Fluoropyridin-2-yl)-2-(2-(6-methylpyridin-3-yl)-5-oxopyrazolo[1,5-a]pyrido[3,2-e]pyrimidin-4(5H)-yl)acetamide

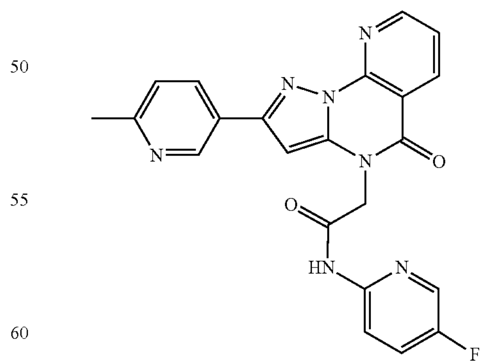

The synthetic method of Example 19 was according to the synthetic method of Example 6. The title compound Example 19 (9 mg, 50%) was obtained.

MS m/z (ESI): 430.4 $[M+H]^+$.

Example 20

N-(5-Fluoropyridin-2-yl)-2-(2-(2-methylpyridin-4-yl)-5-oxopyrazolo[1,5-a]pyrido[3,2-e]pyrimidin-4(5H)-yl)acetamide

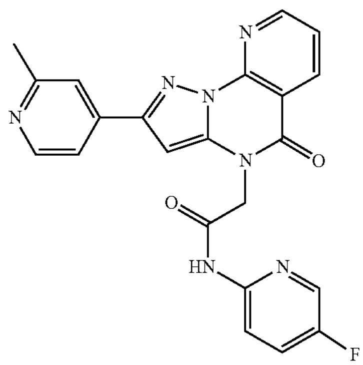 [SMILES: Cc1cc(-c2cc3n(CC(=O)Nc4ccc(F)cn4)c(=O)c4cccnc4n3n2)ccn1]

The synthetic method of Example 20 was according to the synthetic method of Example 6. The title compound Example 20 (13 mg, 50%) was obtained.

MS m/z (ESI): 430.4 [M+H]$^+$.

Example 21

2-(2,5-Dimethylpyridin-4-yl)-5-oxopyrazolo[1,5-a]pyrido[3,2-e]pyrimidin-4(5H)-yl)-N-(5-fluoropyridin-2-yl)acetamide

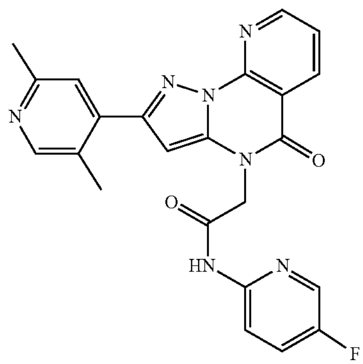 [SMILES: Cc1cc(-c2cc3n(CC(=O)Nc4ccc(F)cn4)c(=O)c4cccnc4n3n2)c(C)cn1]

The synthetic method of Example 21 was according to the synthetic method of Example 6. The title compound Example 21 (18 mg, 56%) was obtained.

MS m/z (ESI): 444.4 [M+H]$^+$.

$^1$H NMR (400 MHz, DMSO-d6) δ 11.21 (s, 1H), 8.90-8.86 (m, 1H), 8.84-8.81 (m, 1H), 8.76-8.74 (m, 1H), 8.38 (s, 1H), 8.30 (s, 1H), 8.06-7.98 (m, 1H), 7.78-7.70 (m, 1H), 7.53-7.47 (m, 1H), 7.35 (s, 1H), 5.44 (s, 2H), 2.78 (s, 3H), 2.74 (s, 3H).

Example 22

2-(2-(Tert-butyl)-8-chloro-5-oxopyrazolo[1,5-a]pyrido[3,2-e]pyrimidin-4(5H)-yl)-N-(5-fluoropyridin-2-yl)acetamide

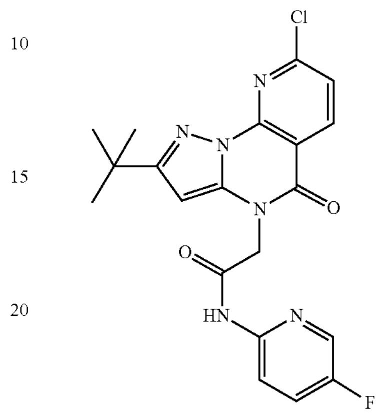

The synthetic method of Example 22 was according to the synthetic method of Example 1. The title compound Example 22 (4 mg, 19%) was obtained.

MS m/z (ESI): 429.8 [M+H]$^+$.

$^1$H NMR (400 MHz, DMSO-d6) δ 11.08 (s, 1H), 8.52 (d, J=8.4 Hz, 1H), 8.38 (d, J=2.8 Hz, 1H), 8.08-8.03 (m, 1H), 7.79-7.74 (m, 1H), 7.62 (d, J=8.4 Hz, 1H), 6.47 (s, 1H), 4.93 (s, 2H), 1.33 (s, 9H).

Example 23

2-(2-(Tert-butyl)-8-methyl-5-oxopyrazolo[1,5-a]pyrido[3,2-e]pyrimidin-4(5H)-yl)-N-(5-fluoropyridin-2-yl)acetamide

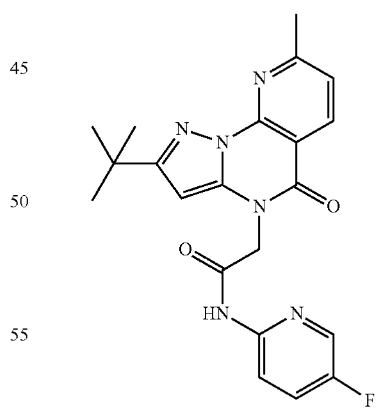

The synthetic method of Example 23 was according to the synthetic method of Example 1. The title compound Example 23 (8 mg, 19%) was obtained.

MS m/z (ESI): 409.4 [M+H]$^+$.

$^1$H NMR (400 MHz, DMSO-d6) δ 11.07 (s, 1H), 8.40 (d, J=8.0 Hz, 1H), 8.37 (d, J=3.2 Hz, 1H), 8.06-8.02 (m, 1H), 7.75 (td, J=8.4, 2.8 Hz, 1H), 7.42 (d, J=8.0 Hz, 1H), 6.38 (s, 1H), 4.93 (s, 2H), 2.68 (s, 3H), 1.33 (s, 9H).

Example 24

2-(2-(Tert-butyl)-7-methyl-5-oxopyrazolo[1,5-a]pyrido[3,2-e]pyrimidin-4(5H)-yl)-N-(5-fluoropyridin-2-yl)acetamide

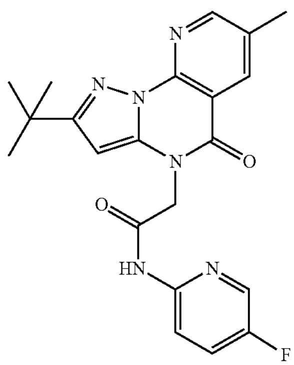 [SMILES: Cc1cnc2c(c1)c(=O)n(CC(=O)Nc1ccc(F)cn1)c1cc(C(C)(C)C)nn21]

The synthetic method of Example 24 was according to the synthetic method of Example 1. The title compound Example 24 (7 mg, 16%) was obtained.

MS m/z (ESI): 409.4 $[M+H]^+$.

$^1$H NMR (400 MHz, DMSO-$d_6$) δ 11.09 (s, 1H), 8.70 (d, J=2.3 Hz, 1H), 8.36 (dd, J=8.7, 2.7 Hz, 2H), 8.04 (s, 1H), 7.76 (dt, J=8.9, 4.5 Hz, 1H), 6.38 (s, 1H), 4.93 (s, 2H), 2.45 (s, 3H), 1.31 (s, 9H).

Example 25

2-(2-(Tert-butyl)-6-methyl-5-oxopyrazolo[1,5-a]pyrido[3,2-e]pyrimidin-4(5H)-yl)-N-(5-fluoropyridin-2-yl)acetamide

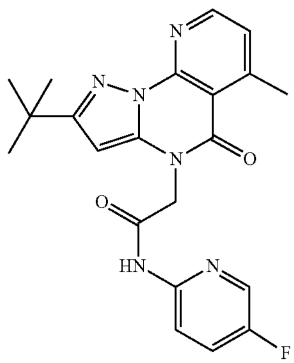 [SMILES: Cc1ccnc2c1c(=O)n(CC(=O)Nc1ccc(F)cn1)c1cc(C(C)(C)C)nn21]

The synthetic method of Example 25 was according to the synthetic method of Example 1. The title compound Example 25 (5 mg, 16%) was obtained.

MS m/z (ESI): 409.4 $[M+H]^+$.

Example 26

2-(2-(Tert-butyl)-5-oxopyrazolo[1,5-a]quinazolin-4(5H)-yl)-N-(5-fluoropyridin-2-yl)acetamide

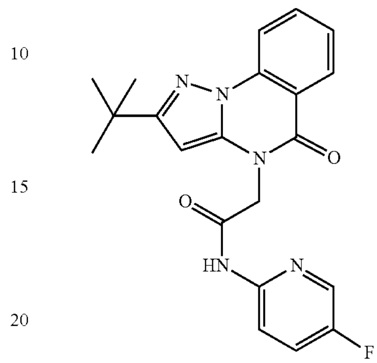

The synthetic method of Example 26 was according to the synthetic method of Example 1. The title compound Example 26 (6 mg, 16%) was obtained.

MS m/z (ESI): 394.4 $[M+H]^+$.

Example 27

2-(2-(Tert-butyl)-5-oxopyrazolo[1,5-a]pyrido[2,3-e]pyrimidin-4(5H)-yl)-N-(5-fluoropyridin-2-yl)acetamide

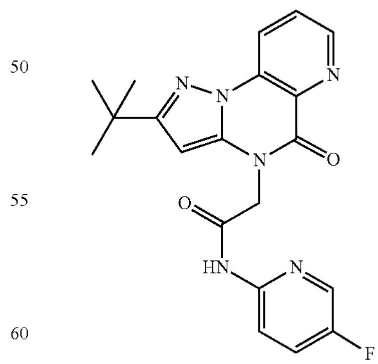

The synthetic method of Example 27 was according to the synthetic method of Example 1. The title compound Example 27 (6 mg, 16%) was obtained.

MS m/z (ESI): 395.4 $[M+H]^+$.

Example 28

2-(2-(Tert-butyl)-7-methyl-5-oxopyrazolo[1,5-a]pyrido[2,3-e]pyrimidin-4(5H)-yl)-N-(5-fluoropyridin-2-yl)acetamide

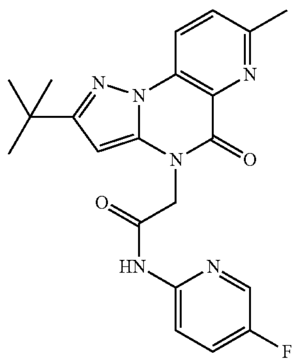

The synthetic method of Example 28 was according to the synthetic method of Example 1. The title compound Example 28 (9 mg, 21%) was obtained.

MS m/z (ESI): 409.4 [M+H]$^+$.

Example 29

2-(2-(Tert-butyl)-7-chloro-5-oxopyrazolo[1,5-a]pyrido[3,2-e]pyrimidin-4(5H)-yl)-N-(5-fluoropyridin-2-yl)acetamide

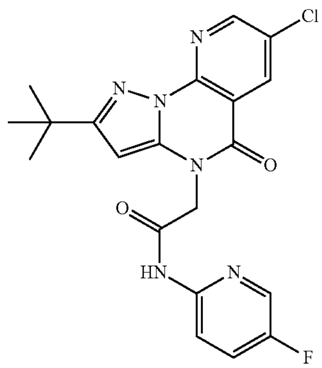

The synthetic method of Example 29 was according to the synthetic method of Example 1. The title compound Example 29 (15 mg, 32%) was obtained.

MS m/z (ESI): 429.1 [M+H]$^+$.

$^1$H NMR (400 MHz, DMSO-d6) δ 11.09 (s, 1H), 8.91 (d, J=2.4, 1H), 8.54 (d, J=2.4 Hz, 1H), 8.38 (d, J=2.8 Hz, 1H), 8.08-8.02 (m, 1H), 7.79-7.74 (m, 1H), 6.47 (s, 1H), 4.94 (s, 2H), 1.32 (s, 9H).

Example 30

2-(2-(Tert-butyl)-5-oxo-8-(trifluoromethyl)pyrazolo[1,5-a]pyrido[3,2-e]pyrimidin-4(5H)-yl)-N-(5-fluoropyridin-2-yl)acetamide

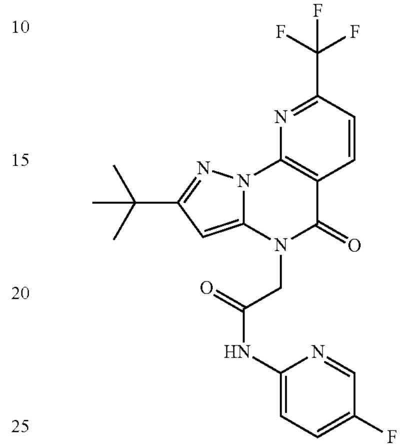

The synthetic method of Example 30 was according to the synthetic method of Example 1. The title compound Example 30 (25 mg, 46%) was obtained by using 2-chloro-6-trifluoromethylnicotinic acid as the starting material.

MS m/z (ESI): 463.1 [M+H]$^+$.

$^1$H NMR (400 MHz, DMSO-$d_6$) δ 11.09 (s, 1H), 7.78 (d, J=8.0 Hz, 1H), 8.38 (d, J=2.8 Hz, 1H), 8.09-8.04 (m, 1H), 8.00 (d, J=8.0 Hz, 1H), 7.79-7.74 (m, 1H), 6.52 (s, 1H), 4.95 (s, 2H), 1.34 (s, 9H).

Example 31

2-(Tert-butyl)-4-(4-chlorobenzyl)pyrazolo[1,5-a]pyrido[3,2-e]pyrimidin-5(4H)-one

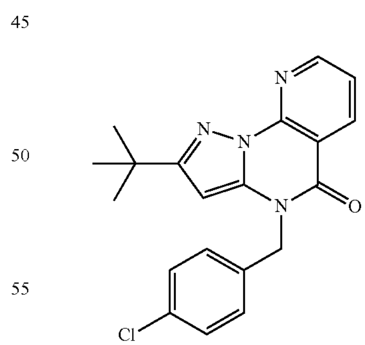

The synthetic method of Example 31 was according to the synthetic method of Example 1. The title compound Example 31 (12 mg, 24%) was obtained.

MS m/z (ESI): 367.1 [M+H]$^+$.

$^1$H NMR (400 MHz, DMSO-$d_6$) δ 8.83 (dd, J=4.8, 1.6 Hz, 1H), 8.56 (dd, J=8.0, 1.6 Hz, 1H), 7.55 (dd, J=8.0, 4.8 Hz, 1H), 7.45 (d, J=8.4 Hz, 1H), 7.39 (d, J=8.4 Hz, 1H), 6.31 (s, 1H), 5.25 (s, 2H), 1.30 (s, 9H).

Example 32

2-(2-(Tert-butyl)-7-isopropyl-5,8-dioxo-5,6,7,8-tetrahydro-4H-pyrazolo[1,5-a]pyrrolo[3,4-e]pyrimidin-4-yl)-N-(5-fluoropyridin-2-yl)acetamide

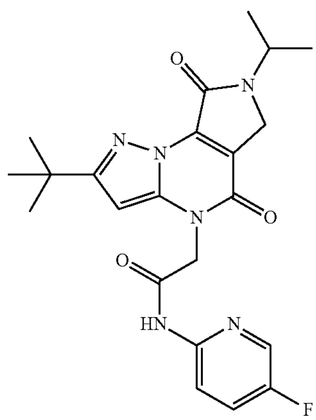

Step 1: Preparation of 4-hydroxy-1-isopropyl-5-oxo-2,5-dihydro-1H-pyrrole-3-carboxylic acid

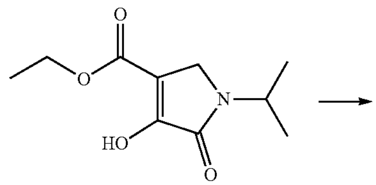

Example 32-1

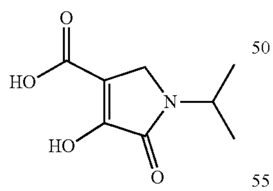

Example 32-2

LiOH (0.23 g, 9.4 mmol) was added to a solution of Example 32-1 (2.0 g, 9.4 mmol) in $CH_3OH$ (30 mL) under an ice bath condition. The ice bath was removed, and the reaction solution was stirred for 1 h. The reaction solution was adjusted to pH 5 to 6 with 1 mol/L aqueous hydrochloric acid solution, and extracted with ethyl acetate (10 mL*3). The organic phase was dried and concentrated to obtain Example 32-2 (1.5 g, 73%).

MS m/z (ESI): 184.7 $[M-H]^+$.

Step 2: Preparation of N-(3-(tert-butyl)-1H-pyrazol-5-yl)-4-hydroxy-1-isopropyl-5-oxo-2,5-dihydro-1H-pyrrole-3-carboxamide

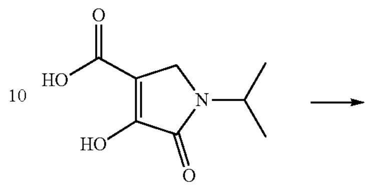

Example 32-2

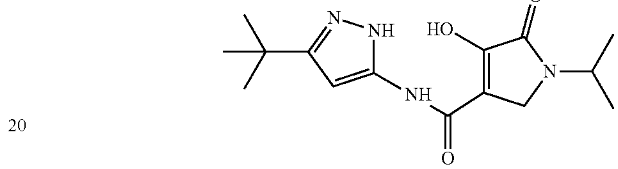

Example 32-3

The synthetic method of Example 32-3 was according to the synthetic method of Example 1-1. The title compound Example 32-3 (0.26 g, 44%) was obtained by using Example 32-2 as the starting material.

MS m/z (ESI): 307.2 $[M+H]^+$.

Step 3: Preparation of 2-(tert-butyl)-7-isopropyl-6,7-dihydro-4H-pyrazolo[1,5-a]pyrrolo[3,4-e]pyrimidine-5,8-dione

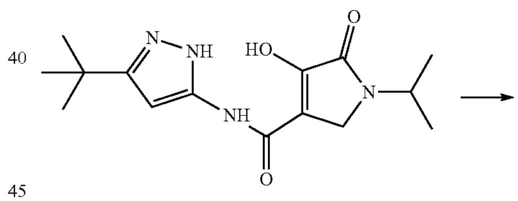

Example 32-3

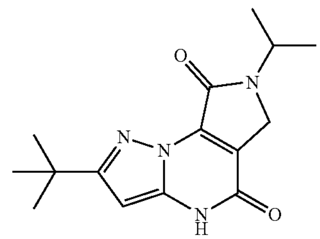

Example 32-4

The synthetic method of Example 32-4 was according to the synthetic method of Example 1-2. The title compound Example 32-4 (0.18 g, 78%) was obtained by using Example 32-3 as the starting material.

MS m/z (ESI): 289.2 $[M+H]^+$.

Step 4: Preparation of 2-(2-(tert-butyl)-7-isopropyl-5,8-dioxo-5,6,7,8-tetrahydro-4H-pyrazolo[1,5-a]pyrrolo[3,4-e]pyrimidin-4-yl)-N-(5-fluoropyridin-2-yl)acetamide

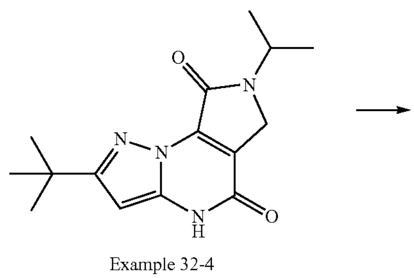

Example 32-4

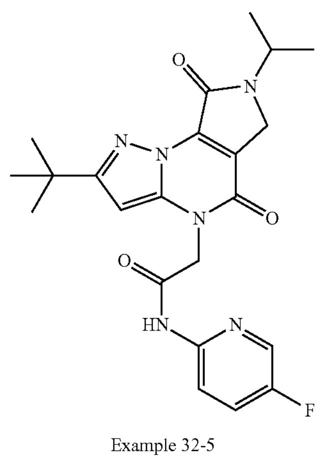

Example 32-5

The synthetic method of Example 32-4 was according to the synthetic method of Example 1. The title compound Example 32-5 (0.12 g, 65%) was obtained by using Example 32-4 as the starting material.

MS m/z (ESI): 441.2 [M+H]+.

Example 33

N-(5-Fluoropyridin-2-yl)-2-(2-methyl-5-oxo-8-(trifluoromethyl)pyrazolo[1,5-a]pyrido[3,2-e]pyrimidin-4(5H)-yl)acetamide

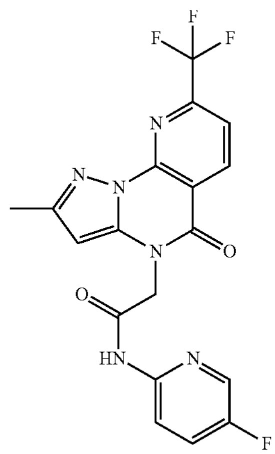

The synthetic method of Example 33 was according to the synthetic method of Example 2. The title compound Example 33 (18 mg, 30%) was obtained.

MS m/z (ESI): 421.1 [M+H]+.

$^1$H NMR (400 MHz, DMSO-d6) δ 11.06 (s, 1H), 8.80 (d, J=8.0 Hz, 1H), 8.37 (s, 1H), 8.07-8.03 (m, 1H), 8.00 (d, J=8.0 Hz, 1H), 7.79-7.73 (m, 1H), 6.28 (s, 1H), 4.95 (s, 2H), 2.33 (s, 3H).

Example 34

2-(2-Ethyl-5-oxo-8-(trifluoromethyl)pyrazolo[1,5-a]pyrido[3,2-e]pyrimidin-4(5H)-yl)-N-(5-fluoropyridin-2-yl)acetamide

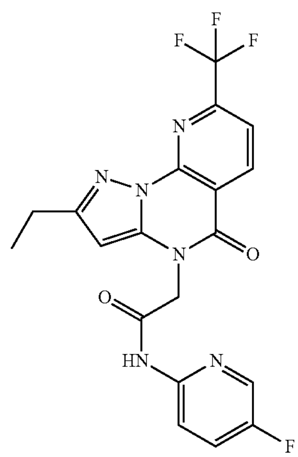

Step 1: Preparation of tert-butyl 5-amino-3-ethyl-1H-pyrazole-1-carboxylate

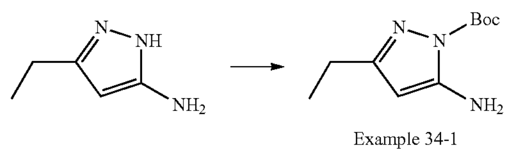

Example 34-1

3-Ethyl-1H-pyrazol-5-amine (2.0 g, 18.0 mmol) was dissolved in anhydrous dichloromethane (50 mL), followed by addition of triethylamine (2.2 g, 21.6 mmol) and di-tert-butyl dicarbonate (4.7 g, 21.6 mmol). The reaction solution was reacted at room temperature for 16 hours. The reaction solution was washed successively with water (50 mL*2) and saturated sodium chloride solution (50 mL), dried over anhydrous sodium sulfate and filtered. The filtrate was concentrated under reduced pressure, and the resulting crude product was purified by column chromatography (ethyl acetate/dichloromethane=0 to 20%) to obtain the title product Example 34-1 (3.4 g), yield: 89.5%.

MS: m/z (ESI): 212.1 [M+H]+.

Step 2: Preparation of tert-butyl 5-amino-3-ethyl-1H-pyrazole-1-carboxylate

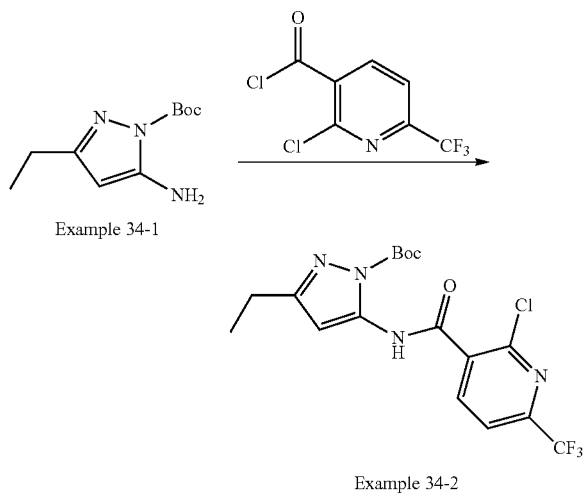

Example 34-1

Example 34-2

Example 34-1 (3.4 g, 16.1 mmol) was dissolved in anhydrous dichloromethane (60 mL), followed by addition of triethylamine (5.4 g, 53.1 mmol). A solution (50 mL) of freshly prepared 2-chloro-6-(trifluoromethyl)nicotinoyl chloride (4.3 g, 17.7 mmol) in dichloromethane was added dropwise under a nitrogen atmosphere at 0° C. After completion of the addition, the reaction solution was reacted at room temperature for 30 minutes. The reaction solution was washed successively with water (200 mL*2) and saturated sodium chloride solution (200 mL), dried over anhydrous sodium sulfate and filtered. The filtrate was concentrated under reduced pressure, and the resulting crude product was purified by silica gel column chromatography (ethyl acetate/petroleum ether=0 to 20%) to obtain Example 34-2 (2.6 g), yield: 38.2%.

MS: m/z (ESI): 319.1 $[M\text{-}Boc+H]^+$.

Step 3: Preparation of N-(3-ethyl-1H-pyrazol-5-yl)-2-chloro-6-(trifluoromethyl)nicotinamide

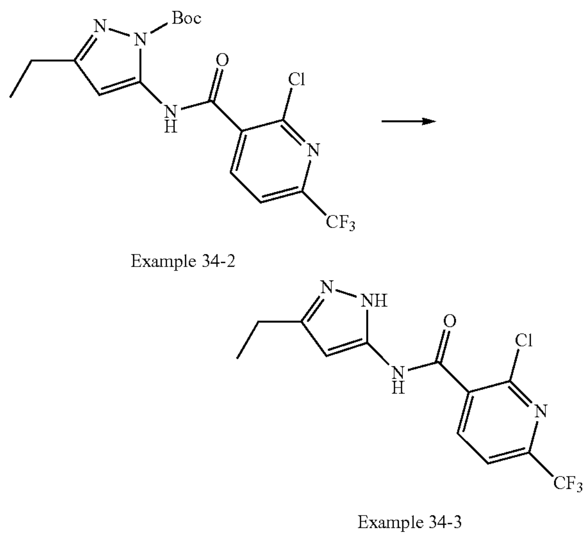

Example 34-2

Example 34-3

Example 34-2 (2.6 g, 6.2 mmol) was dissolved in anhydrous dichloromethane (10 mL), followed by addition of a solution (4 M, 20 mL) of hydrochloric acid in dioxane. The reaction solution was reacted at room temperature for 4 hours. The reaction solution was directly concentrated to dryness by rotary evaporation to obtain Example 34-3 (1.9 g), yield: 96.0%.

MS: m/z (ESI): 319.0 $[M+H]^+$.

Step 4: 2-Ethyl-8-(trifluoromethyl)pyrazolo[1,5-a]pyrido[3,2-e]pyrimidin-5(4H)-one

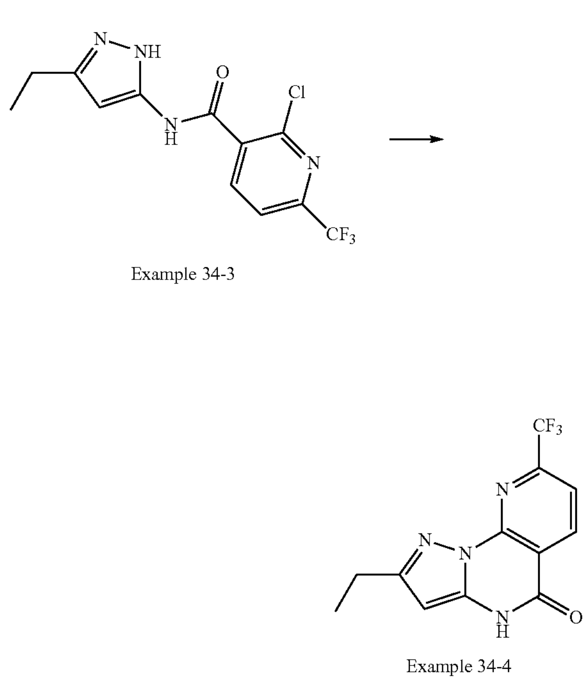

Example 34-3

Example 34-4

Example 34-3 (1.9 g, 6.0 mmol) was dissolved in N,N-dimethylformamide (20 mL), followed by addition of potassium carbonate (2.5 g, 18.0 mmol). The reaction solution was heated to 120° C. and reacted for 2 hours. The reaction solution was cooled to room temperature and used directly in the next step.

MS: m/z (ESI): 283.1$[M+H]^+$.

Step 5: 2-(2-Ethyl-5-oxo-8-(trifluoromethyl)pyrazolo[1,5-a]pyrido[3,2-e]pyrimidin-4(5H)-yl)-N-(5-fluoropyridin-2-yl)acetamide

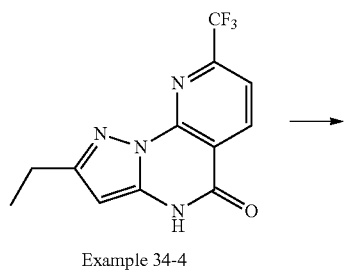

Example 34-4

-continued

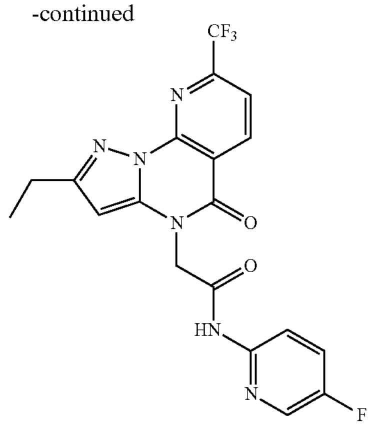

Example 34

Potassium carbonate (1.5 g, 10.6 mmol) and 2-bromo-N-(5-fluoropyridin-2-yl)acetamide (0.99 g, 4.2 mmol) were added to the reaction solution of Example 34-4 (1.0 g, 3.5 mmol) in N,N-dimethylformamide (20 mL), and reacted at 40° C. for 2 hours. The reaction solution was cooled to room temperature, poured into 300 mL of water, and extracted with ethyl acetate (200 mL*3). The organic phases were combined, washed successively with water (200 mL*2) and saturated sodium chloride solution (200 mL), dried over anhydrous sodium sulfate and filtered. The filtrate was concentrated under reduced pressure, and the resulting crude product was recrystallized from ethyl acetate to obtain Example 34.

$^1$H NMR (400 MHz, DMSO-$d_6$) δ 11.06 (s, 1H), 8.79 (d, J=7.6 Hz, 1H), 8.37 (s, 1H), 8.07-8.03 (m, 1H), 8.00 (d, J=8.0 Hz, 1H), 7.79-7.72 (m, 1H), 6.36 (s, 1H), 4.96 (s, 2H), 2.70 (q, J=7.6 Hz, 2H), 1.25 (t, J=7.6 Hz, 3H).

MS m/z (ESI): 435.1 [M+H]$^+$.

Example 35

2-(2-Cyclopropyl-5-oxo-8-(trifluoromethyl)pyrazolo[1,5-a]pyrido[3,2-e]pyrimidin-4(5H)-yl)-N-(5-fluoropyridin-2-yl)acetamide

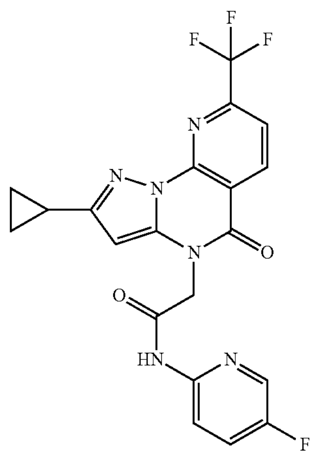

The synthetic method of Example 35 was according to the synthetic method of Example 1. The title compound Example 35 (17 mg, 28%) was obtained.

$^1$H NMR (400 MHz, DMSO-d6) δ 11.05 (s, 1H), 8.78 (d, J=8.0 Hz, 1H), 8.37 (s, 1H), 8.08-8.02 (m, 1H), 7.98 (d, J=8.4 Hz, 1H), 7.79-7.73 (m, 1H), 6.23 (s, 1H), 4.91 (s, 2H), 2.11-2.04 (m, 1H), 1.04-0.98 (m, 2H), 0.82-0.78 (m, 2H).

MS m/z (ESI): 447.1 [M+H]$^+$.

Example 36

N-(5-Fluoropyridin-2-yl)-2-(2-isopropyl-5-oxo-8-(trifluoromethyl)pyrazolo[1,5-a]pyrido[3,2-e]pyrimidin-4(5H)-yl)acetamide

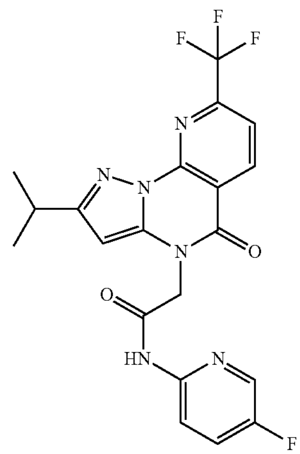

The synthetic method of Example 36 was according to the synthetic method of Example 4. The title compound Example 36 (10 mg, 22%) was obtained.

MS m/z (ESI): 449.1 [M+H]$^+$.

$^1$H NMR (400 MHz, DMSO-d6) δ 11.06 (s, 1H), 8.79 (d, J=8.0 Hz, 1H), 8.37 (s, 1H), 8.09-8.03 (m, 1H), 8.00 (d, J=8.0 Hz, 1H), 7.79-7.74 (m, 1H), 6.42 (s, 1H), 4.96 (s, 2H), 3.08-3.01 (m, 1H), 1.29 (s, 3H), 1.27 (s, 3H).

Example 37

2-(2-Cyclopentyl-5-oxo-8-(trifluoromethyl)pyrazolo[1,5-a]pyrido[3,2-e]pyrimidin-4(5H)-yl)-N-(5-fluoropyridin-2-yl)acetamide

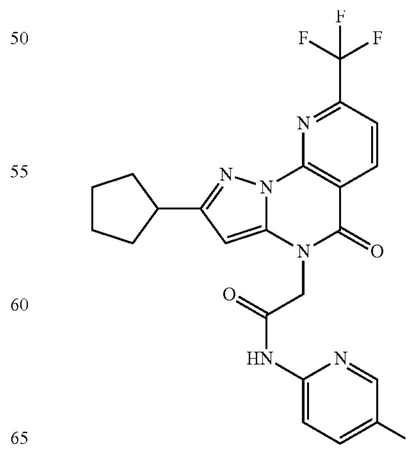

The synthetic method of Example 37 was according to the synthetic method of Example 1. The title compound Example 37 (18 mg, 30%) was obtained.

MS m/z (ESI): 475.1 $[M+H]^+$.

$^1$H NMR (400 MHz, DMSO) δ 11.07 (s, 1H), 8.79 (d, J=8.0 Hz, 1H), 8.38 (s, 1H), 8.14-7.89 (m, 2H), 7.77 (s, 1H), 6.42 (s, 1H), 4.96 (s, 2H), 3.17 (s, 1H), 2.14-1.93 (m, 3H), 1.67 (m, 5H).

Example 38

2-(2-(4,4-Difluorocyclohexyl)-5-oxo-8-(trifluoromethyl)pyrazolo[1,5-a]pyrido[3,2-e]pyrimidin-4(5H)-yl)-N-(5-fluoropyridin-2-yl)acetamide

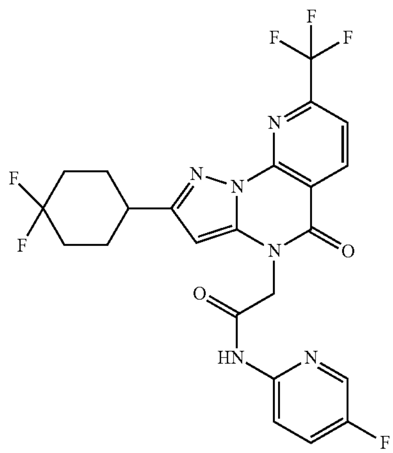

The synthetic method of Example 38 was according to the synthetic method of Example 1. The title compound Example 38 (8 mg, 20%) was obtained.

MS m/z (ESI): 525.1 $[M+H]^+$.

$^1$H NMR (400 MHz, DMSO-$d_6$) δ 11.05 (s, 1H), 8.79 (d, J=8.2 Hz, 1H), 8.37 (d, J=3.0 Hz, 1H), 8.01 (d, J=8.0 Hz, 2H), 7.76 (t, J=9.0 Hz, 1H), 6.49 (s, 1H), 4.95 (s, 2H), 2.95 (s, 1H), 2.05 (q, J=19.1, 17.8 Hz, 6H), 1.74 (d, J=13.1 Hz, 2H).

Example 39

N-(5-Fluoropyridin-2-yl)-2-(2-(6-methylpyridin-3-yl)-5-oxo-8-(trifluoromethyl)pyrazolo[1,5-a]pyrido[3,2-e]pyrimidin-4(5H)-yl)acetamide

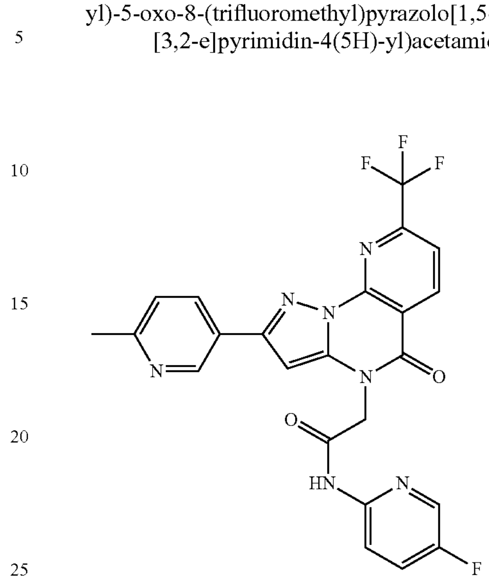

The synthetic method of Example 39 was according to the synthetic method of Example 1. The title compound Example 39 (15 mg, 28%) was obtained.

MS m/z (ESI): 498.1 $[M+H]^+$.

$^1$H NMR (400 MHz, DMSO-$d_6$) δ 11.11 (s, 1H), 9.01 (s, 1H), 8.85 (d, J=8.0 Hz, 1H), 8.37 (d, J=2.8 Hz, 1H), 8.25 (dd, J=8.0, 2.4 Hz, 1H), 8.13-8.03 (m, 2H), 7.79-7.74 (m, 1H), 7.41 (d, J=8.0 Hz, 1H), 7.15 (s, 1H), 5.02 (s, 2H), 2.54 (s, 3H).

Example 40

2-(2,5-Dimethylpyridin-4-yl)-5-oxo-8-(trifluoromethyl)pyrazolo[1,5-a]pyrido[3,2-e]pyrimidin-4(5H)-yl)-N-(5-fluoropyridin-2-yl)acetamide

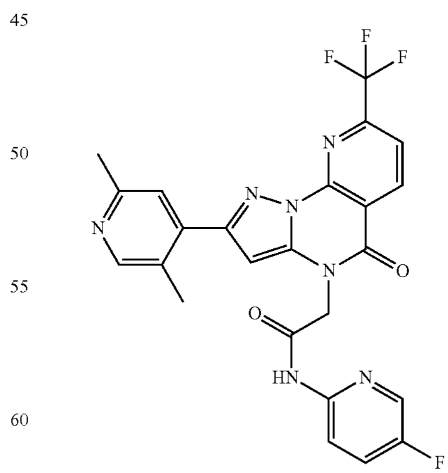

The synthetic method of Example 40 was according to the synthetic method of Example 1. The title compound Example 40 (22 mg, 45%) was obtained.

MS m/z (ESI): 512.1 $[M+H]^+$.

$^1$H NMR (400 MHz, DMSO-$d_6$) δ 11.09 (s, 1H), 8.86 (d, J=8.4 Hz, 1H), 8.46-8.43 (m, 2H), 8.39-8.36 (m, 1H), 8.12-8.03 (m, 2H), 7.79-7.74 (m, 1H), 7.57 (s, 1H), 7.02 (s, 1H), 5.05 (s, 2H), 2.53 (s, 3H), 2.51 (s, 3H).

Example 41

2-(2-Amino-5-oxo-8-(trifluoromethyl)pyrazolo[1,5-a]pyrido[3,2-e]pyrimidin-4(5H)-yl)-N-(5-fluoropyridin-2-yl)acetamide

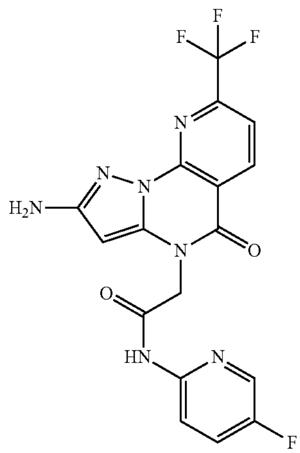

The synthetic method of Example 41 was according to the synthetic method of Example 1. The title compound Example 41 (12 mg, 26%) was obtained.

MS m/z (ESI): 422.1 [M+H]$^+$.

Example 42

2-(2-(Cyclopentylamino)-5-oxo-8-(trifluoromethyl)pyrazolo[1,5-a]pyrido[3,2-e]pyrimidin-4(5H)-yl)-N-(5-fluoropyridin-2-yl)acetamide

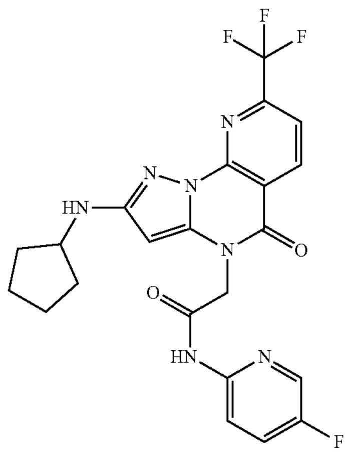

The synthetic method of Example 42 was according to the synthetic method of Example 8. The title compound Example 42 (9 mg, 19%) was obtained.

MS m/z (ESI): 489.2 [M+H]$^+$.

Example 43

N-(5-Fluoropyridin-2-yl)-2-(2-(oxetan-3-ylamino)-5-oxo-8-(trifluoromethyl)pyrazolo[1,5-a]pyrido[3,2-e]pyrimidin-4(5H)-yl)acetamide

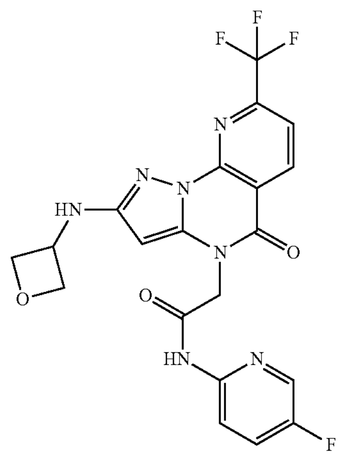

The synthetic method of Example 43 was according to the synthetic method of Example 14. The title compound Example 43 (15 mg, 25%) was obtained.

MS m/z (ESI): 478.1 [M+H]$^+$.

Example 44

2-(8-Amino-2-(tert-butyl)-5-oxopyrazolo[1,5-a]pyrido[3,2-e]pyrimidin-4(5H)-yl)-N-(5-fluoropyridin-2-yl)acetamide

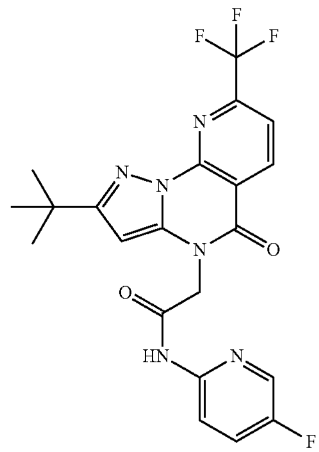

Step 1: Preparation of 2-(8-amino-2-(tert-butyl)-5-oxopyrazolo[1,5-a]pyrido[3,2-e]pyrimidin-4(5H)-yl)-N-(5-fluoropyridin-2-yl)acetamide

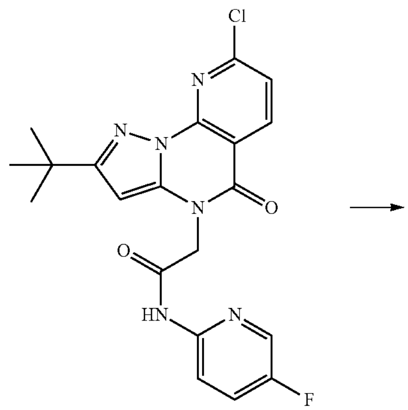

Example 22

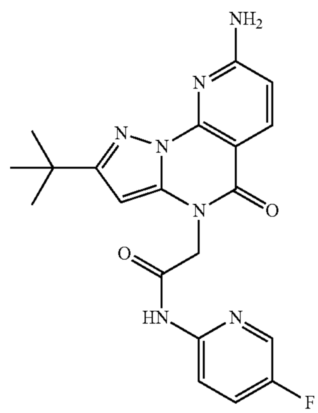

Example 44

Example 22 (100 mg, 0.234 mmol) and aqueous ammonia (5 mL) were added to a round-bottomed flask at room temperature, and the mixture was stirred at 80° C. for 5 h. After completion of the reaction, the reaction solution was purified by HPLC to obtain Example 44 (52 mg, 54%).

MS m/z (ESI): 410.2 $[M+H]^+$.

$^1$H NMR (400 MHz, DMSO-$d_6$) δ 10.96 (s, 1H), 8.41 (s, 1H), 8.02-7.95 (m, 1H), 7.93 (d, J=8.8 Hz, 1H), 7.68 (s, 1H), 7.45 (s, 2H), 6.43 (d, J=8.7 Hz, 1H), 6.15 (s, 1H), 4.79 (s, 2H), 1.23 (s, 9H).

Example 45

2-(2-(Tert-butyl)-8-cyano-5-oxopyrazolo[1,5-a]pyrido[3,2-e]pyrimidin-4(5H)-yl)-N-(5-fluoropyridin-2-yl)acetamide

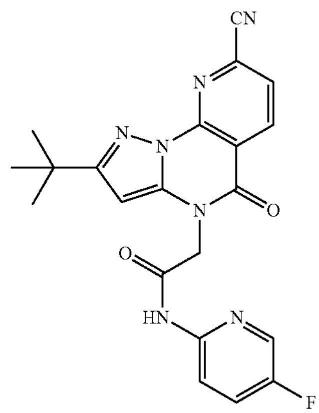

Step 1: Preparation of 2-(2-(tert-butyl)-8-cyano-5-oxopyrazolo[1,5-a]pyrido[3,2-e]pyrimidin-4(5H)-yl)-N-(5-fluoropyridin-2-yl)acetamide

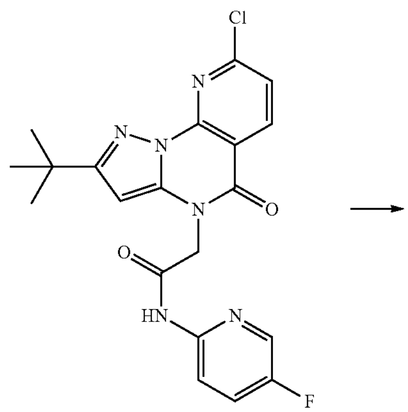

Example 22

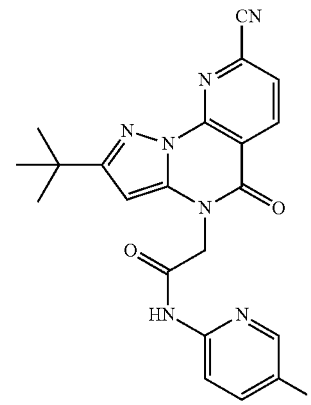

Example 45

Example 22 (80 mg, 0.187 mmol), CuCN (45 mg, 0.5 mmol) and DMF (2 mL) were added to a round-bottomed flask at room temperature, and the mixture was stirred at 150° C. for 5 h under a nitrogen atmosphere. After completion of the reaction, the reaction solution was purified by HPLC to obtain Example 45 (26 mg, 33%).

MS m/z (ESI): 420.1 $[M+H]^+$.

$^1$H NMR (400 MHz, DMSO) δ 11.06 (s, 1H), 8.72 (d, J=8.0 Hz, 1H), 8.37 (s, 1H), 8.17-7.98 (m, 2H), 7.77 (d, J=8.3 Hz, 1H), 6.51 (s, 1H), 4.94 (s, 2H), 1.28 (s, 9H).

Example 46

2-(2-(Tert-butyl)-8-methoxy-5-oxopyrazolo[1,5-a]pyrido[3,2-e]pyrimidin-4(5H)-yl)-N-(5-fluoropyridin-2-yl)acetamide

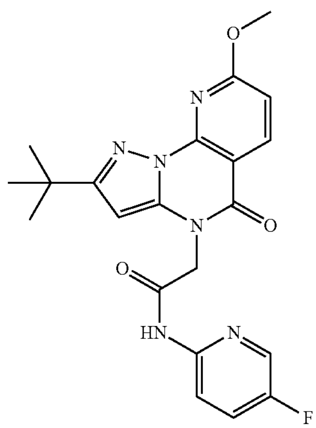

Step 1: Preparation of 2-(2-(tert-butyl)-8-methoxy-5-oxopyrazolo[1,5-a]pyrido[3,2-e]pyrimidin-4(5H)-yl)-N-(5-fluoropyridin-2-yl)acetamide

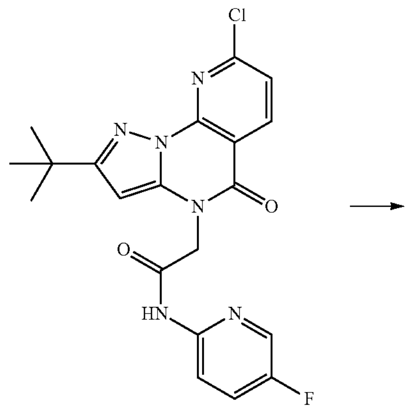

Example 22

-continued

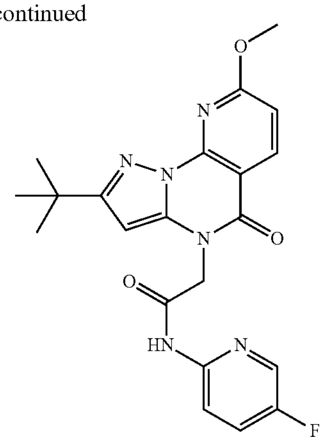

Example 46

Example 22 (80 mg, 0.187 mmol), MeONa (43 mg, 0.8 mmol) and DMF (2 mL) were added to a round-bottomed flask at room temperature, and the mixture was stirred at 80° C. for 3 h under a nitrogen atmosphere. After completion of the reaction, the reaction solution was purified by HPLC to obtain Example 46 (35 mg, 45%).

MS m/z (ESI): 425.0 $[M+H]^+$.

$^1$H NMR (400 MHz, DMSO-d6) δ 11.20 (s, 1H), 8.45 (d, J=8.8 Hz, 1H), 8.37 (d, J=3.2 Hz, 1H), 8.06-8.00 (m, 1H), 7.76-7.71 (m, 1H), 6.75 (d, J=8.8 Hz, 1H), 6.55 (s, 1H), 5.24 (s, 2H), 3.88 (s, 3H), 1.33 (s, 9H).

Example 47

2-(2-(Tert-butyl)-5-oxo-7-(trifluoromethyl)pyrazolo[1,5-a]pyrido[3,2-e]pyrimidin-4(5H)-yl)-N-(5-fluoropyridin-2-yl)acetamide

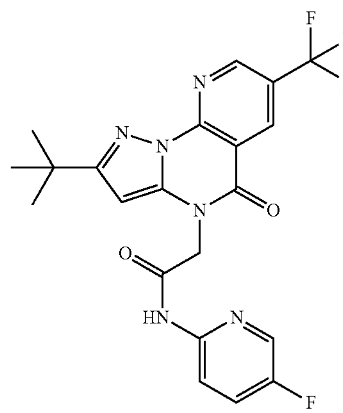

Example 47 was synthesized according to the method of Example 1. Example 47 (36 mg, 52%) was obtained by replacing 2-chloronicotinic acid with 2-chloro-5-(trifluoromethyl)nicotinic acid.

MS m/z (ESI): 463.1 $[M+H]^+$.

$^1$H NMR (400 MHz, $DMSO-d_6$) δ 11.05 (s, 1H), 9.24 (s, 1H), 8.73 (s, 1H), 8.36 (d, J=3.1 Hz, 1H), 8.04 (s, 1H), 7.75 (td, J=8.8, 3.2 Hz, 1H), 6.51 (d, J=2.7 Hz, 1H), 4.96 (s, 2H), 1.33 (s, 9H).

Example 48

Acetamide 2-(2-(Tert-butyl)-6-chloro-5-oxopyrazolo[1,5-a]pyrido[3,2-e]pyrimidin-4 (5H)-yl)-N-(5-fluoropyridin-2-yl)acetamide

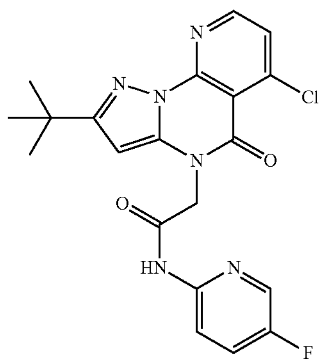

Example 48 was synthesized according to the method of Example 1. Example 48 (52 mg, 46%) was obtained by replacing 2-chloronicotinic acid with 2,4-dichloronicotinic acid.

MS m/z (ESI): 429.2 [M+H]$^+$.

Example 49

2-(2-(Tert-butyl)-6-isopropyl-5-oxopyrazolo[1,5-a]pyrido[3,2-e]pyrimidin-4(5H)-yl)-N-(5-fluoropyridin-2-yl)acetamide

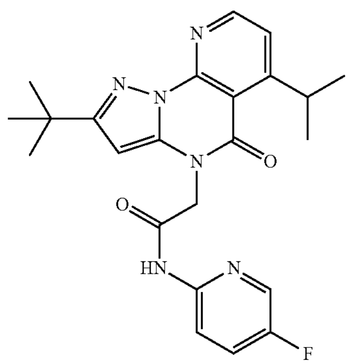

Step 1: Preparation of 2-(2-(tert-butyl)-6-isopropyl-5-oxopyrazolo[1,5-a]pyrido[3,2-e]pyrimidin-4(5H)-yl)-N-(5-fluoropyridin-2-yl)acetamide

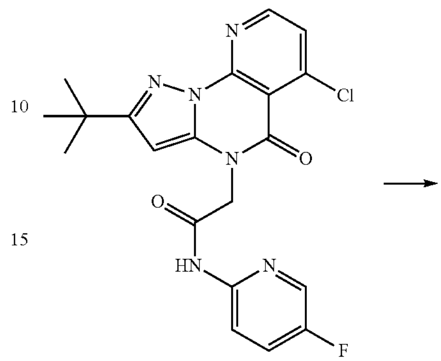

Example 48

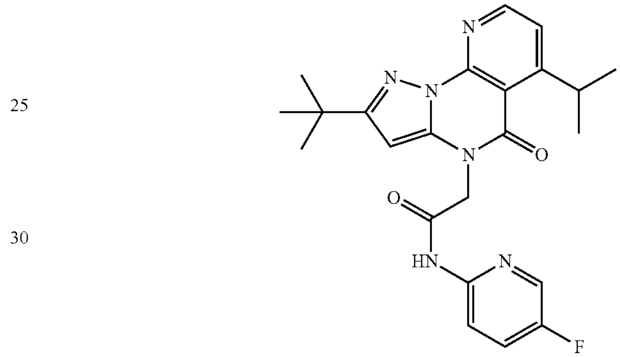

Example 49

Isopropylmagnesium bromide (1 M, 1 mL) was added dropwise to a solution of Example 48 (100 mg, 0.233 mmol) in THE (5 mL) at −70° C. under a nitrogen atmosphere, and the mixture was stirred at room temperature for 3 h. After completion of the reaction, the reaction solution was purified by HPLC to obtain Example 49 (62 mg, 60%).

MS m/z (ESI): 437.0 [M+H]$^+$.

Example 50

2-(2-(Tert-butyl)-6-cyclopropyl-5-oxopyrazolo[1,5-a]pyrido[3,2-e]pyrimidin-4(5H)-yl)-N-(5-fluoropyridin-2-yl)acetamide

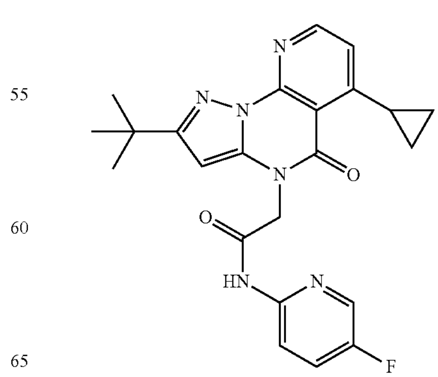

Example 50 was synthesized according to the method of Example 49. Example 50 (36 mg, 58%) was obtained by replacing isopropylmagnesium bromide with cyclopropylmagnesium bromide.

MS m/z (ESI): 435.2 $[M+H]^+$.

Example 51

2-(2-(Tert-butyl)-5-oxo-6-(trifluoromethyl)pyrazolo[1,5-a]pyrido[3,2-e]pyrimidin-4(5H)-yl)-N-(5-fluoropyridin-2-yl)acetamide

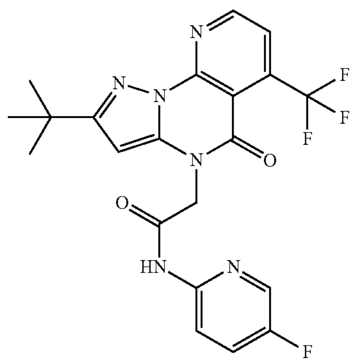

Example 51 was synthesized according to the method of Example 1. Example 51 (36 mg, 52%) was obtained by replacing 2-chloronicotinic acid with 2-chloro-4-(trifluoromethylnicotinic acid.

MS m/z (ESI): 463.1 $[M+H]^+$.

Example 52

2-(6-Amino-2-(tert-butyl)-5-oxopyrazolo[1,5-a]pyrido[3,2-e]pyrimidin-4(5H)-yl)-N-(5-fluoropyridin-2-yl)acetamide

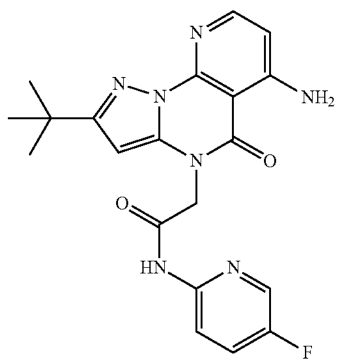

Example 52 was synthesized according to the method of Example 44. Example 52 (36 mg, 52%) was obtained by replacing Example 22 with Example 48.

MS m/z (ESI): 410.2 $[M+H]^+$.

Example 53

2-(7-(Tert-butyl)-4-oxopyrazolo[1,5-a]thiazolo[5,4-e]pyrimidin-5(4H)-yl)-N-(5-fluoropyrid in-2-yl)acetamide

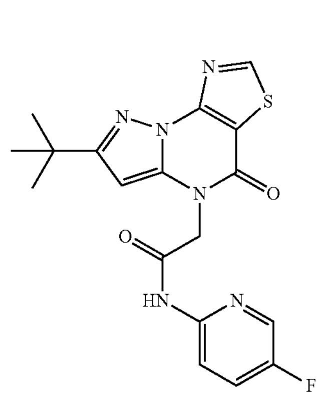

The synthetic method of Example 53 was according to the synthetic method of Example 1. The title compound (19 mg, 21%) was obtained.

MS m/z (ESI): 401.4 $[M+H]^+$.

Example 54

2-(7-(Tert-butyl)-3-isopropyl-4-oxo-3,4-dihydro-5H-pyrazolo[5,1-b]purin-5-yl)-N-(5-fluoro pyridin-2-yl)acetamide

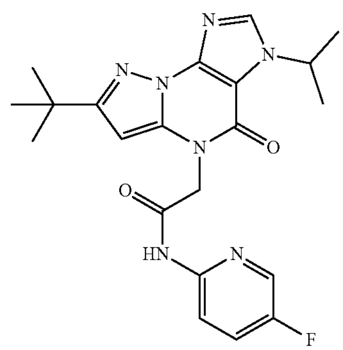

The synthetic method of Example 54 was according to the synthetic method of Example 1. The title compound (11 mg, 28%) was obtained.

MS m/z (ESI): 426.5 $[M+H]^+$.

Example 55

2-(2-(Tert-butyl)-6-ethyl-5-oxo-5,6-dihydro-4H-dipyrazolo[1,5-a:3',4'-e]pyrimidin-4-yl)-N-(5-fluoro-pyridin-2-yl)acetamide

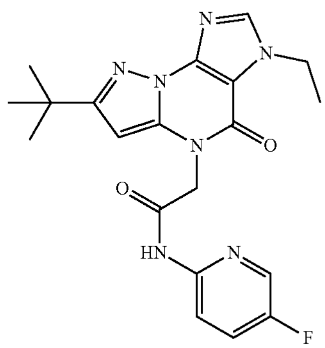

The synthetic method of Example 55 was according to the synthetic method of Example 1. The title compound (26 mg, 28%) was obtained.

MS m/z (ESI): 412.4 $[M+H]^+$.

Example 56

2-(7-(Tert-butyl)-3-methyl-4-oxoisoxazolo[4,3-e]pyrazolo[1,5-a]pyrimidin-5(4H)-yl)-N-(5-fluoropyridin-2-yl)acetamide

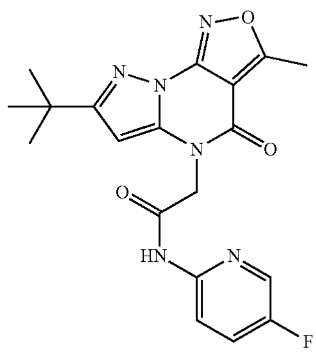

The synthetic method of Example 56 was according to the synthetic method of Example 1. The title compound (23 mg, 25%) was obtained.

MS m/z (ESI): 399.4 $[M+H]^+$.

Example 57

2-(7-(Tert-butyl)-3-methyl-4-oxoisothiazolo[4,3-e]pyrazolo[1,5-a]pyrimidin-5(4H)-yl)-N-(5-fluoropyridin-2-yl)acetamide

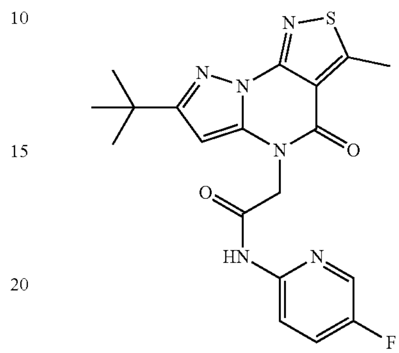

The synthetic method of Example 57 was according to the synthetic method of Example 1. The title compound (19 mg, 29%) was obtained.

MS m/z (ESI): 415.5$[M+H]^+$.

Example 58

2-(2-(Tert-butyl)-5-thioxopyrazolo[1,5-a]pyrido[3,2-e]pyrimidin-4(5H)-yl)-N-(5-fluoropyridin-2-yl)acetamide

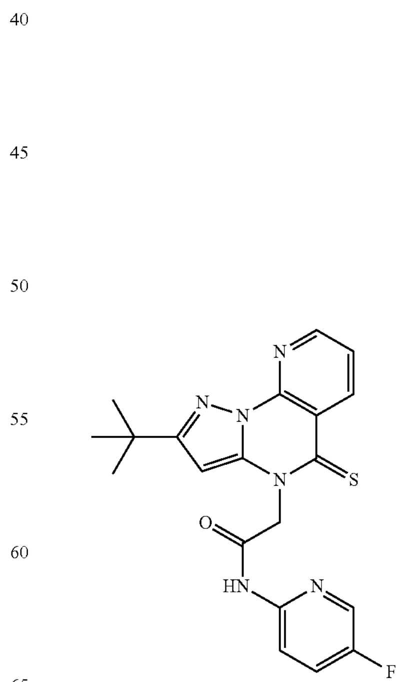

Step 1: Preparation of 2-(2-(tert-butyl)-5-thioxopyrazolo[1,5-a]pyrido[3,2-e]pyrimidin-4(5H)-yl)-N-(5-fluoropyridin-2-yl)acetamide

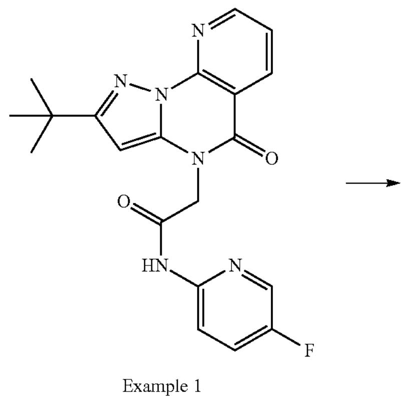

Example 1

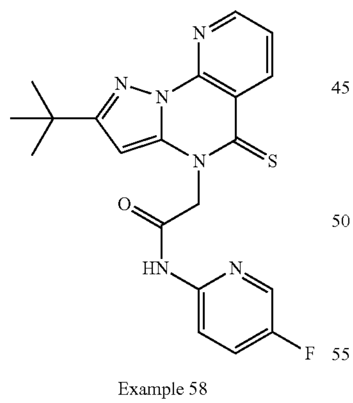

Example 58

Lawson's reagent (158 mg, 0.39 mmol) was added to a solution of Example 1 (50 mg, 0.13 mmol) in toluene (2 mL) at room temperature, and the reaction solution was heated by microwave at 115 degrees for 1 hour. LCMS indicated the completion of the reaction, and the reaction solution was purified by p-HPLC(HCOOH) to obtain Example 58 (5 mg, 10%).

MS m/z (ESI): 411.13 $[M+H]^+$.

Example 59

N-(5-Fluoropyridin-2-yl)-2-(2-(1-methylcyclopropyl)-5-oxo-8-(trifluoromethyl)pyrazolo[1,5-a]pyrido[3,2-e]pyrimidin-4(5H)-yl)acetamide

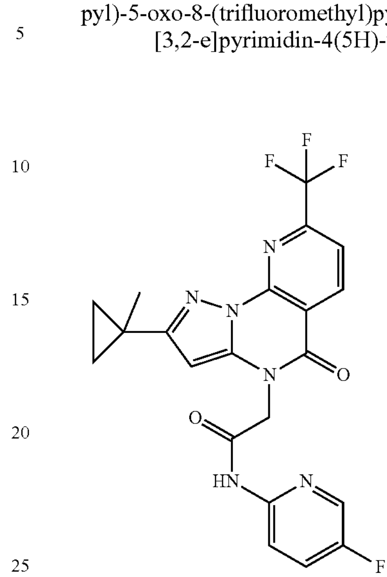

The synthetic method of Example 59 was according to the synthetic method of Example 1. The title compound Example 59 (21 mg, 40%) was obtained.

MS m/z (ESI): 461.4 $[M+H]^+$.

$^1$H NMR (400 MHz, DMSO) δ 11.04 (s, 1H), 8.78 (d, J=7.6 Hz, 1H), 8.37 (s, 1H), 8.17-7.90 (m, 2H), 7.76 (t, J=8.1 Hz, 1H), 6.35 (s, 1H), 4.93 (s, 2H), 1.47 (s, 3H), 1.03 (s, 2H), 0.85 (s, 2H).

Example 60

N-(5-Fluoropyridin-2-yl)-2-(5-oxo-8-(trifluoromethyl)-2-(1-(trifluoromethyl)cyclopropyl)pyrazolo[1,5-a]pyrido[3,2-e]pyrimidin-4(5H)-yl)acetamide

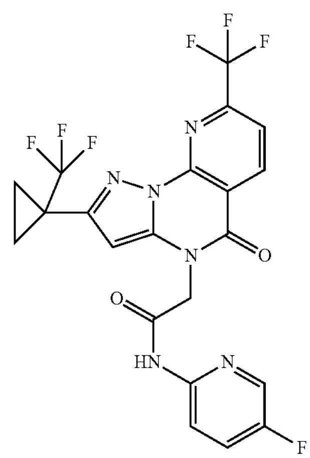

The synthetic method of Example 60 was according to the synthetic method of Example 1. The title compound Example 60 (15 mg, 31%) was obtained.

MS m/z (ESI): 515.4 $[M+H]^+$.

Example 61

2-(2-(2,2-Difluoroethyl)azetidin-3-yl)-5-oxo-8-(trifluoromethyl)pyrazolo[1,5-a]pyrido[3,2-e]pyrimidin-4(5H)-yl)-N-(5-fluoropyridin-2-yl)acetamide

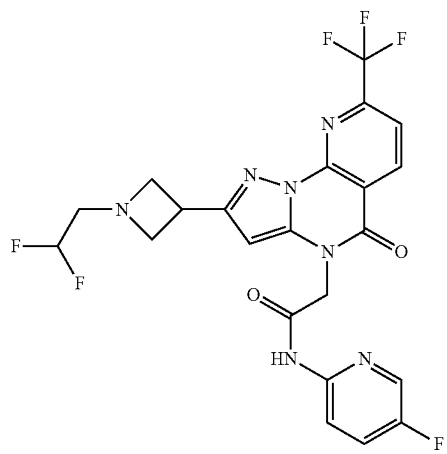

Step 1: Preparation of tert-butyl 5-amino-3-bromo-1H-pyrazole-1-carboxylate

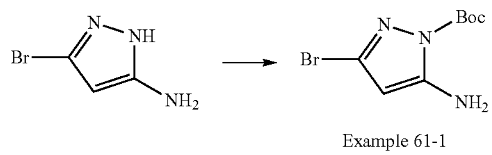

Example 61-1

3-Bromo-1H-pyrazol-5-amine (10.0 g, 61.7 mmol) was dissolved in anhydrous dichloromethane (100 mL), followed by addition of triethylamine (7.48 g, 74.1 mmol) and di-tert-butyl dicarbonate (16.0 g, 74.1 mmol). The reaction solution was reacted at room temperature for 16 hours. The reaction solution was washed successively with water (50 mL*2) and saturated sodium chloride solution (50 mL), dried over anhydrous sodium sulfate and filtered. The filtrate was concentrated under reduced pressure, and the resulting crude product was purified by column chromatography (ethyl acetate/dichloromethane=0 to 20%) to obtain the title product tert-butyl 5-amino-3-bromo-1H-pyrazole-1-carboxylate Example 61-1 (14.5 g), yield: 89.5%.

MS: m/z (ESI): 262.0 $[M+H]^+$ $^1$H NMR (400 MHz, DMSO-$d_6$) δ 6.62 (s, 2H), 5.41 (s, 1H), 1.56 (s, 9H).

Step 2: Preparation of tert-butyl 5-amino-3-bromo-1H-pyrazole-1-carboxylate

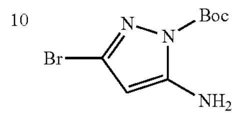

Example 61-1

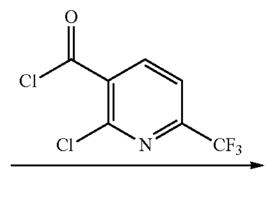

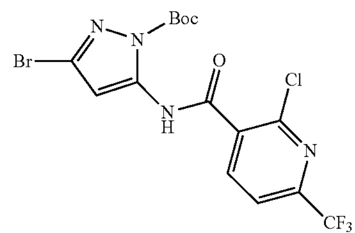

Example 61-2

Tert-butyl 5-amino-3-bromo-1H-pyrazole-1-carboxylate Example 61-1 (14.5 g, 55.3 mmol) was dissolved in anhydrous dichloromethane (200 mL), followed by addition of triethylamine (18.5 g, 183 mmol). A solution (50 mL) of freshly prepared 2-chloro-6-(trifluoromethyl)nicotinoyl chloride (13.0 g, 61.0 mmol) in dichloromethane was added dropwise under a nitrogen atmosphere at 0° C. After completion of the addition, the reaction solution was reacted at room temperature for 30 minutes. The reaction solution was washed successively with water (200 mL*2) and saturated sodium chloride solution (200 mL), dried over anhydrous sodium sulfate and filtered. The filtrate was concentrated under reduced pressure, and the resulting crude product was purified by silica gel column chromatography (ethyl acetate/petroleum ether=0 to 20%) to obtain tert-butyl 5-amino-3-bromo-1H-pyrazole-1-carboxylate Example 61-2 (9.5 g), yield: 38.2%.

MS: m/z (ESI): 371.0 $[M-Boc+H]^+$ $^1$H NMR (400 MHz, DMSO-$d_6$) δ 11.08 (s, 1H), 8.40 (d, J=7.6 Hz, 1H), 8.14 (d, J=7.6 Hz, 1H), 6.96 (s, 1H), 1.58 (s, 9H).

Step 3: Preparation of N-(3-bromo-1H-pyrazol-5-yl)-2-chloro-6-(trifluoromethyl)nicotinamide

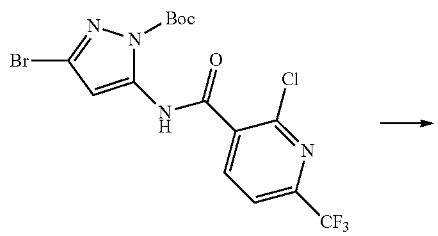

Example 61-2

-continued

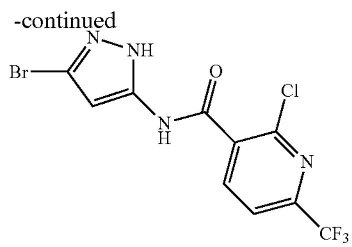

Example 61-3

Tert-butyl 5-amino-3-bromo-1H-pyrazole-1-carboxylate Example 61-2 (8.0 g, 17.1 mmol) was dissolved in anhydrous dichloromethane (20 mL), followed by addition of a solution (4 M, 40 mL) of hydrochloric acid in dioxane. The reaction solution was reacted at room temperature for 4 hours. The reaction solution was directly concentrated to dryness by rotary evaporation to obtain N-(3-bromo-1H-pyrazol-5-yl)-2-chloro-6-(trifluoromethyl)nicotinamide Example 61-3 (6.2 g), yield: 98.4%.

MS: m/z (ESI): 368.9 $[M+H]^+$ $^1$H NMR (400 MHz, DMSO-$d_6$) δ 11.50 (s, 1H), 8.39 (d, J=7.6 Hz, 1H), 8.10 (d, J=7.6 Hz, 1H), 6.53 (s, 1H).

Step 4: Preparation of 2-bromo-8-(trifluoromethyl)pyrazolo[1,5-a]pyrido[3,2-e]pyrimidin-5(4H)-one

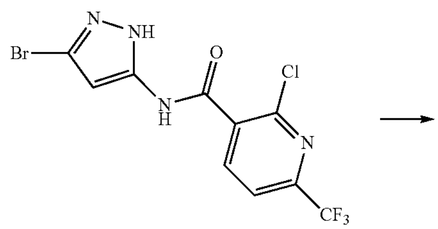

Example 61-3

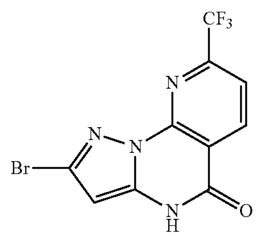

Example 61-4

N-(3-Bromo-1H-pyrazol-5-yl)-2-chloro-6-(trifluoromethyl)nicotinamide Example 61-3 (6.2 g, 16.8 mmol) was dissolved in N,N-dimethylformamide (80 mL), followed by addition of potassium carbonate (6.96 g, 50.4 mmol). The reaction solution was heated to 120° C. and reacted for 2 hours. The reaction solution was cooled to room temperature and used directly in the next step.

MS: m/z (ESI): 333.0 $[M+H]^+$

Step 5: Preparation of 2-(2-bromo-5-oxo-8-(trifluoromethyl)pyrazolo[1,5-a]pyrido[3,2-e]pyrimidin-4(5H)-yl)-N-(5-fluoropyridin-2-yl)acetamide

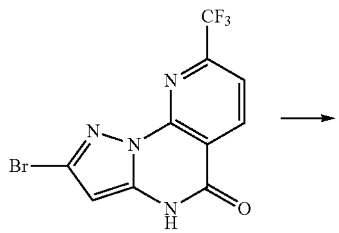

Example 61-4

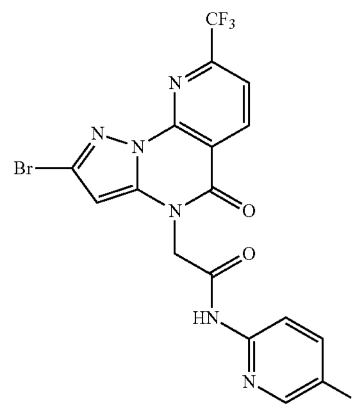

Example 61-A

Potassium carbonate (6.96 g, 50.4 mmol) and 2-bromo-N-(5-fluoropyridin-2-yl)acetamide (4.7 g, 20.2 mmol) were added to the reaction solution of 2-bromo-8-(trifluoromethyl)pyrazolo[1,5-a]pyrido[3,2-e]pyrimidin-5(4H)-one Example 61-4 (NA, 16.8 mmol) in N,N-dimethylformamide (80 mL), and reacted at 40° C. for 2 hours. The reaction solution was cooled to room temperature, poured into 300 mL of water, and extracted with ethyl acetate (200 mL*3). The organic phases were combined, washed successively with water (200 mL*2) and saturated sodium chloride solution (200 mL), dried over anhydrous sodium sulfate and filtered. The filtrate was concentrated under reduced pressure, and the resulting crude product was recrystallized from ethyl acetate to obtain the title product 2-(2-bromo-5-oxo-8-(trifluoromethyl)pyrazolo[1,5-a]pyrido[3,2-e]pyrimidin-4(5H)-yl)-N-(5-fluoropyridin-2-yl)acetamide Example 61-A.

$^1$H NMR (400 MHz, DMSO-$d_6$) δ 11.05 (s, 1H), 8.84 (d, J=8.0 Hz, 1H), 8.37 (s, 1H), 8.09 (d, J=8.0 Hz, 1H), 8.07-8.02 (m, 1H), 7.80-7.73 (m, 1H), 6.78 (s, 1H), 4.96 (s, 2H).

MS m/z (ESI): 486.2 $[M+H]^+$.

Step 6: Preparation of tert-butyl 3-(4-(2-(((5-fluoropyridin-2-yl)amino)-2-oxoethyl)-5-oxo-8-(trifluoromethyl)-4,5-dihydropyrazolo[1,5-a]pyrido[3,2-e]pyrimidin-2-yl)azetidine-1-carboxylate

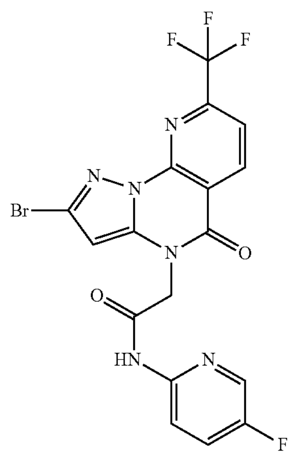

Example 61-A

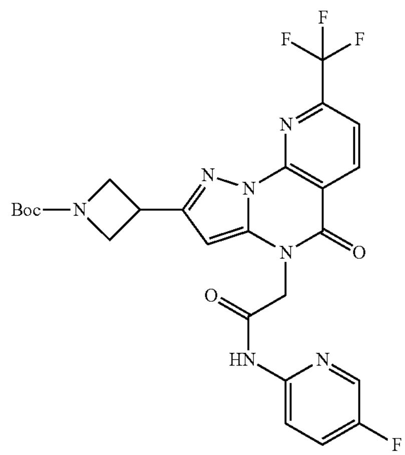

Example 61-B

Zinc dust (<10 μM, 20.3 g) was stirred with 1 M HCl (100 mL). After 2 hours, the suspension was filtered, and the resulting solid was washed with water (×2), then ethanol (×2) and finally ether (×2). The solid was dried under vacuum and stored under a nitrogen atmosphere. Zinc dust (washed, 0.60 g, 9.16 mmol) was vigorously stirred in dimethylacetamide (4 mL) under a nitrogen atmosphere, and the resulting suspension was heated to 65° C. Trimethylchlorosilane (0.12 g, 0.14 mL, 1.14 mmol) and 1,2-dibromoethane (0.098 mL, 1.14 mmol) were added, and the reaction solution was stirred for 40 minutes. A solution of tert-butyl 3-iodoazetidine-1-carboxylate (2.0 g, 7.06 mmol) in dimethylacetamide (4 mL) was added dropwise to the reaction mixture within 0.5 hour. The resulting suspension was stirred at 65° C. for 0.5 h, and then cooled to room temperature. The reaction mixture was used in the next step without treatment. A solution of Example 2 (200 mg, 0.41 mmol) and $Pd(dppf)Cl_2$ (33 mg, 0.04 mmol) in DMA (3 mL) were added to the above solution, heated to 85° C. and reacted for 16 h. The mixture was treated to obtain Example 61-B (100 mg, 43%).

MS m/z (ESI): 562.17 $[M+H]^+$.

Step 7: Preparation of 2-(2-(azetidin-3-yl)-5-oxo-8-(trifluoromethyl)pyrazolo[1,5-a]pyrido[3,2-e]pyrimidin-4(5H)-yl)-N-(5-fluoropyridin-2-yl)acetamide

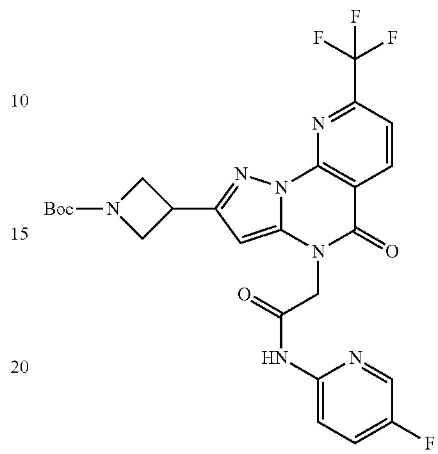

Example 61-B

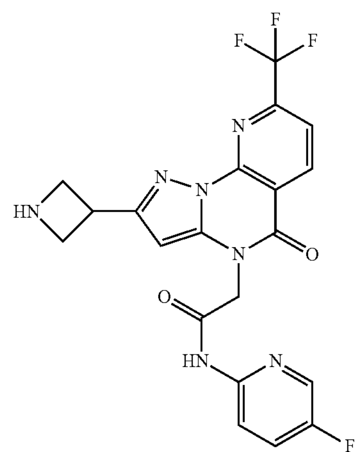

Example 61-C

4 M/L HCl/methanol (6 mL) was added to a solution of Example 61-B (100 mg, 0.18 mmol) in DCM (2 mL). The reaction solution was stirred at room temperature for 2 hours. The reaction solution was directly concentrated to dryness by rotary evaporation to obtain Example 61-C (80 mg, 97%).

MS m/z (ESI): 462.17 $[M+H]^+$.

Step 8: Preparation of 2-(2-(1-(2,2-difluoroethyl) azetidin-3-yl)-5-oxo-8-(trifluoromethyl)pyrazolo[1,5-a]pyrido[3,2-e]pyrimidin-4(5H)-yl)-N-(5-fluoropyridin-2-yl)acetamide

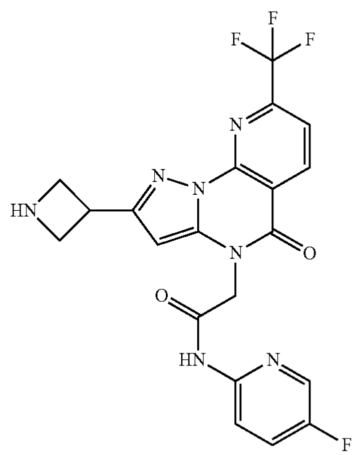

Example 61-C

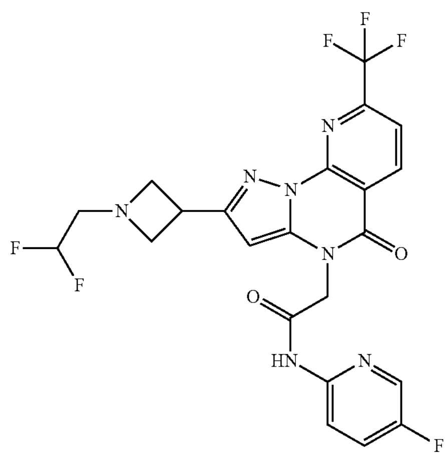

Example 61

Potassium carbonate (46 mg, 0.33 mmol) and difluoroiodoethane (42 mg, 0.22 mmol) were added to a solution of Example 61-C (50 mg, 0.11 mmol) in DMF (5 mL) at room temperature. The mixture was heated to 40° C. and stirred for 2 h. The reaction solution was cooled followed by addition of water. The precipitate was filtered, washed with ethyl acetate, and purified to obtain Example 61 (26 mg, yield: 46%).

MS m/z (ESI): 526.4 $[M+H]^+$.

Example 62

2-(2-Cyclohexyl-5-oxo-8-(trifluoromethyl)pyrazolo[1,5-a]pyrido[3,2-e]pyrimidin-4(5H)-yl)-N-(5-fluoropyridin-2-yl)acetamide

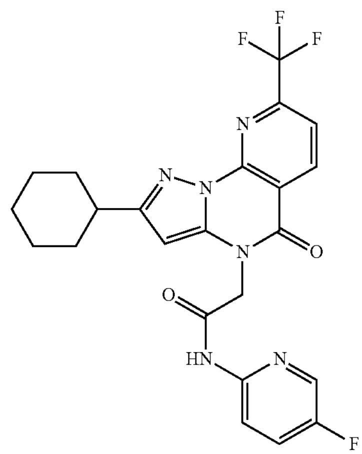

The synthetic method of Example 62 was according to the synthetic method of Example 4. The title compound Example 62 (15 mg, 31%) was obtained.

MS m/z (ESI): 489.5 $[M+H]^+$.

$^1H$ NMR (400 MHz, DMSO-$d_6$) δ 11.01 (s, 1H), 8.74 (d, J=8.0 Hz, 1H), 8.33 (s, 1H), 8.04-7.93 (m, 2H), 7.72 (t, J=9.1 Hz, 1H), 6.36 (s, 1H), 4.91 (s, 2H), 2.69 (s, 1H), 1.90 (d, J=12.5 Hz, 3H), 1.70 (dd, J=34.4, 12.4 Hz, 3H), 1.40 (td, J=24.5, 12.0 Hz, 4H).

Example 63

N-(5-Fluoropyridin-2-yl)-2-(2-(3-methylpyridin-4-yl)-5-oxo-8-(trifluoromethyl)pyrazolo[1,5-a]pyrido[3,2-e]pyrimidin-4(5H)-yl)acetamide

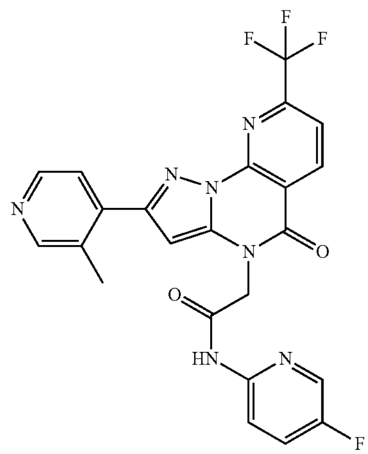

The synthetic method of Example 63 was according to the synthetic method of Example 1. The title compound Example 63 (15 mg, 30%) was obtained.

MS m/z (ESI): 498.4 $[M+H]^+$.

$^1$H NMR (400 MHz, DMSO-$d_6$) δ 11.12 (s, 1H), 8.95-8.74 (m, 3H), 8.38 (s, 1H), 8.27-8.00 (m, 3H), 7.76 (t, J=9.0 Hz, 1H), 7.25 (s, 1H), 5.09 (s, 2H), 2.72 (s, 3H).

Example 64

N-(5-Fluoropyridin-2-yl)-2-(2-(2-methylpyridin-3-yl)-5-oxo-8-(trifluoromethyl)pyrazolo[1,5-a]pyrido[3,2-e]pyrimidin-4(5H)-yl)acetamide

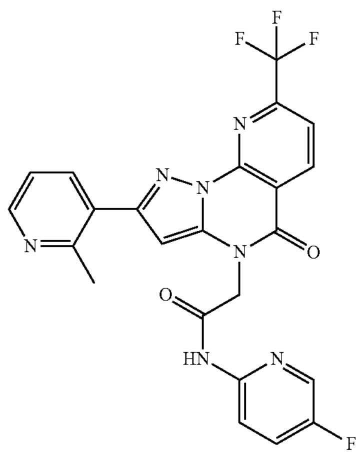

The synthetic method of Example 64 was according to the synthetic method of Example 1. The title compound Example 64 (15 mg, 30%) was obtained.

MS m/z (ESI): 498.4 $[M+H]^+$.

$^1$H NMR (400 MHz, DMSO-$d_6$) δ 11.13 (s, 1H), 8.90-8.62 (m, 3H), 8.36 (s, 1H), 8.15-7.99 (m, 2H), 7.93-7.68 (m, 2H), 7.11 (s, 1H), 5.08 (s, 2H), 2.96 (s, 3H).

Example 65

2-(2,4-Dimethylpyridin-3-yl)-5-oxo-8-(trifluoromethyl)pyrazolo[1,5-a]pyrido[3,2-e]pyrimidin-4(5H)-yl)-N-(5-fluoropyridin-2-yl)acetamide

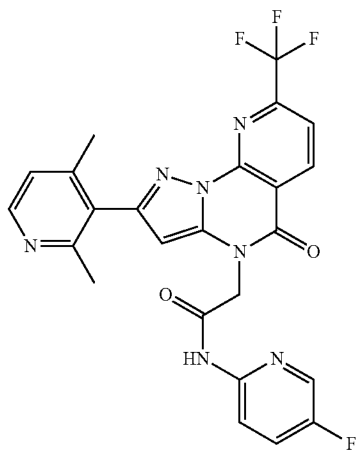

The synthetic method of Example 65 was according to the synthetic method of Example 1. The title compound Example 65 (10 mg, 33%) was obtained.

MS m/z (ESI): 512.4 $[M+H]^+$.

Example 66

N-(5-Fluoropyridin-2-yl)-2-(5-oxo-2,8-bis(trifluoromethyl)pyrazolo[1,5-a]pyrido[3,2-e]pyrimidin-4(5H)-yl)acetamide

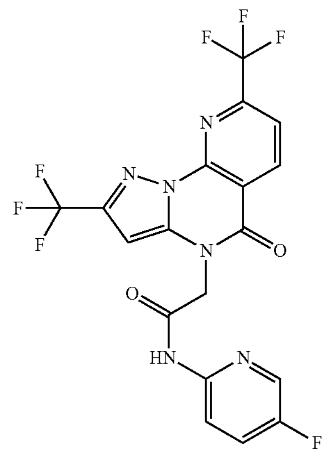

The synthetic method of Example 66 was according to the synthetic method of Example 1. The title compound Example 66 (10 mg, 33%) was obtained.

MS m/z (ESI): 475.3 $[M+H]^+$.

$^1$H NMR (400 MHz, DMSO-$d_6$) δ 11.07 (s, 1H), 8.91 (d, J=8.0 Hz, 1H), 8.37 (d, J=3.1 Hz, 1H), 8.19 (d, J=8.1 Hz, 1H), 8.14-7.98 (m, 1H), 7.76 (t, J=8.8 Hz, 1H), 7.13 (s, 1H), 5.04 (s, 2H).

Example 68

2-(2-Cyano-5-oxo-8-(trifluoromethyl)pyrazolo[1,5-a]pyrido[3,2-e]pyrimidin-4(5H)-yl)-N-(5-fluoropyridin-2-yl)acetamide

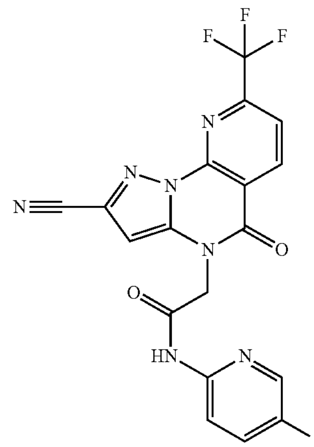

Step 1: Preparation of 2-(2-cyano-5-oxo-8-(trifluoromethyl)pyrazolo[1,5-a]pyrido[3,2-e]pyrimidin-4(5H)-yl)-N-(5-fluoropyridin-2-yl)acetamide

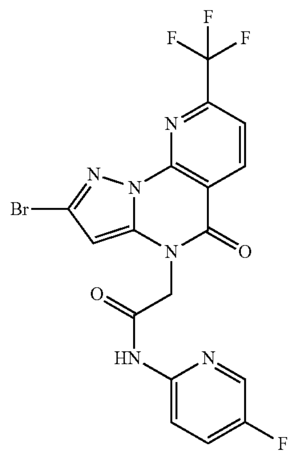

Example 61-A

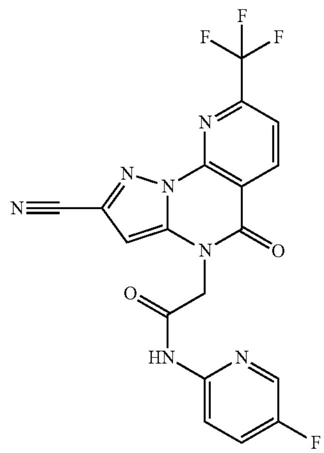

Example 68

Example 61-A (300 mg, 0.619 mmol), $Zn(CN)_2$ (300 mg, 2.56 mmol), $Pd_2(dba)_3$ (20 mg, 0.022 mmol), $Pd(dppf)Cl_2$ (30 mg, 0.036 mmol) and Zn powder (10 mg, 0.154 mmol) were dissolved in DMA (10 mL) at room temperature, followed by purging nitrogen for 2 minutes. The reaction solution was heated by microwave to 140 degrees and reacted for 8 hours. The reaction solution was cooled to room temperature and extracted with ethyl acetate (50 mL). The organic phase was washed twice with saturated brine. The organic phase was dried ($Na_2SO_4$), concentrated under reduced pressure, and purified by p-HPLC (FA) to obtain 100 mg of the title compound (yield: 38%).

$^1$H NMR (400 MHz, DMSO-$d_6$) δ 11.07 (s, 1H), 8.92 (d, J=8.2 Hz, 1H), 8.37 (d, J=3.1 Hz, 1H), 8.22 (d, J=7.9 Hz, 1H), 8.05 (s, 1H), 7.77 (t, J=8.6 Hz, 1H), 7.24 (s, 1H), 5.01 (s, 2H).

MS m/z (ESI): 432.3 $[M+H]^+$.

Example 69

N-(5-Fluoropyridin-2-yl)-2-(2-(2-hydroxypropan-2-yl)-5-oxo-8-(trifluoromethyl)pyrazolo[1,5-a]pyrido[3,2-e]pyrimidin-4(5H)-yl)acetamide

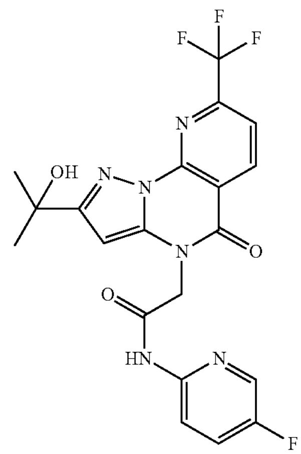

Step 1: Preparation of N-(5-fluoropyridin-2-yl)-2-(2-(2-hydroxypropan-2-yl)-5-oxo-8-(trifluoromethyl)pyrazolo[1,5-a]pyrido[3,2-e]pyrimidin-4(5H)-yl)acetamide

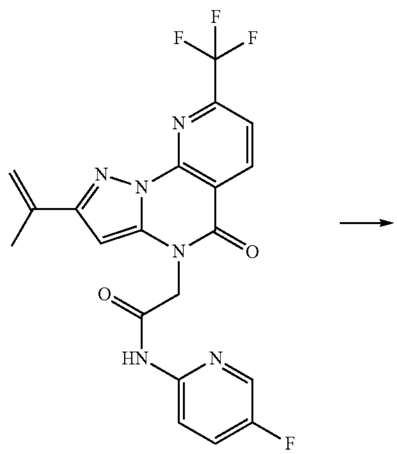

Example 69-1

-continued

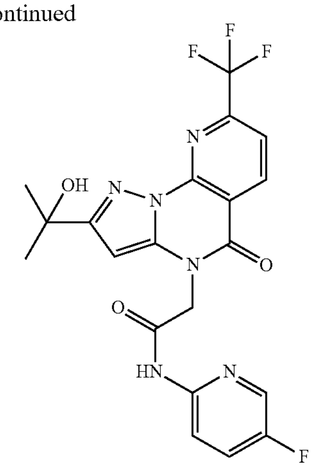

Example 69

Example 69-1 (100 mg, 0.22 mmol) (Example 69-1 was synthesized according to the operation of Example 6) was dissolved in dimethoxyethane (2 ml)/MeOH (2 ml) at 25° C., followed by successively adding cobalt(II) isotetraphenylporphyrin (1.3 mg, 0.002 mmol) and tetraethylammonium borohydride (80.2 mg, 0.55 mmol). The reaction mixture was stirred for 1.25 hours. The reaction was stopped and quenched by saturated aqueous ammonium chloride solution (50 mL). The mixture was extracted with ethyl acetate (3×40 mL). The combined organic phases were washed with saturated aqueous solution of sodium chloride (1×80 mL), dried over anhydrous sodium sulfate, filtered and evaporated under reduced pressure to remove the solvent. The crude product was purified to obtain the title compound (42 mg, yield: 42%).

MS m/z (ESI): 465.1 $[M+H]^+$.

$^1$H NMR (400 MHz, DMSO) δ 11.07 (s, 1H), 8.81 (d, J=7.9 Hz, 1H), 8.37 (s, 1H), 8.12-7.92 (m, 2H), 7.76 (s, 1H), 6.44 (s, 1H), 4.99 (s, 2H), 1.51 (s, 6H).

Example 70

N-(5-Fluoropyridin-2-yl)-2-(2-isobutyl-5-oxo-8-(trifluoromethyl)pyrazolo[1,5-a]pyrido[3,2-e]pyrimidin-4(5H)-yl)acetamide

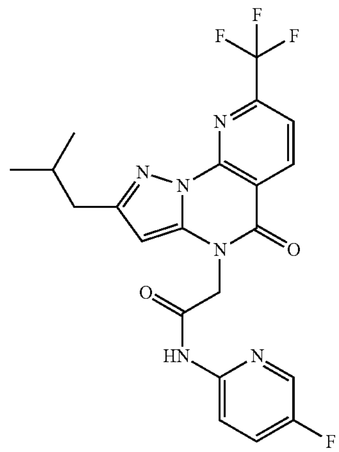

Example 70 was synthesized according to the method of Example 1. The target compound (26 mg, yield: 26%) was obtained by replacing 3-(tert-butyl)-1H-pyrazol-5-amine with 3-(isobutyl)-1H-pyrazol-5-amine.

MS m/z (ESI): 463.4 $[M+H]^+$.

$^1$H NMR (400 MHz, DMSO-$d_6$) δ 11.05 (s, 1H), 8.79 (d, J=8.0 Hz, 1H), 8.37 (s, 1H), 8.07-8.03 (m, 1H), 8.00 (d, J=8.0 Hz, 1H), 7.78-7.73 (m, 1H), 6.33 (s, 1H), 4.96 (s, 2H), 2.55 (d, J=8.2 Hz, 2H), 2.04-1.93 (m, 1H), 0.95 (d, J=6.4 Hz, 6H).

Example 71

N-(5-Fluoropyridin-2-yl)-2-(2-morpholino-5-oxo-8-(trifluoromethyl)pyrazolo[1,5-a]pyrido[3,2-e]pyrimidin-4(5H)-yl)acetamide

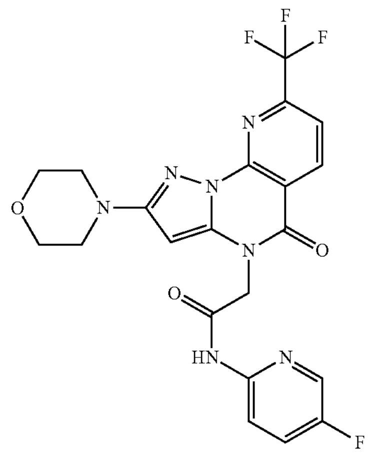

Example 71 was synthesized according to the method of Example 1. The target compound (14 mg, yield: 35%) was obtained by replacing 3-(tert-butyl)-1H-pyrazol-5-amine with 3-(morpholinyl)-1H-pyrazol-5-amine.

MS m/z (ESI): 492.4 $[M+H]^+$.

Example 74

2-(2-(Azetidine-1-carbonyl)-5-oxo-8-(trifluoromethyl)pyrazolo[1,5-a]pyrido[3,2-e]pyrimidin-4(5H)-yl)-N-(5-fluoropyridin-2-yl)acetamide

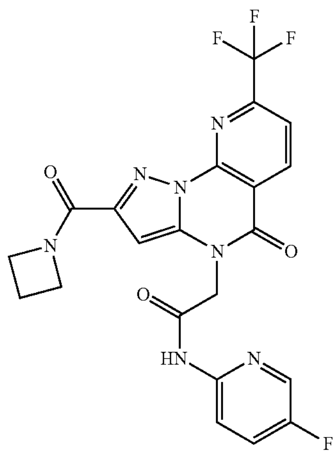

Step 1: Preparation of 2-(2-(azetidine-1-carbonyl)-5-oxo-8-(trifluoromethyl)pyrazolo[1,5-a]pyrido[3,2-e]pyrimidin-4(5H)-yl)-N-(5-fluoropyridin-2-yl)acetamide

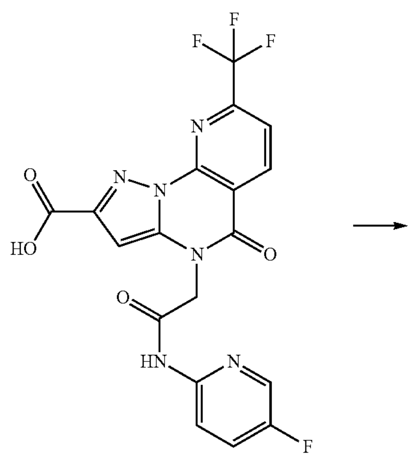

Example 74-1

-continued

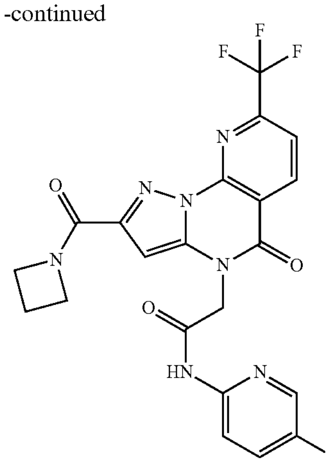

Example 74

DIPEA (0.1 mL, 0.6 mmol) was added to a solution of Example 74-0 mg, 0.22 mmol) (Example 74-1 was synthesized according to Example 8-3) and HATU (83.4 mg, 0.22 mmol) in DMF (2 mL). The mixture was stirred at room temperature for 30 minutes, followed by addition of azetidine (12.5 mg, 0.22 mmol). The reaction solution was stirred at room temperature for 18 hours. Water (40 mL) was added to the reaction solution. The mixture was extracted with ethyl acetate (2×20 mL). The organic layer was dried over anhydrous sodium sulfate, filtered, concentrated and purified to obtain Example 74 (56 mg, yield: 52%).

MS m/z (ESI): 490.1 $[M+H]^+$.

$^1$H NMR (400 MHz, DMSO-$d_6$) δ 11.04 (s, 1H), 8.86 (d, J=8.1 Hz, 1H), 8.37 (s, 1H), 8.15-8.08 (m, 1H), 8.04 (s, 1H), 7.75 (t, J=9.4 Hz, 1H), 6.81 (s, 1H), 5.04 (s, 2H), 4.68-4.52 (m, 2H), 4.08 (t, J=7.5 Hz, 2H), 2.34 (d, J=9.1 Hz, 2H).

Example 78

N-(5-Fluoropyridin-2-yl)-2-(5-oxo-8-(trifluoromethyl)pyrazolo[1,5-a]pyrido[3,2-e]pyrimidin-4(5H)-yl)acetamide

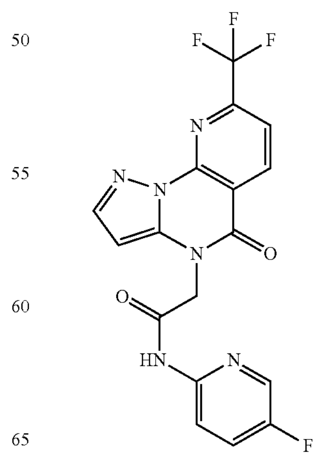

Step 1: Preparation of 2-chloro-N-(1H-pyrazol-5-yl)-6-(trifluoromethyl) nicotinamide

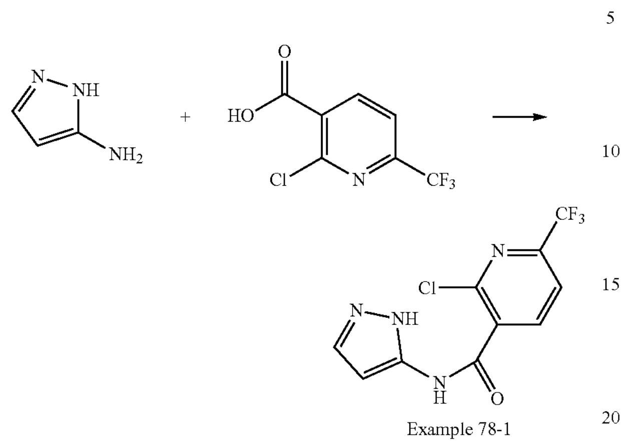

Example 78-1

1H-Pyrazol-5-amine (1.66 g, 19.93 mmol), DIPEA (6.2 g, 49.8 mmol) and HATU (5.4 g, 0.144 mmol) were added successively to a solution of 2-chloronicotinic acid (1.57 g, 9.96 mmol) in DMF (30 mL) under an ice bath condition. The ice bath was removed, and the reaction solution was stirred for 1 h. The mixture was treated to obtain Example 78-1 (2.0 g, 90%).

MS m/z (ESI): 291.0 $[M+H]^+$.

Step 2: Preparation of 8-(trifluoromethyl)pyrazolo[1,5-a]pyrido[3,2-e]pyrimidin-5(4H)-one

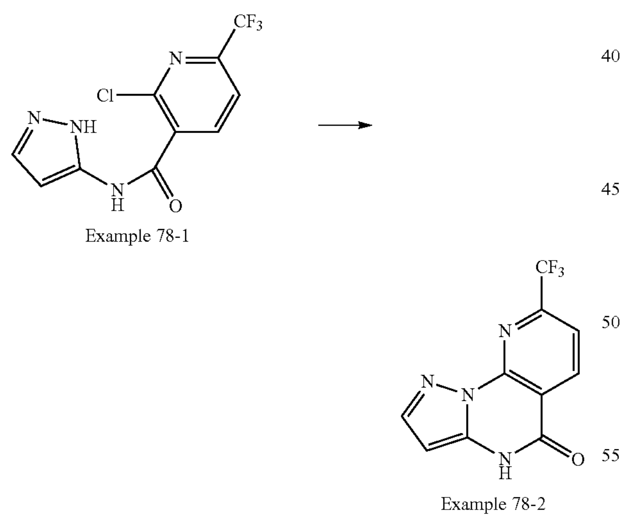

Example 78-1

Example 78-2

Potassium carbonate (1.61 g, 11.66 mmol) and 1,4-diazabicyclo[2.2.2]octane (DABCO) (150.9 mg, 1.35 mmol) were added to a solution of Example 78-1 (2.0 g, 8.97 mmol) in DMF (50 mL). The reaction solution was stirred at room temperature for 16 hours. The mixture was treated to obtain Example 78-2 (1.6 g, 97%).

MS m/z (ESI): 255.0 $[M+H]^+$.

Step 3: Preparation of N-(5-fluoropyridin-2-yl)-2-(5-oxo-8-(trifluoromethyl)pyrazolo[1,5-a]pyrido[3,2-e]pyrimidin-4(5H)-yl)acetamide

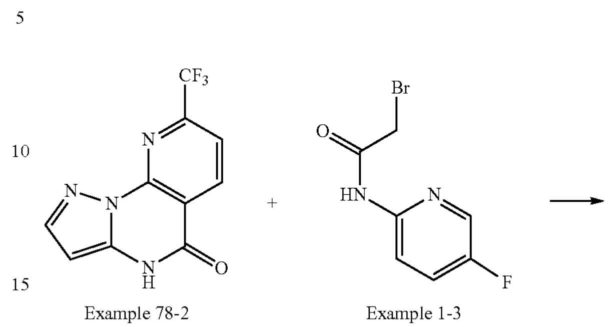

Example 78-2

Example 1-3

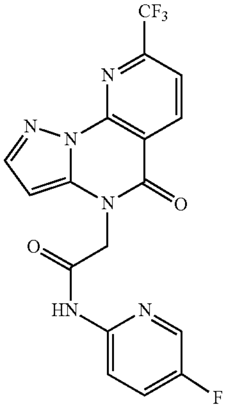

Example 78

Potassium carbonate (2.23 g, 16.11 mmol) and Example 1-3 (2.25 g, 9.67 mmol) were added to a solution of Example 78-2 (1.5 g, 8.06 mmol) in DMF (30 mL) at room temperature. The mixture was heated to 80° C. and stirred for 2 h. The reaction solution was cooled followed by addition of water. The precipitate was filtered, washed with ethyl acetate, and purified to obtain Example 78 (2.1 g, yield: 78%).

$^1H$ NMR (400 MHz, DMSO-$d_6$) δ 11.06 (s, 1H), 8.83 (d, J=8.0 Hz, 1H), 8.37 (d, J=3.2 Hz, 1H), 8.06 (d, J=8.0 Hz, 1H), 8.05-8.02 (m, 1H), 7.98 (d, J=2.0 Hz, 1H), 7.78-7.73 (m, 1H), 6.46 (s, 1H), 5.00 (s, 2H).

MS m/z (ESI): 407.3 $[M+H]^+$.

Example 79

2-(2-Chloro-5-oxo-8-(trifluoromethyl)pyrazolo[1,5-a]pyrido[3,2-e]pyrimidin-4(5H)-yl)-N-(5-fluoropyridin-2-yl)acetamide

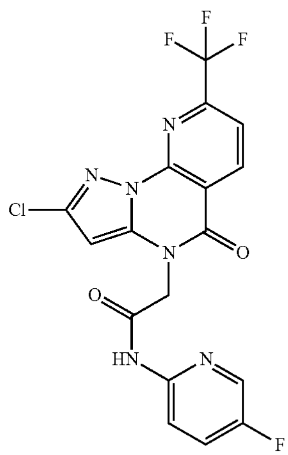

Example 79 was synthesized according to the method of Example 1. The target compound (31 mg, yield: 26%) was obtained by replacing 3-(tert-butyl)-1H-pyrazol-5-amine with 3-chloro-1H-pyrazol-5-amine.

$^1$H NMR (400 MHz, DMSO-$d_6$) δ 11.05 (s, 1H), 8.84 (d, J=8.1 Hz, 1H), 8.36 (s, 1H), 8.15-7.99 (m, 2H), 7.76 (t, J=9.0 Hz, 1H), 6.73 (s, 1H), 4.96 (s, 2H).

MS m/z (ESI): 441.7 [M+H]$^+$.

Example 80

2-(3-Cyano-5-oxo-8-(trifluoromethyl)pyrazolo[1,5-a]pyrido[3,2-e]pyrimidin-4(5H)-yl)-N-(5-fluoropyridin-2-yl)acetamide

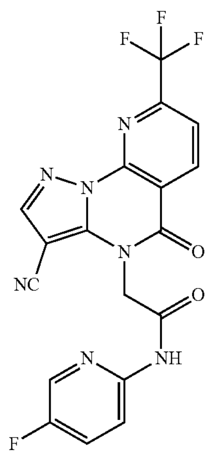

Example 80 was synthesized according to the method of Example 1. The target compound was obtained by replacing 3-(tert-butyl)-1H-pyrazol-5-amine with 4-cyano-1H-pyrazol-5-amine.

Step 1: Preparation of tert-butyl 3-amino-4-cyano-1H-pyrazole-1-carboxylate

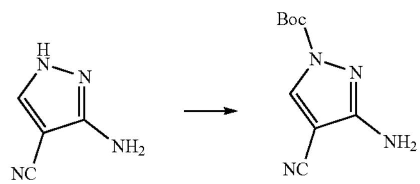

Example 80-1

5-Amino-1H-pyrazole-4-carbonitrile (2.0 g, 18.5 mmol) was dissolved in anhydrous dichloromethane (40 mL), followed by addition of triethylamine (3.74 g, 37.0 mmol) and di-tert-butyl dicarbonate (4.44 g, 20.4 mmol). The reaction solution was reacted at room temperature for 16 hours. The reaction solution was concentrated under reduced pressure, and made slurry in petroleum ether (50 mL) to obtain the title product tert-butyl 3-amino-4-cyano-1H-pyrazole-1-carboxylate Example 80-1 (3.5 g), yield: 90.9%.

$^1$H NMR (400 MHz, DMSO-$d_6$) δ 7.77 (s, 1H), 7.63 (s, 2H), 1.56 (s, 9H).

Step 2: Preparation of tert-butyl-(2-chloro-6-(trifluoromethyl)nicotinamido)-4-cyano-1H-pyrazole-1-carboxylate

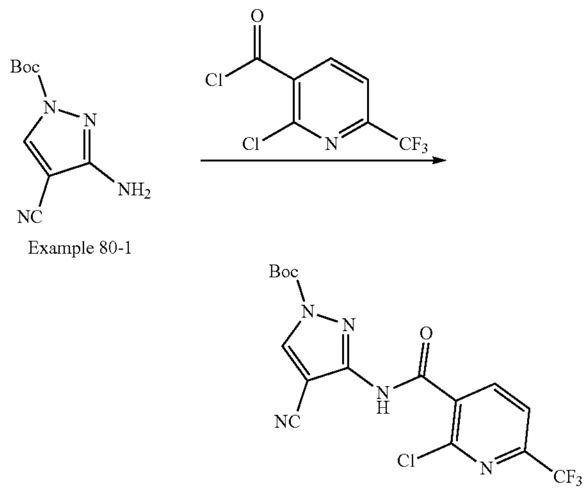

Example 80-1

Example 80-2

Tert-butyl 3-amino-4-cyano-1H-pyrazole-1-carboxylate Example 80-1 (3.5 g, 16.8 mmol) was dissolved in anhydrous dichloromethane (50 mL), followed by addition of triethylamine (5.35 g, 7.37 mmol). A solution (50 mL) of freshly prepared 2-chloro-6-(trifluoromethyl)nicotinoyl chloride (4.3 g, 17.6 mmol) in dichloromethane was added dropwise under a nitrogen atmosphere at 0° C. After completion of the addition, the reaction solution was reacted at room temperature for 1 hour. The reaction solution was washed successively with water (50 mL*2) and saturated sodium chloride solution (50 mL), dried over anhydrous sodium sulfate and filtered. The filtrate was concentrated under reduced pressure, and the resulting crude product was purified by silica gel column chromatography (ethyl acetate/petroleum ether=0 to 40%) to obtain tert-butyl 3-(2-chloro-6-(trifluoromethyl)nicotinamido)-4-cyano-1H-pyrazole-1-carboxylate Example 80-2 (2.8 g), yield: 38.2%.

MS: m/z (ESI): 432.8 [M+NH$_4$]

$^1$H NMR (400 MHz, DMSO-d$_6$) δ 11.87 (s, 1H), 9.23 (s, 1H), 8.43 (d, J=7.6 Hz, 1H), 8.13 (d, J=7.6 Hz, 1H), 1.59 (s, 9H).

Step 3: Preparation of 2-chloro-N-4-cyano-1H-pyrazol-5-yl)-6-(trifluoromethyl)nicotinamide

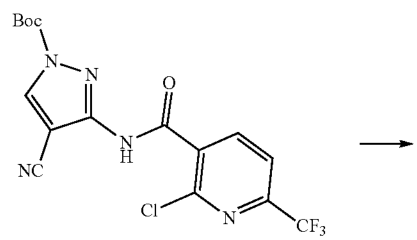

Example 80-2

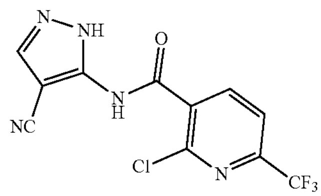

Example 80-3

Tert-butyl 3-(2-chloro-6-(trifluoromethyl)nicotinamido)-4-cyano-1H-pyrazole-1-carboxylate Example 80-2 (2.8 g, 6.73 mmol) was dissolved in anhydrous dichloromethane (10 mL), followed by addition of a solution (4 M, 30 mL) of hydrochloric acid in dioxane. The reaction solution was reacted at room temperature for 5 hours. The reaction solution was directly concentrated to dryness by rotary evaporation to obtain 2-chloro-N-(4-cyano-1H-pyrazol-5-yl)-6-(trifluoromethyl)nicotinamide Example 80-3 (2.1 g), yield: 98.8%.

MS: m/z (ESI): 315.8 [M+H]$^+$

Step 4: Preparation of 5-oxo-8-(trifluoromethyl)-4,5-dihydropyrazolo[1,5-a]pyrido[3,2-e]pyrimidine-3-carbonitrile

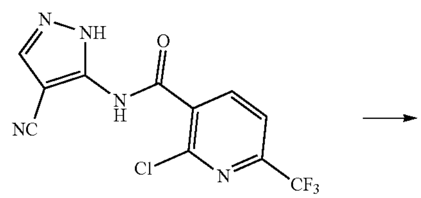

Example 80-3

-continued

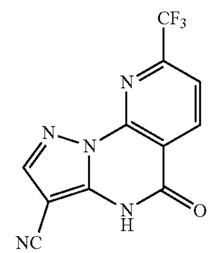

Example 80-4

2-Chloro-N-(4-cyano-1H-pyrazol-5-yl)-6-(trifluoromethyl)nicotinamide Example 80-3 (2.1 g, 6.65 mmol) was dissolved in N,N-dimethylformamide (40 mL), followed by addition of potassium carbonate (1.84 g, 13.3 mmol). The reaction solution was heated to 120° C. and reacted for 2 hours. The reaction solution was cooled to room temperature, adjusted to pH 5 to 6 with 1M dilute hydrochloric acid, and extracted with ethyl acetate (100 mL*2). The organic phases were combined, washed successively with water (100 mL*2) and saturated sodium chloride solution (100 mL), dried over anhydrous sodium sulfate and filtered. The filtrate was concentrated under reduced pressure, and made slurry in ethyl acetate (15 mL) to obtain 5-oxo-8-(trifluoromethyl)-4,5-dihydropyrazolo[1,5-a]pyrido[3,2-e]pyrimidine-3-carbonitrile Example 80-4 (1.3 g), yield: 69.9%.

MS: m/z (ESI): 279.8 [M+H]$^+$

Step 4: Preparation of 2-(3-cyano-5-oxo-8-(trifluoromethyl)pyrazolo[1,5-a]pyrido[3,2-e]pyrimidin-4(5H)-yl)-N-(5-fluoropyridin-2-yl)acetamide

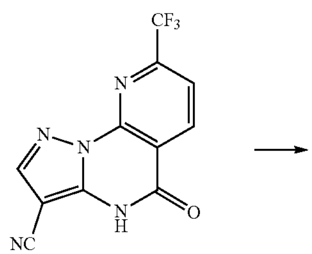

Example 80-4

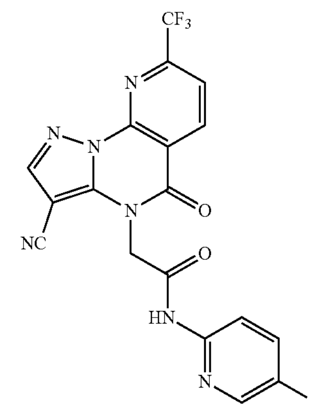

Example 80

5-Oxo-8-(trifluoromethyl)-4,5-dihydropyrazolo[1,5-a]pyrido[3,2-e]pyrimidine-3-carbo nitrile Example 80-4 (500 mg, 1.79 mmol) was dissolved in N,N-dimethylformamide (20 mL), followed by addition of potassium carbonate (371 mg, 2.69 mmol) and 2-bromo-N-(5-fluoropyridin-2-yl)acetamide (501 mg, 2.15 mmol). The reaction solution was reacted at 40° C. and for 2 hours. The reaction solution was cooled to room temperature, poured into 100 mL of water, and extracted with ethyl acetate (50 mL*2). The organic phases were combined, washed successively with water (50 mL*2) and saturated sodium chloride solution (50 mL), dried over anhydrous sodium sulfate and filtered. The filtrate was concentrated under reduced pressure, and the resulting crude product was made slurry in ethyl acetate. The resulting mother liquor was concentrated under reduced pressure, and purified by reverse HPLC to obtain the title product 2-(3-cyano-5-oxo-8-(trifluoromethyl)pyrazolo[1,5-a]pyrido[3,2-e]pyrimidin-4(5H)-yl)-N-(5-fluoropyridin-2-yl)acetamide Example 80.

MS m/z (ESI): 432.3[M+H]$^+$.

$^1$H NMR (400 MHz, DMSO-$d_6$) δ 11.2 (s, 1H), 8.93 (d, J=8.0 Hz, 1H), 8.58 (s, 1H), 8.38 (d, J=3.2 Hz, 1H), 8.20 (d, J=8.0 Hz, 1H), 8.07-8.04 (m, 1H), 7.81-7.75 (m, 1H), 5.19 (s, 2H).

Example 81

4-(2-((5-Fluoropyridin-2-yl)amino)-2-oxoethyl)-N-methyl-5-oxo-8-(trifluoromethyl)-4,5-dihydropyrazolo[1,5-a]pyrido[3,2-e]pyrimidine-2-carboxamide

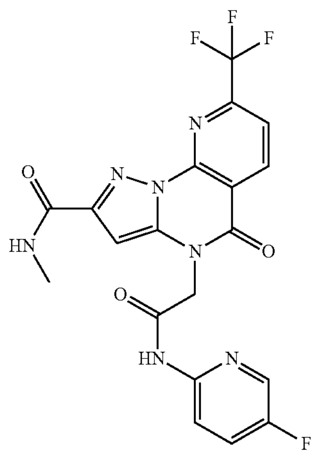

Example 81 was synthesized according to the method of Example 74. The target compound (48 mg, yield: 61%) was obtained by replacing azacyclobutylamine with methylamine.

MS m/z (ESI): 464.1[M+H]$^+$.

$^1$H NMR (400 MHz, DMSO-$d_6$) δ 11.04 (s, 1H), 8.88 (d, J=8.0 Hz, 1H), 8.53 (d, J=5.4 Hz, 1H), 8.37 (s, 1H), 8.13 (d, J=8.1 Hz, 1H), 8.04 (s, 1H), 7.76 (t, J=8.9 Hz, 1H), 6.84 (s, 1H), 5.05 (s, 2H), 2.80 (d, J=4.6 Hz, 3H).

Example 82

N-(5-Fluoropyridin-2-yl)-2-(2-(hydroxymethyl)-5-oxo-8-(trifluoromethyl)pyrazolo[1,5-a]pyrido[3,2-e]pyrimidin-4(5H)-yl)acetamide

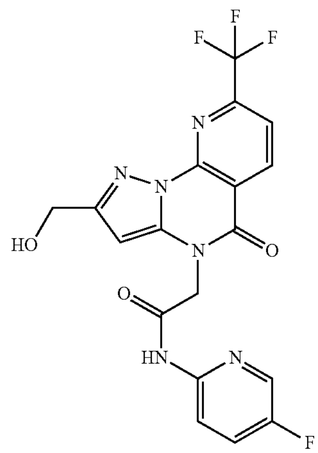

Step 1: Preparation of N-(5-fluoropyridin-2-yl)-2-(2-(hydroxymethyl)-5-oxo-8-(trifluoromethyl)pyrazolo[1,5-a]pyrido[3,2-e]pyrimidin-4(5H)-yl)acetamide

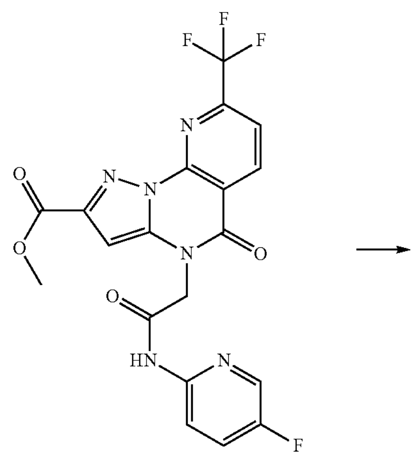

Example 82-1

-continued

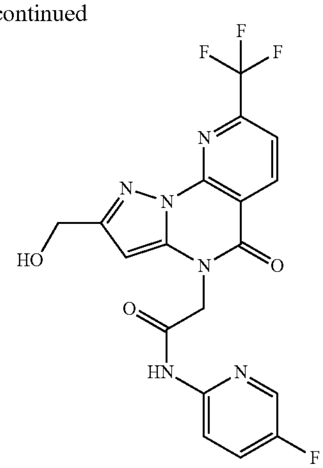

Example 82

Diisobutylaluminum hydride (1M in toluene, 0.66 mL, 0.66 mmol) was added to a solution of Example 82-1 (100 mg, 0.22 mmol) (Example 82-1 was synthesized according to Example 8-2) in THE (2 mL) at 0° C. The mixture was stirred at room temperature overnight. Rochelle's salt solution (1.0 M, 5 ml) was added, followed by addition of ethyl acetate (5 mL). The resulting suspension was stirred at room temperature until clear phase separation was achieved. The organic phase was separated, and the aqueous phase was extracted with EtOAc (3×40 ml). The combined organic layers were washed with saturated aqueous solution of sodium bicarbonate (50 mL) and saturated brine (50 mL), dried over anhydrous sodium sulfate, concentrated and purified to obtain the target compound (32 mg, yield: 34%).

MS m/z (ESI): 437.1$[M+H]^+$.

$^1$H NMR (400 MHz, DMSO) δ 11.06 (s, 1H), 8.82 (d, J=7.9 Hz, 1H), 8.37 (s, 1H), 8.02 (m, 2H), 7.76 (s, 1H), 6.40 (s, 1H), 5.44 (s, 1H), 5.00 (s, 2H), 4.56 (s, 2H).

Example 83

N-(5-Chloropyridin-2-yl)-2-(5-oxo-8-(trifluoromethyl)pyrazolo[1,5-a]pyrido[3,2-e]pyrimidin-4(5H)-yl)acetamide

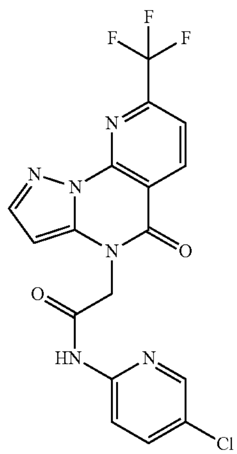

Example 83 was synthesized according to the method of Example 78. The target compound (23 mg, yield: 54%) was obtained by replacing 5-fluoropyridin-2-amine with 5-chloropyridin-2-amine.

MS m/z (ESI): 423.1$[M+H]^+$.

$^1$H NMR (400 MHz, DMSO-$d_6$) δ 11.14 (s, 1H), 8.84 (d, J=8.0 Hz, 1H), 8.42 (d, J=2.6 Hz, 1H), 8.05 (t, J=9.3 Hz, 2H), 7.99-7.89 (m, 2H), 6.47 (d, J=2.0 Hz, 1H), 5.02 (s, 2H).

Example 84

N-(5-Chloropyrimidin-2-yl)-2-(5-oxo-8-(trifluoromethyl)pyrazolo[1,5-a]pyrido[3,2-e]pyrimidin-4(5H)-yl)acetamide

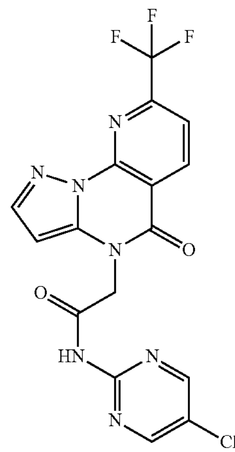

Example 84 was synthesized according to the method of Example 78. The target compound (21 mg, yield: 53%) was obtained by replacing 5-fluoropyridin-2-amine with 5-chloropyrimidine-2-amine.

MS m/z (ESI): 424.1$[M+H]^+$.

$^1$H NMR (400 MHz, DMSO-$d_6$) δ 11.29 (s, 1H), 8.95-8.72 (m, 3H), 8.06 (d, J=8.0 Hz, 1H), 7.98 (d, J=2.0 Hz, 1H), 6.46 (d, J=2.0 Hz, 1H), 5.16 (s, 2H).

Example 85

N-(3,5-Difluoropyridin-2-yl)-2-(5-oxo-8-(trifluoromethyl)pyrazolo[1,5-a]pyrido[3,2-e]pyrimidin-4(5H)-yl)acetamide

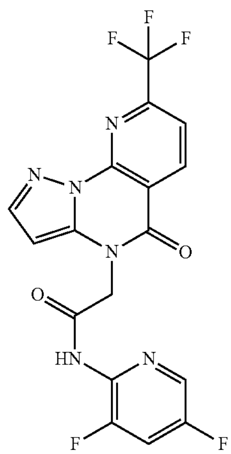

Example 85 was synthesized according to the method of Example 78. The target compound (25 mg, yield: 46%) was obtained by replacing 5-fluoropyridin-2-amine with 3,5-difluoropyridine.

MS m/z (ESI): 425.1[M+H]$^+$.

$^1$H NMR (400 MHz, DMSO-$d_6$) δ 11.32 (s, 1H), 8.82 (d, J=8.0 Hz, 1H), 8.56 (dd, J=10.2, 2.2 Hz, 1H), 8.12-7.91 (m, 3H), 6.45 (d, J=2.0 Hz, 1H), 5.01 (s, 2H).

Biological Assay and Evaluation

The present invention is further illustrated below in combination with the following test examples, which are not intended to limit the scope of the present invention.

Test Example 1. Determination of the Effect of the Compounds of the Present Invention on Calcium Ion Mobility in Cells Stably Expressing 1321N1-hP2X3 Receptors Experimental Objective:

To determine the inhibitory activity of the compounds on 1321N1-hP2X3 receptor.

Experimental Instruments:

384-well cell plate (Corning; 3712);
384-well compound plate (Corning; 3657);
384-well assay plate (LABCYTE; P-05525);
FLIPR (Molecular Devices).

Experimental Reagents:

DMEM (Gibco; 11965);
FBS (Gibco; 10099-141);
Hygromycin B (Invitrogen, 10687010);
Matrix (Thermo; 5416);
DMSO (Sigma; D2650);
HBSS (Invitrogen; 14025);
HEPES (Invitrogen; 15630080);
Probenecid (Sigma; P8761);
Versene (Gibco; 15040066);
G418 (Sigma; G5013);
FLIPR® Calcium 4 Assay Kit (Molecular Devices; R8141);
α,β-meATP (Sigma; M6517);
ATP hydrolytic enzyme (Sigma; A7646);
Stably transfected cell line: 1321N1-hP2X3 (supplied by Shanghai ChemPartner Chemical Research Co., Ltd.).

Experimental Method:

1. Formulation of the Reagents:
   Assay buffer: 1*HBSS+20 mM HEPES;
   Cell culture medium: DMEM+10% FBS+75 g/mL Hygromycin B+300 g/mL G418;
   Plating medium: DMEM+10% DPBS;
   0.5*Dye: 10*Dye stock+1.25 Probenecid+1*assay buffer+0.5 U/mL ATP hydrolytic enzyme;
2. The cells were cultured to 70%-90% confluency in the cell culture medium at 37° C., 5% $CO_2$. The medium was discarded, and the cells were added with 2 mL of Versene, and the cells were placed in an incubator at 37° C. for 2 to 5 min. The cells were collected by addition of 10 mL of plating medium and counted. The cells were seeded to the 384-well assay plate by addition of 50 μL solution (a density of $1\times10^4$ cells/well) to each well, and incubated for 16 to 24 hours (at least overnight).
3. The medium was discarded, and 30 μL of 1× dye was added. The cells were incubated at 37° C. in the dark for 60 min.
4. The compound powder was dissolved in DMSO to obtain a 20 mM stock solution. 180× compound with required concentration was formulated, and diluted in gradient for concentration points.
5. Preparation of compound plate: 500 nL of 180× compound was transferred to the compound plate (source plate for FLIPR) using ECHO. 30 μL of assay buffer was added to each well, and the plate was shaken gently for 20 to 40 minutes.
6. Determination: 15 μL of 3× compound was taken from each well and added to the cell plate. The samples were added by FLIPR instrument, and the calcium signals were detected. After 15 minutes, 22.5 μL of 3× agonist ($EC_{80}$ concentration) was added to each well and the calcium signals were detected.

Processing Method of the Experimental Data:

The calcium signal values were determined by FLIPR. The ratio of the 340/510 nm wavelength signals to 380/510 nm wavelength signals was used as the calculated results for each sampling time point in the experiment. The calculation of maximum minus minimum was derived from the ratio signal curve.

The percent inhibition rate and ten-point concentration data were fitted to the parametric nonlinear logistic equation by using GraphPad prism to calculate the $IC_{50}$ values of the compounds.

Experimental Results:

The results of the compounds of the Examples of the present invention in the 1321N1-hP2X3 receptor cell function calcium ion mobility assay are shown in Table 1:

TABLE 1

| Example No. | 1321N1-hP2X3 $IC_{50}$ (nM) |
|---|---|
| 1 | 16.19 |
| 21 | 304.8 |
| 30 | 88.20 |
| 34 | 63.38 |
| 35 | 77.69 |
| 36 | 185.0 |
| 37 | 336.7 |

TABLE 1-continued

| Example No. | 1321N1-hP2X3 $IC_{50}$ (nM) |
|---|---|
| 40 | 292.5 |
| 59 | 259.2 |
| 61-A | 76.40 |
| 62 | 384.7 |
| 63 | 238.5 |
| 64 | 149.5 |
| 66 | 130.4 |
| 68 | 32.45 |
| 74 | 203.1 |
| 78 | 49.00 |
| 79 | 34.70 |
| 80 | 64.35 |
| 83 | 136.7 |

Experimental Conclusion:

The above data indicate that the compounds of the present invention show good inhibitory effect in the 1321N1-hP2X3 receptor cell function calcium ion mobility assay.

Test Example 2. Determination of the Effect of the Compounds of the Present Invention on Calcium Ion Mobility in Cells Stably Expressing 1321N1-hP2X2/3 Receptors Experimental Objective:

To determine the inhibitory activity of the compounds on 1321N1-hP2X2/3 receptor.

Experimental Instruments:

384-well cell plate (Corning; 3712);

384-well compound plate (Corning; 3657);

384-well assay plate (LABCYTE; P-05525);

FLIPR (Molecular Devices).

Experimental Reagents:

DMEM (Gibco; 11965);

FBS (Gibco; 10099-141);

Hygromycin B (Invitrogen, 10687010);

Matrix (Thermo; 5416);

DMSO (Sigma; D2650);

HBSS (Invitrogen; 14025);

HEPES (Invitrogen; 15630080);

Probenecid (Sigma; P8761);

Versene (Gibco; 15040066);

G418 (Sigma; G5013);

FLIPR® Calcium 4 Assay Kit (Molecular Devices; R8141);

α,β-meATP (Sigma; M6517);

ATP hydrolytic enzyme (Sigma; A7646);

Stably transfected cell line: 1321N1-hP2X2/3 (supplied by Shanghai ChemPartner Chemical Research Co., Ltd.).

Experimental Method:

1. Formulation of the Reagents:

Assay buffer: 1*HBSS+20 mM HEPES;

Cell culture medium: DMEM+10% FBS+75 μg/mL Hygromycin B+150 μg/mL G418;

Plating medium: DMEM+10% DPBS;

0.5*Dye: 10*Dye stock+1.25 Probenecid+1*assay buffer+0.5 U/mL ATP hydrolytic enzyme;

2. The cells were cultured to 70%-90% confluency in the cell culture medium at 37° C., 5% $CO_2$. The medium was discarded, and the cells were added with 2 mL of Versene, and the cells were placed in an incubator at 37° C. for 2 to 5 min. The cells were collected by addition of 10 mL of plating medium and counted. The cells were seeded to the 384-well assay plate by addition of 50 μL solution (a density of $1\times10^4$ cells/well) to each well, and incubated for 16 to 24 hours (at least overnight).

3. The medium was discarded, and 30 μL of 1× dye was added. The cells were incubated at 37° C. in the dark for 60 min.

4. The compound powder was dissolved in DMSO to obtain a 20 mM stock solution. 180× compound with required concentration was formulated, and diluted in gradient for concentration points.

5. Preparation of compound plate: 500 nL of 180× compound was transferred to the compound plate (source plate for FLIPR) using ECHO. 30 μL of assay buffer was added to each well, and the plate was shaken gently for 20 to 40 minutes.

6. Determination: 15 μL of 3× compound was taken from each well and added to the cell plate. The samples were added by FLIPR instrument, and the calcium signals were detected. After 15 minutes, 22.5 μL of 3× agonist ($EC_{80}$ concentration) was added to each well and the calcium signals were detected.

Processing Method of the Experimental Data:

The calcium signal values were determined by FLIPR. The ratio of the 340/510 nm wavelength signals to 380/510 nm wavelength signals was used as the calculated results for each sampling time point in the experiment. The calculation of maximum minus minimum was derived from the ratio signal curve.

The percent inhibition rate and ten-point concentration data were fitted to the parametric nonlinear logistic equation by using GraphPad prism to calculate the $IC_{50}$ values of the compounds.

Experimental Results:

The results of the compounds of the Examples of the present invention in the 1321N1-hP2X2/3 receptor cell function calcium ion mobility assay are shown in Table 2:

TABLE 2

| Example No. | 1321N1-hP2X2/3 $IC_{50}$ (nM) |
|---|---|
| 1 | 64390 |
| 30 | 14540 |
| 34 | 25240 |
| 35 | >30000 |
| 40 | 16660 |
| 59 | 32170 |
| 61-A | 6363 |
| 68 | 5629 |
| 78 | 4523 |
| 80 | 3037 |
| 83 | >30000 |

Experimental Conclusion:

The above data indicate that the compounds of the present invention show weak inhibitory effect in the 1321N1-h2X2/3 receptor cell function calcium ion mobility assay.

Test Example 3. Pharmacokinetic Assay in Balb/C Mice

1. Study Objective:

Balb/C mice were used as test animals. The pharmacokinetic behavior of the compounds of Examples was studied in mouse body (plasma) by orally administration at a dose of 5 mg/kg.

2. Experimental Protocol 2.1 Test Compounds:

Compounds of the Examples of the present invention, prepared by the applicant.

2.2 Test Animals:

Male Balb/C mice (6 mice per group), purchased from Shanghai Jiesijie Laboratory Animal Co., LTD, with Certificate No.: SCXK (Shanghai) 2013-0006 N0.311620400001794.

2.3 Formulation of the Compound:

5 g of hydroxyethyl cellulose (HEC, CMC-Na, viscosity: 800-1200 Cps) was weighed and dissolved in 1000 mL of purified water, followed by addition of 10 g of Tween80.

The mixture was mixed well to obtain a clear solution.

2.4 Administration:

After an overnight fast, male Balb/C mice were administered p.o. with the test compound at a dose of 5 mg/kg and a volume of 10 mL/kg.

2.5 Sample Collection:

0.04 mL of blood was taken from the orbit of the mouse before administration and at 0, 0.5, 1, 2, 4, 6, 8 and 24 hours after administration. The samples were stored in EDTA-K2 tubes, and centrifuged for 6 minutes at 4° C., 6000 rpm to separate the plasma. The plasma samples were stored at −80° C.

2.6 Sample process:

1) 160 μL of acetonitrile was added to 20 μL of the plasma sample for precipitation, and then the mixture was centrifuged at 3500×g for 5 to 20 minutes.

2) After the above process, 100 μL of the supernatant was taken to analyze the concentration of the test compound by LC/MS/MS.

2.7 Liquid Chromatography Analysis

Liquid chromatography condition: Shimadzu LC-20AD pump

Mass spectrometry condition: AB Sciex API 4000 mass spectrometer

Chromatographic column: phenomenex Gemiu 5 um C18 50×4.6 mm

Mobile phase: Eluent A was 0.1% formic acid in water, and Eluent B was acetonitrile Flow rate: 0.8 mL/min Elution time: 0-4.0 minutes the eluent is as follows:

| Time/minute | Eluent A | Eluent B |
|---|---|---|
| 0.01 | 90% | 10% |
| 0.5 | 90% | 10% |
| 0.8 | 5% | 95% |
| 2.4 | 5% | 95% |
| 2.5 | 90% | 10% |
| 4.0 | Stop | |

3. Experimental Results and Analysis

The main parameters of pharmacokinetics were calculated by WinNonlin 8.2. The results of pharmacokinetic test in mice are shown in the following Table 3:

TABLE 3

Results of pharmacokinetic test in mice

| Example No. | Pharmacokinetic test (5 mg/kg) Peak time $t_{max}$(h) | Area under curve $AUC_{0-t}$ (ng/mL*h) | Plasma concentration $C_{max}$(ng/mL) | Half life $t_{1/2}$(h) | Average residence time $MRT_{0-\infty}$(h) |
|---|---|---|---|---|---|
| 30 | 0.50 | 10943.63 | 3546.70 | 1.36 | 2.16 |
| 34 | 1.00 | 7584.0 | 2360.0 | 1.4 | 2.3 |
| 61-A | 2.00 | 30539.48 | 3433.3 | 4.60 | 5.60 |
| 68 | 2.00 | 10160.1 | 1826.7 | 1.8 | 3.8 |
| 78 | 1.00 | 5043.0 | 1293.3 | 1.6 | 2.5 |

Note:
0.5% CMC-Na (1% Tween 80)

Experimental Conclusion:

It can be seen from the results of pharmacokinetic test in mice in the table that the compounds of the Examples of the present invention show good pharmacokinetic properties, and both the exposure AUC and maximum plasma concentration Cmax are good.

Test Example 4. Pharmacokinetic Assay in Rats

1. Study Objective:

SD rats were used as test animals. The pharmacokinetic behavior of the compounds of Examples was studied in rat body (plasma) by orally administration at a dose of 5 mg/kg.

2. Experimental Protocol 2.1 Test Compounds:

Compounds of the Examples of the present invention, prepared by the applicant.

2.2 Test Animals:

Male SD rats (3 rats per group), purchased from Shanghai Jiesijie Laboratory Animal Co., LTD, with Certificate No.: SCXK (Shanghai) 2013-0006 N0.311620400001794.

2.3 Formulation of the Compound:

5 g of hydroxyethyl cellulose (HEC, CMC-Na, viscosity: 800-1200 Cps) was weighed and dissolved in 1000 mL of purified water, followed by addition of 10 g of Tween80.

The mixture was mixed well to obtain a clear solution.

2.4 Administration:

After an overnight fast, male SD rats (3 rats per group) were administered p.o. with the test compound at a dose of 5 mg/kg and a volume of 10 mL/kg.

2.5 Sample Collection:

0.2 mL of blood was taken from the jugular vein of the rat before administration and at 0, 0.5, 1, 2, 4, 6, 8 and 24 hours after administration. The samples were stored in EDTA-K2 tubes, and centrifuged for 6 minutes at 4° C., 6000 rpm to separate the plasma. The plasma samples were stored at −80° C.

2.6 Sample Process:

1) 160 μL of acetonitrile was added to 40 μL of the plasma sample for precipitation, and then the mixture was centrifuged at 3500×g for 5 to 20 minutes.

2) After the above process, 100 μL of the supernatant was taken to analyze the concentration of the test compound by LC/MS/MS.

2.7 Liquid Chromatography Analysis

Liquid chromatography condition: Shimadzu LC-20AD pump

Mass spectrometry condition: AB Sciex API 4000 mass spectrometer

Chromatographic column: phenomenex Gemiu 5 um C18 50×4.6 mm

Mobile phase: Eluent A was 0.1% formic acid in water, and Eluent B was acetonitrile Flow rate: 0.8 mL/min Elution time: 0-4.0 minutes, the eluent is as follows:

| Time/minute | Eluent A | Eluent B |
|---|---|---|
| 0.01 | 90% | 10% |
| 0.5 | 90% | 10% |
| 0.8 | 5% | 95% |
| 2.4 | 5% | 95% |
| 2.5 | 90% | 10% |
| 4.0 | Stop | |

3. Experimental Results and Analysis

The main parameters of pharmacokinetics were calculated by WinNonlin 8.2. The results of pharmacokinetic test in rats are shown in the following Table 4:

TABLE 4

Results of pharmacokinetic test in rats

| | Pharmacokinetic test (5 mg/kg) | | | | |
|---|---|---|---|---|---|
| Example No. | Peak time $t_{max}$(h) | Area under curve $AUC_{0-t}$ (ng/mL*h) | Plasma concentration $C_{max}$(ng/mL) | Half life $t_{1/2}$(h) | Average residence time $MRT_{0-\infty}$(h) |
| 34 | 4.00 | 5783 | 904 | 3.5 | 6.2 |
| 61-A | 2.00 | 11977 | 1547 | 8.0 | 5.8 |
| 68 | 4.00 | 9852 | 1877 | 1.8 | 3.5 |
| 78 | 2.00 | 6811 | 1217 | 1.7 | 3.7 |
| 80 | 4.00 | 21252 | 2193 | 11.3 | 13.6 |

Note:
0.5% CMC-Na (1% Tween 80)

4. Experimental Conclusion:

It can be seen from the results of pharmacokinetic test in rats in the table that the compounds of the Examples of the present invention show good pharmacokinetic properties at the dose of 5 mg/kg, and both the exposure AUC and maximum plasma concentration $C_{max}$ are good.

Test Example 5. Assay of Metabolic Stability in Liver Microsome

1. Experimental Objective:

The objective of the experiment is to determine the stability of the compounds of the Examples in liver microsome of mouse, rat, dog and human.

2. Experimental Procedure:

2.1 Formulation of the Working Solution of the Compound

Formulation of the working solution of the compound: The stock solution of the compound was added to phosphate buffer, and the final concentration was 20 μM.

2.2 Formulation of the Working Solution of Liver Microsome

Liver microsome was diluted with 100 mM phosphate buffer to obtain a final concentration of 0.625 mg/mL.

2.3 Formulation of NADPH and UDPGA

NADPH (reduced nicotinamide adenine dinucleotide phosphate) and UDPGA (uridine diphosphate glucuronic acid) were weighed respectively, followed by addition of 100 mM phosphate buffer. The final concentrations were 20 mM.

2.4 Formulation of the Channel-Forming Reagent 1 mg of Alamethicin was weighed, to which 200 μL of DMSO was added to obtain a 5 mg/mL solution. The solution was diluted with phosphate buffer to obtain a final concentration of 50 μg/mL.

2.5 Formulation of the Reaction Stop Solution

Stop solution: Cold acetonitrile containing 100 ng/mL labetalol hydrochloride and 400 ng/mL tolbutamide as internal standards.

2.6 Incubation Procedure

400 μL of the prepared liver microsome, 25 μL of the working solution of the compound and 25 μL of Alamethicin were added to a 96-well plate successively, which was then pre-incubated at 37° C. for 10 min. 50 μL of the prepared NADPH/UDPGA was added to initiate the reaction, and the plate was incubated at 37° C. The total volume of the reaction system was 500 μL. The final contents of the components were as follows:

| Components | Content |
|---|---|
| Liver microsome | 0.5 mg/mL |
| Compound | 1 μM |
| NADPH | 2 mM |
| UDPGA | 2 mM |
| Alamethicin | 2.5 μg/mL |

2.7 Sample Analysis 2.7.1 Chromatographic Conditions:

Instrument: Shimadzu LC-30 AD;

Chromatographic column: XBridge® C18 (50*4.6 mm, particle size: 5 μm);

Mobile phase: A: 0.1% formic acid solution, B: methanol

Eluent gradient: 0.2-1.6 min 5% A to 95% A, 3.0-3.1 min 95% A to 5% A

Running time: 4.0 min.

2.7.2 Mass Spectrometry Conditions:

Instrument: API5500 liquid chromatography-mass spectrometer, AB Sciex;

Ion source: Electrospray ionization source (ESI);

Drying gas: N2, temperature: 500° C.;

Electrospray voltage: 5000V;

Detection method: Positive ion detection;

Scanning mode: Mode of reaction monitoring (MRM).

3. Experimental Results:

TABLE 5

Results of the metabolic stability assay of the compounds of the Examples in liver microsome

| | Mouse | | Rat | | Dog | | Human | |
|---|---|---|---|---|---|---|---|---|
| Example No. | $t_{1/2}$ (min) | Remaining (%, 60 min) | $t_{1/2}$ (min) | Remaining (%, 60 min) | $t_{1/2}$ (min) | Remaining (%, 60 min) | $t_{1/2}$ (min) | Remaining (%, 60 min) |
| 34 | 186.6 | 81.3 | 1735.0 | 104.4 | / | / | ∞ | 113.9 |
| 61-A | 409.1 | 92.5 | 941.8 | 102.3 | 937.5 | 96.0 | ∞ | 100.4 |
| 68 | 165.0 | 91.6 | ∞ | 106.4 | 1352.9 | 99.0 | 1405.4 | 101.2 |
| 78 | 34099.6 | 99.3 | 1964.7 | 98.9 | 671.0 | 93.4 | 884.7 | 97.5 |

4. Experimental Conclusion:

The above data show that the compounds of the Examples of the present invention have good metabolic stability in liver microsome of mouse, rat, dog and human.

Test Example 6. Assay of Plasma Protein Binding Rate

1. Experimental Objective:

The objective of the experiment is to determine the plasma protein binding of the compounds of the Examples in plasma.

2. Experimental Instruments and Materials:

Liquid chromatography-mass spectrometer, centrifuge, vortex mixer, pipette, continuous pipette, 96-well plate, tissue homogenizer (used for tissue sample analysis), 50% aqueous solution of methanol, acetonitrile solution containing internal standard, blank medium (plasma, urine or tissue homogenate, etc.)

3. Experimental Procedure:

3.1 Formulation of the Stock Solution a of the Test Compound

The compound of the Example was formulated into 1 mM solution A with DMSO;

3.2 Formulation of the Plasma Solution B

The solution A was added to the plasma solution to obtain 5 μM solution B;

3.3 Operation Procedure 1) 200 μL of solution B was added to the inside of the membrane;
2) 350 L of PBS was added to the outside of the membrane;
3) Incubation in a water bath at 37° C. for 6 h;
4) The sample was diluted and analyzed by mass spectrometry.

4. Chromatographic Conditions:

Instrument: Shimadzu LC-20 AD;

Chromatographic column: Phenomenex Gemiu® C18 (50*4.6 mm, particle size: 5 μm);

Mobile phase: A: acetonitrile, B: 0.1% formic acid solution; 0~0.5 min: 5% A→90% A, 2.0~2.1 min: 90% A→5% A; flow rate: 0.8 mL/min; running time: 5.0 min; injection volume: 5 μL.

5. Mass Spectrometry Conditions:

Instrument: API4000 liquid chromatography-mass spectrometer, AB Co., USA;

The ion source was electrospray ionization source (ESI);

The temperature of the drying gas (N2) was 500° C.;

The electrospray voltage was 5500V;

The detection method was positive ion detection;

The scanning mode was mode of reaction monitoring (MRM); the scan time was 0.1 is.

6. Experimental Results:

TABLE 6

Results of the plasma protein binding rate assay of the compounds of the Examples

| Example No. | Mouse % Unbound | Rat % Unbound | Dog % Unbound | Human % Unbound |
|---|---|---|---|---|
| 34 | 4.3 | 4.4 | 3.2 | 1.5 |
| 61-A | 4.4 | 2.7 | 3.7 | 1.6 |
| 68 | 16.2 | 11.0 | 8.4 | 6.6 |
| 78 | 8.4 | 6.1 | 14.7 | 10.3 |
| 80 | 25.6 | 23.4 | 13.5 | 13.5 |

7. Experimental Conclusion:

The above data show that the compounds of the Examples of the present invention have high plasma protein binding rate with little species variation.

Test Example 7. CYP Enzyme Single-Point Inhibition Assay

1. Experimental Objective

The inhibition of the compounds on CYP450 enzyme isoformwas rapidly predicted by single-point method using human liver microsome incubation system.

2. Experimental Procedure 2.1 Solution Formulation 2.5 mM NADPH: 4.165 mg of NADPH (reduced nicotinamide adenine dinucleotide phosphate) was weighed, followed by addition of 100 mM phosphate buffer to 2 mL. 0.25 mg/mL microsome solution: 4 mL of 100 mM phosphate buffer was added to 50 μL of 20 mg/mL microsome solution and mixed well.

Formulation of the reaction solution of the test compound:

The test compound of the Example was weighed, diluted to 10 mM with DMSO and then to 100 μM with 100 mM phosphate buffer.

2.2 Experimental Procedure:

1. 40 μL of liver microsome, 10 μL of substrate and 10 μL of the test compound were added to a 96-well plate and pre-incubated for 3 min.
2. 40 μL of NADPH was added.
3. 300 μL of acetonitrile stop solution containing internal standard was added at 20 min.
4. The sample was centrifuged and injected.

3. Experimental Results:

TABLE 7

Results of the CYP enzyme single-point inhibition assay of the compounds of the Examples

| | $IC_{50}$ (μM) | | | | | |
|---|---|---|---|---|---|---|
| Compound | 1A2 | 2C9 | 2C19 | 2D6 | 3A4-M | 3A4-T |
| 34 | 24.9 | >100 | >100 | >100 | >100 | >100 |
| 61-A | 72.1 | >100 | >100 | >100 | >100 | >100 |
| 68 | >100 | >100 | >100 | >100 | >100 | >100 |
| 78 | >100 | >100 | >100 | >100 | >100 | >100 |

Note:
Strong inhibition: $IC_{50}$ < 1 μM; moderate inhibition: 1 μM < $IC_{50}$ < 10 μM; weak inhibition: $IC_{50}$ > 10 μM 4. Experimental Conclusion:

The above data show that the compounds of the Examples of the present invention have no strong inhibition on CYP enzyme isoforms, and the risk of DDI is low.

Test Example 8. hERG Potassium Channel Inhibition Activity Assay

1. Cell Preparation 7.1.1 CHO-hERG cells were cultured in a 175 $cm^2$ culture flask. After the cell density reached 60-80%, the culture solution was removed. The cells were washed with 7 mL of PBS once, and dissociated with 3 mL of Detachin.

7.1.2 After completion of dissociation, the cells were neutralized with 7 mL of culture solution. The solution was centrifuged, and the supernate was removed. The cells were resuspended in 5 mL of culture solution. The cell indensity is ensured as 2~5×$10^6$/mL.

2. Solution Formulation

TABLES 8

| Components of intracellular and extracellular fluids | | |
|---|---|---|
| Reagents | Extracellular fluid (mM) | Intracellular fluid (mM) |
| $CaCl_2$ | 2 | 5.374 |
| $MgCl_2$ | 1 | 1.75 |
| KCl | 4 | 120 |
| NaCl | 145 | — |
| Glucose | 10 | — |
| HEPES | 10 | 10 |
| EGTA | — | 5 |
| Na-ATP | — | 4 |
| pH | 7.40 (adjusted with NaOH), Osmolarity~305 mOsm | 7.25 (adjusted with KOH), Osmolarity~290 mOsm |

3. Electrophysiological Recording Process

Single cell sealing impedance and formation of whole-cell mode were automatically performed by Qpatch instrument. After obtaining the whole-cell recording mode, the cell was clamped at −80 mV. The cell first underwent pre-voltage of −50 mV for 50 msec, then underwent depolarization stimulation at +40 mV for 5 sec, and then underwent repolarization at −50 mV for 5 sec, and then the voltage returned to −80 mV The cell underwent the stimulation at the voltage every 15 sec. The data were recorded for 2 min, then extracellular fluid was administrated, and then the data were recorded for 5 min. Then, the administration process begun. The concentration of the test compound started from the lowest concentration, and each test concentration was administrated for 2.5 min. At least three cells (n≥3) were tested for each concentration.

4. Compound Formulation 4.1 20 mM mother liquor of the compound was diluted with extracellular fluid. 2495 L of extracellular fluid was added to 5 μL of 20 mM mother liquor of the compound to obtain a concentration of 40 μM (500-fold dilution). The solution was subjected to a 3-fold serial dilution with extracellular fluid containing 0.2% DMSO to obtain a required final concentration.

4.2 The highest test concentration was 40 μM. The 6 concentrations were 40, 13.33, 4.44, 1.48, 0.49 and 0.16 μM.

4.3 The DMSO content in the final test concentration did not exceed 0.2%. This concentration of DMSO had no effect on hERG potassium channel.

5. Data Analysis

The experimental data was analyzed by XLFit software.

6. Quality Control

Environment: humidity 20~50%, temperature 22-25° C.

Reagents: the reagents used were purchased from Sigma, with a purity of >98%

The experimental data in the report must meet the following criteria:

Whole cell sealing impedance >100 MΩ

Tail current amplitude >400 pA

Pharmacological Parameters:

The inhibition effect of Cisapride at multiple concentrations on hERG channel was used as the positive control.

7. Experimental Results:

TABLE 9

| Results of inhibition effect of the compounds of the Examples at multiple concentrations on hERG current | |
|---|---|
| Example No. | hERG $IC_{50}$ (uM) |
| 61-A | >10 |
| 68 | 18.38 |
| 78 | >10 |
| 80 | >20 |

8. Experimental Conclusion:

Inhibition of cardiac hERG potassium channel by drug is the main cause of drug-induced QT prolongation syndrome. It can be seen from the experimental results that the compounds of the Examples of the present invention have no obvious inhibition effect on cardiac hERG potassium channel. Cardiotoxic effects at high doses can thus be avoided.

Test Example 9. Taste Sensitivity Assay in BALB/c Mice

1. Experimental Objective:

In this assay, compounds with less toxic and side effects on animal taste were screened by quinine bitter solution experiment.

2. Main Experimental Instruments and Materials 2.1 Instruments:

1. Ultra-clean workbench (CJ-2F, Suzhou Fengshi Laboratory Animal Equipment Co., Ltd);
2. Electronic balance (CPA2202D, Sartorius);
3. Electronic balance (BSA2202S-CW, Sartorius);
4. Pure water maker (Pacific TII, Thermo).

2.2 Reagents:

Quinine monohydrochloride dihydrate (6119-47-7, Adamas).

2.3 Animals:

BALB/c mice, 6 to 8 weeks old, ♂, purchased from Shanghai SIPPR-BK Laboratory Animal Co., Ltd.

3. Experimental Procedure:

3.1 Animal Screening

One day before the experiment, all BALB/c mice were weighed, and animals with too high or too low body weight were excluded.

3.2 Grouping and Water Deprivation

BALB/c mice were randomly grouped according to body weight, and were deprived of water 12 to 16 hours before administration with no fasting.

3.3 Formulation of Aqueous Solution of Quinine

An appropriate amount of quinine monohydrochloride dihydrate was weighed and formulated into an aqueous solution quinine hydrochloride (concentration: 3 mmol/L) with ultrapure water for later use.

3.4 Formulation of Test Compound

An appropriate amount of the test compound was weighed and formulated into the target concentration with the corresponding solvent according to the experimental design for later use.

3.5 Administration and Quinine Solution Intake Assay in Animal

Administration and fasting: On the day of the experiment, the animals were weighed and fasted, bedding was changed, and the compounds were administered according to the experimental design.

Quinine Solution Intake Assay:

1. The corresponding clean mouse drinking bottle was rinsed 2 to 3 times with ultrapure water and the formulated 3 mmol/L aqueous solution of quinine hydrochloriderespectively. The bottle was filled and weighed, and the weight was recorded as $Wi_0$.

2. According to the experimental design, a certain period after administration, the filled bottle was gently placed in the corresponding mouse cage, and the timing was started. After 30 min, the bottle was gently taken out and weighed, and the weight was recorded as $Wi_{30}$.
3. Calculation of solution consumption of animals in each group: $\Delta WW(g)=Wi_{30}-Wi_0$; calculation of solution consumption of single mouse: $\Delta pWW(g)=\Delta WW/N$, N is the number of animals in each group.
4. Dysgeusia rate=(ΔpWW of the group in which the drinking water was the aqueous solution of quinine hydrochlorideand the test compound was administered at the same time−ΔpWW of the group in which the drinking water was aqueous solution of quinine hydrochlorideand the solvent control was administered at the same time)/(ΔpWW of the group in which the drinking water was ultrapure water and the solvent control was administered at the same time−ΔpWW of the group in which the drinking water was aqueous solution of quinine hydrochloride and the solvent control was administered at the same time)×100%. Data processing was performed with software such as Excel.
5. The animals were euthanized after completion of the experiment.

4. Experimental Results:

TABLE 10

Results of the taste sensitivity assay of the compounds of the Examples

| Compound | Solution consumption of single mouse (g) Ultrapure water | Quinine solution | Dysgeusia rate |
|---|---|---|---|
| Solvent group (20% HP-B-CD) | 0.598 | / | / |
| Solvent group (20% HP-B-CD) | / | 0.068 | / |
| 61-A @30 mpk | / | 0.048 | −3.77% |
| 68 @30 mpk | / | 0.056 | −2.26% |
| 78 @30 mpk | / | 0.016 | −9.81% |

5. Experimental Conclusion:

It can be seen from the above results that the compounds of the present application have low toxic and side effects on the taste of mice.

Test Example 10. Pharmacodynamic Study on Citric Acid-Induced Acute Cough of Guinea Pigs 1. Experimental Objective The objective of this experiment is to evaluate the efficacy of the compounds on a citric acid-induced acute cough model of guinea pigs.

2. Experimental Instruments and Reagents 2.1 Key Instruments

| Instrument name | Manufacturer | Model/Specification | Device number |
|---|---|---|---|
| WBP | DSI | Whole Body Plethysmography | 100301, 100249 |
| Electronic balance | Changzhou Tianzhiping Instrument Equipment Co., Ltd. | EL-2KL | 6072710 |
| Ultrasonic cell poulverizer | Ningbo Scientz Biotechnology Co., Ltd. | SCIENTZ-IID | 10192149 |
| Electronic balance | Mettler Toledo | MS205DL | B844687071 |
| Pipette | Eppendorf | 5 mL | I19578I |
| Pipette | Eppendorf | 1000 μL | Q12774H |
| Pipette | Eppendorf | 200 μL | L33188I |
| Pipette | Eppendorf | 100 μL | R12555H |

2.2 Key Reagents

| Reagent name | Manufacturer | Article number |
|---|---|---|
| Sodium carboxymethyl cellulose | Sigma | C5678 |
| Tween 80 | Sigma | P4780 |
| ATP | Sigma | A2383 |
| Citric acid | Sigma | C2404 |

3. Experimental Operation and Data Processing:

3.1 Animals

Hartley Guinea Pigs, male, purchased from Beijing Vital River Laboratory Animal Technology Co., Ltd.

3.2 Experimental Procedure

The animals were adaptively feed. After their body weight reached the standard (300 to 400 g), the animals were serially numbered and randomly grouped according to their body weight.

Cough induction method: The guinea pig was put into the whole body plethysmography box to adapt for 3-5 minutes. ATP atomization was performed for 2 minutes. After an interval of 3 minutes, citric acid atomization was performed for 5 minutes. From the beginning of citric acid atomization, the number of coughs and the cough latency of the animals were recorded within 10 min.

3.3 Administration Regimen and Monitoring of Cough Indicators

The test compound was administered to the guinea pig by a single gavage 2 hours before citric acid atomization. The guinea pig was put into the respiratory plethysmography chamber of the DSI Buxco whole body plethysmography (WBP) at the predetermined time, and subjected to cough induction by citric acid atomization. From the beginning of citric acid atomization, the total number of coughs (CCnt) and cough latency (CIP) in the guinea pig within 10 minutes were recorded by the WBP system.

3.4 Data Processing

All data were entered into Excel files and expressed as mean±standard error. The data of each group were analyzed and compared by one-way ANOVA. If the statistical analysis results showed $p<0.05$, then there was a significant difference. Pairwise comparisons were carried out by t-test method to compare the differences.

The results show that the compounds of the Examples of the present invention can effectively improve cough symptoms in the citric acid-induced acute cough model of guinea pigs, and the reduction rate of the total number of coughs is over 59%.

What is claimed is:

1. A compound of formula (I), a stereoisomer thereof or a pharmaceutically acceptable salt thereof:

(I)

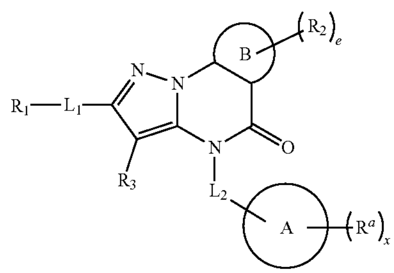

wherein:

$L_1$ is selected from the group consisting of a bond, $-(CH_2)_{n1}-$, $-(CH_2)_{n1}C(O)(CR_{aa}R_{bb})_{n2}-$, $-(CH_2)_{n1}C(O)NR_{aa}(CH_2)_{n2}-$, $-(CH_2)_{n1}(CR_{aa}R_{bb})_{n2}-$, $-(CR_{aa}R_{bb})_{n1}O(CH_2)_{n2}-$, $-(CH_2)_{n1}O(CR_{aa}R_{bb})_{n2}-$, $-(CR_{aa}R_{bb})_{n1}S(CH_2)_{n2}-$, $-(CH_2)_{n1}S(CR_{aa}R_{bb})_{n2}-$, $-(CR_{aa}R_{bb})_{n1}(CH_2)_{n2}NR_{cc}-$, $-(CH_2)_{n1}NR_{aa}(CR_{bb}R_{cc})_{n2}-$, $-(CH_2)_{n1}NR_{aa}C(O)-$, $-(CH_2)_{n1}P(O)R_{aa}-$, $-(CH_2)_{n1}S(O)_{n2}-$, $-(CH_2)_{n1}S(O)_{n2}NR_{aa}-$ and $-(CH_2)_{n1}NR_{aa}S(O)_{n2}-$;

$R_{aa}$, $R_{bb}$, $R_{cc}$ are each independently selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

or, any two of $R_{aa}$, $R_{bb}$, $R_{cc}$ are bonded to form a cycloalkyl, heterocyclyl, aryl or heteroaryl, wherein the cycloalkyl, heterocyclyl, aryl or heteroaryl can be optionally further substituted;

$L_2$ is selected from the group consisting of $-(CH_2)_{n3}C(O)(CR_{dd}R_{ee})_{n4}-$, $-(CH_2)_{n3}C(O)NR_{dd}(CH_2)_{n4}-$, $-(CR_{dd}R_{ee})_{n3}O(CH_2)_{n4}-$, $-(CH_2)_{n3}O(CR_{dd}R_{ee})_{n4}-$, $-(CR_{dd}R_{ee})_{n3}S(CH_2)_{n4}-$, $-(CH_2)_{n3}S(CR_{dd}R_{ee})_{n4}-$, $-(CR_{dd}R_{ee})_{n3}(CH_2)_{n4}NR_{ff}-$, $-(CH_2)_{n3}NR_{dd}(CR_{ee}R_{ff})_{n4}-$, $-(CH_2)_{n3}NR_{dd}C(O)-$, $-(CH_2)_{n3}P(O)R_{dd}-$, $-(CH_2)_{n3}S(O)_{n4}-$, $-(CH_2)_{n3}S(O)_{n4}NR_{dd}-$ and $-(CH_2)_{n3}NR_{dd}S(O)_{n4}-$;

$R_{dd}$, $R_{ee}$, $R_{ff}$ are each independently selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

or, any two of $R_{dd}$, $R_{ee}$, $R_{ff}$ are bonded to form a cycloalkyl, heterocyclyl, aryl or heteroaryl, wherein the cycloalkyl, heterocyclyl, aryl or heteroaryl can be optionally further substituted;

ring A is selected from the group consisting of cycloalkyl, heterocyclyl, aryl and heteroaryl;

$R_1$ is selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

ring B is selected from the group consisting of cycloalkyl, heterocyclyl and heteroaryl;

$R_2$ is selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

$R_3$ is selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl and heteroaryl can be each optionally further substituted;

$R^a$ is selected from the group consisting of hydrogen, deuterium, halogen, amino, nitro, hydroxy, cyano, oxo, thioxo, alkyl, deuterated alkyl, haloalkyl, hydroxyalkyl, alkoxy, haloalkoxy, alkenyl, alkynyl, heterocyclylalkyl, cycloalkyl, heterocyclyl, aryl, heteroaryl, $—(CH_2)_{n5}R_{gg}$, $—(CH_2)_{n5}OR_{gg}$, $—(CH_2)_{n5}C(O)OR_{gg}$, $—(CH_2)_{n5}SR_{gg}$, $—(CH_2)_{n5}NR_{gg}C(O)(CH_2)_{n6}R_{hh}$, $—(CH_2)_{n5}NR_{gg}C(O)OR_{hh}$, $—(CH_2)_{n5}NR_{gg}C(O)NR_{hh}R_{ii}$, $—(CH_2)_{n5}NR_{gg}R_{hh}$, $—NR_{gg}(CH_2)_{n5}R_{hh}$, $—(CH_2)_{n5}C(O)NR_{gg}(CH_2)_{n6}R_{hh}$, $—(CH_2)_{n5}S(O)_{n6}R_{gg}$, $—(CH_2)_{n5}NR_{gg}S(O)_{n6}R_{hh}$, $—CH{=}CH(CH_2)_{n5}R_{gg}$, $—CH{=}CH(CH_2)_{n5}NR_{gg}R_{hh}$, $—CH{=}CH(CH_2)_{n5}NR_{gg}C(O)R_{hh}$ and $—CH{=}CH(CH_2)_{n5}NR_{gg}C(O)NR_{hh}R_{ii}$, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl and heteroaryl can be each optionally further substituted;

$R_{gg}$, $R_{hh}$, $R_{ii}$ are each independently selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

or, any two of $R_{gg}$, $R_{hh}$, $R_{ii}$ are bonded to form a cycloalkyl, heterocyclyl, aryl or heteroaryl, wherein the cycloalkyl, heterocyclyl, aryl or heteroaryl can be optionally further substituted;

x is an integer from 0 to 6;

e is an integer from 0 to 6;

n1, n3, and n5 are each independently an integer from 0 to 3; and n2, n4, and n6 are each independently an integer from 0 to 2.

2. The compound, a stereoisomer thereof or a pharmaceutically acceptable salt thereof according to claim 1, wherein $L_1$ is selected from the group consisting of a bond, $—(CH_2)_{n1}—$, $—(CH_2)_{n1}C(O)(CR_{aa}R_{bb})_{n2}—$, $—(CH_2)_{n1}C(O)NR_{aa}(CH_2)_{n2}—$, $—(CH_2)_{n1}(CR_{aa}R_{bb})_{n2}—$, $—(CR_{aa}R_{bb})_{n1}O(CH_2)_{n2}—$, $—(CH_2)_{n1}O(CR_{aa}R_{bb})_{n2}—$, $—(CR_{aa}R_{bb})_{n1}S(CH_2)_{n2}—$, $—(CH_2)_{n1}S(CR_{aa}R_{bb})_{n2}—$, $—(CR_{aa}R_{bb})_{n1}(CH_2)_{n2}NR_{cc}—$, $—(CH_2)_{n1}NR_{aa}(CR_{bb}R_{cc})_{n2}—$, $—(CH_2)_{n1}NR_{aa}C(O)—$, $—(CH_2)_{n1}P(O)R_{aa}—$, $—(CH_2)_{n1}S(O)_{n2}—$, $—(CH_2)_{n1}S(O)_{n2}NR_{aa}—$ and $—(CH_2)_{n1}NR_{aa}S(O)_{n2}—$;

$R_{aa}$, $R_{bb}$, $R_{cc}$ are each independently selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

or, any two of $R_{aa}$, $R_{bb}$, $R_{cc}$ are bonded to form a $C_{3-12}$ cycloalkyl, 3 to 12 membered heterocyclyl, $C_{6-14}$ aryl or 5 to 14 membered heteroaryl, wherein the $C_{3-12}$ cycloalkyl, 3 to 12 membered heterocyclyl, $C_{6-14}$ aryl or 5 to 14 membered heteroaryl is optionally substituted by one or more substituents selected from the group consisting of deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

n1 is an integer from 0 to 3; and n2 is an integer from 0 to 2.

3. The compound, a stereoisomer thereof or a pharmaceutically acceptable salt thereof according to claim 1, wherein $L_2$ is selected from the group consisting of $—(CH_2)_{n3}C(O)(CR_{dd}R_{ee})_{n4}—$, $—(CH_2)_{n3}C(O)NR_{dd}(CH_2)_{n4}—$, $—(CR_{dd}R_{ee})_{n3}O(CH_2)_{n4}—$, $—(CH_2)_{n3}O(CR_{dd}R_{ee})_{n4}—$, $—(CR_{dd}R_{ee})_{n3}S(CH_2)_{n4}—$, $—(CH_2)_{n3}S(CR_{dd}R_{ee})_{n4}—$, $—(CR_{dd}R_{ee})_{n3}(CH_2)_{n4}NR_{ff}—$, $—(CH_2)_{n3}NR_{dd}(CR_{ee}R_{ff})_{n4}—$, $—(CH_2)_{n3}NR_{dd}C(O)—$, $—(CH_2)_{n3}P(O)R_{dd}—$, $—(CH_2)_{n3}S(O)_{n4}—$, $—(CH_2)_{n3}S(O)_{n4}NR_{dd}—$ and $—(CH_2)_{n3}NR_{dd}S(O)_{n4}—$;

$R_{dd}$, $R_{ee}$, $R_{ff}$ are each independently selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

or, any two of $R_{dd}$, $R_{ee}$, $R_{ff}$ are bonded to form a $C_{3-12}$ cycloalkyl, 3 to 12 membered heterocyclyl, $C_{6-14}$ aryl or 5 to 14 membered heteroaryl, wherein the $C_{3-12}$ cycloalkyl, 3 to 12 membered heterocyclyl, $C_{6-14}$ aryl or 5 to 14 membered heteroaryl is optionally substituted by one or more substituents selected from the group consisting of deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

n3 is an integer from 0 to 3; and n4 is an integer from 0 to 2.

4. The compound, a stereoisomer thereof or a pharmaceutically acceptable salt thereof according to claim 1, wherein ring A is selected from the group consisting of $C_{3-8}$ cycloalkyl, 3 to 12 membered heterocyclyl, $C_{6-14}$ aryl and 5 to 14 membered heteroaryl.

5. The compound, a stereoisomer thereof or a pharmaceutically acceptable salt thereof according to claim 1, wherein $R_1$ is selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl, $C_{6-14}$ aryloxy, 5 to 14 membered heteroaryl and 5 to 14 membered heteroaryloxy, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl, $C_{6-14}$ aryloxy, 5 to 14 membered heteroaryl and 5 to 14 membered heteroaryloxy are each optionally substituted by one or more substituents selected from the group consisting of deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl, $C_{6-14}$ aryloxy, 5 to 14 membered heteroaryl, 5 to 14 membered heteroaryloxy, $-(CH_2)_{m1}OR_a$, $-(CH_2)_{m1}SR_a$, $-(CH_2)_{m1}C(O)R_a$, $-(CH_2)_{m1}NR_aR_b$, $-(CH_2)_{m1}C(O)NR_aR_b$, $-(CH_2)_{m1}NR_aC(O)R_b$ and $-(CH_2)_{m1}S(O)_{m2}R_a$;

$R_a$ and $R_b$ are each independently selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

or, $R_a$ and $R_b$ are bonded to form a $C_{3-12}$ cycloalkyl, 3 to 12 membered heterocyclyl, $C_{6-14}$ aryl or 5 to 14 membered heteroaryl, wherein the $C_{3-12}$ cycloalkyl, 3 to 12 membered heterocyclyl, $C_{6-14}$ aryl or 5 to 14 membered heteroaryl is optionally substituted by one or more substituents selected from the group consisting of deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

m1 is an integer from 0 to 3; and m2 is an integer from 0 to 2.

6. The compound, a stereoisomer thereof or a pharmaceutically acceptable salt thereof according to claim 1, wherein $R_2$ is selected from the group consisting of hydrogen, deuterium, halogen, amino, hydroxy, cyano, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl and 5 to 14 membered heteroaryl.

7. The compound, a stereoisomer thereof or a pharmaceutically acceptable salt thereof according to claim 1, wherein, $R_3$ is selected from the group consisting of hydrogen, deuterium, halogen, amino, hydroxy, cyano, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl and 5 to 14 membered heteroaryl.

8. The compound, a stereoisomer thereof or a pharmaceutically acceptable salt thereof according to claim 1, wherein, $R^a$ is selected from the group consisting of hydrogen, deuterium, halogen, amino, hydroxy, cyano, oxo, thioxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl, 5 to 14 membered heteroaryl, $-(CH_2)_{n5}R_{gg}$, $-(CH_2)$ n5OR$_{gg}$, $-(CH_2)_{n5}C(O)OR_{gg}$, $-(CH_2)_{n5}SR_{gg}$, $-(CH_2)_{n5}NR_{gg}C(O)(CH_2)_{n6}R_{hh}$, $-(CH_2)_{n5}NR_{gg}C(O)OR_{hh}$, $-(CH_2)_{n5}NR_{gg}C(O)NR_{hh}R_{ii}$, $(CH_2)_{n5}NR_{gg}R_{hh}$, $-NR_{gg}(CH_2)_{n5}R_{hh}$, and $-(CH_2)_{n5}C(O)NR_{gg}(CH_2)_{n6}R_{hh}$;

$R_{gg}$, $R_{hh}$, $R_{ii}$ are each independently selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

or, any two of $R_{gg}$, $R_{hh}$, $R_{ii}$ are bonded to form a $C_{3-12}$ cycloalkyl, 3 to 12 membered heterocyclyl, $C_{6-14}$ aryl or 5 to 14 membered heteroaryl, wherein the $C_{3-12}$ cycloalkyl, 3 to 12 membered heterocyclyl, $C_{6-14}$ aryl or 5 to 14 membered heteroaryl is optionally substituted by one or more substituents selected from the group consisting of deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

n5 is an integer from 0 to 3; and n6 is an integer from 0 to 2.

9. The compound, a stereoisomer thereof or a pharmaceutically acceptable salt thereof according to claim 1, wherein ring B is shown as following:

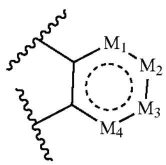

wherein:

$M_1$, $M_2$, $M_3$ and $M_4$ are each independently selected from the group consisting of —$CR_{A1}$—, —C(O)—, —N—, —$CR_{A1}R_{A2}$— and —$NR_{A3}$—; and at least one of $M_1$, $M_2$, $M_3$ and $M_4$ is N;

$R_{A1}$, $R_{A2}$, $R_{A3}$ are each independently selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted.

10. The compound, a stereoisomer thereof or a pharmaceutically acceptable salt thereof according to claim 9, wherein, $M_1$ is N, and $M_2$, $M_3$ and $M_4$ are each independently $CR_{A1}$;

$R_{A1}$ is selected from the group consisting of hydrogen, deuterium, halogen, amino, hydroxy, cyano, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 8 membered heterocyclyl containing 1 to 3 atoms selected from the group consisting of N, O and S, $C_{6-10}$ aryl and 5 to 10 membered heteroaryl containing 1 to 3 atoms selected from the group consisting of N, O and S.

11. The compound, a stereoisomer thereof or a pharmaceutically acceptable salt thereof according to claim 1, wherein ring B is shown as following:

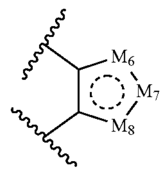

wherein:

$M_6$, $M_7$ and $M_8$ are each independently selected from the group consisting of —$CR_{A4}$—, —C(O)—, —N—, —O—, —S—, —$CR_{A4}R_{A5}$— and —$NR_{A6}$—;

$R_{A4}$, $R_{A5}$, $R_{A6}$ are each independently selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted.

12. The compound, a stereoisomer thereof or a pharmaceutically acceptable salt thereof according to claim 1, wherein, ring A is selected from

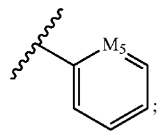

;

$M_5$ is selected from the group consisting of —N— and —$CR_4$—;

$R_4$ is selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_6$-14 aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-12}$ aryl and 5 to 12 membered heteroaryl.

13. The compound, a stereoisomer thereof or a pharmaceutically acceptable salt thereof according to claim 1, wherein the compound is further shown as formula (II):

(II)

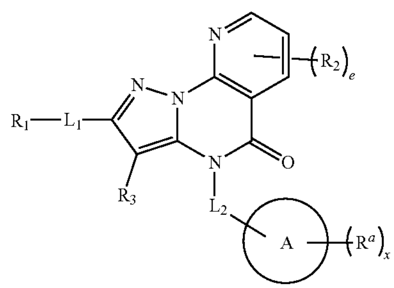

wherein e is an integer from 0 to 3.

14. The compound, a stereoisomer thereof or a pharmaceutically acceptable salt thereof according to claim 13, wherein the compound is further shown as formula (III):

(III)

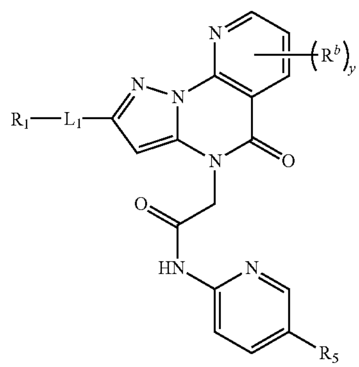

wherein:

$R_5$ is selected from the group consisting of hydrogen, deuterium, halogen, amino, hydroxy, cyano, oxo, thioxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl and 5 to 14 membered heteroaryl;

$R^b$ is selected from the group consisting of hydrogen, deuterium, halogen, amino, hydroxy, cyano, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl and 5 to 14 membered heteroaryl; and y is an integer from 0 to 3.

15. The compound, a stereoisomer thereof or a pharmaceutically acceptable salt thereof according to claim 14, wherein the compound is further shown as formula (IV):

(IV)

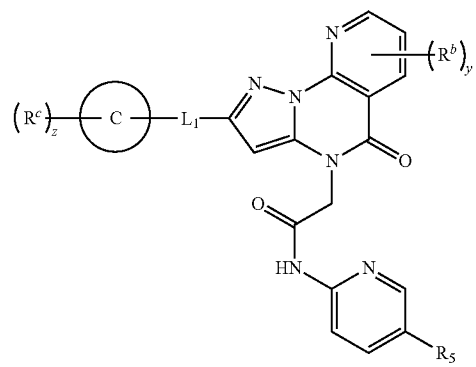

wherein:

ring C is selected from the group consisting of $C_{3-12}$ cycloalkyl, 3 to 12 membered heterocyclyl, $C_{6-14}$ aryl and 5 to 14 membered heteroaryl, or ring C is absent;

$R^c$ is selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl, $C_{6-14}$ aryloxy, 5 to 14 membered heteroaryl, 5 to 14 membered heteroaryloxy, $—(CH_2)_{m3}OR_c$, $—(CH_2)_{m3}SR_c$, $—(CH_2)_{m3}C(O)R_c$, $—(CH_2)_{m3}NR_cR_d$, $—(CH_2)_{m3}C(O)NR_cR_d$, $—(CH_2)_{m3}NR_cC(O)R_d$ and $—(CH_2)_{m3}S(O)_{m4}R_c$, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl, $C_{6-14}$ aryloxy, 5 to 14 membered heteroaryl and 5 to 14 membered heteroaryloxy are each optionally substituted by one or more substituents selected from the group consisting of deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl, $C_{6-14}$ aryloxy, 5 to 14 membered heteroaryl and 5 to 14 membered heteroaryloxy;

$R_c$ and $R_d$ are each independently selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

or, $R_c$ and $R_d$ are bonded to form a $C_{3-12}$ cycloalkyl, 3 to 12 membered heterocyclyl, $C_{6-14}$ aryl or 5 to 14 membered heteroaryl, wherein the $C_{3-12}$ cycloalkyl, 3 to 12 membered heterocyclyl, $C_{6-14}$ aryl or 5 to 14 membered heteroaryl is optionally substituted by one or more substituents selected from the group consisting of deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-14}$ aryl and 5 to 14 membered heteroaryl;

m3 is an integer from 0 to 3;

m4 is an integer from 0 to 2; and z is an integer from 0 to 6.

16. The compound, a stereoisomer thereof or a pharmaceutically acceptable salt thereof according to claim 13, wherein the compound is further shown as formula (V):

(V)

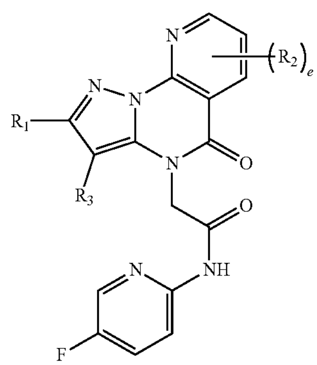

wherein:

$R_1$ is selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of deuterium, halogen, amino, hydroxy, cyano, nitro, oxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-12}$ aryl and 5 to 12 membered heteroaryl;

$R_2$ is selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl and 5 to 14 membered heteroaryl are each optionally substituted by one or more substituents selected from the group consisting of deuterium, halogen, amino, hydroxy, cyano, nitro, oxo, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3 to 12 membered heterocyclyl, $C_{6-12}$ aryl and 5 to 12 membered heteroaryl;

$R_3$ is selected from the group consisting of hydrogen, deuterium, halogen, amino, hydroxy, cyano, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{3-8}$ cycloalkyl, 3 to 12 membered heterocyclyl, $C_{6-14}$ aryl and 5 to 14 membered heteroaryl; and e is an integer from 0 to 3.

17. The compound, a stereoisomer thereof or a pharmaceutically acceptable salt thereof according to claim 16, wherein:

$R_1$ is selected from the group consisting of hydrogen, deuterium, halogen, amino, hydroxy, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3 to 12 membered heterocyclyl, $C_{6-14}$ aryl and 5 to 14 membered heteroaryl, wherein the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-8}$ cycloalkyl, 3 to 8 membered heterocyclyl, $C_{6-10}$ aryl and 5 to 10 membered heteroaryl are each optionally substituted by one or more substituents selected from the group consisting of deuterium, halogen, amino, hydroxy, cyano, nitro, oxo, $C_{1-3}$ alkyl, $C_{2-3}$ alkenyl, $C_{2-3}$ alkynyl, $C_{1-3}$ deuterated alkyl, $C_{1-3}$ haloalkyl, $C_{1-3}$ alkoxy, $C_{1-3}$ haloalkoxy, $C_{1-3}$ hydroxyalkyl, cyano-substituted $C_{1-3}$ alkyl, $C_{3-8}$ cycloalkyl, 3 to 8 membered heterocyclyl, $C_{6-10}$ aryl and 5 to 10 membered heteroaryl;

$R_2$ is selected from the group consisting of hydrogen, deuterium, halogen, amino, hydroxy, cyano, nitro, $C_{1-3}$ alkyl, $C_{2-3}$ alkenyl, $C_{2-3}$ alkynyl, $C_{1-3}$ deuterated alkyl, $C_{1-3}$ haloalkyl, $C_{1-3}$ alkoxy, $C_{1-3}$ haloalkoxy, $C_{1-3}$ hydroxyalkyl, $C_{3-8}$ cycloalkyl, 3 to 8 membered heterocyclyl, $C_{6-10}$ aryl and 5 to 10 membered heteroaryl;

$R_3$ is selected from the group consisting of hydrogen, deuterium, halogen, amino, hydroxy, cyano, $C_{1-3}$ alkyl, $C_{2-3}$ alkenyl, $C_{2-3}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-8}$ cycloalkyl, 3 to 8 membered heterocyclyl, $C_{6-10}$ aryl and 5 to 10 membered heteroaryl; and e is an integer from 0 to 3.

18. A compound, a stereoisomer thereof or a pharmaceutically acceptable salt thereof, wherein the specific structure of the compound is as follows:

1

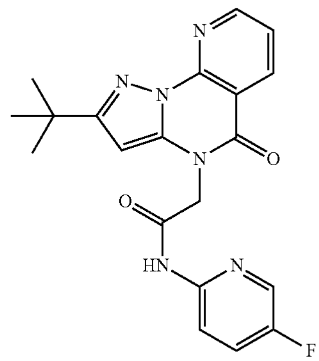

-continued
2
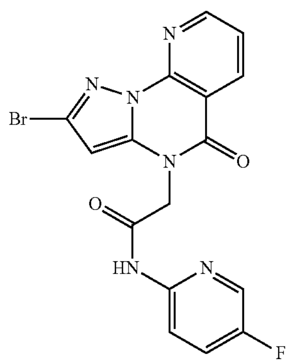
3
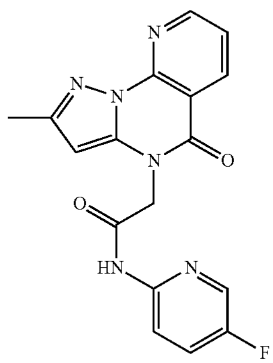
4
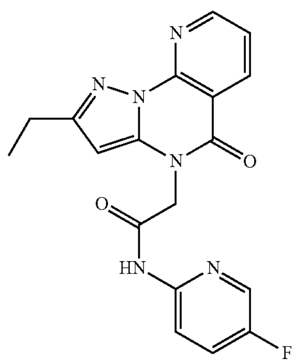
5
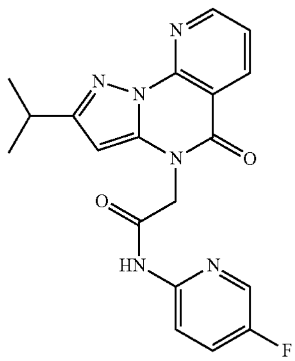
-continued
6
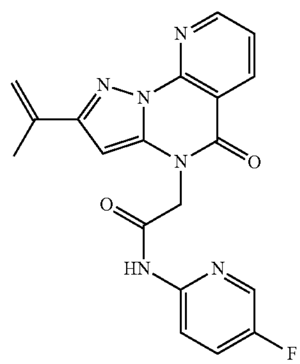
7
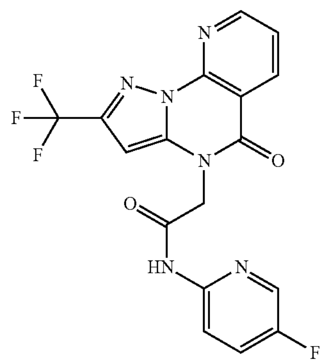
8
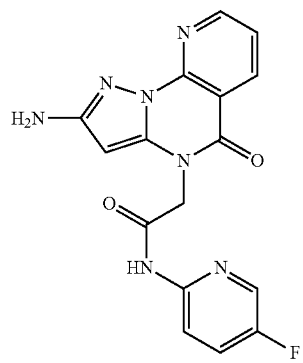
9
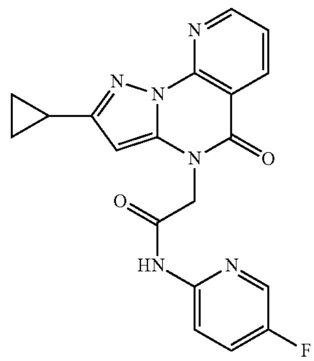

10
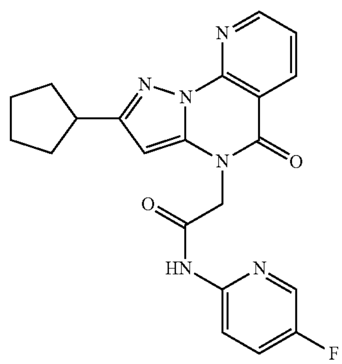
11
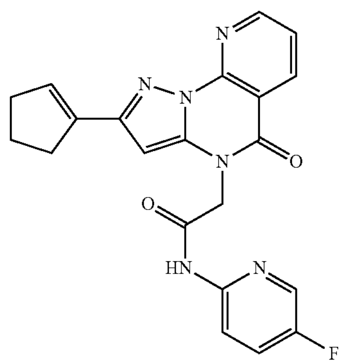
12
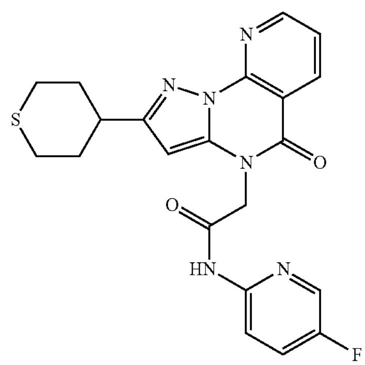
13
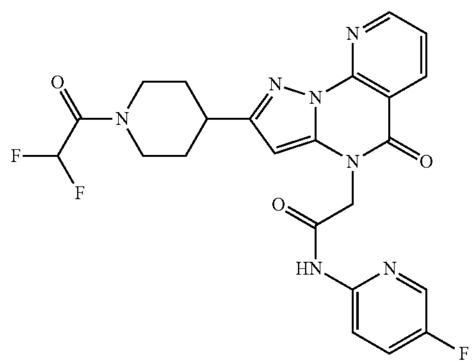
14
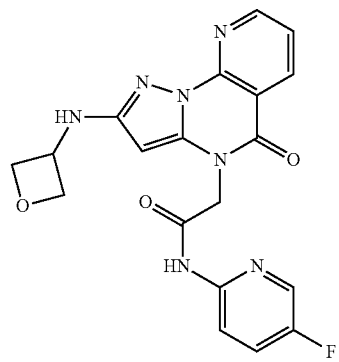
15
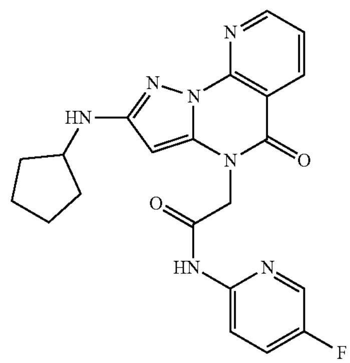
16
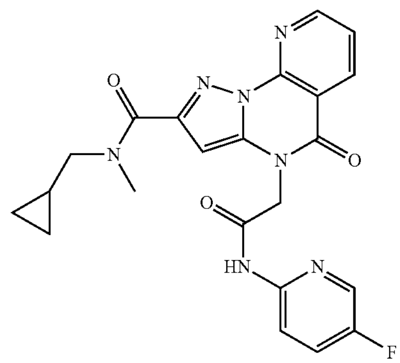
17
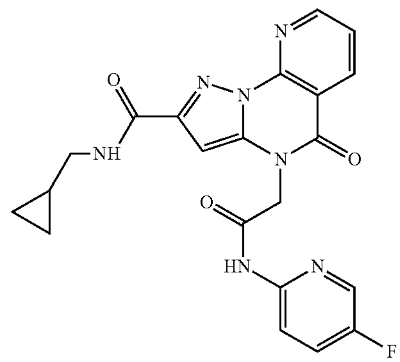

-continued
18
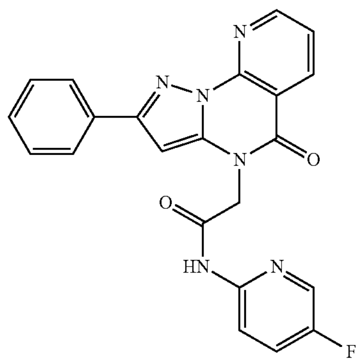
19
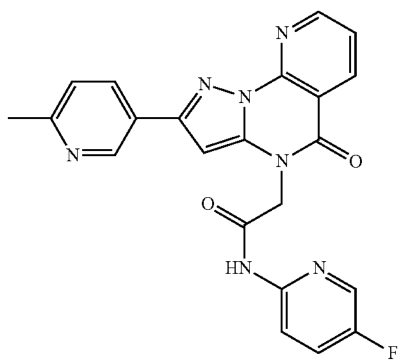
20
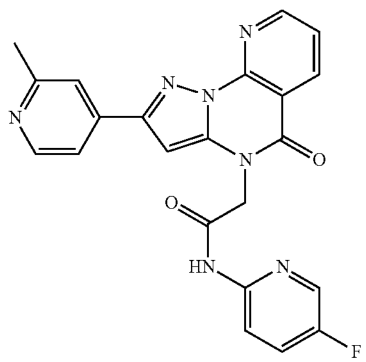
21
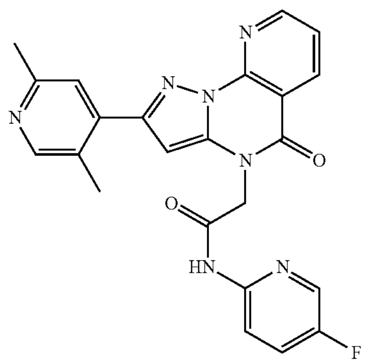
-continued
22
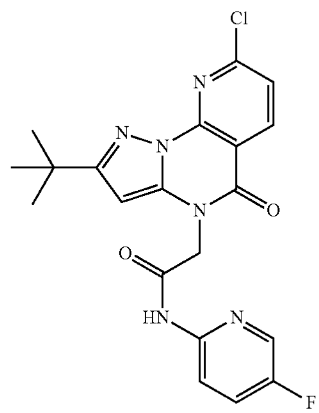
23
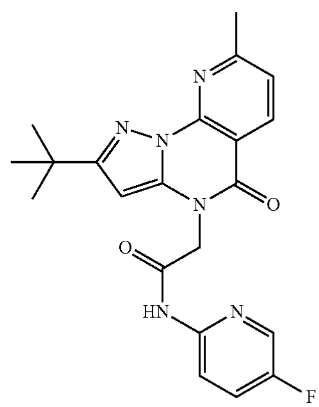
24
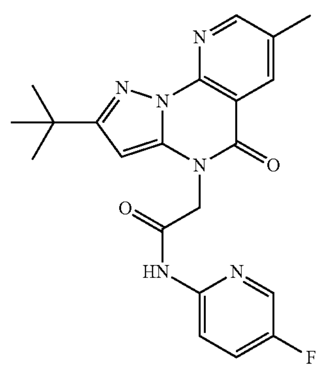
25
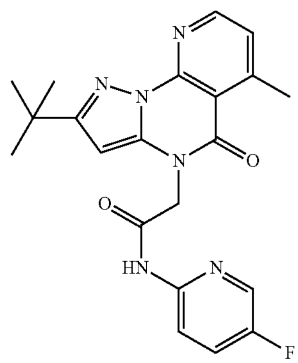

-continued
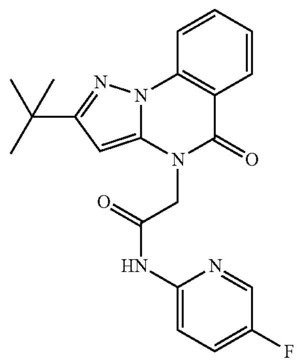 [SMILES: CC(C)(C)c1cc2n(CC(=O)Nc3ccc(F)cn3)c(=O)c3ncccc3n2n1]
26
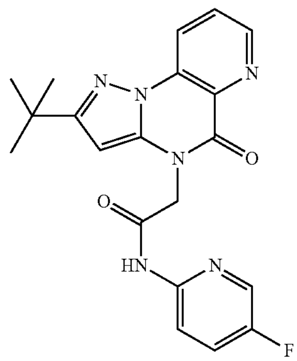
27
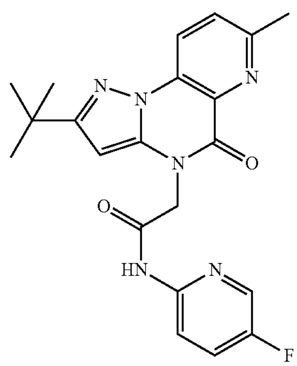 [SMILES: Cc1ccc2c(n1)c(=O)n(CC(=O)Nc1ccc(F)cn1)c1cc(C(C)(C)C)nn21]
28
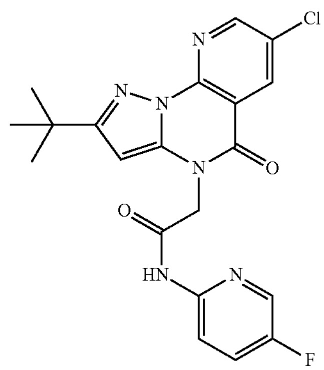 [SMILES: CC(C)(C)c1cc2n(CC(=O)Nc3ccc(F)cn3)c(=O)c3cc(Cl)cnc3n2n1]
29
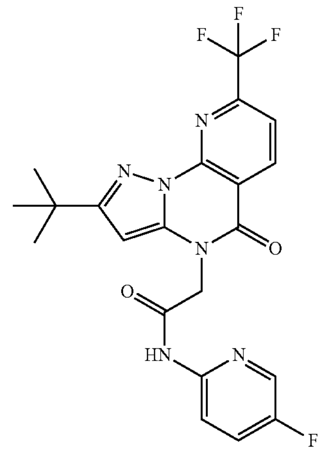 [SMILES: CC(C)(C)c1cc2n(CC(=O)Nc3ccc(F)cn3)c(=O)c3ccc(C(F)(F)F)nc3n2n1]
30
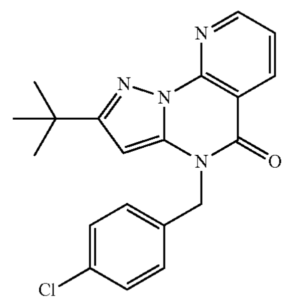 [SMILES: CC(C)(C)c1cc2n(Cc3ccc(Cl)cc3)c(=O)c3cccnc3n2n1]
31
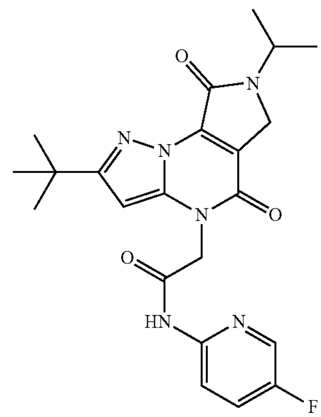 [SMILES: CC(C)N1Cc2c(n3nc(C(C)(C)C)cc3n(CC(=O)Nc3ccc(F)cn3)c2=O)C1=O]
32
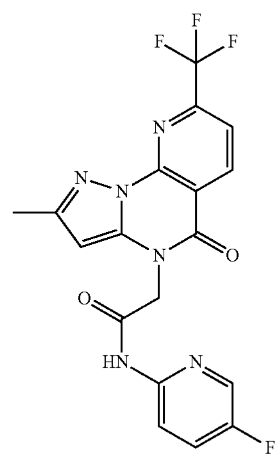 [SMILES: Cc1cc2n(CC(=O)Nc3ccc(F)cn3)c(=O)c3ccc(C(F)(F)F)nc3n2n1]
33

-continued
34
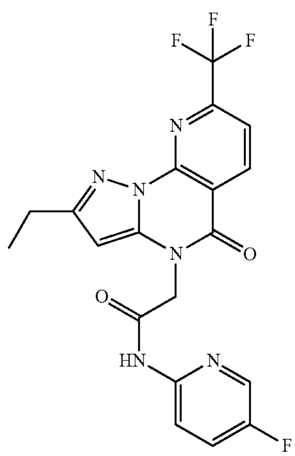 [SMILES: CCc1cc2n(CC(=O)Nc3ccc(F)cn3)c(=O)c3ccc(C(F)(F)F)nc3n2n1]
35
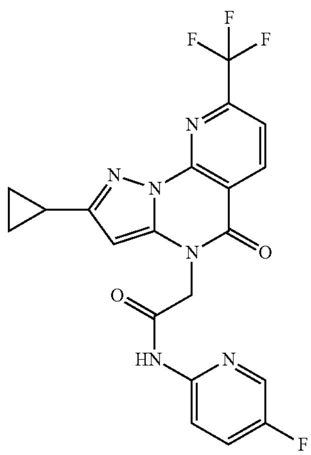 [SMILES: O=C(Cn1c(=O)c2ccc(C(F)(F)F)nc2n2nc(C3CC3)cc12)Nc1ccc(F)cn1]
36
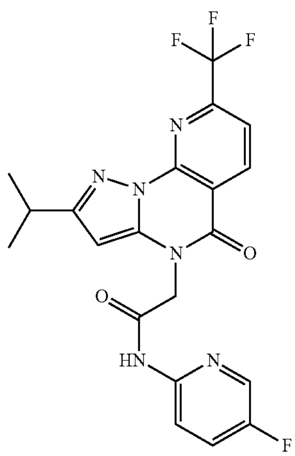 [SMILES: CC(C)c1cc2n(CC(=O)Nc3ccc(F)cn3)c(=O)c3ccc(C(F)(F)F)nc3n2n1]
-continued
37
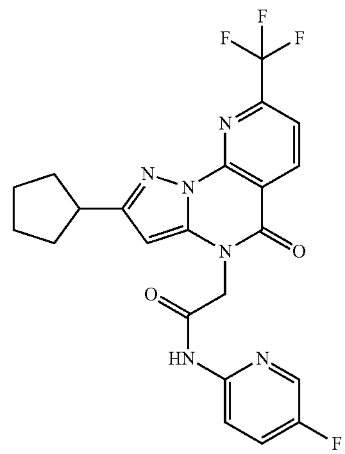 [SMILES: O=C(Cn1c(=O)c2ccc(C(F)(F)F)nc2n2nc(C3CCCC3)cc12)Nc1ccc(F)cn1]
38
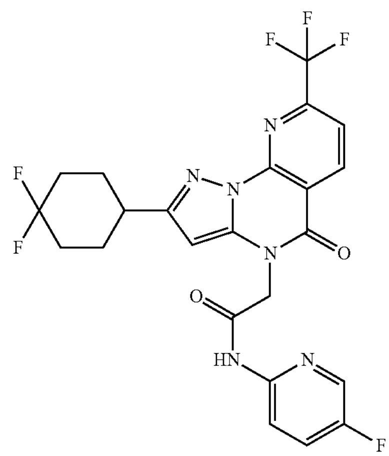
39
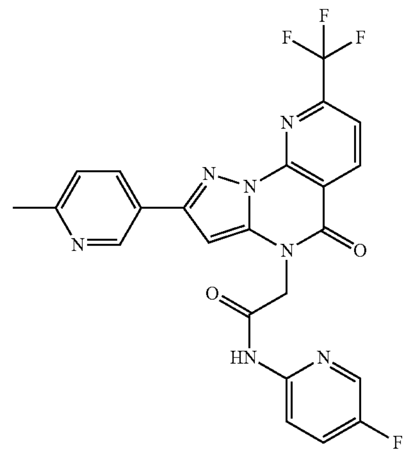 [SMILES: Cc1ccc(-c2cc3n(CC(=O)Nc4ccc(F)cn4)c(=O)c4ccc(C(F)(F)F)nc4n3n2)cn1]

-continued
40
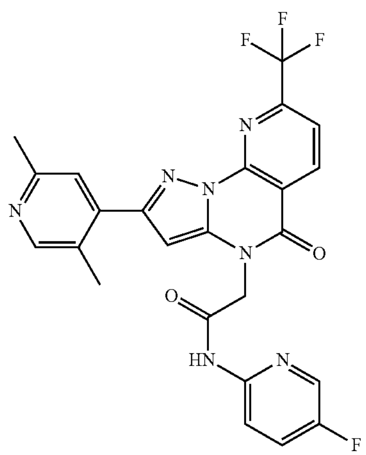 [SMILES: Cc1cc(-c2cc3n(CC(=O)Nc4ccc(F)cn4)c(=O)c4ccc(C(F)(F)F)nc4n3n2)c(C)cn1]
41
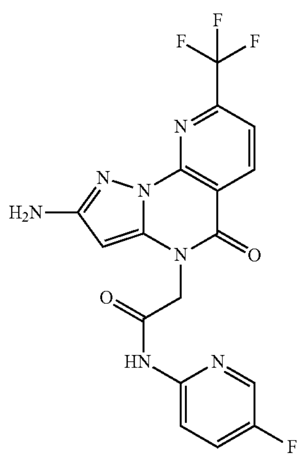 [SMILES: Nc1cc2n(CC(=O)Nc3ccc(F)cn3)c(=O)c3ccc(C(F)(F)F)nc3n2n1]
42
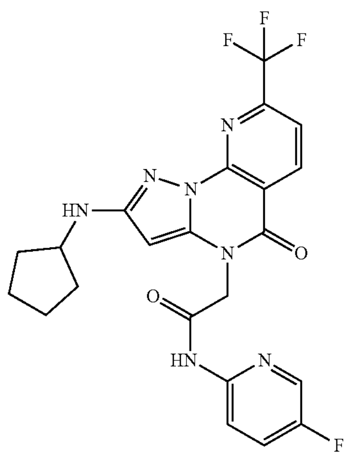 [SMILES: O=C(Cn1c(=O)c2ccc(C(F)(F)F)nc2n2nc(NC3CCCC3)cc12)Nc1ccc(F)cn1]
-continued
43
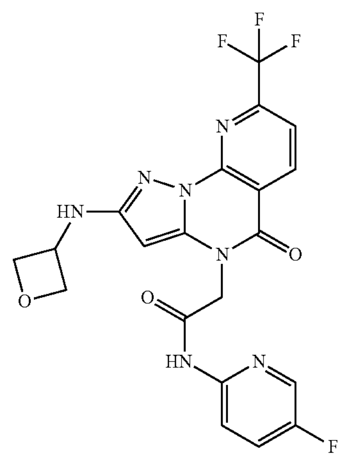 [SMILES: O=C(Cn1c(=O)c2ccc(C(F)(F)F)nc2n2nc(NC3COC3)cc12)Nc1ccc(F)cn1]
44
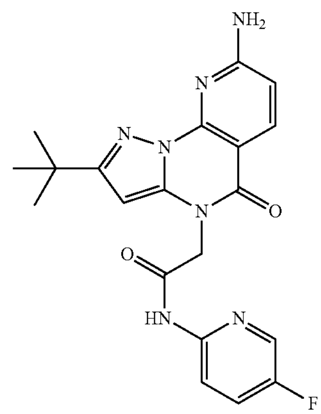
45
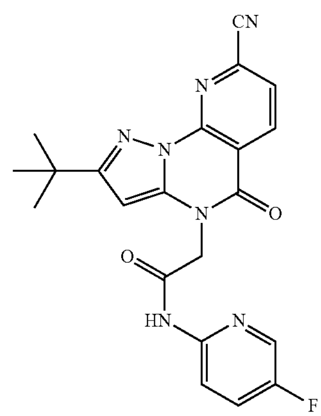 [SMILES: CC(C)(C)c1cc2n(CC(=O)Nc3ccc(F)cn3)c(=O)c3ccc(C#N)nc3n2n1]

-continued
46
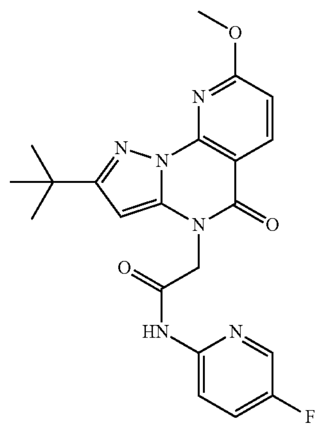 [SMILES: COc1ccc2c(=O)n(CC(=O)Nc3ccc(F)cn3)c3cc(C(C)(C)C)nn3c2n1]
47
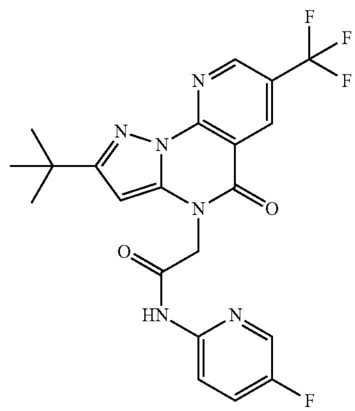 [SMILES: CC(C)(C)c1cc2n(CC(=O)Nc3ccc(F)cn3)c(=O)c3cc(C(F)(F)F)cnc3n2n1]
48
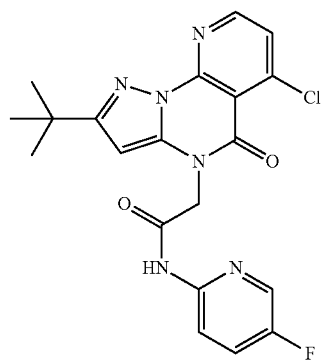 [SMILES: CC(C)(C)c1cc2n(CC(=O)Nc3ccc(F)cn3)c(=O)c3c(Cl)ccnc3n2n1]
49
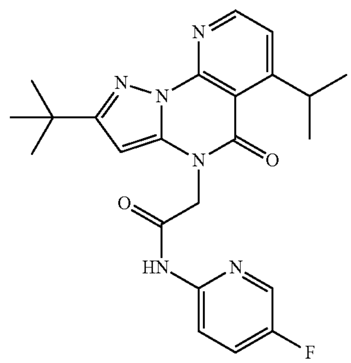 [SMILES: CC(C)c1ccnc2c1c(=O)n(CC(=O)Nc1ccc(F)cn1)c1cc(C(C)(C)C)nn21]
-continued
50
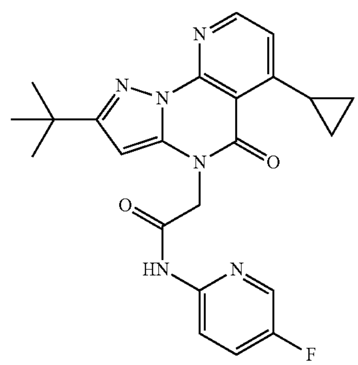 [SMILES: CC(C)(C)c1cc2n(CC(=O)Nc3ccc(F)cn3)c(=O)c3c(C4CC4)ccnc3n2n1]
51
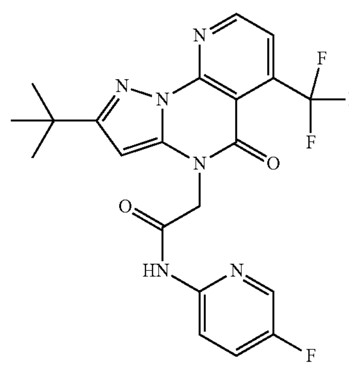
52
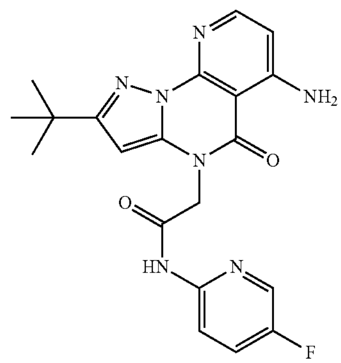 [SMILES: CC(C)(C)c1cc2n(CC(=O)Nc3ccc(F)cn3)c(=O)c3c(N)ccnc3n2n1]
53
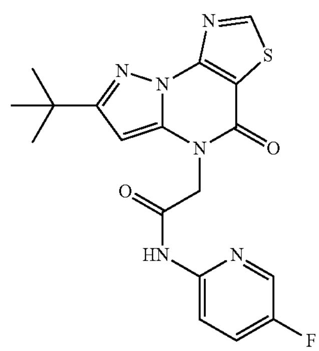 [SMILES: CC(C)(C)c1cc2n(CC(=O)Nc3ccc(F)cn3)c(=O)c3scnc3n2n1]

54
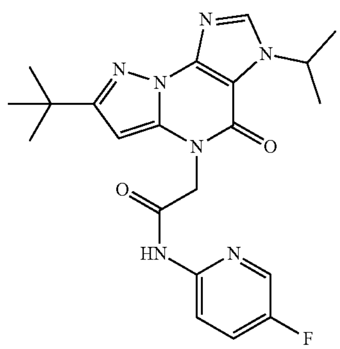 [SMILES: CC(C)n1cnc2c1c(=O)n(CC(=O)Nc1ccc(F)cn1)c1cc(C(C)(C)C)nn21]
55
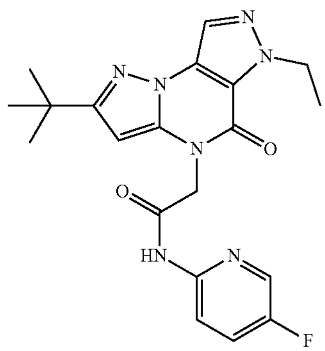
56
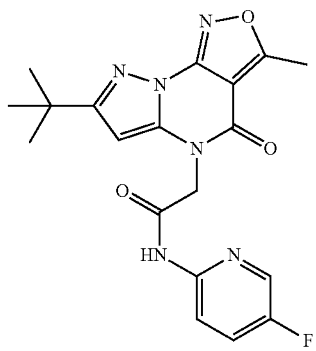 [SMILES: Cc1onc2c1c(=O)n(CC(=O)Nc1ccc(F)cn1)c1cc(C(C)(C)C)nn21]
57
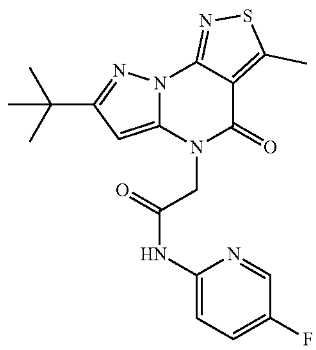 [SMILES: Cc1snc2c1c(=O)n(CC(=O)Nc1ccc(F)cn1)c1cc(C(C)(C)C)nn21]
58
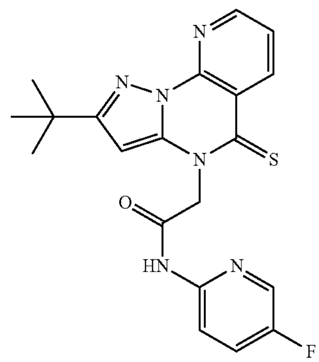 [SMILES: CC(C)(C)c1cc2n(CC(=O)Nc3ccc(F)cn3)c(=S)c3cccnc3n2n1]
59
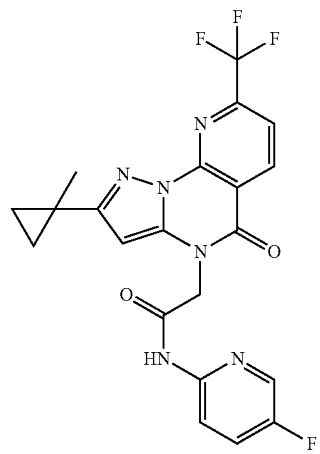
61-0
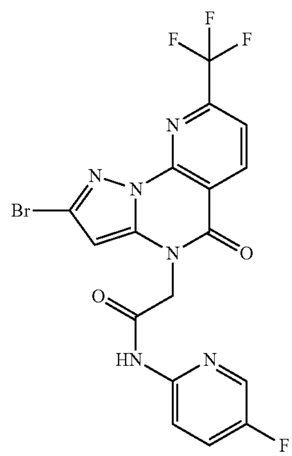

-continued
60
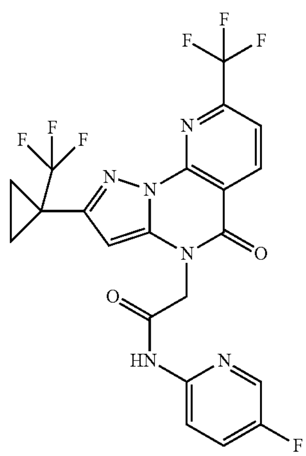
61
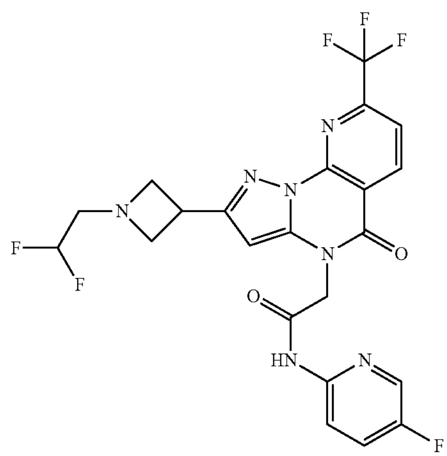 [SMILES: O=C(Cn1c(=O)c2ccc(C(F)(F)F)nc2n2nc(C3CN(CC(F)F)C3)cc12)Nc1ccc(F)cn1]
62
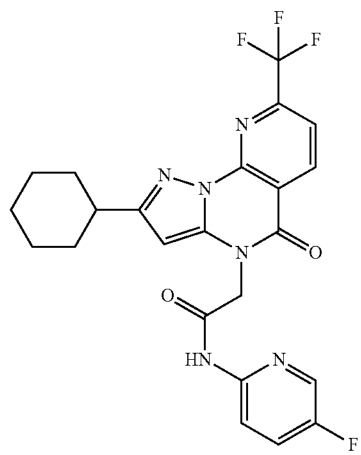 [SMILES: O=C(Cn1c(=O)c2ccc(C(F)(F)F)nc2n2nc(C3CCCCC3)cc12)Nc1ccc(F)cn1]
-continued
63
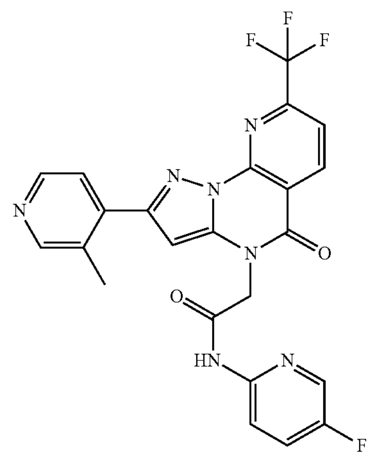 [SMILES: Cc1cnccc1-c1cc2n(CC(=O)Nc3ccc(F)cn3)c(=O)c3ccc(C(F)(F)F)nc3n2n1]
64
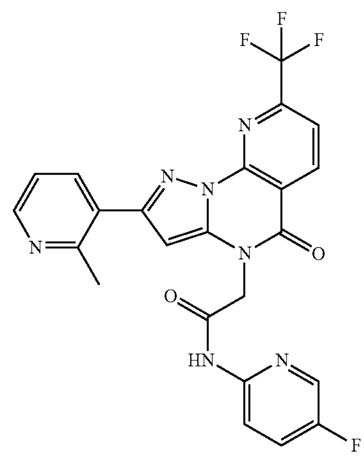 [SMILES: Cc1ncccc1-c1cc2n(CC(=O)Nc3ccc(F)cn3)c(=O)c3ccc(C(F)(F)F)nc3n2n1]
65
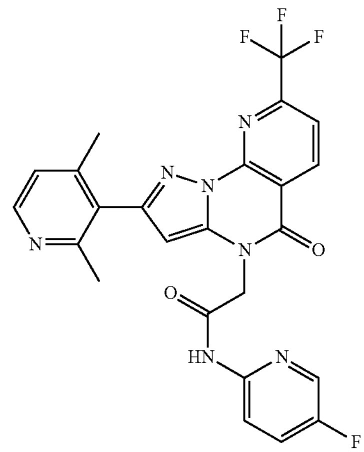 [SMILES: Cc1ccnc(C)c1-c1cc2n(CC(=O)Nc3ccc(F)cn3)c(=O)c3ccc(C(F)(F)F)nc3n2n1]

-continued
66
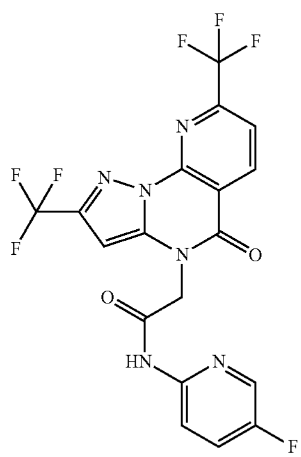
67
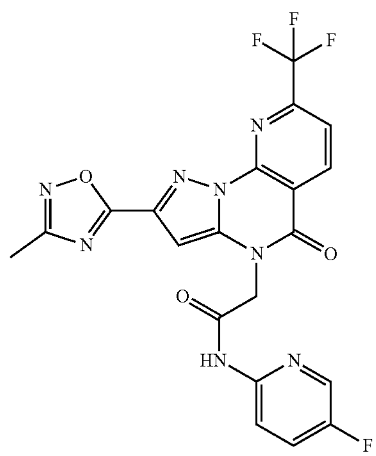
68
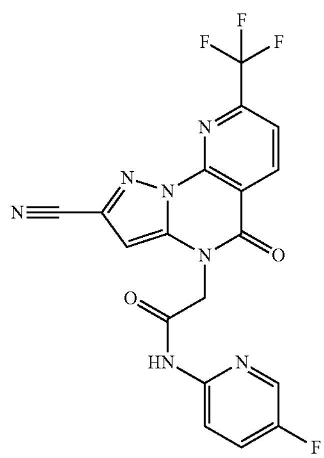 [SMILES: N#Cc1cc2n(CC(=O)Nc3ccc(F)cn3)c(=O)c3ccc(C(F)(F)F)nc3n2n1]
-continued
69
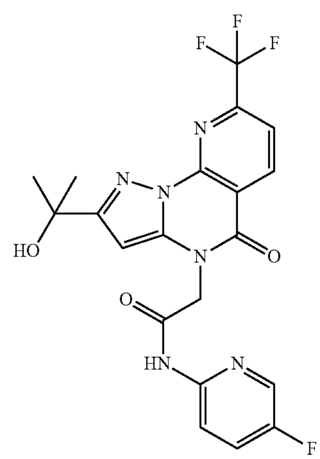
70
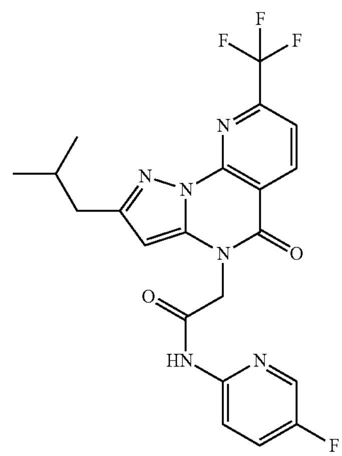 [SMILES: CC(C)Cc1cc2n(CC(=O)Nc3ccc(F)cn3)c(=O)c3ccc(C(F)(F)F)nc3n2n1]
71
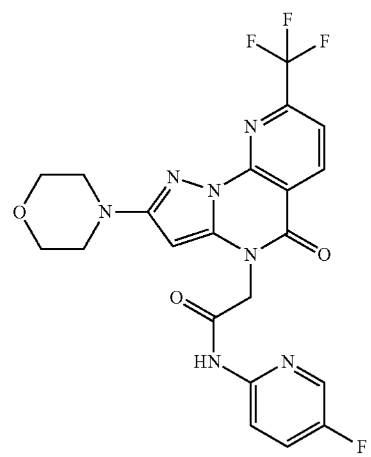 [SMILES: O=C(Cn1c(=O)c2ccc(C(F)(F)F)nc2n2nc(N3CCOCC3)cc12)Nc1ccc(F)cn1]

-continued
72
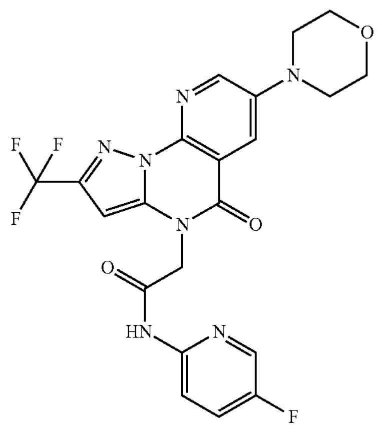
73
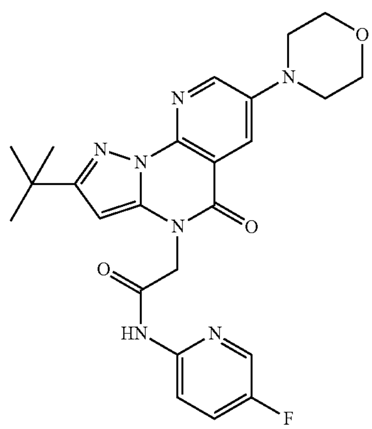
74
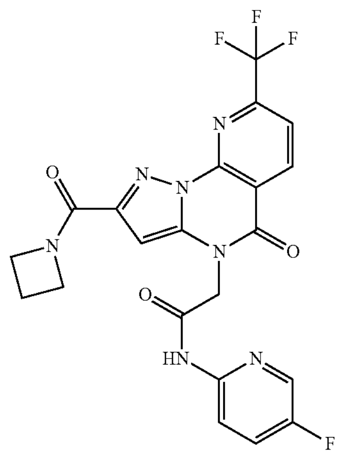 [SMILES: O=C(Cn1c(=O)c2ccc(C(F)(F)F)nc2n2nc(C(=O)N3CCC3)cc12)Nc1ccc(F)cn1]
-continued
75
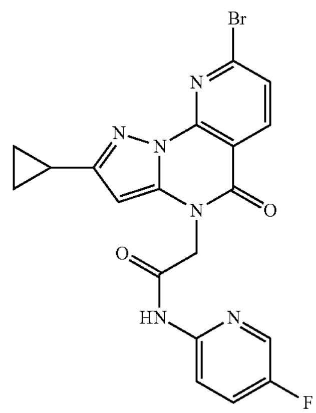
76
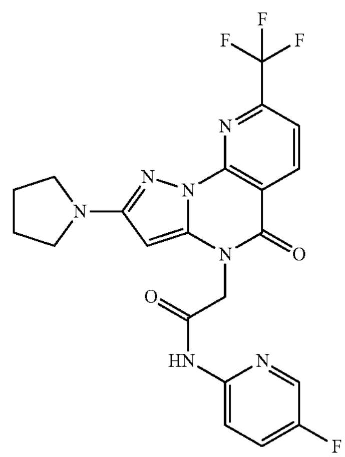
77
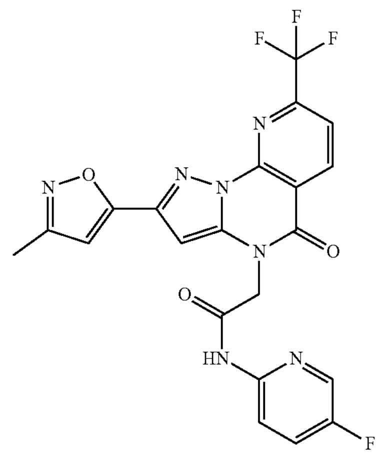

-continued
78
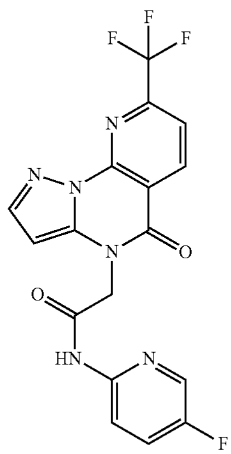 [SMILES: O=C(Cn1c(=O)c2ccc(C(F)(F)F)nc2n2nccc12)Nc1ccc(F)cn1]
79
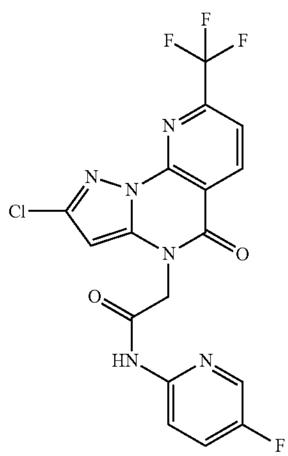 [SMILES: O=C(Cn1c(=O)c2ccc(C(F)(F)F)nc2n2nc(Cl)cc12)Nc1ccc(F)cn1]
80
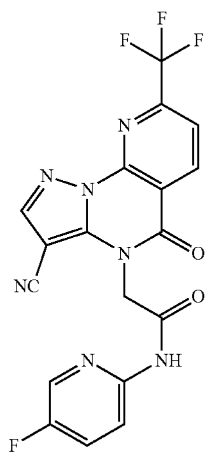
-continued
81
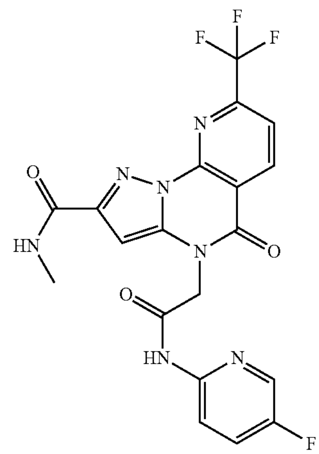 [SMILES: CNC(=O)c1cc2n(CC(=O)Nc3ccc(F)cn3)c(=O)c3ccc(C(F)(F)F)nc3n2n1]
82
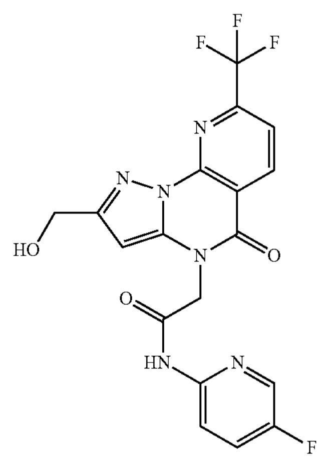 [SMILES: O=C(Cn1c(=O)c2ccc(C(F)(F)F)nc2n2nc(CO)cc12)Nc1ccc(F)cn1]
83
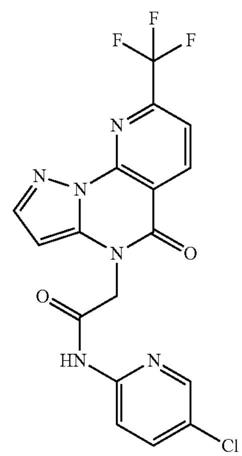 [SMILES: O=C(Cn1c(=O)c2ccc(C(F)(F)F)nc2n2nccc12)Nc1ccc(Cl)cn1]

-continued
84
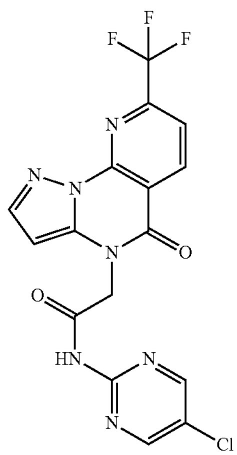 [SMILES: O=C(Cn1c(=O)c2ccc(C(F)(F)F)nc2n2nccc12)Nc1ncc(Cl)cn1]
85
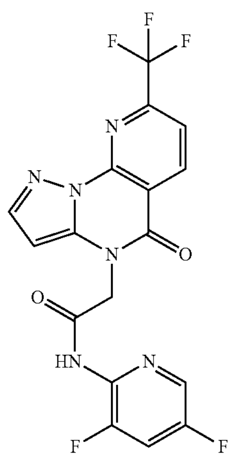 [SMILES: O=C(Cn1c(=O)c2ccc(C(F)(F)F)nc2n2nccc12)Nc1ncc(F)cc1F]
86
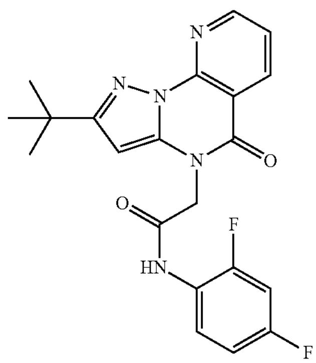
-continued
87
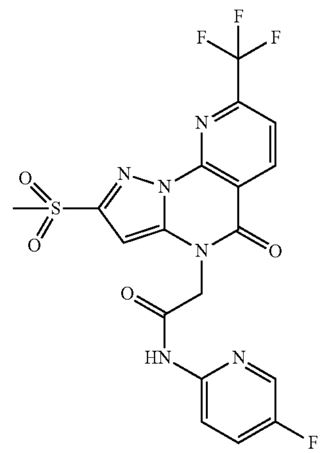
88
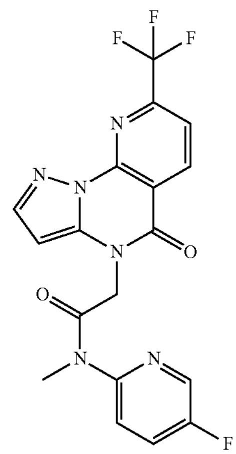
89
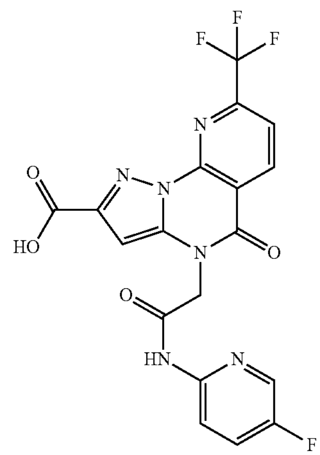

-continued
90
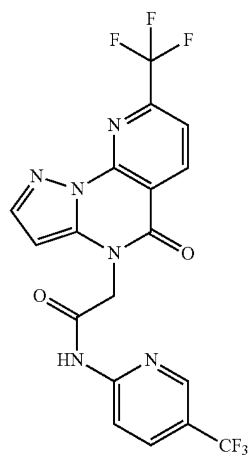
91
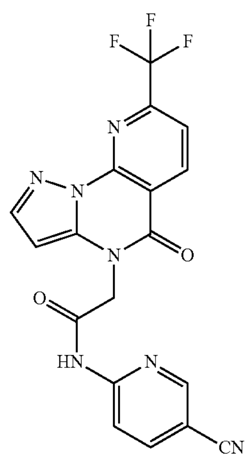
92
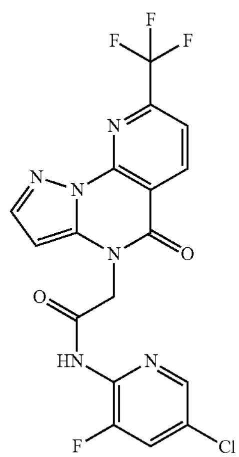
-continued
93
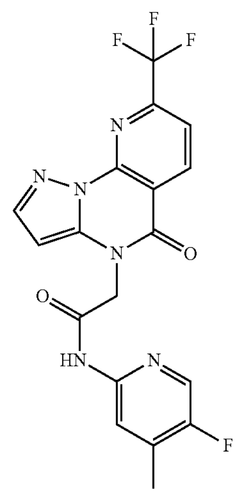
94
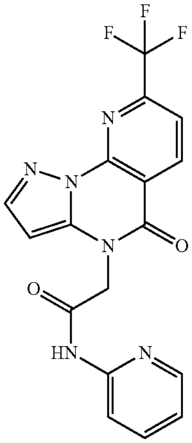
and
95
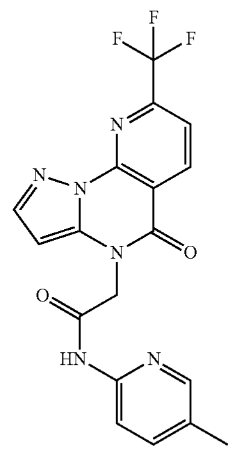
19. A method for preparing the compound of formula (III), a stereoisomer thereof or a pharmaceutically acceptable salt thereof according to claim 14, comprising the following step of:

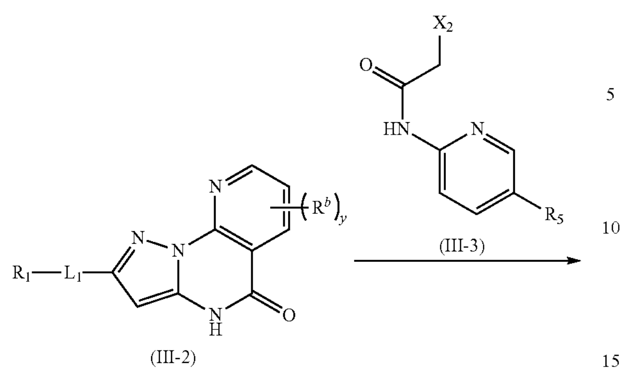

(III-2)

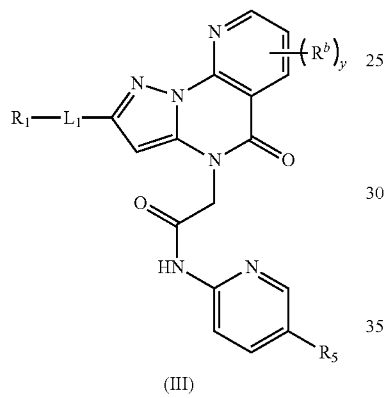

(III)

reacting a compound of formula (III-2) with a compound of formula (III-3) to obtain the target compound of formula (III);

wherein:

$X_2$ is halogen.

20. A method for preparing the compound of formula (V), a stereoisomer thereof or a pharmaceutically acceptable salt thereof according to claim 16, comprising the following step of:

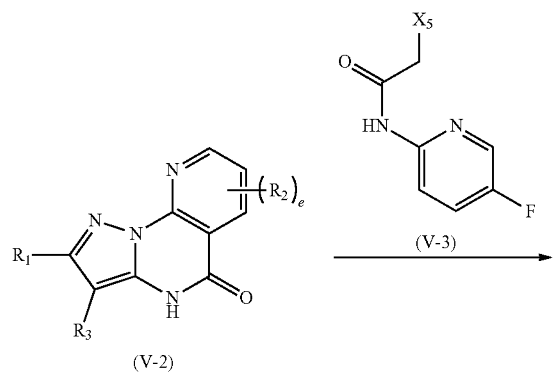

(V-2)

-continued

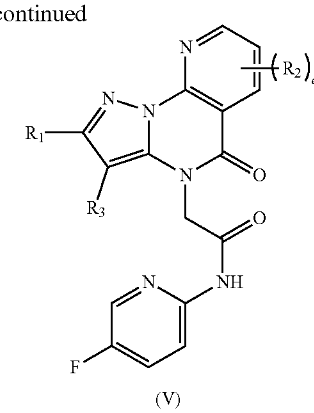

(V)

reacting a compound of formula (V-2) with a compound of formula (V-3) to obtain the target compound of formula (V);

wherein:

$X_5$ is halogen.

21. A pharmaceutical composition comprising a therapeutically effective dose of the compound, a stereoisomer thereof or a pharmaceutically acceptable salt thereof according to claim 1, and one or more pharmaceutically acceptable carriers or excipients.

22. A method for treating a neurogenic disease in a patient in need thereof, the method comprising administering to the patient a therapeutically effective dose of the compound, a stereoisomer thereof or a pharmaceutically acceptable salt thereof according to claim 1, wherein the neurogenic disease is selected from neuropathic pain or pain and discomfort related to uterine fibroid.

23. The compound, a stereoisomer thereof or a pharmaceutically acceptable salt thereof according to claim 14, wherein:

$R^b$ is selected from the group consisting of hydrogen, deuterium, halogen, amino, hydroxy, cyano, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3 to 10 membered heterocyclyl, $C_{6-12}$ aryl and 5 to 12 membered heteroaryl.

24. The compound, a stereoisomer thereof or a pharmaceutically acceptable salt thereof according to claim 14, wherein:

$R^b$ is selected from the group consisting of hydrogen, deuterium, fluorine, chlorine, bromine, amino, hydroxy, cyano, methyl, ethyl, propyl, vinyl, propenyl, allyl, ethynyl, propynyl, propargyl, deuterated methyl, deuterated ethyl, deuterated propyl, fluoromethyl, fluoroethyl, fluoropropyl, chloromethyl, chloroethyl, chloropropyl, bromomethyl, bromoethyl, bromopropyl, hydroxymethyl, hydroxyethyl, hydroxypropyl, methoxy, ethoxy, propoxy, fluoromethoxy, fluoroethoxy, fluoropropoxy, chloromethoxy, chloroethoxy, chloropropoxy, cyclopropyl, cyclobutyl, cyclopentyl, cyclohexyl, cycloheptyl, oxiranyl, oxetanyl, tetrahydrofuryl, tetrahydropyranyl, oxepanyl, aziridinyl, azetidinyl, azacyclopentyl, azacyclohexyl, azacycloheptyl, thienyl, pyrrolyl, pyridyl, pyranyl, piperazinyl, phenyl and naphthyl.

25. A compound of formula (I), a stereoisomer thereof or a pharmaceutically acceptable salt thereof:

(I)

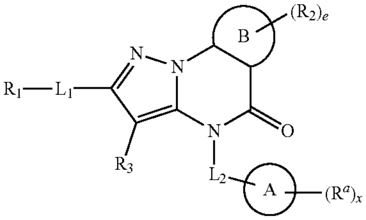

wherein:

$L_1$ is selected from the group consisting of a bond, $-(CH_2)_{n1}-$, $-(CH_2)_{n1}C(O)(CR_{aa}R_{bb})_{n2}-$, $-(CH_2)_{n1}C(O)NR_{aa}(CH_2)_{n2}-$, $-(CH_2)_{n1}(CR_{aa}R_{bb})_{n2}-$, $-(CR_{aa}R_{bb})_{n1}O(CH_2)_{n2}-$, $-(CH_2)_{n1}O(CR_{aa}R_{bb})_{n2}-$, $-(CR_{aa}R_{bb})_{n1}S(CH_2)_{n2}-$, $-(CH_2)_{n1}S(CR_{aa}R_{bb})_{n2}-$, $-(CR_{aa}R_{bb})_{n1}(CH_2)_{n2}NR_{cc}-$, $-(CH_2)_{n1}NR_{aa}(CR_{bb}R_{cc})_{n2}-$, $-(CH_2)_{n1}NR_{aa}C(O)-$, $-(CH_2)_{n1}P(O)R_{aa}-$, $-(CH_2)_{n1}S(O)_{n2}-$, $-(CH_2)_{n1}S(O)_{n2}NR_{aa}-$ and $-(CH_2)_{n1}NR_{aa}S(O)_{n2}-$;

$R_{aa}$, $R_{bb}$, $R_{cc}$ are each independently selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

or, any two of $R_{aa}$, $R_{bb}$, $R_{cc}$ are bonded to form a cycloalkyl, heterocyclyl, aryl or heteroaryl, wherein the cycloalkyl, heterocyclyl, aryl or heteroaryl can be optionally further substituted;

$L_2$ is selected from the group consisting of $-(CH_2)_{n3}C(O)(CR_{dd}R_{ee})_{n4}-$, $(CH_2)_{n3}C(O)NR_{dd}(CH_2)_{n4}-$, $-(CR_{dd}R_{ee})_{n3}O(CH_2)_{n4}-$, $-(CH_2)_{n3}O(CR_{dd}R_{ee})_{n4}-$, $-(CR_{dd}R_{ee})_{n3}S(CH_2)_{n4}-$, $-(CH_2)_{n3}S(CR_{dd}R_{ee})_{n4}-$, $-(CR_{dd}R_{ee})_{n3}(CH_2)_{n4}NR_{ff}-$, $-(CH_2)_{n3}NR_{dd}(CR_{ee}R_{ff})_{n4}-$, $-(CH_2)_{n3}NR_{dd}C(O)-$, $-(CH_2)_{n3}P(O)R_{dd}-$, $-(CH_2)_{n3}S(O)_{n4}-$, $-(CH_2)_{n3}S(O)_{n4}NR_{dd}-$ and $-(CH_2)_{n3}NR_{dd}S(O)_{n4}-$;

$R_{dd}$, $R_{ee}$, $R_{ff}$ are each independently selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

or, any two of $R_{dd}$, $R_{ee}$, $R_{ff}$ are bonded to form a cycloalkyl, heterocyclyl, aryl or heteroaryl, wherein the cycloalkyl, heterocyclyl, aryl or heteroaryl can be optionally further substituted;

ring A is selected from the group consisting of cycloalkyl, heterocyclyl, aryl and heteroaryl;

$R_1$ is selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

ring B is selected from the group consisting of cycloalkyl, heterocyclyl and heteroaryl;

$R_2$ is selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

$R_3$ is selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl and heteroaryl can be each optionally further substituted;

$R^a$ is selected from the group consisting of hydrogen, deuterium, halogen, amino, nitro, hydroxy, cyano, oxo, thioxo, alkyl, deuterated alkyl, haloalkyl, hydroxyalkyl, alkoxy, haloalkoxy, alkenyl, alkynyl, heterocyclylalkyl, cycloalkyl, heterocyclyl, aryl, heteroaryl, $-(CH_2)_{n5}R_{gg}$, $-(CH_2)_{n5}OR_{gg}$, $-(CH_2)_{n5}C(O)OR_{gg}$, $-(CH_2)_{n5}SR_{gg}$, $-(CH_2)_{n5}NR_{gg}C(O)(CH_2)_{n6}R_{hh}$, $-(CH_2)_{n5}NR_{gg}C(O)OR_{hh}$, $-(CH_2)_{n5}NR_{gg}C(O)NR_{hh}R_{ii}$, $-(CH_2)_{n5}NR_{gg}R_{hh}$, $-NR_{gg}(CH_2)_{n5}R_{hh}$, $-(CH_2)_{n5}C(O)NR_{gg}(CH_2)_{n6}R_{hh}$, $-(CH_2)_{n5}C(O)R_{gg}$, $-(CH_2)_{n5}S(O)_{n6}R_{gg}$, $-(CH_2)_{n5}NR_{gg}S(O)_{n6}R_{hh}$, $-CH{=}CH(CH_2)_{n5}R_{gg}$, $-CH{=}CH(CH_2)_{n5}NR_{gg}R_{hh}$, $-CH{=}CH(CH_2)_{n5}NR_{gg}C(O)R_{hh}$ and $CH{=}CH(CH_2)_{n5}NR_{gg}C(O)NR_{hh}R_{ii}$, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl and heteroaryl can be each optionally further substituted;

$R_{gg}$, $R_{hh}$, $R_{ii}$ are each independently selected from the group consisting of hydrogen, deuterium, halogen, amino, nitro, hydroxy, cyano, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy, wherein the amino, alkyl, deuterated alkyl, haloalkyl, hydroxyalkyl, alkoxy, haloalkoxy, alkenyl, alkynyl, heterocyclylalkyl, cycloalkyl, heterocyclyl, aryl, aryloxy, heteroaryl and heteroaryloxy can be each optionally further substituted;

or, any two of $R_{gg}$, $R_{hh}$, $R_{ii}$ are bonded to form a cycloalkyl, heterocyclyl, aryl or heteroaryl, wherein the cycloalkyl, heterocyclyl, aryl or heteroaryl can be optionally further substituted;

x is an integer from 0 to 6;

e is an integer from 0 to 6;

n1, n3, and n5 are each independently an integer from 0 to 3; and n2, n4, and n6 are each independently an integer from 0 to 2.

* * * * *